US011291710B2

(12) United States Patent
Khalili et al.

(10) Patent No.: US 11,291,710 B2
(45) **Date of Patent: *Apr. 5, 2022**

(54) METHODS AND COMPOSITIONS FOR RNA-GUIDED TREATMENT OF HIV INFECTION

(71) Applicant: Temple University of The Commonwealth System of Higher Education, Philadelphia, PA (US)

(72) Inventors: Kamel Khalili, Bala Cynwyd, PA (US); Wenhui Hu, Cherry Hill, NJ (US)

(73) Assignee: Temple University—of the Commonwealth System of Higher Education, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/874,295

(22) Filed: May 14, 2020

(65) Prior Publication Data

US 2021/0069303 A1 Mar. 11, 2021

Related U.S. Application Data

(63) Continuation of application No. 15/950,236, filed on Apr. 11, 2018, now abandoned, which is a continuation of application No. 15/148,261, filed on May 6, 2016, now Pat. No. 9,981,020, which is a continuation of application No. 14/838,057, filed as application No. PCT/US2014/053441 on Aug. 29, 2014, now Pat. No. 9,925,248.

(60) Provisional application No. 62/026,103, filed on Jul. 18, 2014, provisional application No. 62/018,441, filed on Jun. 27, 2014, provisional application No. 61/871,626, filed on Aug. 29, 2013.

(51) Int. Cl.

| | |
|---|---|
| ***A61K 38/46*** | (2006.01) |
| ***C12N 15/11*** | (2006.01) |
| ***A61K 48/00*** | (2006.01) |
| ***A61K 9/00*** | (2006.01) |
| ***A61K 35/12*** | (2015.01) |
| ***A61K 45/06*** | (2006.01) |
| ***C12N 7/00*** | (2006.01) |
| ***C12N 9/22*** | (2006.01) |

(52) U.S. Cl.

CPC .......... *A61K 38/465* (2013.01); *A61K 9/0034* (2013.01); *A61K 35/12* (2013.01); *A61K 45/06* (2013.01); *A61K 48/00* (2013.01); *A61K 48/005* (2013.01); *C12N 7/00* (2013.01); *C12N 9/22* (2013.01); *C12N 15/111* (2013.01); *C12N 2310/20* (2017.05); *C12N 2320/30* (2013.01); *C12N 2740/16063* (2013.01); *C12Y 301/21* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 6,392,029 | B1 | 5/2002 | Ludwig et al. |
| 6,727,240 | B1 | 4/2004 | Neurath et al. |
| 8,871,516 | B2 | 10/2014 | Hauber et al. |
| 8,895,308 | B1 | 11/2014 | Zhang et al. |
| 9,023,649 | B2 | 5/2015 | Mali et al. |
| 9,925,248 | B2 | 3/2018 | Khalili et al. |
| 9,981,020 | B2 | 5/2018 | Khalili et al. |
| 2003/0087817 | A1 | 5/2003 | Cox et al. |
| 2003/0180756 | A1 | 9/2003 | Shi et al. |
| 2004/0132161 | A1 | 7/2004 | Finkel et al. |
| 2007/0175484 | A1 | 8/2007 | Staab |
| 2011/0171733 | A1 | 7/2011 | Luo et al. |
| 2014/0357530 | A1 | 12/2014 | Zhang et al. |
| 2015/0020223 | A1 | 1/2015 | Zhang et al. |

(Continued)

FOREIGN PATENT DOCUMENTS

| | | | |
|---|---|---|---|
| CN | 103060378 | A | 12/2002 |
| EP | 3 038 661 | A1 | 4/2013 |

(Continued)

OTHER PUBLICATIONS

Chen et al. (Jan. 2003) "Expression of ssDNA in Mammalian Cells", Biotechniques, 34(1):4 pages.

Chenna et al. (Jul. 2003) "Multiple Sequence Alignment with the Clustal Series of Programs", Nucleic Acids Research, 31(13):3497-3500.

Curiel et al. (Oct. 1991) "Adenovirus Enhancement of Transferrin-Polylysine-Mediated Gene Delivery", PNAS, 88:8850-8854.

Database Genbank, "Expression Vector pCas9, Complete Sequence", Genbank Accession No. KM099231.1, Aug. 9, 2014, 4 pages.

(Continued)

*Primary Examiner* — Nancy J Leith

(74) *Attorney, Agent, or Firm* — Mintz Levin Cohn Ferris Glovsky and Popeo, P.C.; Nicholas A. Zachariades

(57) ABSTRACT

A method of preventing transmission of a retrovirus from a mother to her offspring, by administering to the mother a therapeutically effective amount of a composition comprising a Clustered Regularly Interspaced Short Palindromic Repeat (CRISPR)-associated endonuclease, and the two or more different multiplex gRNAs, wherein each of the at least two gRNAs is complementary to a different target nucleic acid sequence in a long terminal repeat (LTR) of proviral DNA of the virus that is unique from the genome of the host cell, cleaving a double strand of the proviral DNA at a first target protospacer sequence with the CRISPR-associated endonuclease, cleaving a double strand of the proviral DNA at a second target protospacer sequence with the CRISPR-associated endonuclease, excising an entire HIV-1 proviral genome, eradicating the HIV-1 proviral DNA from the host cell, and preventing transmission of the proviral DNA to the offspring.

15 Claims, 30 Drawing Sheets

Specification includes a Sequence Listing.

(56) References Cited

U.S. PATENT DOCUMENTS

| | | | |
|---|---|---|---|
| 2016/0017301 | A1 | 1/2016 | Khalili et al. |
| 2016/0040165 | A1 | 2/2016 | Howell et al. |
| 2016/0250300 | A1 | 9/2016 | Khalili et al. |
| 2018/0169193 | A1 | 6/2018 | Khalili et al. |
| 2018/0169194 | A1 | 6/2018 | Khalili et al. |
| 2018/0169195 | A1 | 6/2018 | Khalili et al. |
| 2018/0200343 | A1 | 7/2018 | Khalili et al. |
| 2018/0207243 | A1 | 7/2018 | Khalili et al. |
| 2018/0208914 | A1 | 7/2018 | Khalili et al. |
| 2018/0214521 | A1 | 8/2018 | Khalili et al. |
| 2018/0221458 | A1 | 8/2018 | Khalili et al. |
| 2018/0228874 | A1 | 8/2018 | Khalili et al. |
| 2018/0228875 | A1 | 8/2018 | Khalili et al. |
| 2018/0228876 | A1 | 8/2018 | Khalili et al. |
| 2018/0236041 | A1 | 8/2018 | Khalili et al. |
| 2018/0236042 | A1 | 8/2018 | Khalili et al. |
| 2018/0236043 | A1 | 8/2018 | Khalili et al. |
| 2018/0236044 | A1 | 8/2018 | Khalili et al. |
| 2018/0236045 | A1 | 8/2018 | Khalili et al. |
| 2018/0236046 | A1 | 8/2018 | Khalili et al. |
| 2018/0296649 | A1 | 10/2018 | Khalili et al. |
| 2018/0303915 | A1 | 10/2018 | Khalili et al. |
| 2019/0032057 | A1 | 1/2019 | Khalili et al. |
| 2019/0038770 | A1 | 2/2019 | Khalili et al. |
| 2019/0083656 | A1 | 3/2019 | Khalili et al. |
| 2019/0085326 | A1 | 3/2019 | Khalili et al. |
| 2019/0093091 | A1 | 3/2019 | Khalili et al. |
| 2019/0093092 | A1 | 3/2019 | Khalili et al. |
| 2019/0225963 | A1 | 7/2019 | Khalili et al. |
| 2019/0247470 | A1 | 8/2019 | Khalili et al. |
| 2019/0256844 | A1 | 8/2019 | Khalili et al. |
| 2019/0273576 | A1 | 9/2019 | Zhang et al. |
| 2019/0365862 | A1 | 12/2019 | Khalili et al. |
| 2019/0367910 | A1 | 12/2019 | Khalili et al. |
| 2019/0367924 | A1 | 12/2019 | Khalili et al. |
| 2020/0140865 | A1 | 5/2020 | Khalili et al. |
| 2020/0282025 | A1 | 9/2020 | Khalili |

FOREIGN PATENT DOCUMENTS

| | | | |
|---|---|---|---|
| JP | 2016-501531 | A | 6/2014 |
| JP | 2016-514479 | A | 3/2015 |
| WO | 9737005 | A1 | 10/1997 |
| WO | 0066759 | A1 | 11/2000 |
| WO | 2013098244 | A1 | 7/2013 |
| WO | 2014165349 | A1 | 10/2014 |
| WO | 02/096349 | A2 | 12/2015 |
| WO | 2014/093622 | A2 | 1/2016 |
| WO | 2015/031775 | A1 | 5/2016 |
| WO | 2015/184259 | A1 | 7/2016 |

OTHER PUBLICATIONS

Database Genbank (Aug. 9, 2014) "Expression Vector pCas9_eba175 sgRNA, Complete Sequence", Genbank Accession Nos. KM099233.1, 4 pages.

Database Genbank (Aug. 9, 2014) "Expression Vector pCas9_kahrp sgRNA, Complete Sequence", Genbank Accession Nos. KM099232.1, 4 pages.

Davidson et al. (Mar. 1993) "A Model System for in Vivo Gene Transfer into the Central Nervous System Using an Adenoviral Vector", Nature Genetics, 3(3):219-223.

Davis et al. (Apr. 1993) "Direct Gene Transfer into Skeletal Muscle In Vivo: Factors Affecting Efficiency of Transfer and Stability of Expression", Human Gene Therapy, 4(2): 151-159.

Yang et al. (Apr. 1995) "Cellular and Humoral Immune Responses to Viral Antigens Create Barriers to Lung-Directed Gene Therapy with Recombinant Adenoviruses", Journal of Virology, 69(4):2004-2015.

Felgner et al. (1989) "Cationic Liposome-Mediated Transfection", Bethesda Research Laboratories Focus, 11(2):21-25.

Geller et al. (Feb. 1995) "An HSV-1 Vector Expressing Tyrosine Hydroxylase Causes Production and Release of I-DOPA from Cultured Rat Striatal Cells", Journal of Neurochemistry, 64(2):19 pages.

Geller et al. (1990) "Infection of Cultured Central Nervous System Neurons with a Defective Herpes Simplex Virus 1 Vector Results in Stable Expression of *Escherichia coli* β-galactosidase", PNAS, 87(3):1149-1153.

Geller et al. (Aug. 1993) "Long-Term Increases in Neurotransmitter Release from Neuronal Cells Expressing a Constitutively Active Adenylate Cyclase from a Herpes Simplex Virus Type 1 Vector", PNAS, 90(16):7603-7607.

Hu et al. (Jul. 21, 2014) "RNA-Directed Gene Editing Specifically Eradicates Latent and Prevents New HIV-1 Infection", PNAS, 111 (31):11461-11466.

Hu et al. (Oct. 1, 2013) "RNA-Mediated Excision of the HIV-1 Genome from Latently Infected Cells in Nervous System", Journal of NeuroVirology, 19(Suppl 1):1 page.

Jiang et al. (Mar. 2013) "RNA-Guided Editing of Bacterial Genomes Using CRISPR-Cas Systems", Nature Biotechnology, 31(3):233-239.

Kaplitt et al. (Oct. 1994) "Long-Term Gene Expression and Phenotypic Correction Using Adeno-Associated Virus Vectors in the Mammalian Brain", Nature Genetics, 8(2):148-154.

Koonin et al. (2017) "Diversity, Classification and Evolution of CRISPR-Cas Systems", Current Opinion in Microbiology, 37:67-78.

La Salle et al. (Feb. 12, 1993) "An Adenovirus Vector for Gene Transfer into Neurons and Glia in the Brain", Science, 259(5097):988-990.

Mannino et al. (Jul. 1, 1988) "Liposome Mediated Gene Transfer", BioTechniques, 6(7):682-690.

Stratford-Perricadet (Aug. 1, 1992) "Widespread Long-term Gene Transfer to Mouse Skeletal Muscles and Heart", Journal of Clinical Investigation, 90(2):626-630.

Quantin et al. (Apr. 1992) "Adenovirus as an Expression Vector in Muscle Cells in Vivo", PNAS, 89:2581-2584.

Rosenfeld et al. (Jan. 10, 1992) "In Vivo Transfer of the Human Cystic Fibrosis Transmembrane Conductance Regulator Gene to the Airway Epithelium", Cell, 68(1):143-155.

Smith et al. (Aug. 1, 2005) "HIV Superinfection", The Journal of Infectious Diseases, 192(3):438-444.

Sorek et al. (2013) "CRISPR-Mediated Adaptive Immune Systems in Bacteria and Archaea", Annual Review of Biochemistry, 82:237-266.

Maurer et al. (1989) "Cationic Liposome-Mediated Transfection of Primary Cultures of Rat Pituitary Cells", Bethesda Research Laboratories Focus, 11(2):25-27.

Ebina et al., "Harnessing the CRISPr/Cas9 System to Disrupt Latent HIV-1 Provirus," Scientific Reports, 3:2510, Internal pp. 1-7, pp. 1-4, Aug. 26, 2013.

Ramalingham et al., "A CRISPR way to Engineer the Human Genome," Genome Biology, 14:2, Article No. 107, Internal pp. 1-4, Feb. 26, 2013.

Richeter et al., "Exploiting CRISPR/Cas: Interference Mechanisms and Applications," International Journal of Molecular Sciences, vol. 14, pp. 14518-14531, Jul. 12, 2013.

Mcintyre et al., "96 shRNAs Designed for Maximal Coverage of HIV-1 Variants," 6 Retrovirology 55 1-15 (2009).

Maggio et al., "Adenoviral Vector Delivery of RNA-Guided CRISPR/Cas9 Nuclease Complexes Induces Targeted Mutagenesis in a Diverse Array of Human Cells," Scientific Reports (Online Journal), 5151, DOI: 10,1038/srep05105. Nature Publishing Group 2014.

Manjunath et al., "Newer Gene Editing Technologies Toward HIV Gene Therapy," MDPI (online journal). Viruses 5:2748-2766, Doi: 10.3390/v5112748. Multidisciplinary Digital Publishing Institute. 2013.

Yi et al., "Management of Mother-to-Child Transmission of Hepatitis B Virus: Propositions and Challenges," 77 Journal of Clinical Virology 32-39 (2016).

Vrazo et al., "Interventions to Significantly Improve Service Uptake and Retention of HIV-Positive Pregnant Women and HIV-Exposed Infants Along the Prevention of Mother-to-Child Transmission Continuum of Care: Systematic Review," 23(2) Tropical Medicine and International Health 136-148 (2018).

(56) References Cited

OTHER PUBLICATIONS

Davis et al., "Cytomegalovirus Infection in Pregnancy," 109 Birth Defects Research 336-346 (2017).
Sorek et al., "CRISPR-Mediated Adaptive Immune Systems in Bacteria and Archaea," 82 Annual Review of Biochemistry, 237-266 (2013).
Koonin et al., "Diversity, Classification and Evolution of CRISPR-CAS Systems," 37 Current Opinion in Microbiology, pp. 67-78 (2017).
Cong et al. (Feb. 15, 2013) "Multiplex Genome Engineering Using CRISPR/Cas Systems", Science, 339 (6121):819-823.

Uninduced
TSA induced
U6-CAG
LTR-A
LTR-B
2.0 ±0.14 %
76.3 ±0.21 %
0.3 ±0.07 %
17.1 ±0.49 %
0.0 ±0.03 %
3.9 ±0.28 % bp
Cell
U6-CAG
LTR-A
LTR-B
- + - + - +
500
400
300
200
100

U6-CAG
LTR-A/B

LTR-A
LTR-B
PAM
GCCAGGGATCAGATATCCACTGACCTTTGG----
TCCGGAGTACTTCAAGAACTGCTGACATCGAGCT
C C A C T G A C T A C T T C A A G A A
840
845
850
855
SEQ ID NO:1
SEQ ID NO:2
SEQ ID NO:3
190 bp excision junction ICC
WB
Cas9
GAPDH c1 c2 c3 c4 c5 c6 c7
500
300
100
LTR-Luciferase (-Fold)
20
15
10
5
0

EGFP Positive Cells (%)
80
60
40
20
0
MOI=0.3
MOI=0.9
*
*
U6-CAG
LTR-A/B

U6-CAG
LTR-A/B

Fig. 4A

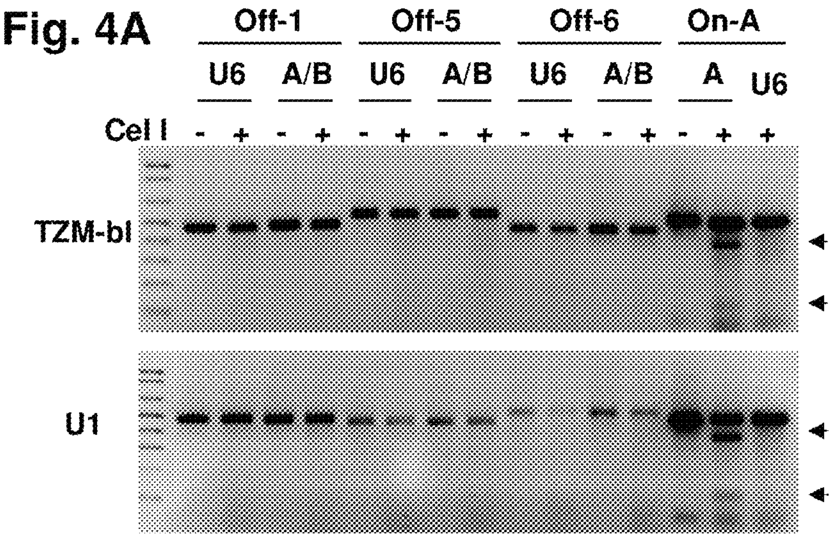

Fig. 4B

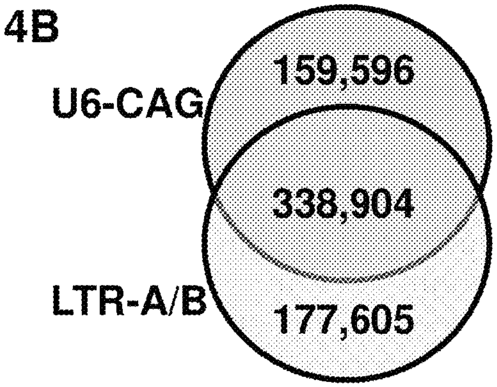

Fig. 4D

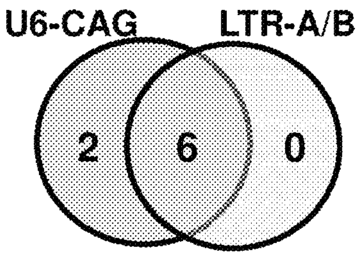

Fig. 4C nt 1-22 of SEQ ID NO:14

| Name | gRNA Target Site | | | | Indels | | | | | | | Genotype | |
|---|---|---|---|---|---|---|---|---|---|---|---|---|---|
| | genome | start | end | strand | genome | start | end | reference | quality | filter | mutation | U6-CAG | LTR-A/B |
| LTRA | chr11 | 103532094 | 103532108 | + | chr11 | 1.04E+08 | 103532209 | ATC | 272.76 | PASS | A | 1/1 | 1/1 |
| LTRA | chr14 | 24193180 | 24193194 | - | chr14 | 24192852 | 24192875 | [illegible] | 86.74 | PASS | G | 0/1 | 0/0 |
| LTRA | chr6 | 98901053 | 98901068 | + | chr6 | 98901264 | 98901267 | CACA | 323.75 | PASS | C | 1/1 | 1/1 |
| LTRA | chr6 | 98901053 | 98901068 | + | chr6 | 98901280 | 98901282 | GCA | 208.27 | PASS | G | 1/1 | 1/1 |
| LTRA | chr7 | 72210628 | 72210642 | - | chr7 | 72210827 | 72210828 | GT | 111.24 | LowQual | G | 0/1 | 0/1 |
| LTRA | chr7 | 72210628 | 72210642 | - | chr7 | 72210829 | 72210832 | GTGT | 25.74 | LowQual | G | 0/1 | 0/0 |
| LTRA | chr9 | 95871690 | 95871704 | + | chr9 | 95871594 | 95871596 | CCA | 456.73 | PASS | C | 0/1 | 0/1 |
| LTRA | HIV | 162 | 184 | + | HIV | 371 | 375 | CTACA | 14.87 | LowQual | C | 0/0 | 0/1 |
| LTRB | chr15 | 82132445 | 82132459 | + | chr15 | 82132704 | 82132704 | T | 109.78 | PASS | [illegible] | 1/1 | 1/1 |
| LTRB | HIV | 9091 | 9313 | - | HIV | 9616 | 9616 | A | 174.06 | PASS | [illegible] | 0/0 | 0/1 |

SEQ ID NO:15

13% (4/30) mutated (LTR-D) in TZMbI cells

5'-primer (T492)
SEQ ID NO:35
3'-primer (T493)

kb
10
5
1.5
1.0
0.7
0.5
0.3
0.1
LTR-A/B
U6-CAG
Parent
467 + 9709bp
467 + 635bp
NS
467bp
NS Ct Value
R=0.97,
P<0.0001
Log[pNL4-3] Copy#

Proviral DNA load
(Gag copies)
U6-CAG
LTR-A/B
** bp
c1 c2 c3 c4 c5 c6 c7
500
200
LTR-A
LTR-B
β-actin

Cas9 DNA Levels (%)
100
80
60
40
20
0
c1 c2 c3 c4 c5 c6
LTR-A/B Subclones

LTR-A/B Subclones
c1 c2 c3 c4 c5 c6
Cas9
Cas9
tCas9
tCas9
GAPDH
WB: anti-Flag

LTR-A/B subclone C3
LTR-A/B subclone C4
ICC: anti-Flag

U6-CAG
LTR-A/B
EGFP Positive Cells (%)
2.5
2.0
1.5
1.0
0.5
0.0
*
**
**
0
1/18
1/6
1/2
NL4-3-EGFP virus concentration U6-CAG
LTR-A/B
Viral RNA levels (Gag, %)
100
50
0
**
**
SF162
JRFL U6-CAG
LTR-A/B
Proviral DNA load (Gag, %)
100
50
0
*
**
**
SF162
JRFL
NL4-3-EGFP U6-CAG
LTR-A/B
Luciferase Activity (RLU)
6.0×10⁶
4.0×10⁶
2.0×10⁶
500000
400000
300000
200000
100000
0
*
**
**
**
Vehicle
SF162
JRFL
NL4-3-EGFP

Fig. 13 Predicted LTR gRNAs and their off-target numbers (100% match)

| Name | No. | gRNA sequence | 20 | 19 | 18 | 17 | 16 | 15 | 14 | 13 | 12 |
|---|---|---|---|---|---|---|---|---|---|---|---|
| | | Sense | | | | | | | | | |
| SEQ ID NO: 79 | 1 | TCAGACCCTTTTAGTCAGTGTGG | 0 | 0 | 0 | 0 | 0 | 0 | 0 | 2 | 25 |
| SEQ ID NO: 80 | 2 | TTGCTTGTACTGGGTCTCTCTGG | 0 | 0 | 0 | 0 | 0 | 0 | 0 | 3 | 10 |
| SEQ ID NO: 81 | 3 | CAGCTGCTTTTTGCTTGTACTGG | 0 | 0 | 0 | 0 | 0 | 0 | 2 | 4 | 11 |
| SEQ ID NO: 82 | 4 | CTGACATCGAGCTTGCTACAAGG | 0 | 0 | 0 | 0 | 0 | 0 | 0 | 0 | 17 |
| SEQ ID NO: 83 | 5 | CCGCCTAGCATTTCATCACATGG | 0 | 0 | 0 | 0 | 0 | 1 | 2 | 9 | 55 |
| SEQ ID NO: 84 | 6 | CGGAGAGAGAAGTATTAGAGTGG | 0 | 0 | 0 | 0 | 0 | 0 | 0 | 3 | 18 |
| SEQ ID NO: 85 | 7 | AGTACCAGTTGAGCAAGAGAAGG | 0 | 0 | 0 | 0 | 0 | 0 | 0 | 1 | 18 |
| SEQ ID NO: 86 | 8 | GATATCCACTGACCTTTGGATGG | 0 | 0 | 0 | 0 | 0 | 1 | 3 | 22 | 211 |
| SEQ ID NO: 87 LTR-C | 9 | [redacted] | [redacted] | [redacted] | [redacted] | [redacted] | [redacted] | [redacted] | [redacted] | [redacted] | [redacted] |
| SEQ ID NO: 88 | 10 | CACAAGGCTACTTCCCTGATTGG | 0 | 0 | 0 | 0 | 0 | 0 | 0 | 2 | 11 |
| SEQ ID NO: 89 | 11 | CTGTGGATCTACCACACACAAGG | 0 | 0 | 0 | 0 | 0 | 2 | 5 | 12 | 37 |
| SEQ ID NO: 90 | 12 | TGGGAGCTCTCTGGCTAACTAGG | 0 | 0 | 0 | 0 | 0 | 0 | 0 | 4 | 14 |
| SEQ ID NO: 91 | 13 | GGTTAGACCAGATCTGAGCCTGG | 0 | 0 | 0 | 0 | 0 | 0 | 0 | 9 | 33 |
| SEQ ID NO: 92 | 14 | TGCTACAAGGGACTTTCCGCTGG | 0 | 0 | 0 | 0 | 0 | 0 | 0 | 2 | 5 |
| SEQ ID NO: 93 | 15 | AGAGAGAAGTATTAGAGTGGAGG | 0 | 0 | 0 | 0 | 0 | 0 | 5 | 7 | 16 |
| SEQ ID NO: 94 | 16 | TTACACCCTGTGAGCCTGCATGG | 0 | 0 | 0 | 0 | 0 | 0 | 3 | 14 | 35 |
| SEQ ID NO: 95 | 17 | AAGGTAGAAGAAGCCAATGAAGG | 0 | 0 | 0 | 0 | 0 | 0 | 4 | 36 | 75 |
| SEQ ID NO: 96 LTR-A | 18 | [redacted] | [redacted] | [redacted] | [redacted] | [redacted] | [redacted] | [redacted] | [redacted] | [redacted] | [redacted] |
| SEQ ID NO: 97 | 19 | GACAAGATATCCTTGATCTGTGG | 0 | 0 | 0 | 0 | 0 | 0 | 0 | 0 | 10 |
| SEQ ID NO: 98 | 20 | GCCCGTCTGTTGTGTGACTCTGG | 0 | 0 | 0 | 0 | 0 | 0 | 3 | 7 | 35 |
| SEQ ID NO: 99 | 21 | ATCTGAGCCTGGGAGCTCTCTGG | 0 | 0 | 0 | 0 | 1 | 2 | 9 | 32 | 78 |
| SEQ ID NO: 100 | 22 | CTTTCCGCTGGGGACTTTCCAGG | 0 | 0 | 0 | 0 | 0 | 0 | 0 | 0 | 4 |
| SEQ ID NO: 101 | 23 | CAGAACTACACACCAGGGCCAGG | 0 | 0 | 0 | 0 | 0 | 0 | 0 | 3 | 20 |
| SEQ ID NO: 102 | 24 | CCTGCATGGGATGGATGACCCGG | 0 | 0 | 0 | 0 | 2 | 2 | 2 | 5 | 21 |

Fig. 13 cont'd.

| Name | No. | gRNA sequence | 20 | 19 | 18 | 17 | 16 | 15 | 14 | 13 | 12 |
|---|---|---|---|---|---|---|---|---|---|---|---|
| | | Sense | | | | | | | | | |
| SEQ ID NO: 103 | 25 | CCCTGTGAGCCTGCATGGGATGG | 0 | 0 | 0 | 0 | 1 | 1 | 2 | 9 | 30 |
| SEQ ID NO: 104 | 26 | CTTTCCAGGGAGGCGTGGCCTGG | 0 | 0 | 0 | 0 | 0 | 8 | 15 | 32 | 75 |
| SEQ ID NO: 105 | 27 | GGGGACTTTCCAGGGAGGCGTGG | 0 | 0 | 0 | 0 | 0 | 0 | 0 | 5 | 24 |
| SEQ ID NO: 106 | 28 | CCGCTGGGGACTTTCCAGGGAGG | 0 | 0 | 0 | 0 | 0 | 1 | 3 | 9 | 25 |
| SEQ ID NO: 107 | 29 | CATGGCCCGAGAGCTGCATCCGG | 0 | 0 | 0 | 0 | 0 | 0 | 0 | 0 | 16 |
| SEQ ID NO: 108 | 30 | GCCTGGGCGGGACTGGGGAGTGG | 0 | 0 | 0 | 0 | 1 | 2 | 7 | 18 | 250 |
| SEQ ID NO: 109 | 31 | AGGCGTGGCCTGGGCGGGACTGG | 0 | 0 | 0 | 0 | 0 | 0 | 0 | 2 | 6 |
| SEQ ID NO: 110 LTR-D | 32 | [redacted] | [redacted] | [redacted] | [redacted] | [redacted] | [redacted] | [redacted] | [redacted] | [redacted] | [redacted] |
| SEQ ID NO: 111 | 33 | CCAGGGAGGCGTGGCCTGGGCGG | 0 | 0 | 0 | 0 | 2 | 2 | 2 | 11 | 22 |
| | | Antisense | | | | | | | | | |
| SEQ ID NO: 112 | 1 | TGTGGTAGATCCACAGATCAAGG | 0 | 0 | 0 | 0 | 0 | 0 | 0 | 3 | 13 |
| SEQ ID NO: 113 | 2 | GGTGTGTAGTTCTGCCAATCAGG | 0 | 0 | 0 | 0 | 0 | 0 | 0 | 8 | 11 |
| SEQ ID NO: 114 | 3 | GTCAGTGGATATCTGATCCCTGG | 0 | 0 | 0 | 0 | 0 | 0 | 0 | 2 | 10 |
| SEQ ID NO: 115 | 4 | TAGCACCATCCAAAGGTCAGTGG | 0 | 0 | 0 | 0 | 0 | 0 | 2 | 3 | 10 |
| SEQ ID NO: 116 | 5 | TAGCTTGTAGCACCATCCAAAGG | 0 | 0 | 0 | 0 | 0 | 1 | 1 | 6 | 12 |
| SEQ ID NO: 117 | 6 | TCTACCTTCTCTTGCTCAACTGG | 0 | 0 | 0 | 0 | 0 | 0 | 1 | 1 | 6 |
| SEQ ID NO: 118 | 7 | CACTCTAATACTTCTCTCTCCGG | 0 | 0 | 0 | 0 | 0 | 0 | 0 | 1 | 26 |
| SEQ ID NO: 119 | 8 | CCATGTGATGAAATGCTAGGCGG | 0 | 0 | 0 | 0 | 0 | 1 | 1 | 5 | 17 |
| SEQ ID NO: 120 | 9 | GGGCCATGTGATGAAATGCTAGG | 0 | 0 | 0 | 0 | 0 | 0 | 0 | 3 | 48 |
| SEQ ID NO: 121 LTR-B | 10 | [redacted] | [redacted] | [redacted] | [redacted] | [redacted] | [redacted] | [redacted] | [redacted] | [redacted] | [redacted] |
| SEQ ID NO: 122 | 11 | CTGCTTATATGCAGCATCTGAGG | 0 | 0 | 0 | 0 | 0 | 0 | 0 | 4 | 39 |
| SEQ ID NO: 123 | 12 | CACACTACTTGAAGCACTCAAGG | 0 | 0 | 0 | 0 | 0 | 0 | 0 | 3 | 19 |
| SEQ ID NO: 124 | 13 | TACCAGAGTCACACAACAGACGG | 0 | 0 | 0 | 0 | 0 | 0 | 0 | 2 | 12 |

Fig. 13 cont'd.

| Name | No. | gRNA sequence | 20 | 19 | 18 | 17 | 16 | 15 | 14 | 13 | 12 |
|---|---|---|---|---|---|---|---|---|---|---|---|
| | | Antisense | | | | | | | | | |
| SEQ ID NO: 125 | 14 | ACACTGACTAAAAGGGTCTGAGG | 0 | 0 | 0 | 0 | 1 | 2 | 3 | 4 | 15 |
| SEQ ID NO: 126 | 15 | CAAGGATATCTTGTCTTCGTTGG | 0 | 0 | 0 | 0 | 0 | 0 | 0 | 1 | 5 |
| SEQ ID NO: 127 | 16 | CAGGGAAGTAGCCTTGTGTGTGG | 0 | 0 | 0 | 0 | 0 | 1 | 2 | 4 | 17 |
| SEQ ID NO: 128 | 17 | GCGGGTGTTCTCTCCTTCATTGG | 0 | 0 | 0 | 0 | 0 | 2 | 2 | 15 | 49 |
| SEQ ID NO: 129 | 18 | TAGTTAGCCAGAGAGCTCCCAGG | 0 | 0 | 0 | 0 | 0 | 2 | 4 | 24 | 93 |
| SEQ ID NO: 130 | 19 | CTTTATTGAGGCTTAAGCAGTGG | 0 | 0 | 0 | 0 | 0 | 0 | 0 | 4 | 25 |
| SEQ ID NO: 131 | 20 | ACTCAAGGCAAGCTTTATTGAGG | 0 | 0 | 0 | 0 | 0 | 0 | 0 | 1 | 28 |
| SEQ ID NO: 132 | 21 | GGATATCTGATCCCTGGCCCTGG | 0 | 0 | 0 | 0 | 0 | 1 | 2 | 8 | 43 |
| SEQ ID NO: 133 | 22 | GGCTCACAGGGTGTAACAAGCGG | 0 | 0 | 0 | 0 | 0 | 0 | 0 | 2 | 5 |
| SEQ ID NO: 134 | 23 | TCCATCCCATGCAGGCTCACAGG | 0 | 0 | 0 | 0 | 0 | 3 | 3 | 8 | 20 |
| SEQ ID NO: 135 | 24 | AGTACTCCGGATGCAGCTCTCGG | 0 | 0 | 0 | 0 | 0 | 0 | 1 | 5 | 48 |
| SEQ ID NO: 136 | 25 | AGAGCTCCCAGGCTCAGATCTGG | 0 | 0 | 0 | 0 | 0 | 0 | 4 | 15 | 38 |
| SEQ ID NO: 137 | 26 | GATTTTCCACACTGACTAAAAGG | 0 | 0 | 0 | 0 | 0 | 0 | 0 | 8 | 21 |
| SEQ ID NO: 138 | 27 | CCGGGTCATCCATCCCATGCAGG | 0 | 0 | 0 | 0 | 0 | 0 | 0 | 4 | 36 |
| SEQ ID NO: 139 | 28 | CCTCCCTGGAAAGTCCCCAGCGG | 0 | 0 | 0 | 0 | 0 | 0 | 3 | 14 | 37 |
| SEQ ID NO: 140 | 29 | GCCACTCCCCAGTCCCGCCCAGG | 0 | 0 | 0 | 0 | 0 | 0 | 1 | 4 | 14 |
| SEQ ID NO: 141 | 30 | CCGCCCAGGCCACGCCTCCCTGG | 0 | 0 | 0 | 0 | 0 | 1 | 1 | 6 | 19 |

Fig. 14

| Target name | Direction | Sequences (5' to 3') | SEQ ID NOS. |
|---|---|---|---|
| LTR-A | T353: Sense | aaacAGGGCCAGGGATCAGATATCCACTGACCTTgt | SEQ ID NO: 36 |
| | T354: Antisense | taaacAAGGTCAGTGGATATCTGATCCCTGGCCCT | SEQ ID NO: 37 |
| LTR-B | T355: Anti-sense | aaacAGCTCGATGTCAGCAGTTCTTGAAGTACTCgt | SEQ ID NO: 38 |
| | T356: Sense | taaacGAGTACTTCAAGAACTGCTGACATCGAGCT | SEQ ID NO: 39 |
| LTR-C | T357: Sense | caccGATTGGCAGAACTACACACC | SEQ ID NO: 40 |
| | T358: Antisense | aaacGGTGTGTAGTTCTGCCAATC | SEQ ID NO: 41 |
| LTR-D | T359: Sense | caccGCGTGGCCTGGGCGGGACTG | SEQ ID NO: 42 |
| | T360: Antisense | aaacCAGTCCCGCCCAGGCCACGC | SEQ ID NO: 43 |
| **PCR primer** | | | |
| LTR -453/F | Sense | TGGAAGGGCTAATTCACTCCCAAC | SEQ ID NO: 44 |
| LTR +43/R | Anti-sense | CCGAGAGCTCCCAGGCTCAGATCT | SEQ ID NO: 45 |
| LTR -411/F | T361: Sense | caccGATCTGTGGATCTACCACACACA | SEQ ID NO: 46 |
| LTR +129/R | T363: Anti-sense | aaacGAGTCACACAACAGACGGGC | SEQ ID NO: 47 |
| Cas-hU6/5'/XhoBm | T351: Sense | cgcctcgaggatccGAGGGCCTATTTCCCATGATTCC | SEQ ID NO: 48 |
| Cas-CAG/3'/EcoR | T352: Anti-sense | tgtgaattcAGGCGGGCCATTTACCGTAAGTTATG | SEQ ID NO: 49 |
| U1-Chromosome X | T485: Sense | ACGACTATCTTATCAATCCTTCCTG | SEQ ID NO: 50 |
| | T486: Anti-sense | CTAGGTGATTAGGATATTCTACAATC | SEQ ID NO: 51 |
| U1-Chromosome 2 | T492: Sense | GCTATTGTATCTGATCACAAGCTG | SEQ ID NO: 52 |
| | T493: Anti-sense | TTGATTGTGTGTCCAGGTCCTAGG | SEQ ID NO: 53 |
| d2EGFP | T494: Sense | GCAAGGGCGAGGAGCTGTTCACC | SEQ ID NO: 54 |
| | T495: Anti-sense | TTGTAGTTGCCGTCGTCCTTGAAG | SEQ ID NO: 55 |
| Gag | T457: Sense | AATGGTACATCAGGCCATATCAC | SEQ ID NO: 56 |
| | T458: Anti-sense | CCCACTGTGTTTAGCATGGTATT | SEQ ID NO: 57 |
| Cas9 | T477: Sense | CACAGCATCAAGAAGAACCTGAT | SEQ ID NO: 58 |
| | T491: Anti-sense | TCTTCCGTCTGGTGTATCTTCTTC | SEQ ID NO: 59 |
| RRE | Sense | CGCCAAGCTTGAATAGGAGCTTTGTTCC | SEQ ID NO: 60 |
| | Antisense | CTAGGATCCAGGAGCTGTTGATCCTTTAGG | SEQ ID NO: 61 |

Fig. 14 cont'd.

| Target name | Direction | Sequences (5' to 3') | SEQ ID NOS. |
|---|---|---|---|
| **Off-Target (OT)** | | | |
| LTR-A-OT-1 | T465: Sense | GTGGACTTTGGATGGTGAGATAG | SEQ ID NO: 62 |
| | T466: Anti-sense | GCCTGGCAAGAGTGAACTGAGTC | SEQ ID NO: 63 |
| LTR-A-OT-2 | T467: Sense | AAGATAATGAGTTGTGGCAGAGC | SEQ ID NO: 64 |
| | T468: Anti-sense | TCTACCTGGTAATCCAGCATCTGG | SEQ ID NO: 65 |
| LTR-A-OT-3 | T469: Sense | ATAGGAGGAAGGCACCAAGAGGG | SEQ ID NO: 66 |
| | T470: Anti-sense | AATGATGCTTTGGTCCTACTCCT | SEQ ID NO: 67 |
| LTR-A-OT-4 | T471: Sense | TGCTCTTGCTACTCTGGCATGTAC | SEQ ID NO: 68 |
| | T472: Anti-sense | AATCTACCTCTGAGAGCTGCAGG | SEQ ID NO: 69 |
| LTR-A-OT-5 | T473: Sense | TCAGACACAGCTGAAGCAGAGGC | SEQ ID NO: 70 |
| | T474: Anti-sense | ATGCCAGTGTCAGTAGATGTCAG | SEQ ID NO: 71 |
| LTR-A-OT-6 | T475: Sense | TCAAGATCAGCCAGAGTGCACATG | SEQ ID NO: 72 |
| | T476: Anti-sense | TGCTCTTCCGAGCCTCTCTGGAG | SEQ ID NO: 73 |
| **Others** | | | |
| hU6-sequence | T428: Sense | ATGGACTATCATATGCTTACCG | SEQ ID NO: 74 |
| LSP1 | Sense | GCTTCAGCAAGCCGAGTCCTGCGTCGAG | SEQ ID NO: 75 |
| LSP2 | Anti-sense | GCTCCTCTGGTTTCCCTTTCGCTTTCAA | SEQ ID NO: 76 |
| AP1 | Sense | GTAATACGACTCACTATAGGGC | SEQ ID NO: 77 |
| AP2 | Anti-sense | ACTATAGGGCACGCGTGGT | SEQ ID NO: 78 |

Fig. 15

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRA | ATCAGATATCCACTGACCTTTGG | 142 | HIV | 100 | 7.00E-04 | 162 | 184 | + | ATCAGATATCCACTGACCTTTGG | 253 | 0 |
| LTRA | TCAGATATCCACTGACCTTTGG | 143 | HIV | 100 | 0.003 | 163 | 184 | + | TCAGATATCCACTGACCTTTGG | 254 | 0 |
| LTRA | TCAGATATCCACTGACCTTTGG | 144 | HIV | 100 | 0.003 | 9091 | 9112 | + | TCAGATATCCACTGACCTTTGG | 255 | 0 |
| LTRA | CAGATATCCACTGACCTTTGG | 145 | HIV | 100 | 0.009 | 164 | 184 | + | CAGATATCCACTGACCTTTGG | 256 | 0 |
| LTRA | CAGATATCCACTGACCTTTGG | 146 | HIV | 100 | 0.009 | 9092 | 9112 | + | CAGATATCCACTGACCTTTGG | 257 | 0 |
| LTRA | AGATATCCACTGACCTTTGG | 147 | HIV | 100 | 0.033 | 165 | 184 | + | AGATATCCACTGACCTTTGG | 258 | 0 |
| LTRA | AGATATCCACTGACCTTTGG | 148 | HIV | 100 | 0.033 | 9093 | 9112 | + | AGATATCCACTGACCTTTGG | 259 | 0 |
| LTRA | GATATCCACTGACCTTTGG | 149 | HIV | 100 | 0.12 | 166 | 184 | + | GATATCCACTGACCTTTGG | 260 | 0 |
| LTRA | GATATCCACTGACCTTTGG | 150 | HIV | 100 | 0.12 | 9094 | 9112 | + | GATATCCACTGACCTTTGG | 261 | 0 |
| LTRA | ATATCCACTGACCTTTGG | 151 | HIV | 100 | 0.42 | 167 | 184 | + | ATATCCACTGACCTTTGG | 262 | 0 |
| LTRA | ATATCCACTGACCTTTGG | 152 | HIV | 100 | 0.42 | 9095 | 9112 | + | ATATCCACTGACCTTTGG | 263 | 0 |
| LTRA | TATCCACTGACCTTGGG | 153 | chr5 | 100 | 1.5 | 21926317 | 21926333 | + | TATCCACTGACCTTGGG | 264 | 0 |
| LTRA | TATCCACTGACCTTTGG | 154 | HIV | 100 | 1.5 | 168 | 184 | + | TATCCACTGACCTTTGG | 265 | 0 |
| LTRA | TATCCACTGACCTTTGG | 155 | HIV | 100 | 1.5 | 9096 | 9112 | + | TATCCACTGACCTTTGG | 266 | 0 |
| LTRA | TATCCACTGACCTTAAG | 156 | chr3 | 100 | 1.5 | 116712577 | 116712593 | + | TATCCACTGACCTTAAG | 267 | 0 |
| LTRA | TATCCACTGACCTTGAG | 157 | chr6 | 100 | 1.5 | 32460607 | 32460623 | + | TATCCACTGACCTTGAG | 268 | 0 |
| LTRA | ATCCACTGACCTTAGG | 158 | chr3 | 100 | 5.4 | 2669092 | 2669107 | + | ATCCACTGACCTTAGG | 269 | 0 |
| LTRA | ATCCACTGACCTTAGG | 159 | chr3 | 100 | 5.4 | 158293369 | 158293384 | + | ATCCACTGACCTTAGG | 270 | 0 |
| LTRA | ATCCACTGACCTTGGG | 160 | chr20 | 100 | 5.4 | 46918344 | 46918359 | + | ATCCACTGACCTTGGG | 271 | 0 |
| LTRA | ATCCACTGACCTTGGG | 161 | chr14 | 100 | 5.4 | 86310067 | 86310082 | - | ATCCACTGACCTTGGG | 272 | 0 |
| LTRA | ATCCACTGACCTTGGG | 162 | chr5 | 100 | 5.4 | 21926318 | 21926333 | + | ATCCACTGACCTTGGG | 273 | 0 |
| LTRA | ATCCACTGACCTTGGG | 163 | chr4 | 100 | 5.4 | 95491921 | 95491936 | - | ATCCACTGACCTTGGG | 274 | 0 |
| LTRA | ATCCACTGACCTTTGG | 164 | HIV | 100 | 5.4 | 169 | 184 | + | ATCCACTGACCTTTGG | 275 | 0 |
| LTRA | ATCCACTGACCTTTGG | 165 | HIV | 100 | 5.4 | 9097 | 9112 | + | ATCCACTGACCTTTGG | 276 | 0 |
| LTRA | ATCCACTGACCTTTGG | 166 | chr6 | 100 | 5.4 | 98901053 | 98901068 | + | ATCCACTGACCTTTGG | 277 | 0 |
| LTRA | ATCCACTGACCTTAAG | 167 | chr7 | 100 | 5.4 | 155511293 | 155511308 | - | ATCCACTGACCTTAAG | 278 | 0 |
| LTRA | ATCCACTGACCTTAAG | 168 | chr3 | 100 | 5.4 | 116712578 | 116712593 | + | ATCCACTGACCTTAAG | 279 | 0 |
| LTRA | ATCCACTGACCTTCAG | 169 | chr5 | 100 | 5.4 | 152371289 | 152371304 | + | ATCCACTGACCTTCAG | 280 | 0 |

Fig. 15, cont'd.

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRA | ATCCACTGACCTTCAG | 170 | chr4 | 100 | 5.4 | 110823169 | 110823184 | - | ATCCACTGACCTTCAG | 281 | 0 |
| LTRA | ATCCACTGACCTTGAG | 171 | chrX | 100 | 5.4 | 74260260 | 74260275 | + | ATCCACTGACCTTGAG | 282 | 0 |
| LTRA | ATCCACTGACCTTGAG | 172 | chr6 | 100 | 5.4 | 32460608 | 32460623 | + | ATCCACTGACCTTGAG | 283 | 0 |
| LTRA | TCCACTGACCTTAGG | 173 | chr12 | 100 | 20 | 14485012 | 14485026 | - | TCCACTGACCTTAGG | 284 | 0 |
| LTRA | TCCACTGACCTTAGG | 174 | chr7 | 100 | 20 | 72210628 | 72210642 | - | TCCACTGACCTTAGG | 285 | 0 |
| LTRA | TCCACTGACCTTAGG | 175 | chr6 | 100 | 20 | 160845640 | 160845654 | + | TCCACTGACCTTAGG | 286 | 0 |
| LTRA | TCCACTGACCTTAGG | 176 | chr3 | 100 | 20 | 2669093 | 2669107 | + | TCCACTGACCTTAGG | 287 | 0 |
| LTRA | TCCACTGACCTTAGG | 177 | chr3 | 100 | 20 | 158293370 | 158293384 | + | TCCACTGACCTTAGG | 288 | 0 |
| LTRA | TCCACTGACCTTAGG | 178 | chr2 | 100 | 20 | 237551230 | 237551244 | - | TCCACTGACCTTAGG | 289 | 0 |
| LTRA | TCCACTGACCTTGGG | 179 | chr20 | 100 | 20 | 46918345 | 46918359 | + | TCCACTGACCTTGGG | 290 | 0 |
| LTRA | TCCACTGACCTTGGG | 180 | chr14 | 100 | 20 | 86310067 | 86310081 | - | TCCACTGACCTTGGG | 291 | 0 |
| LTRA | TCCACTGACCTTGGG | 181 | chr12 | 100 | 20 | 116054688 | 116054702 | + | TCCACTGACCTTGGG | 292 | 0 |
| LTRA | TCCACTGACCTTGGG | 182 | chr11 | 100 | 20 | 103532094 | 103532108 | + | TCCACTGACCTTGGG | 293 | 0 |
| LTRA | TCCACTGACCTTGGG | 183 | chr10 | 100 | 20 | 132186431 | 132186445 | - | TCCACTGACCTTGGG | 294 | 0 |
| LTRA | TCCACTGACCTTGGG | 184 | chr8 | 100 | 20 | 144600475 | 144600489 | - | TCCACTGACCTTGGG | 295 | 0 |
| LTRA | TCCACTGACCTTGGG | 185 | chr5 | 100 | 20 | 21926319 | 21926333 | + | TCCACTGACCTTGGG | 296 | 0 |
| LTRA | TCCACTGACCTTGGG | 186 | chr4 | 100 | 20 | 95491921 | 95491935 | - | TCCACTGACCTTGGG | 297 | 0 |
| LTRA | TCCACTGACCTTTGG | 187 | HIV | 100 | 20 | 170 | 184 | + | TCCACTGACCTTTGG | 298 | 0 |
| LTRA | TCCACTGACCTTTGG | 188 | HIV | 100 | 20 | 9098 | 9112 | + | TCCACTGACCTTTGG | 299 | 0 |
| LTRA | TCCACTGACCTTTGG | 189 | chr16 | 100 | 20 | 86962569 | 86962583 | + | TCCACTGACCTTTGG | 300 | 0 |
| LTRA | TCCACTGACCTTTGG | 190 | chr11 | 100 | 20 | 68156214 | 68156228 | + | TCCACTGACCTTTGG | 301 | 0 |
| LTRA | TCCACTGACCTTTGG | 191 | chr6 | 100 | 20 | 98901054 | 98901068 | + | TCCACTGACCTTTGG | 302 | 0 |
| LTRA | TCCACTGACCTTTGG | 192 | chr5 | 100 | 20 | 72600080 | 72600094 | + | TCCACTGACCTTTGG | 303 | 0 |
| LTRA | TCCACTGACCTTTGG | 193 | chr5 | 100 | 20 | 136458169 | 136458183 | + | TCCACTGACCTTTGG | 304 | 0 |
| LTRA | TCCACTGACCTTTGG | 194 | chr4 | 100 | 20 | 25353030 | 25353044 | + | TCCACTGACCTTTGG | 305 | 0 |
| LTRA | TCCACTGACCTTTGG | 195 | chr2 | 100 | 20 | 207833373 | 207833387 | + | TCCACTGACCTTTGG | 306 | 0 |
| LTRA | TCCACTGACCTTAAG | 196 | chr15 | 100 | 20 | 67850506 | 67850520 | - | TCCACTGACCTTAAG | 307 | 0 |
| LTRA | TCCACTGACCTTAAG | 197 | chr7 | 100 | 20 | 155511293 | 155511307 | - | TCCACTGACCTTAAG | 308 | 0 |
| LTRA | TCCACTGACCTTAAG | 198 | chr5 | 100 | 20 | 25142541 | 25142555 | - | TCCACTGACCTTAAG | 309 | 0 |

Fig. 15, cont'd.

| name | query Seq | SEQ ID NO: | Subj. ID | Iden tity (%) | E-Val ue | start | end | strand | ref Seq | SEQ ID NO: | mismatch (12bp seed) |
|---|---|---|---|---|---|---|---|---|---|---|---|
| LTRA | TCCACTGACCTTAAG | 199 | chr3 | 100 | 20 | 116712579 | 116712593 | + | TCCACTGACCTTAAG | 310 | 0 |
| LTRA | TCCACTGACCTTAAG | 200 | chr1 | 100 | 20 | 163298514 | 163298528 | + | TCCACTGACCTTAAG | 311 | 0 |
| LTRA | TCCACTGACCTTCAG | 201 | chr20 | 100 | 20 | 22136764 | 22136778 | - | TCCACTGACCTTCAG | 312 | 0 |
| LTRA | TCCACTGACCTTCAG | 202 | chr19 | 100 | 20 | 50519462 | 50519476 | - | TCCACTGACCTTCAG | 313 | 0 |
| LTRA | TCCACTGACCTTCAG | 203 | chr18 | 100 | 20 | 74623621 | 74623635 | - | TCCACTGACCTTCAG | 314 | 0 |
| LTRA | TCCACTGACCTTCAG | 204 | chr16 | 100 | 20 | 71402733 | 71402747 | + | TCCACTGACCTTCAG | 315 | 0 |
| LTRA | TCCACTGACCTTCAG | 205 | chr14 | 100 | 20 | 24193180 | 24193194 | - | TCCACTGACCTTCAG | 316 | 0 |
| LTRA | TCCACTGACCTTCAG | 206 | chr11 | 100 | 20 | 133664063 | 133664077 | + | TCCACTGACCTTCAG | 317 | 0 |
| LTRA | TCCACTGACCTTCAG | 207 | chr9 | 100 | 20 | 140394271 | 140394285 | + | TCCACTGACCTTCAG | 318 | 0 |
| LTRA | TCCACTGACCTTCAG | 208 | chr6 | 100 | 20 | 47685256 | 47685270 | - | TCCACTGACCTTCAG | 319 | 0 |
| LTRA | TCCACTGACCTTCAG | 209 | chr5 | 100 | 20 | 152371290 | 152371304 | + | TCCACTGACCTTCAG | 320 | 0 |
| LTRA | TCCACTGACCTTCAG | 210 | chr4 | 100 | 20 | 110823169 | 110823183 | - | TCCACTGACCTTCAG | 321 | 0 |
| LTRA | TCCACTGACCTTCAG | 211 | chr3 | 100 | 20 | 46255327 | 46255341 | + | TCCACTGACCTTCAG | 322 | 0 |
| LTRA | TCCACTGACCTTCAG | 212 | chr3 | 100 | 20 | 186757301 | 186757315 | + | TCCACTGACCTTCAG | 323 | 0 |
| LTRA | TCCACTGACCTTGAG | 213 | chrX | 100 | 20 | 74260261 | 74260275 | + | TCCACTGACCTTGAG | 324 | 0 |
| LTRA | TCCACTGACCTTGAG | 214 | chr11 | 100 | 20 | 76052171 | 76052185 | - | TCCACTGACCTTGAG | 325 | 0 |
| LTRA | TCCACTGACCTTGAG | 215 | chr9 | 100 | 20 | 33927660 | 33927674 | - | TCCACTGACCTTGAG | 326 | 0 |
| LTRA | TCCACTGACCTTGAG | 216 | chr9 | 100 | 20 | 71035331 | 71035345 | + | TCCACTGACCTTGAG | 327 | 0 |
| LTRA | TCCACTGACCTTGAG | 217 | chr9 | 100 | 20 | 95871690 | 95871704 | + | TCCACTGACCTTGAG | 328 | 0 |
| LTRA | TCCACTGACCTTGAG | 218 | chr7 | 100 | 20 | 137681847 | 137681861 | + | TCCACTGACCTTGAG | 329 | 0 |
| LTRA | TCCACTGACCTTGAG | 219 | chr6 | 100 | 20 | 32460609 | 32460623 | + | TCCACTGACCTTGAG | 330 | 0 |
| LTRA | TCCACTGACCTTGAG | 220 | chr3 | 100 | 20 | 42344237 | 42344251 | + | TCCACTGACCTTGAG | 331 | 0 |
| LTRA | TCCACTGACCTTGAG | 221 | chr2 | 100 | 20 | 64643586 | 64643600 | + | TCCACTGACCTTGAG | 332 | 0 |
| LTRA | TCCACTGACCTTTAG | 222 | chr16 | 100 | 20 | 55133552 | 55133566 | - | TCCACTGACCTTTAG | 333 | 0 |
| LTRA | TCCACTGACCTTTAG | 223 | chr15 | 100 | 20 | 90072212 | 90072226 | - | TCCACTGACCTTTAG | 334 | 0 |
| LTRA | TCCACTGACCTTTAG | 224 | chr12 | 100 | 20 | 69006300 | 69006314 | + | TCCACTGACCTTTAG | 335 | 0 |
| LTRA | TCCACTGACCTTTAG | 225 | chr3 | 100 | 20 | 170680338 | 170680352 | - | TCCACTGACCTTTAG | 336 | 0 |
| LTRA | TCCACTGACCTTTAG | 226 | chr2 | 100 | 20 | 215414950 | 215414964 | - | TCCACTGACCTTTAG | 337 | 0 |

Fig. 15, cont'd.

| name | query Seq | SEQ ID NO: | Subj. ID | Identity (%) | E-Value | start | end | strand | ref Seq | SEQ ID NO: | mismatch (12bp seed) |
|---|---|---|---|---|---|---|---|---|---|---|---|
| LTRB | CAGCAGTTCTTGAAGTACTCCGG | 227 | HIV | 100 | 7.00E-04 | 9291 | 9313 | - | CAGCAGTTCTTGAAGTACTCCGG | 338 | 0 |
| LTRB | AGCAGTTCTTGAAGTACTCCGG | 228 | HIV | 100 | 0.003 | 9291 | 9312 | - | AGCAGTTCTTGAAGTACTCCGG | 339 | 0 |
| LTRB | GCAGTTCTTGAAGTACTCCGG | 229 | HIV | 100 | 0.009 | 9291 | 9311 | - | GCAGTTCTTGAAGTACTCCGG | 340 | 0 |
| LTRB | CAGTTCTTGAAGTACTCCGG | 230 | HIV | 100 | 0.033 | 9291 | 9310 | - | CAGTTCTTGAAGTACTCCGG | 341 | 0 |
| LTRB | AGTTCTTGAAGTACTCCGG | 231 | HIV | 100 | 0.12 | 9291 | 9309 | - | AGTTCTTGAAGTACTCCGG | 342 | 0 |
| LTRB | GTTCTTGAAGTACTCCGG | 232 | HIV | 100 | 0.42 | 9291 | 9308 | - | GTTCTTGAAGTACTCCGG | 343 | 0 |
| LTRB | TTCTTGAAGTACTCCGG | 233 | HIV | 100 | 1.5 | 9291 | 9307 | - | TTCTTGAAGTACTCCGG | 344 | 0 |
| LTRB | TCTTGAAGTACTCCGG | 234 | HIV | 100 | 5.4 | 9291 | 9306 | - | TCTTGAAGTACTCCGG | 345 | 0 |
| LTRB | TCTTGAAGTACTCTAG | 235 | chr11 | 100 | 5.4 | 91845834 | 91845849 | - | TCTTGAAGTACTCTAG | 346 | 0 |
| LTRB | CTTGAAGTACTCAGG | 236 | chr19 | 100 | 20 | 45672789 | 45672803 | - | CTTGAAGTACTCAGG | 347 | 0 |
| LTRB | CTTGAAGTACTCAGG | 237 | chr15 | 100 | 20 | 82132445 | 82132459 | + | CTTGAAGTACTCAGG | 348 | 0 |
| LTRB | CTTGAAGTACTCAGG | 238 | chr11 | 100 | 20 | 94282411 | 94282425 | + | CTTGAAGTACTCAGG | 349 | 0 |
| LTRB | CTTGAAGTACTCAGG | 239 | chr2 | 100 | 20 | 193312744 | 193312758 | - | CTTGAAGTACTCAGG | 350 | 0 |
| LTRB | CTTGAAGTACTCCGG | 240 | HIV | 100 | 20 | 9291 | 9305 | - | CTTGAAGTACTCCGG | 351 | 0 |
| LTRB | CTTGAAGTACTCTGG | 241 | chr15 | 100 | 20 | 61274973 | 61274987 | - | CTTGAAGTACTCTGG | 352 | 0 |
| LTRB | CTTGAAGTACTCAAG | 242 | chrX | 100 | 20 | 36051764 | 36051778 | - | CTTGAAGTACTCAAG | 353 | 0 |
| LTRB | CTTGAAGTACTCAAG | 243 | chr15 | 100 | 20 | 31316465 | 31316479 | - | CTTGAAGTACTCAAG | 354 | 0 |
| LTRB | CTTGAAGTACTCAAG | 244 | chr13 | 100 | 20 | 23054474 | 23054488 | - | CTTGAAGTACTCAAG | 355 | 0 |
| LTRB | CTTGAAGTACTCAAG | 245 | chr9 | 100 | 20 | 83208046 | 83208060 | + | CTTGAAGTACTCAAG | 356 | 0 |
| LTRB | CTTGAAGTACTCAAG | 246 | chr8 | 100 | 20 | 13956368 | 13956382 | + | CTTGAAGTACTCAAG | 357 | 0 |
| LTRB | CTTGAAGTACTCCAG | 247 | chr16 | 100 | 20 | 57449025 | 57449039 | - | CTTGAAGTACTCCAG | 358 | 0 |
| LTRB | CTTGAAGTACTCCAG | 248 | chr15 | 100 | 20 | 41397831 | 41397845 | - | CTTGAAGTACTCCAG | 359 | 0 |
| LTRB | CTTGAAGTACTCCAG | 249 | chr11 | 100 | 20 | 70255488 | 70255502 | - | CTTGAAGTACTCCAG | 360 | 0 |
| LTRB | CTTGAAGTACTCCAG | 250 | chr3 | 100 | 20 | 134149643 | 134149657 | + | CTTGAAGTACTCCAG | 361 | 0 |
| LTRB | CTTGAAGTACTCTAG | 251 | chr11 | 100 | 20 | 91845834 | 91845848 | - | CTTGAAGTACTCTAG | 362 | 0 |
| LTRB | CTTGAAGTACTCTAG | 252 | chr1 | 100 | 20 | 224520600 | 224520614 | + | CTTGAAGTACTCTAG | 363 | 0 |

-644
-453
-411
-10
+1
+78
U3
AR
Firefly Luc
Protospace(E)
Protospace(C)
Protospace(A)
Protospace(B)
Protospace(D)
Protospace(F)
(SEQ ID NO: 16)

Luciferase Activity (RLU)
U6-CAG
U6-LTR C
U6-LTR D
U6-LTR C/D

Control
TSA/PMA
Luciferase Activity (%)

Luciferase Activity (%)
U6-CAG
LTR-C
LTR-D
LTR-C/D

Luciferase Activity (Flod)
U6-CAG
LTR-C
LTR-D
LTR-C/D

-456
C A
B
D
+1
+98
+182
U3
R
U5
AP1
NFAT
USF
Ets
TCF1α
NFκB
NFAT
SP1
TATA
-418
-18
AU3
pHR'-NL43-Env-EGFP

Control
TSA
EGFP positive cells (%)
EGFP intensity (Grn Hlog)
EGFP intensity (GRN Hlog)
U6-CAG
U6-LTR A
U6-LTR B
U6-LTR A/B
U6-LTR C
U6-LTR D
U6-LTR C/D

Fig. 18

HIV-1 LTR (634 bp)

Human immunodeficiency virus type 1, NY5/BRU (LAV-1) recombinant clone pNL4-3.
ACCESSION number: M19921

TGGAAGGGCTAATTCACTCCCAACGAAGACAAGATATCCTTGATCTGTGGATCTACCACACACAA

GGCTACTTCCCTGATTGGCAGAACTACACACCAGGGCCAGGGATCAGATATCCACTGACCTTTGG

U3 region

ATGGTGCTACAAGCTAGTACCAGTTGAGCAAGAGAAGGTAGAAGAAGCCAATGAAGGAGAGAACA

CCCGCTTGTTACACCCTGTGAGCCTGCATGGGATGGATGACCCGGAGAGAGAAGTATTAGAGTGG

AGGTTTGACAGCCGCCTAGCATTTCATCACATGGCCCGAGAGCTGCATCCGGAGTACTTCAAGAA

CTGCTGACATCGAGCTTGCTACAAGGGACTTTCCGCTGGGGACTTTCCAGGGAGGCGTGGCCTGG

GCGGGACTGGGGAGTGGCGAGCCCTCAGATGCTGCATATAAGCAGCTGCTTTTTGCTTGTACTGG

R region

GTCTCTCTGGTTAGACCAGATCTGAGCCTGGGAGCTCTCTGGCTAACTAGGGAACCCACTGCTTA

U5 region

AGCCTCAATAAAGCTTGCCTTGAGTGCTTCAAGTAGTGTGTGCCCGTCTGTTGTGTGACTCTGGT

AACTAGAGATCCCTCAGACCCTTTTAGTCAGTGTGGAAAATCTCTAGCA (SEQ ID NO: 376)

Fig. 19

SIVmm239-LTR(818bp)

Simian (macaque) immunodeficiency virus, isolate 239
Genebank number: M33262

TGGAAGGGATTTATTACAGTGCAAGAAGACATAGAATCTTAGACATATACTTAGAAAAGGAAGAAGGCATCAT

ACCAGATTGGCAGGATTACACCTCAGGACCAGGAATTAGATACCCAAAGACATTTGGCTGGCTATGGAAATTA

U3 region

GTCCCTGTAAATGTATCAGATGAGGCACAGGAGGATGAGGAGCATTATTTAATGCATCCAGCTCAAACTTCCC

AGTGGGATGACCCTTGGGGAGAGGTTCTAGCATGGAAGTTTGATCCAACTCTGGCCTACACTTATGAGGCATA

TGTTAGATACCCAGAAGAGTTTGGAAGCAAGTCAGGCCTGTCAGAGGAAGAGGTTAGAAGAAGGCTAACCGCA

AGAGGCCTTCTTAACATGGCTGACAAGAAGGAAACTCGCTGAAACAGCAGGGACTTTCCACAAGGGGATGTTA

CGGGGAGGTACTGGGGAGGAGCCGGTCGGGAACGCCCACTTTCTTGATGTATAAATATCACTGCATTTCGCTC

TGTATTCAGTCGCTCTGCGGAGAGGCTGGCAGATTGAGCCCTGGGAGGTTCTCTCCAGCACTAGCAGGTAGAG

R region

CCTGGGTGTTCCCTGCTAGACTCTCACCAGCACTTGGCCGGTGCTGGGCAGAGTGACTCCACGCTTGCTTGCT

TAAAGCCCTCTTCAATAAAGCTGCCATTTTAGAAGTAAGCTAGTGTGTGTTCCCATCTCTCCTAGCCGCCGCC

U5 region

TGGTCAACTCGGTACTCAATAATAAGAAGACCCTGGTCTGTTAGGACCCTTTCTGCTTTGGGAAACCGAAGCA

GGAAAATCCCTAGCA (SEQ ID NO: 380)

METHODS AND COMPOSITIONS FOR RNA-GUIDED TREATMENT OF HIV INFECTION

CROSS-REFERENCE TO RELATED APPLICATIONS

This application is a continuation of U.S. application Ser. No. 15/950,236, filed Apr. 11, 2018, which is a continuation of U.S. application Ser. No. 15/148,261, filed May 6, 2016, now U.S. Pat. No. 9,981,020, issued May 29, 2018, which is a continuation of U.S. application Ser. No. 14/838,057, filed Dec. 11, 2015, now U.S. Pat. No. 9,925,248, issued Mar. 27, 2018, which is a National Stage Application filed under 35 U.S.C. § 371, of International Patent Application No PCT/US2014/053441, filed on Aug. 29, 2014, which claims the benefit of and priority to U.S. Provisional Application No. 61/871,626, filed Aug. 29, 2013, U.S. Provisional Application No. 62/018,441, filed Jun. 27, 2014 and U.S. Provisional Application No. 62/026,103, filed Jul. 18, 2014. The entire contents of which are incorporated herein by reference in their entirety.

STATEMENT REGARDING FEDERALLY SPONSORED RESEARCH

This invention was made with U.S. government support under grant numbers R01MH093271, R01NS087971, and P30MH092177 awarded by the National Institutes of Health. The U.S. government may have certain rights in the invention.

SEQUENCE LISTING

The instant application contains a Sequence Listing which has been submitted electronically in ASCII format and is hereby incorporated by reference in its entirety. Said ASCII copy, created on Aug. 31, 2020, is named 062851-502C12US_SL.txt and is 174,536 bytes in size.

BACKGROUND OF THE INVENTION

1. Technical Field

The present invention relates to compositions that specifically cleave target sequences in retroviruses, for example human immunodeficiency virus (HIV). Such compositions, which can include nucleic acids encoding a Clustered Regularly Interspace Short Palindromic Repeat (CRISPR) associated endonuclease and a guide RNA sequence complementary to a target sequence in a human immunodeficiency virus, can be administered to a subject having or at risk for contracting an HIV infection.

2. Background Art

For more than three decades since the discovery of HIV-1, AIDS remains a major public health problem affecting greater than 35.3 million people worldwide. AIDS remains incurable due to the permanent integration of HIV-1 into the host genome. Current therapy (highly active antiretroviral therapy or HAART) for controlling HIV-1 infection and impeding AIDS development profoundly reduces viral replication in cells that support HIV-1 infection and reduces plasma viremia to a minimal level. But HAART fails to suppress low level viral genome expression and replication in tissues and fails to target the latently-infected cells, for example, resting memory T cells, brain macrophages, microglia, and astrocytes, gut-associated lymphoid cells, that serve as a reservoir for HIV-1. Persistent HIV-1 infection is also linked to co-morbidities including heart and renal diseases, osteopenia, and neurological disorders. There is a continuing need for curative therapeutic strategies that target persistent viral reservoirs.

SUMMARY OF THE INVENTION

The present invention provides fora method of treating a subject at risk for having a virus infection, by administering to the subject a prophylactically effective amount of a composition comprising a vector encoding a CRISPR-associated endonuclease and at least two guide RNAs, wherein the guide RNAs are complementary to two target sequences spanning from the 5'- to 3'-LTRs of the sequence in the virus, and preventing a retroviral infection.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1D discloses SEQ ID NOS 1-3, respectively, in order of appearance. (1E-1G) Subcloning of LTR-AB stable clones reveals complete loss of reporter reactivation determined by EGFP flow cytometry (1E) and elimination of pNL4-3-ΔGag-d2EGFP proviral genome detected by standard (1F) and real-time (1G) PCR amplification of genomic DNA for EGFP and HIV-1 Rev response element (RRE); (3-actin is a DNA purification and loading control. (1H) PCR genotyping of LTR-AB subclones (#8, 13) using primers to amplify DNA fragment covering HIV-1 LTR U3/R/U5 regions (−411 to +129) shows indels (a, deletion; c, insertion) and "intact" or combined LTR (b).

FIG. 2B discloses SEQ ID NOS 4-13, respectively, in order of appearance. (2C) Functional analysis of LTR-AB-induced eradication of HIV-1 genome, showing substantial blockade of TSA/PMA reactivation-induced p24 virion release. U1 cells were transfected with pX260-LTRs-A, -B, or -A/B. After 2-week puromycin selection, cells were treated with TSA (250 nM)/PMA for 2 days before p24 Gag ELISA was performed.

(FIG. 3A) Immunocytochemistry (ICC) and Western blot (WB) analyses with anti-Flag antibody confirm the expression of Flag-Cas9 in TZM-bl stable clones puromycin (2 μg/ml)-selected for 2 weeks. (FIG. 3B) PCR genotyping of Cas9/LTR-A/B stable clones (c1-c7) reveals a close correlation of LTR excision with repression of LTR luciferase reporter activation. Fold changes represent TSA/PMA-induced levels over corresponding non-induction levels. (FIG. 3C) Stable Cas9/LTR-AB-expressing cells (c4) were infected with pseudotyped-pNL4-3-Nef-EGFP lentivirus at indicated multiplicity of infection (M01) and infection efficiency measured by EGFP flow cytometry, 2 d post-infection. (FIG. 3D) Representative phase-contrast/fluorescence micrographs show that LTR-AB stable, but not control (U6-CAG; black) cells, are resistant to new infection (right panel) by pNL4-3-ΔE-EGFP HIV-1 reporter virus (gray).

FIGS. 4A-4D illustrate the off-target effects of Cas9/LTR-A/B on the human genome. (4A) SURVEYOR assay shows no indel mutations in predicted/potential off-target regions in human TZM-bl and U1 cells. LTR-A on-target region (A) was used as a positive control and empty U6-CAG vector (U6) as a negative control. (4B-4D) Whole-genome sequencing of LTR-AB stable TZM-bl subclone showing the numbers of called indels in the U6-CAG control and LTR-A/B samples (4B), detailed information on 10 called indels near gRNA target sites in both samples (4C), and distribution of off-target called indels (4D). FIG. 4C discloses SEQ ID NOS 14-15, respectively, in order of appearance.

FIG. 5 discloses SEQ ID NO: 16.

FIG. 7C discloses SEQ ID NOS 17-25, respectively, in order of appearance. FIG. 7D discloses SEQ ID NOS 26-30, respectively, in order of appearance. (7E) PCR-restriction fragment length polymorphism (RFLP) analysis using BsaJ Ito cut 5 sites (96, 102, 372, 386, 482) of the PCR product covering −453 to +43 of LTR showing two major bands (96 bp and 270 bp) in the U6-CAG control sample, but an additional 372 bp band (upper arrow) after LTR-C-induced indel mutation at the 96/102 sites, a 290 bp band (middle arrow) after LTR-D-induced mutations at the 372 site and a 180 bp fragment (lower arrow) after LTR-C/D-induced excision. (7F) Example chromatograms showing the deletion of a 302 bp fragment between LTR-C and LTR-D (top) and an additional 17 bp deletion (bottom). Red arrows indicate the junction sites. *$P<0.05$ indicates a significant decrease in LTR-C or LTR-D-mediated luciferase activation compared to U6-CAG control. FIG. 7F discloses SEQ ID NOS 31-32, respectively, in order of appearance.

FIG. 8C discloses SEQ ID NOS 33-34, respectively, in order of appearance.

FIG. 9A discloses SEQ ID NO: 35. (9B) The representative DNA gel picture shows specific eradication of the HIV-1 genome. NS, non-specific band. (9C, 9D) Quantitative PCR analysis using the primer pair targeting the Gag gene (T457/T458) shows 85% efficiency of entire HIV-1 genome eradication in Cas9/LTR-A/B-expressing U1 cells. U1 cells were transfected with pX260 empty vector (U6-CAG) or LTRs-AB-encoding vectors. After 2-week puromycin selection, the cellular genomic DNAs were used for absolute quantitative qPCR analysis using spiked pNL4-3-AE-EGFP human genomic DNA as a standard. **P<0.01 indicates a significant decrease compared to the U6-CAG control.

FIG. 13 shows the predicted LTR gRNAs and their off-target numbers (100% match). The 5'-LTR sense and antisense sequences (SEQ ID NOS 79-111 and 112-141, respectively) (634 bp) of pHR'-CMV-LacZ lentiviral vector (AF105229) were utilized to search for Cas9/gRNA target sites containing a 20-bp guide sequence (protospacer) plus the protospacer adjacent motif sequence (NGG) using Jack Lin's CRISPR/Cas9 gRNA finder tool (spot.colorado.edu/~slin/cas9). Each gRNA plus NGG (AGG, TGG, GGG, CGG) was blasted against available human genomic and transcript sequences with 1000 aligned sequences being displayed. After pressing Control+F, copy/paste the target sequence (1-23 through 9-23 nucleotides) and find the number of genomic targets with 100% match. The number of off-targets for each searching was divided by 3 because of repeated genome library. The number shown indicates the sum of 4 searches (NGG). The top number (for example, for gRNA sequence (sense): 20, 19, 19, 17, 16, 15, 14, 13, 12) indicates the gRNA target sequences farthest from NGG. The sequence and off-target numbers for the selected LTR-A/B and LTR-C/D are highlighted red and green respectively.

FIG. 14 depicts the oligonucleotides for gRNA targeting sites and primers (SEQ ID NOS 36-78, respectively, in order of appearance) used for PCR and sequencing.

FIG. 15 shows the locations of predicted gRNA targeting sites of LTR-A and LTR-B and discloses "query Seq" sequences as SEQ ID NOS 142-252, and "ref Seq" sequences as SEQ ID NOS 253-363, all respectively, in order of appearance.

FIG. 16A discloses SEQ ID NO: 16. TZMBI cells were cotransfected with Cas9-EGFP and chimera gRNA expression cassette (PCR products) by LIPOFECTAMINE 2000. After 3 d, EGFP-positive cells were sorted through FACS and 2000 cells per group were collected for luciferase assay (FIG. 16B). The population sorted cells were cultured for 2 d and treated with TSA/PMA for 1 d before luciferase assay (FIG. 16C). The single cells were sorted into 96-well plate and cultured till confluence for luciferase assay in the absence (FIG. 16D) or presence (FIG. 1E) of TSA/PMA for 1 d. The PCR product from the population sorted cells were analyzed with Surveyor Cel-I nuclease assay (FIG. 1F) and restriction fragment length polymorphism with Bsajl (FIG. 16G) showing mutation (FIG. 16F) or uncut (FIG. 16G) band (red arrow). A 200 bp fragment (FIGS. 16F, 16G, black arrow) resulting from the deletion of 321 bp region between LTR-C and LTR-D as predicted (FIG. 16A, red arrowhead) was validated by TA-cloning and sequencing showing precise genomic excision (FIG. 16H). FIG. 16H discloses SEQ ID NO: NO: 31. Sanger sequencing of PCR products from individual LTR-C and -D identified % and % indel mutation efficiency respectively (FIG. 16I). * p<0.05 indicates statistically significant reduction using a student's t test compared to the corresponding U6-CAG control. Protospace(E), Protospace(C), Protospace(A), Protospace(B), Protospace(D), and Protospace(F) correspond to SEQ ID NOS 365, 367, 369, 371, 373, and 375, respectively, in order of appearance.

FIG. 17H discloses SEQ ID NOS 1-3, respectively, in order of appearance.

FIG. 18 shows LTR of a representative HIV-1 sequence (SEQ ID NO: 376). The U3 region extends from nucleotide 1 to nucleotide 432 (SEQ ID NO: 377), the R region extends from nucleotide 432 to nucleotide 559 (SEQ ID NO: 378), and the U5 region extends from 560 to nucleotide 634 (SEQ ID NO: 379).

FIG. 19 shows LTR of a representative SIV sequence (SEQ ID NO: 380). The U3 region extends from nucleotide 1 to nucleotide 517 (SEQ ID NO: 381), the R region extends from nucleotide 518 to nucleotide 693 (SEQ ID NO: 382), and the U5 region extends from 694 to nucleotide 818 (SEQ ID NO: 383).

DETAILED DESCRIPTION OF THE INVENTION

Figures 1A, 1B, 1C, 1D:
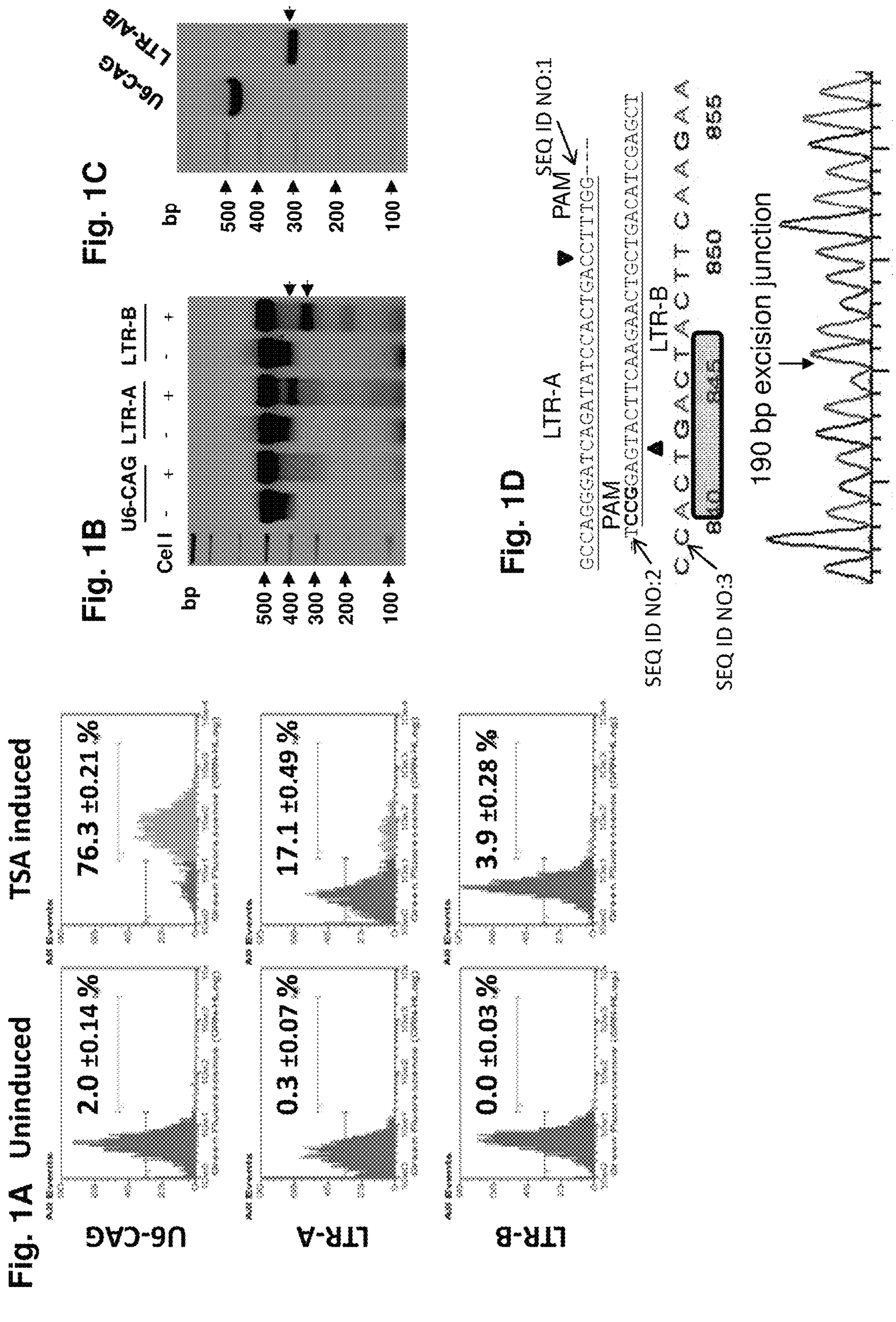
FIGS. 1A-1H show that Cas9/LTR-gRNA suppresses HIV-1 reporter virus production in CHME5 microglial cells latently infected with HIV-1. (1A) Representative gating diagram of EGFP flow cytometry shows a dramatic reduction in TSA-induced reactivation of latent pNL4-3-ΔGag-d2EGFP reporter virus by stably expressed Cas9 plus LTR-A or —B, vs. empty U6-driven gRNA expression vector (U6-CAG). (1B) SURVEYOR Cel-I nuclease assay of PCR product (−453 to +43 within LTR) from selected LTR-A- or -B-expressing stable clones shows dramatic indel mutation patterns (arrows). (1C, 1D) PCR fragment analysis shows a precise deletion of 190-bp region between LTRs A and B cutting sites (arrowhead and arrow in 1D), leaving 306-bp fragment (arrow in 1C) validated by TA-cloning and sequencing results.

The present invention is based, in part, on our discovery that we could eliminate the integrated HIV-1 genome from HIV-1 infected cells by using the RNA-guided Clustered Regularly Interspace Short Palindromic Repeat (CRISPR)-Cas 9 nuclease system (Cas9/gRNA) in single and multiplex configurations. We identified highly specific targets within the HIV-1 LTR U3 region that were efficiently edited by Cas9/gRNA, inactivating viral gene expression and replication in latently-infected microglial, promonocytic and T cells. Cas9/gRNAs caused neither genotoxicity nor off-target editing to the host cells, and completely excised a 9709-bp fragment of integrated proviral DNA that spanned from its 5'- to 3T-LTRs. Furthermore, the presence of multiplex gRNAs within Cas9-expressing cells prevented HIV-1 infection. Our results suggest that Cas9/gRNA can be engineered to provide a specific, efficacious prophylactic and therapeutic approach against AIDS.

Accordingly, the invention features compositions comprising a nucleic acid encoding a CRISPR-associated endonuclease and a guide RNA that is complementary to a target sequence in a retrovirus, e.g., HIV, as well as pharmaceutical formulations comprising a nucleic acid encoding a CRISPR-associated endonuclease and a guide RNA that is complementary to a target sequence in HIV. Also featured are compositions comprising a CRISPR-associated endonuclease polypeptide and a guide RNA that is complementary to a target sequence in HIV, as well as pharmaceutical formulations comprising a CRISPR-associated endonuclease polypeptide and a guide RNA that is complementary to a target sequence in HIV.

Also featured are methods of administering the compositions to treat a retroviral infection, e.g., HIV infection, methods of eliminating viral replication, and methods of preventing HIV infection. The therapeutic methods described herein can be carried out in connection with other antiretroviral therapies (e.g., HAART).

The clinical course of HIV infection can vary according to a number of factors, including the subject's genetic background, age, general health, nutrition, treatment received, and the HIV subtype. In general, most individuals develop flu-like symptoms within a few weeks or months of infection. The symptoms can include fever, headache, muscle aches, rash, chills, sore throat, mouth or genital ulcers, swollen lymph glands, joint pain, night sweats, and diarrhea. The intensity of the symptoms can vary from mild to severe depending upon the individual. During the acute phase, the HIV viral particles are attracted to and enter cells expressing the appropriate CD4 receptor molecules. Once the virus has entered the host cell, the HIV encoded reverse transcriptase generates a proviral DNA copy of the HIV RNA and the pro-viral DNA becomes integrated into the host cell genomic DNA. It is this HIV provirus that is replicated by the host cell, resulting in the release of new HIV virions which can then infect other cells. The methods and compositions of the invention are generally and variously useful for excision of integrated HIV proviral DNA, although the invention is not so limited, and the compositions may be administered to a subject at any stage of infection or to an uninfected subject who is at risk for HIV infection.

The primary HIV infection subsides within a few weeks to a few months, and is typically followed by a long clinical "latent" period which may last for up to 10 years. The latent period is also referred to as asymptomatic HIV infection or chronic HIV infection. The subject's CD4 lymphocyte numbers rebound, but not to pre-infection levels and most subjects undergo seroconversion, that is, they have detectable levels of anti-HIV antibody in their blood, within 2 to 4 weeks of infection. During this latent period, there can be no detectable viral replication in peripheral blood mononuclear cells and little or no culturable virus in peripheral blood. During the latent period, also referred to as the clinical latency stage, people who are infected with HIV may experience no HIV-related symptoms, or only mild ones. But, the HIV virus continues to reproduce at very low levels. In subjects who have treated with anti-retroviral therapies, this latent period may extend for several decades or more. However, subjects at this stage are still able to transmit HIV to others even if they are receiving antiretroviral therapy, although anti-retroviral therapy reduces the risk of transmission. As noted above, anti-retroviral therapy does not suppress low levels of viral genome expression nor does it efficiently target latently infected cells such as resting memory T cells, brain macrophages, microglia, astrocytes and gut associated lymphoid cells.

Clinical signs and symptoms of AIDS (acquired immunodeficiency syndrome) appear as CD4 lymphocyte numbers decrease, resulting in irreversible damage to the immune system. Many patients also present with AIDS-related complications, including, for example, opportunistic infections such as tuberculosis, salmonellosis, cytomegalovirus, candidiasis, cryptococcal meningitis, toxoplasmosis, and cryptosporidiosis, as well as certain kinds of cancers, including for example, Kaposi's sarcoma, and lymphomas, as well as wasting syndrome, neurological complications, and HIV-associated nephropathy.

Compositions

The compositions of the invention include nucleic acids encoding a CRISPR-associated endonuclease, e.g., Cas9, and a guide RNA that is complementary to a target sequence in a retrovirus, e.g., HIV. In bacteria the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA). The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or Hi-promoted RNA expression vector, although cleavage efficiencies of the artificial sgRNA are lower than those for systems with the crRNA and tracrRNA expressed separately.

The compositions of the invention can include a nucleic acid encoding a CRISPR-associated endonuclease. In some embodiments, the CRISPR-associated endonuclease can be a Cas9 nuclease. The Cas9 nuclease can have a nucleotide sequence identical to the wild type *Streptococcus pyrogenes* sequence. In some embodiments, the CRISPR-associated endonuclease can be a sequence from other species, for example other *Streptococcus* species, such as *thermophilus; Psuedomona aeruginosa, Escherichia coli*, or other sequenced bacteria genomes and archaea, or other prokaryotic microorganisms. Alternatively, the wild type *Streptococcus* pyrogenes Cas9 sequence can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

The Cas9 nuclease sequence can be a mutated sequence. For example the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

In some embodiments, compositions of the invention can include a CRISPR-associated endonuclease polypeptide encoded by any of the nucleic acid sequences described above. The terms "peptide," "polypeptide," and "protein" are used interchangeably herein, although typically they refer to peptide sequences of varying sizes. We may refer to the amino acid-based compositions of the invention as "polypeptides" to convey that they are linear polymers of amino acid residues, and to help distinguish them from full-length proteins. A polypeptide of the invention can "constitute" or "include" a fragment of a CRISPR-associated endonuclease, and the invention encompasses polypeptides that constitute or include biologically active variants of a CRISPR-associated endonuclease. It will be understood that the polypeptides can therefore include only a fragment of a CRISPR-associated endonuclease (or a biologically active variant thereof) but may include additional residues as well. Biologically active variants will retain sufficient activity to cleave target DNA.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a CRISPR-associated endonuclease can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

One or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine (2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

Alternatively, or in addition, one or more of the amino acid residues in a biologically active variant can be a naturally occurring residue that differs from the naturally occurring residue found in the corresponding position in a wildtype sequence. In other words, biologically active variants can include one or more amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a CRISPR-associated endonuclease can be characterized in terms of the extent to which their sequence is similar to or identical to the corresponding wild-type polypeptide. For example, the sequence of a biologically active variant can be at least or about 80% identical to corresponding residues in the wild-type polypeptide. For example, a biologically active variant of a CRISPR-associated endonuclease can have an amino acid sequence with at least or about 80% sequence identity (e.g., at least or about 85%, 90%, 95%, 97%, 98%, or 99% sequence identity) to a CRISPR-associated endonuclease or to a homolog or ortholog thereof.

A biologically active variant of a CRISPR-associated endonuclease polypeptide will retain sufficient biological activity to be useful in the present methods. The biologically active variants will retain sufficient activity to function in targeted DNA cleavage. The biological activity can be assessed in ways known to one of ordinary skill in the art and includes, without limitation, in vitro cleavage assays or functional assays.

Polypeptides can be generated by a variety of methods including, for example, recombinant techniques or chemical synthesis. Once generated, polypeptides can be isolated and purified to any desired extent by means well known in the art. For example, one can use lyophilization following, for example, reversed phase (preferably) or normal phase HPLC, or size exclusion or partition chromatography on polysaccharide gel media such as Sephadex G-25. The composition of the final polypeptide may be confirmed by amino acid analysis after degradation of the peptide by standard means, by amino acid sequencing, or by FAB-MS techniques. Salts, including acid salts, esters, amides, and N-acyl derivatives of an amino group of a polypeptide may be prepared using methods known in the art, and such peptides are useful in the context of the present invention.

The compositions of the invention include sequence encoding a guide RNA (gRNA) comprising a sequence that is complementary to a target sequence in a retrovirus. The retrovirus can be a lentivirus, for example, a human immunodeficiency virus, a simian immunodeficiency virus, a feline immunodeficiency virus or a bovine immunodeficiency virus. The human immunodeficiency virus can be HIV-1 or HIV-2. The target sequence can include a sequence from any HIV, for example, HIV-1 and HIV-2, and any circulating recombinant form thereof. The genetic variability of HIV is reflected in the multiple groups and subtypes that have been described. A collection of HIV sequences is compiled in the Los Alamos HIV databases and compendiums. The methods and compositions of the invention can be applied to HIV from any of those various groups, subtypes, and circulating recombinant forms. These include for example, the HIV-1 major group (often referred to as Group M) and the minor groups, Groups N, O, and P, as well as but not limited to, any of the following subtypes, A, B, C, D, F, G, H, J and K. or group (for example, but not limited to any of the following Groups, N, O and P) of HIV. The methods and compositions can also be applied to HIV-2 and any of the A, B, C, F or G clades (also referred to as "subtypes" or "groups"), as well as any circulating recombinant form of HIV-2.

The guide RNA can be a sequence complimentary to a coding or a non-coding sequence. For example, the guide RNA can be an HIV sequence, such as a long terminal repeat (LTR) sequence, a protein coding sequence, or a regulatory sequence. In some embodiments, the guide RNA comprises a sequence that is complementary to an HIV long terminal repeat (LTR) region. The HIV-1 LTR is approximately 640 bp in length. An exemplary HIV-1 LTR is the sequence of SEQ ID NO: 376. An exemplary SIV LTR is the sequence of SEQ ID NO: 380. HIV-1 long terminal repeats (LTRs) are divided into U3, R and U5 regions. Exemplary HIV-1 LTR U3, R and U5 regions are SEQ ID NOs: 377, 378 and 379, respectively. Exemplary SIV LTR U3, R and U5 regions are SEQ ID NOs: 381, 382, and 383, respectively. The configuration of the U1, R, U5 regions for exemplary HIV-1 and SIV sequences are shown in FIGS. 18 and 19, respectively. LTRs contain all of the required signals for gene expression and are involved in the integration of a provirus into the genome of a host cell. For example, the basal or core promoter, a core enhancer and a modulatory region is found within U3 while the transactivation response element is found within R. In HIV-1, the U5 region includes several sub-regions, for example, TAR or trans-acting responsive element, which is involved in transcriptional activation; Poly A, which is involved in dimerization and genome packaging; PBS or primer binding site; Psi or the packaging signal; DIS or dimer initiation site.

Useful guide sequences are complementary to the U3, R, or U5 region of the LTR. Exemplary guide RNA sequences that target the U3 region of HIV-1 are shown in FIG. 13. A guide RNA sequence can comprise, for example, a sequence complementary to the target protospacer sequence of:

```
LTR A:
                              (SEQ ID NO: 96)
ATCAGATATCCACTGACCTTTGG,

LTR B:
                             (SEQ ID NO: 121)
CAGCAGTTCTTGAAGTACTCCGG,

LTR C
                              (SEQ ID NO: 87)
GATTGGCAGAACTACACACCAGG,
or

LTR D:
                             (SEQ ID NO: 110)
GCGTGGCCTGGGCGGGACTGGGG.
```

Figure 5:
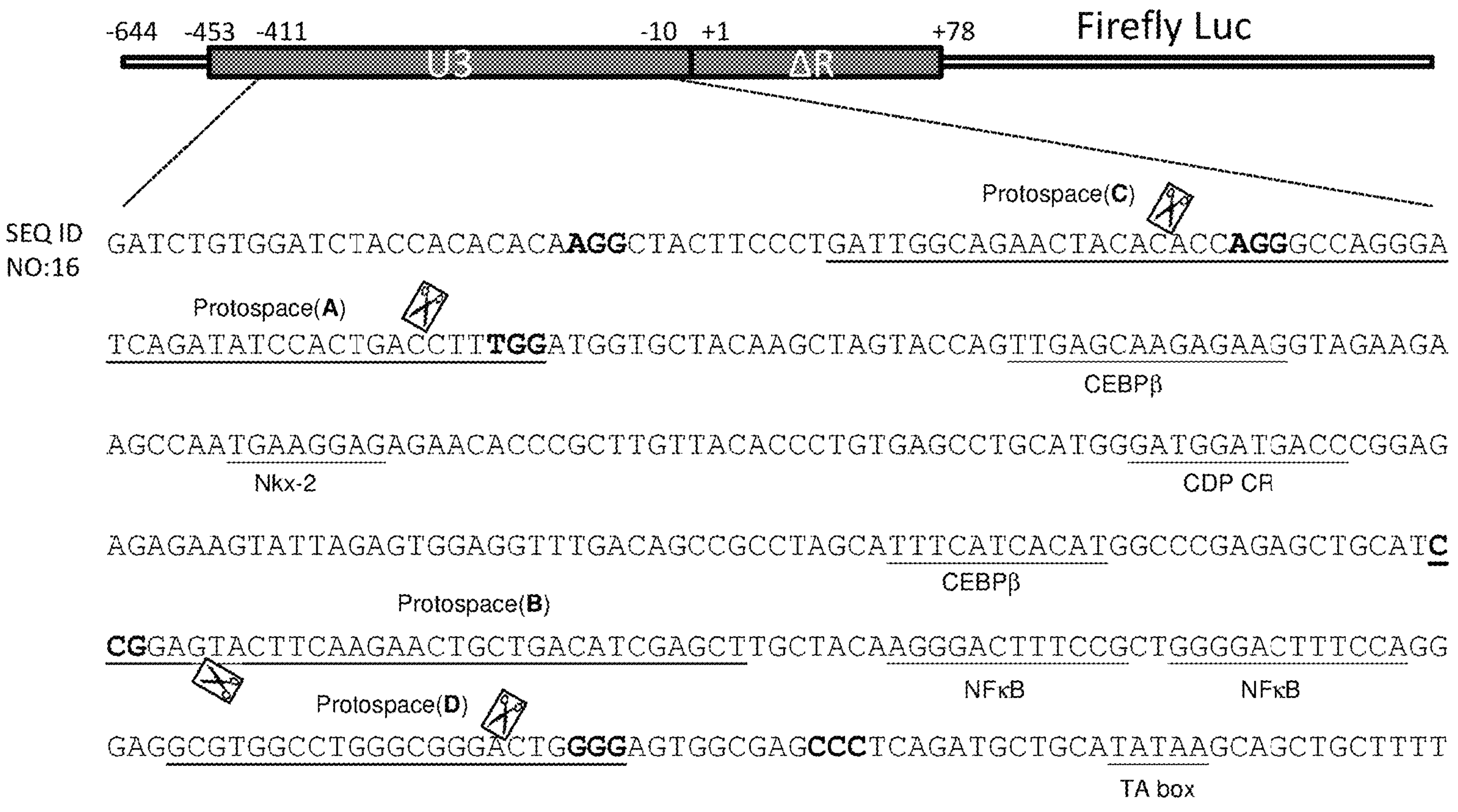
FIG. 5 shows the LTR U3 sequence of the integrated lentiviral LTR-firefly luciferase reporter identified by TA-cloning and sequencing of PCR product (−411 to −10) from the genomic DNA of human TZM-bl cells. The protospacer and PAM (NGG) sequences of 4 gRNAs (LTR-A to D) and the predicted binding sites of indicated transcription factors are highlighted. The precise cleavage sites are marked with scissors. +1 indicates the transcriptional start site.

The locations of LTR A (SEQ ID NO: 96), LTR B (SEQ ID NO: 121), LTR C (SEQ ID NO: 87) and LTR D (SEQ ID NO: 110) within the U3 (SEQ ID NO: 16) region are shown FIG. 5. Additional exemplary guide RNA sequences that target the U3 region are listed in the table shown in FIG. 13 and can have the sequence of any of SEQ ID NOs: 79-111 and SEQ ID NOs: 111-141. In some embodiments, the guide sequence can comprise a sequence having 95% identity to any of SEQ ID NOs: 79-111 and SEQ ID NOs: 111-141. Thus, a guide RNA sequence can comprise, for example, a sequence having 95% identity to a sequence complementary to the target protospacer sequence of:

```
LTR A:
                              (SEQ ID NO: 96)
ATCAGATATCCACTGACCTTTGG,

LTR B:
                             (SEQ ID NO: 121)
CAGCAGTTCTTGAAGTACTCCGG,

LTR C:
                              (SEQ ID NO: 87)
GATTGGCAGAACTACACACCAGG,
or

LTR D:
                             (SEQ ID NO: 110)
GCGTGGCCTGGGCGGGACTGGGG.
```

We may also be refer to the guide RNA sequence as a spacer, e.g., spacer (A), spacer (B), spacer (C), and spacer (D).

The guide RNA sequence can be complementary to a sequence found within an HIV-1 U3, R, or U5 region reference sequence or consensus sequence. The invention is not so limiting however, and the guide RNA sequences can be selected to target any variant or mutant HIV sequence. In some embodiments, more than one guide RNA sequence is employed, for example a first guide RNA sequence and a second guide RNA sequence, with the first and second guide RNA sequences being complimentary to target sequences in any of the above mentioned retroviral regions. In some embodiments, the guide RNA can include a variant sequence or quasi-species sequence. In some embodiments, the guide RNA can be a sequence corresponding to a sequence in the genome of the virus harbored by the subject undergoing treatment. Thus for example, the sequence of the particular U3, R, or U5 region in the HIV virus harbored by the subject can be obtained and guide RNAs complementary to the patient's particular sequences can be used.

In some embodiments, the guide RNA can be a sequence complimentary to a protein coding sequence, for example, a sequence encoding one or more viral structural proteins, (e.g., gag, pol, env and tat). Thus, the sequence can be complementary to sequence within the gag polyprotein, e.g., MA (matrix protein, p17); CA (capsid protein, p24); SP1 (spacer peptide 1, p2); NC (nucleocapsid protein, p'7); SP2 (spacer peptide 2, p1) and P6 protein; pol, e.g., reverse transcriptase (RT) and RNase H, integrase (IN), and HIV protease (PR); env, e.g., gp160, or a cleavage product of gp160, e.g., gp120 or SU, and gp41 or TM; or tat, e.g., the 72-amino acid one-exon Tat or the 86-101 amino-acid two-exon Tat. In some embodiments, the guide RNA can be a sequence complementary to a sequence encoding an accessory protein, including for example, vif, nef (negative factor) vpu (Virus protein U) and tev.

In some embodiments, the sequence can be a sequence complementary to a structural or regulatory element, for example, an LTR, as described above; TAR (Target sequence for viral transactivation), the binding site for Tat protein and for cellular proteins, consists of approximately the first 45 nucleotides of the viral mRNAs in HIV-1 (or the first 100 nucleotides in HIV-2) forms a hairpin stem-loop structure; RRE (Rev responsive element) an RNA element encoded within the env region of HIV-1, consisting of approximately 200 nucleotides (positions 7710 to 8061 from the start of transcription in HIV-1, spanning the border of gp120 and gp41); PE (Psi element), a set of 4 stem-loop structures preceding and overlapping the Gag start codon; SLIP, a TTTTTT "slippery site", followed by a stem-loop structure; CRS (Cis-acting repressive sequences); INS Inhibitory/Instability RNA sequences) found for example, at nucleotides 414 to 631 in the gag region of HIV-1.

The guide RNA sequence can be a sense or anti-sense sequence. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. For example, Cas9 from *S. thermophilus* requires 5'-NNAGAA for CRISPR 1 and 5'-NGGNG for CRISPR3) and *Neiseria menigiditis* requires 5'-NNNNGATT). The specific sequence of the guide RNA may vary, but, regardless of the sequence, useful guide RNA sequences will be those that minimize off-target effects while achieving high efficiency and complete ablation of the genomically integrated HIV-1 provirus. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides. Useful selection methods identify regions having extremely low homology between the foreign viral genome and host cellular genome including endogenous retroviral DNA, include bioinformatic screening using 12-bp+NGG target-selection criteria to exclude off-target human transcriptome or (even rarely) untranslated-genomic sites; avoiding transcription factor binding sites within the HIV-1 LTR promoter (potentially conserved in the host genome); selection of LTR-A- and -B-directed, 30-bp gRNAs and also pre-crRNA system reflecting the original bacterial immune mechanism to enhance specificity/efficiency vs. 20-bp gRNA-, chimeric crRNA-tracRNA-based system and WGS, Sanger sequencing and SURVEYOR assay, to identify and exclude potential off-target effects.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs, for example any combination of sequences in U3, R, or U5. In some embodiments, combinations of LTR A, LTR B, LTR C and LTR D can be used. In some embodiments, combinations of any of the sequences LTR A (SEQ ID NO: 96), LTR B (SEQ ID NO: 121), LTR C (SEQ ID NO: 87), and LTR D (SEQ ID NO: 110), can be used. In some embodiments, any combinations of the sequences having the sequence of SEQ ID NOs: 79-111 and SEQ ID NOs: 111-141 can be used. When the compositions are administered in an expression vector, the guide RNAs can be encoded by a single vector. Alternatively, multiple vectors can be engineered to each include two or more different guide RNAs. Useful configurations will result in the excision of viral sequences between cleavage sites resulting in the ablation of HIV genome or HIV protein expression. Thus, the use of two or more different guide RNAs promotes excision of the viral sequences between the cleavage sites recognized by the CRISPR endonuclease. The excised region can vary in size from a single nucleotide to several thousand nucleotides. Exemplary excised regions are described in the examples.

When the compositions are administered as a nucleic acid or are contained within an expression vector, the CRISPR endonuclease can be encoded by the same nucleic acid or vector as the guide RNA sequences. Alternatively or in addition, the CRISPR endonuclease can be encoded in a physically separate nucleic acid from the guide RNA sequences or in a separate vector.

In some embodiments, the RNA molecules e.g. crRNA, tracrRNA, gRNA are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington D.C.). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethyl-2-thiouridine; dihydrouridine; dihydroribosylthymine; 2'-methyladenosine; 2-methyl adenosine; N.sup.6N-methyl adenosine; $N^6$, $N^6$-dimethyladenosine; $N^6$,2'-O-trimethyladenosine; 2-methylthio-$N^6$N-isopentenyladenosine; N6-(cis-hydroxyisopentenyl)-adenosine; 2-methylthio-$N^6$-(cis-hydroxyisopentenyl)-adenosine; $N^6$-glycinylcarbamoyl)adeno sine; $N^6$-threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1; 2'-O-dimethyl inosine; 2'-O-methyl guanosine; 1-methyl guanosine; $N^2$-methyl guanosine; $N^2$,$N^2$-dimethyl guanosine; $N^2$, 2'-O-dimethyl guanosine; $N^2$, $N^2$, 2'-O-trimethyl guanosine; 2'-O-ribosyl guanosine (phosphate); 7-methyl guanosine; $N^2$; 7-dimethyl guanosine; $N^2$; $N^2$; 7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring Cas9 or a biologically active variant thereof and a guide RNA where in the guide RNA is complementary to a sequence in HIV.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a Cas9-encoding DNA (in accordance with, for example, the formula above).

Two nucleic acids or the polypeptides they encode may be described as having a certain degree of identity to one another. For example, a Cas9 protein and a biologically active variant thereof may be described as exhibiting a certain degree of identity. Alignments may be assembled by locating short Cas9 sequences in the Protein Information Research (PIR) site, followed by analysis with the "short nearly identical sequences." Basic Local Alignment Search Tool (BLAST) algorithm on the NCBI website.

As used herein, the term "percent sequence identity" refers to the degree of identity between any given query sequence and a subject sequence. For example, a naturally occurring Cas9 can be the query sequence and a fragment of a Cas9 protein can be the subject sequence. Similarly, a fragment of a Cas9 protein can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., Nucleic Acids Res. 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. for multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express Cas9 and/or a guide RNA complementary to a target sequence in HIV. A recombinant nucleic acid construct comprises a nucleic acid encoding a Cas9 and/or a guide RNA complementary to a target sequence in HIV as described herein, operably linked to a regulatory region suitable for expressing the Cas9 and/or a guide RNA complementary to a target sequence in HIV in the cell. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for Cas9 can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Yeast expression systems can also be used. For example, the non-fusion pYES2 vector (Xbal, Sphl, Shol, Notl, GstXl, EcoRl, BstXl, BamH1, Sacl, Kpnl, and Hindlll cloning sites; Invitrogen) or the fusion pYESHisA, B, C (Xbal, Sphl, Shol, Notl, BstXl, EcoRl, BamH1, Sacl, Kpnl, and Hindlll cloning sites, N-terminal peptide purified with ProBond resin and cleaved with enterokinase; Invitrogen), to mention just two, can be employed according to the invention. A yeast two-hybrid expression system can also be prepared in accordance with the invention.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). A large variety of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function (s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. PNAS 88: 8850-8854, 1991).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., J. Neurochem, 64: 487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A.:90 7603 (1993); Geller, A. I., et al., Proc Natl. Acad. Sci USA: 87:1149 (1990)], Adenovirus Vectors [LeGal LaSalle et al., Science, 259:988 (1993); Davidson, et al., Nat. Genet. 3: 219 (1993); Yang, et al., J. Virol. 69: 2004 (1995)] and Adeno-associated Virus Vectors [Kaplitt, M. G., et al., Nat. Genet. 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV) (Davis, et al., Hum Gene Ther 4:151 (1993)), the SV40 early promoter region, the herpes thymidine kinase promoter, the regulatory sequences of the metallothionein (MMT) gene, prokaryotic expression vectors such as the B-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, BioTechniques, 6:682 (1988). See also, Feigner and Holm, Bethesda Res. Lab. Focus, 11(2):21 (1989) and Maurer, R.A., Bethesda Res. Lab. Focus, 11(2):25 (1989).

Replication-defective recombinant adenoviral vectors, can be produced in accordance with known techniques. See, Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the expressed products intracellularly. See for example, Chen et al, BioTechniques, 34: 167-171 (2003), which is incorporated herein, by reference, in its entirety.

Pharmaceutical Compositions

As described above, the compositions of the present invention can be prepared in a variety of ways known to one of ordinary skill in the art. Regardless of their original source or the manner in which they are obtained, the compositions of the invention can be formulated in accordance with their use. For example, the nucleic acids and vectors described above can be formulated within compositions for application to cells in tissue culture or for administration to a patient or subject. Any of the pharmaceutical compositions of the invention can be formulated for use in the preparation of a medicament, and particular uses are indicated below in the context of treatment, e.g., the treatment of a subject having an HIV infection or at risk for contracting and HIV infection. When employed as pharmaceuticals, any of the nucleic acids and vectors can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, nucleic acids and vectors described herein in combination with one or more pharmaceutically acceptable carriers. We use the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are commonly latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding the an isolated nucleic acid sequence comprising a sequence encoding a CRISPR-associated endonuclease and a guide RNA is operatively linked to a promoter or enhancer-promoter combination. Promoters and enhancers are described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments, the compositions may be formulated as a topical gel for blocking sexual transmission of HIV. The topical gel can be applied directly to the skin or mucous membranes of the male or female genital region prior to sexual activity. Alternatively or in addition the topical gel can be applied to the surface or contained within a male or female condom or diaphragm.

In some embodiments, the compositions can be formulated as a nanoparticle encapsulating a nucleic acid encoding Cas9 or a variant Cas9 and a guide RNA sequence complementary to a target HIV or vector comprising a nucleic acid encoding Cas9 and a guide RNA sequence complementary to a target HIV. Alternatively, the compositions can be formulated as a nanoparticle encapsulating a CRISPR-associated endonuclease polypeptide, e.g., Cas9 or a variant Cas9 and a guide RNA sequence complementary to a target.

The present formulations can encompass a vector encoding Cas9 and a guide RNA sequence complementary to a target HIV. The guide RNA sequence can include a sequence complementary to a single region, e.g. LTR A, B, C, or D or it can include any combination of sequences complementary to LTR A, B, C, and D. Alternatively the sequence encoding Cas9 and the sequence encoding the guide RNA sequence can be on separate vectors.

Methods of Treatment

The compositions disclosed herein are generally and variously useful for treatment of a subject having a retroviral infection, e.g., an HIV infection. We may refer to a subject, patient, or individual interchangeably. The methods are useful for targeting any HIV, for example, HIV-1, HIV-2, and any circulating recombinant form thereof. A subject is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has an HIV infection; and b) providing to the subject a composition comprising a nucleic acid encoding a CRISPR-associated nuclease, e.g., Cas9, and a guide RNA complementary to an HIV target sequence, e.g. an HIV LTR. A subject can be identified using standard clinical tests, for example, immunoassays to detect the presence of HIV antibodies or the HIV polypeptide p24 in the subject's serum, or through HIV nucleic acid amplification assays. An amount of such a composition provided to the subject that results in a complete resolution of the symptoms of the infection, a decrease in the severity of the symptoms of the infection, or a slowing of the infection's progression is considered a therapeutically effective amount. The present methods may also include a monitoring step to help optimize dosing and scheduling as well as predict outcome. In some methods of the present invention, one can first determine whether a patient has a latent HIV-1 infection, and then make a determination as to whether or not to treat the patient with one or more of the compositions described herein. Monitoring can also be used to detect the onset of drug resistance and to rapidly distinguish responsive patients from nonresponsive patients. In some embodiments, the methods can further include the step of determining the nucleic acid sequence of the particular HIV harbored by the patient and then designing the guide RNA to be complementary to those particular sequences. For example, one can determine the nucleic acid sequence of a subject's LTR U3, R or U5 region and then design one or more guide RNAs to be precisely complementary to the patient's sequences.

The compositions are also useful for the treatment, for example, as a prophylactic treatment, of a subject at risk for having a retroviral infection, e.g., an HIV infection. These methods can further include the steps of a) identifying a subject at risk for having an HIV infection; b) providing to the subject a composition comprising a nucleic acid encoding a CRISPR-associated nuclease, e.g., Cas9, and a guide RNA complementary to an HIV target sequence, e.g. an HIV LTR. A subject at risk for having an HIV infection can be, for example, any sexually active individual engaging in unprotected sex, i.e., engaging in sexual activity without the use of a condom; a sexually active individual having another sexually transmitted infection; an intravenous drug user; or an uncircumcised man. A subject at risk for having an HIV infection can be, for example, an individual whose occupation may bring him or her into contact with HIV-infected populations, e.g., healthcare workers or first responders. A subject at risk for having an HIV infection can be, for example, an inmate in a correctional setting or a sex worker, that is, an individual who uses sexual activity for income employment or nonmonetary items such as food, drugs, or shelter.

The compositions can also be administered to a pregnant or lactating woman having an HIV infection in order to reduce the likelihood of transmission of HIV from the mother to her offspring. A pregnant woman infected with HIV can pass the virus to her offspring transplacentally in utero, at the time of delivery through the birth canal or following delivery, through breast milk. The compositions disclosed herein can be administered to the HIV infected mother either prenatally, perinatally or postnatally during the breast-feeding period, or any combination of prenatal, perinatal, and postnatal administration. Compositions can be administered to the mother along with standard antiretroviral therapies as described below. In some embodiments, the compositions of the invention are also administered to the infant immediately following delivery and, in some embodiments, at intervals thereafter. The infant also can receive standard antiretroviral therapy.

The methods and compositions disclosed herein are useful for the treatment of retroviral infections. Exemplary retroviruses include human immunodeficiency viruses, e.g. HIV-1, HIV-2; simian immunodeficiency virus (SIV); feline immunodeficiency virus (Hy); bovine immunodeficiency virus (BIV); equine infectious anemia virus (EIAV); and caprine arthritis/encephalitis virus (CAEV). The methods disclosed herein can be applied to a wide range of species, e.g., humans, non-human primates (e.g., monkeys), horses or other livestock, dogs, cats, ferrets or other mammals kept as pets, rats, mice, or other laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of diseases or conditions as described herein.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

The compositions may also be administered with another therapeutic agent, for example, an anti-retroviral agent, used in HAART. Exemplary antiretroviral agents include reverse transcriptase inhibitors (e.g., nucleoside/nucleotide reverse transcriptase inhibitors, zidovudine, emtricitibine, lamivudine and tenofivir; and non-nucleoside reverse transcriptase inhibitors such as efavarenz, nevirapine, rilpivirine); protease inhibitors, e.g., tipiravir, darunavir, indinavir; entry inhibitors, e.g., maraviroc; fusion inhibitors, e.g., enfuviritide; or integrase inhibitors e.g., raltegrivir, dolutegravir. Exemplary antiretroviral agents can also include multi-class combination agents for example, combinations of emtricitabine, efavarenz, and tenofivir; combinations of emtricitabine; rilpivirine, and tenofivir; or combinations of elvitegravir, cobicistat, emtricitabine and tenofivir.

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks. The therapeutic agents may be administered under a metronomic regimen, e.g., continuous low-doses of a therapeutic agent.

Dosage, toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compositions lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As described, a therapeutically effective amount of a composition (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The compositions described herein are suitable for use in a variety of drug delivery systems described above. Additionally, in order to enhance the in vivo serum half-life of the administered compound, the compositions may be encapsulated, introduced into the lumen of liposomes, prepared as a colloid, or other conventional techniques may be employed which provide an extended serum half-life of the compositions. A variety of methods are available for preparing liposomes, as described in, e.g., Szoka, et U.S. Pat. Nos. 4,235,871, 4,501,728 and 4,837,028 each of which is incorporated herein by reference. Furthermore, one may administer the drug in a targeted drug delivery system, for example, in a liposome coated with a tissue-specific antibody. The liposomes will be targeted to and taken up selectively by the organ.

Also provided, are methods of inactivating a retrovirus, for example a lentivirus such as a human immunodeficiency virus, a simian immunodeficiency virus, a feline immunodeficiency virus, or a bovine immunodeficiency virus in a mammalian cell. The human immunodeficiency virus can be HIV-1 or HIV-2. The human immunodeficiency virus can be a chromosomally integrated provirus. The mammalian cell can be any cell type infected by HIV, including, but not limited to CD4+ lymphocytes, macrophages, fibroblasts, monocytes, T lymphocytes, B lymphocytes, natural killer cells, dendritic cells such as Langerhans cells and follicular dendritic cells, hematopoietic stem cells, endothelial cells, brain microglial cells, and gastrointestinal epithelial cells. Such cell types include those cell types that are typically infected during a primary infection, for example, a CD4+ lymphocyte, a macrophage, or a Langerhans cell, as well as those cell types that make up latent HIV reservoirs, i.e., a latently infected cell.

The methods can include exposing the cell to a composition comprising an isolated nucleic acid encoding a gene editing complex comprising a CRISPR-associated endonuclease and one or more guide RNAs wherein the guide RNA is complementary to a target nucleic acid sequence in the retrovirus. In a preferred embodiment, as previously described, the method of inactivating a proviral DNA integrated into the genome of a host cell latently infected with a retrovirus includes the steps of treating the host cell with a composition comprising a CRISPR-associated endonuclease, and two or more different guide RNAs (gRNAs), wherein each of the at least two gRNAs is complementary to a different target nucleic acid sequence in the proviral DNA; and inactivating the proviral DNA. The at least two gRNAs can be configured as a single sequence or as a combination of one or more different sequences, e.g., a multiplex configuration. Multiplex configurations can include combinations of two, three, four, five, six, seven, eight, nine, ten, or more different gRNAs, for example any combination of sequences in U3, R, or U5. In some embodiments, combinations of LTR A, LTR B, LTR C and LTR D can be used. In some embodiments, combinations of any of the sequences LTR A (SEQ ID NO: 96), LTR B (SEQ ID NO: 121), LTR C (SEQ ID NO: 87), and LTR D (SEQ ID NO: 110), can be used. In experiments described in the Examples, the use of two different gRNAs caused the excision of the viral sequences between the cleavage sites recognized by the CRISPR endonuclease. The excised region can include the entire HIV-1 genome. The treating step can take place in vivo, that is, the compositions can be administered directly to a subject having HIV infection. The methods are not so limited however, and the treating step can take place ex vivo. For example, a cell or plurality of cells, or a tissue explant, can be removed from a subject having an HIV infection and placed in culture, and then treated with a composition comprising a CRISPR-associated endonuclease and a guide RNA wherein the guide RNA is complementary to the nucleic acid sequence in the human immunodeficiency virus. As described above, the composition can be a nucleic acid encoding a CRISPR-associated endonuclease and a guide RNA wherein the guide RNA is complementary to the nucleic acid sequence in the human immunodeficiency virus; an expression vector comprising the nucleic acid sequence; or a pharmaceutical composition comprising a nucleic acid encoding a CRISPR-associated endonuclease and a guide RNA wherein the guide RNA is complementary to the nucleic acid sequence in the human immunodeficiency virus; or an expression vector comprising the nucleic acid sequence. In some embodiments, the gene editing complex can comprise a CRISPR-associated endonuclease polypeptide and a guide RNA wherein the guide RNA is complementary to the nucleic acid sequence in the human immunodeficiency virus.

Regardless of whether compositions are administered as nucleic acids or polypeptides, they are formulated in such a way as to promote uptake by the mammalian cell. Useful vector systems and formulations are described above. In some embodiments the vector can deliver the compositions to a specific cell type. The invention is not so limited however, and other methods of DNA delivery such as chemical transfection, using, for example calcium phosphate, DEAE dextran, liposomes, lipoplexes, surfactants, and perfluoro chemical liquids are also contemplated, as are physical delivery methods, such as electroporation, micro injection, ballistic particles, and "gene gun" systems.

Standard methods, for example, immunoassays to detect the CRISPR-associated endonuclease, or nucleic acid-based assays such as PCR to detect the gRNA, can be used to confirm that the complex has been taken up and expressed by the cell into which it has been introduced. The engineered cells can then be reintroduced into the subject from whom they were derived as described below.

The gene editing complex comprises a CRISPR-associated nuclease, e.g., Cas9, and a guide RNA complementary to the retroviral target sequence, for example, an HIV target sequence. The gene editing complex can introduce various mutations into the proviral DNA. The mechanism by which such mutations inactivate the virus can vary, for example the mutation can affect proviral replication, viral gene expression or proviral excision. The mutations may be located in regulatory sequences or structural gene sequences and result in defective production of HIV. The mutation can comprise a deletion. The size of the deletion can vary from a single nucleotide base pair to about 10,000 base pairs. In some embodiments, the deletion can include all or substantially all of the proviral sequence. In some embodiments the deletion can include the entire proviral sequence. The mutation can comprise an insertion; that is the addition of one or more nucleotide base pairs to the pro-viral sequence. The size of the inserted sequence also may vary, for example from about one base pair to about 300 nucleotide base pairs. The mutation can comprise a point mutation, that is, the replacement of a single nucleotide with another nucleotide. Useful point mutations are those that have functional consequences, for example, mutations that result in the conversion of an amino acid codon into a termination codon or that result in the production of a nonfunctional protein.

In exemplary multiplex methods for inactivating proviral DNA integrated into the genome of a host cell, as demonstrated in Examples 2-5, two different gRNA sequences are deployed, with each gRNA sequence targeting a different site in the proviral DNA. That is, the methods include the steps of exposing the host cell to a composition including an isolated nucleic acid encoding a CRISPR-associated endonuclease; an isolated nucleic acid sequence encoding a first gRNA having a first spacer sequence that is complementary to a first target protospacer sequence in a proviral DNA; and an isolated nucleic acid encoding a second gRNA having a second spacer sequence that is complementary to a second target protospacer sequence in the proviral DNA; expressing in the host cell the CRISPR-associated endonuclease, the first gRNA, and the second gRNA; assembling, in the host cell, a first gene editing complex including the CRISPR-associated endonuclease and the first gRNA; and a second gene editing complex including the CRISPR-associated endonuclease and the second gRNA; directing the first gene editing complex to the first target protospacer sequence by complementary base pairing between the first spacer sequence and the first target protospacer sequence; directing the second gene editing complex to the second target protospacer sequence by complementary base pairing between the second spacer sequence and the second target protospacer sequence; cleaving the proviral DNA at the first target protospacer sequence with the CRISPR-associated endonuclease; cleaving the proviral DNA at the second target protospacer sequence with the CRISPR-associated endonuclease; and inducing at least one mutation in the proviral DNA. The same multiplex method is readily incorporated into methods for treating a subject having a human immunodeficiency virus, and for reducing the risk of a human immunodeficiency virus infection. It will be understood that the term "composition" can include not only a mixture of components, but also separate components that are not necessarily administered simultaneously. As a non-limiting example, a composition according to the present invention can include separate component preparations of nucleic acid sequences encoding a Cas9 nuclease, a first gRNA, and a second gRNA, with each component being administered sequentially in an infusion, during a time frame that results in a host cell being exposed to all three components.

In other embodiments, the compositions comprise a cell which has been transformed or transfected with one or more Cas/gRNA vectors. In some embodiments, the methods of the invention can be applied ex vivo. That is, a subject's cells can be removed from the body and treated with the compositions in culture to excise HIV sequences and the treated cells returned to the subject's body. The cell can be the subject's cells or they can be haplotype matched or a cell line. The cells can be irradiated to prevent replication. In some embodiments, the cells are human leukocyte antigen (HLA)-matched, autologous, cell lines, or combinations thereof. In other embodiments the cells can be a stem cell. For example, an embryonic stem cell or an artificial pluripotent stem cell (induced pluripotent stem cell (iPS cell)). Embryonic stem cells (ES cells) and artificial pluripotent stem cells (induced pluripotent stem cell, iPS cells) have been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

The gRNA expression cassette can be easily delivered to a subject by methods known in the art, for example, methods which deliver siRNA. In some aspects, the Cas may be a fragment wherein the active domains of the Cas molecule are included, thereby cutting down on the size of the molecule. Thus, the, Cas9/gRNA molecules can be used clinically, similar to the approaches taken by current gene therapy. In particular, a Cas9/multiplex gRNA stable expression stem cell or iPS cells for cell transplantation therapy as well as HIV-1 vaccination will be developed for use in subjects.

Transduced cells are prepared for reinfusion according to established methods. After a period of about 2-4 weeks in culture, the cells may number between $1\times10^6$ and $1\times10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces that may include, but are not restricted to, bone marrow or adipose tissues.

Articles of Manufacture

The compositions described herein can be packaged in suitable containers labeled, for example, for use as a therapy to treat a subject having a retroviral infection, for example, an HIV infection or a subject at for contracting a retroviral infection, for example, an HIV infection. The containers can include a composition comprising a nucleic acid sequence encoding a CRISPR-associated endonuclease, for example, a Cas9 endonuclease, and a guide RNA complementary to a target sequence in a human immunodeficiency virus, or a vector encoding that nucleic acid, and one or more of a suitable stabilizer, carrier molecule, flavoring, and/or the like, as appropriate for the intended use. Accordingly, packaged products (e.g., sterile containers containing one or more of the compositions described herein and packaged for storage, shipment, or sale at concentrated or ready-to-use concentrations) and kits, including at least one composition of the invention, e.g., a nucleic acid sequence encoding a CRISPR-associated endonuclease, for example, a Cas9 endonuclease, and a guide RNA complementary to a target sequence in a human immunodeficiency virus, or a vector encoding that nucleic acid and instructions for use, are also within the scope of the invention. A product can include a container (e.g., a vial, jar, bottle, bag, or the like) containing one or more compositions of the invention. In addition, an article of manufacture further may include, for example, packaging materials, instructions for use, syringes, delivery devices, buffers or other control reagents for treating or monitoring the condition for which prophylaxis or treatment is required.

In some embodiments, the kits can include one or more additional antiretroviral agents, for example, a reverse transcriptase inhibitor, a protease inhibitor or an entry inhibitor. The additional agents can be packaged together in the same container as a nucleic acid sequence encoding a CRISPR-associated endonuclease, for example, a Cas9 endonuclease, and a guide RNA complementary to a target sequence in a human immunodeficiency virus, or a vector encoding that nucleic acid or they can be packaged separately. The nucleic acid sequence encoding a CRISPR-associated endonuclease, for example, a Cas9 endonuclease, and a guide RNA complementary to a target sequence in a human immunodeficiency virus, or a vector encoding that nucleic acid and the additional agent may be combined just before use or administered separately.

The product may also include a legend (e.g., a printed label or insert or other medium describing the product's use (e.g., an audio- or videotape)). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents and/or an additional therapeutic agent. Alternatively, the compositions can be provided in a concentrated form with a diluent and instructions for dilution.

Example 1: Materials and Methods

Plasmid Preparation:

Vectors containing human Cas9 and gRNA expression cassette, pX260, and pX330 (Addgene) were utilized to create various constructs, LTR-A, B, C, and D.

Cell Culture and Stable Cell Lines:

TZM-b1 reporter and U1 cell lines were obtained from the NIH AIDS Reagent Program and CHMES microglial cells are known in the art.

Immunohistochemistry and Western Blot:

Standard methods for immunocytochemical observation of the cells and evaluation of protein expression by Western blot were utilized.

Firefly-Luciferase Assay:

Cells were lysed 24 h post-treatment using Passive Lysis Buffer (Promega) and assayed with a Luciferase Reporter Gene Assay kit (Promega) according to the manufacturer's protocol. Luciferase activity was normalized to the number of cells determined by a parallel MTT assay (VYBRANT, Invitrogen)

p24 ELISA:

After infection or reactivation, the levels of HIV-1 viral load in the supernatants were quantified by p24 Gag ELISA (Advanced BioScience Laboratories, Inc) following the manufacturer's protocol. To assess cell viability upon treatments, MTT assay was performed in parallel according to the manufacturer's manual (VYBRANT, Invitrogen).

EGFP Flow Cytometry:

Cells were trypsinized, washed with PBS and fixed in 2% paraformaldehyde for 10 min at room temperature, then washed twice with PBS and analyzed using a GUAVA EASYCYTE Mini flow cytometer (Guava Technologies).

HIV-1 Reporter Virus Preparation and Infections:

HEK293T cells were transfected using LIPOFECTAMINE 2000 reagent (Invitrogen) with pNL4-3-AE-EGFP (NIH AIDS Research and Reference Reagent Program). After 48 h, the supernatant was collected, 0.45 μm filtered and tittered in HeLa cells using EGFP as an infection marker. For viral infection, stable Cas9/gRNA TZM-bl cells were incubated 2 h with diluted viral stock, and then washed twice with PBS. At 2 and 4 d post-infection, cells were collected, fixed and analyzed by flow cytometry for EGFP expression, or genomic DNA purification was performed for PCR and whole genome sequencing.

Genomic DNA Amplification, PCR, TA-Cloning, and Sanger Sequencing, GENOMEWALKER Link PCR:

Standard methods for DNA manipulation for cloning and sequencing were utilized. For identification of the integration sites of HIV-1, we utilized Lenti-X™ integration site analysis kit was used.

Surveyor Assay:

The presence of mutations in PCR products was examined using a SURVEYOR Mutation Detection Kit (Transgenomic) according to the protocol from the manufacturer. Briefly heterogeneous PCR product was denatured for 10 min in 95° C. and hybridized by gradual cooling using a thermocycler. Next, 300 ng of hybridized DNA (9 μl) was subjected to digestion with 0.25 μl of SURVEYOR Nuclease in the presence of 0.25 μl SURVEYOR Enhancer S and 15 mM $MgCl_2$ for 4 h at 42° C. Then Stop Solution was added and samples were resolved in 2% agarose gel together with equal amounts of undigested PCR product controls.

Some PCR products were used for restriction fragment length polymorphism analysis. Equal amounts of the PCR products were digested with BsaJl. Digested DNA was separated on an ethidium bromide-contained agarose gel (2%). For sequencing, PCR products were cloned using a TA Cloning® Kit Dual Promoter with pCRTMIl vector (Invitrogen). The insert was confirmed by digestion with EcoRl and positive clones were sent to Genewiz for Sanger sequencing.

Selection of LTR Target Sites, Whole Genome Sequencing and Bioinformatics and Statistical Analysis.

We utilized Jack Lin's CRISPR/Cas9 gRNA finder tool for initial identification of potential target sites within the LTR.

Plasmid Preparation.

DNA segment expressing LTR-A or LTR-B for pre-crRNA was cloned into the pX260 vector that contains the puromycin selection gene (Addgene, plasmid #42229). DNA segments expressing LTR-C or LTR-D for the chimeric crRNA-tracrRNA were cloned into the pX330 vector (Addgene, plasmid #42230). Both vectors contain a humanized Cas9 coding sequence driven by a CAG promoter and a gRNA expression cassette driven by a human U6 promoter. The vectors were digested with Bbsl and treated with Antarctic Phosphatase, and the linearized vector was purified with a Quick nucleotide removal kit (Qiagen). A pair of oligonucleotides for each targeting site (FIG. 14, AlphaDNA) was annealed, phosphorylated, and ligated to the linearized vector. The gRNA expression cassette was sequenced with U6 sequencing primer (FIG. 14) in GENEWIZ. For pX330 vectors, we designed a pair of universal PCR primers with overhang digestion sites (FIG. 14) that can tease out the gRNA expression cassette (U6-gRNA-crRNA-stem-tracrRNA) for direct transfection or subcloning to other vectors.

Cell Culture.

TZM-bl reporter cell line from Dr John C. Kappes, Dr Xiaoyun Wu and Tranzyme Inc, U1/Hiv-1 cell line from Dr. Thomas Folks and J-Lat full length clone from Dr. Eric Verdin were obtained through the NIH AIDS Reagent Program, Division of AIDS, NIAID, NIH. CHME5/HIV fetal microglia cell line were generated as previously described. TZM-bl and CHMES cells were cultured in Dulbecco's minimal essential medium high glucose supplemented with 10% heat-inactivated fetal bovine serum (FBS) and 1% penicillin/streptomycin. U1 and J-Lat cells were cultured in RPMI 1640 containing 2.0 mM L-glutamine, 10% FBS and 1% penicillin/streptomycin.

Stable Cell Lines and Subcloning.

TZM-bl or CHME5/HIV cells were seeded in 6-well plates at $1.5\times10^5$ cells/well and transfected using LIPOFECTAMINE 2000 reagent (Invitrogen) with 1 μg of pX260 (for LTR-A and B) or 1 μg/0.1 μg of pX330/pX260 (for LTR-C and D) plasmids. Next day, cells were transferred into 100-mm dishes and incubated with growth medium containing 1 μg/ml of puromycin (Sigma). Two weeks later, surviving cell colonies were isolated using cloning cylinders (Corning). U1 cells ($1.5\times10^5$) were electroporated with 1 μg of DNA using 10 μl tip, 3×10 ms 1400 V impulses at The Neon™ Transfection System (Invitrogen). Cells were selected with 0.5 μg/ml of puromycin for two weeks. The stable clones were subcultured using a limited dilution method in 96-well plates and single cell-derived subclones were maintained for further studies.

Immunocytochemistry and Western Blot.

The Cas9/gRNA stable expression TZM-bl cells were cultured in 8-well chamber slides for 2 days and fixed for 10 min in 4% paraformaldehyde/PBS. After three rinses, the cells were treated with 0.5% Triton X-100/PBS for 20 min and blocked in 10% donkey serum for 1 h. Cells were incubated overnight at 4° C. with mouse anti-Flag M2 primary antibody (1:500, Sigma). After rinsing three times, cells were incubated for 1 h with donkey anti-mouse AlexaFluor-594 secondary antibodies, and incubated with Hoechst 33258 for 5 min. After three rinses with PBS, the cells were coverslipped with anti-fading aqueous mounting media (Biomeda) and analyzed under a Leica DMI6000B fluorescence microscope.

TZM-bl cells cultured in 6-well plate were solubilized in 200 μl of Triton X-100-based lysis buffer containing 20 mM Tris-HCl (pH 7.4), 1% Triton X-100, 5 mM ethylenediaminetetraacetic acid, 5 mM dithiothreitol, 150 mM NaCl, 1 mM phenylmethylsulfonyl fluoride, lx nuclear extraction proteinase inhibitor cocktail (Cayman Chemical, Ann Arbor, Mich.), 1 mM sodium orthovanadate and 30 mM NaF. Cell lysates were rotated at 4° C. for 30 min. Nuclear and cellular debris was cleared by centrifugation at 20,000 g for 20 min at 4° C. Equal amounts of lysate proteins (20 μg) were denatured by boiling for 5 min in sodium dodecyl sulphate (SDS) sample buffer, fractionated by SDS-polyacrylamide gel electrophoresis in tris-glycine buffer, and transferred to nitrocellulose membrane (BioRad). The SEEBLUE prestained standards (Invitrogen) were used as a molecular weight reference. Blots were blocked in 5% BSA/tris-buffered saline (pH 7.6) plus 0.1% Tween-20 (TBS-T) for 1 h and then incubated overnight at 4° C. with mouse anti-Flag M2 monoclonal antibody (1:1000, Sigma) or mouse anti-GAPDH monoclonal antibody (1:3000, Santa Cruz Biotechnology). After washing with TBS-T, the blots were incubated with IRDye 680LT-conjugated anti-mouse antibody for 1 h at room temperature. Membranes were scanned and analyzed using an Odyssey Infrared Imaging System (LI-COR Biosciences).

Firefly-Luciferase Assay.

Cells were lysed 24 h post-treatment using Passive Lysis Buffer (Promega) and assayed with a Luciferase Reporter Gene Assay kit (Promega) according to the protocol of the manufacturer. Luciferase activity was normalized to the number of cells determined by parallel MTT assay (VYBRANT, lnvitrogen).

p24 ELISA.

After infection or reactivation, the HIV-1 viral load levels in the supernatants were quantified by p24 Gag ELISA (Advanced BioScience Laboratories, Inc) following the manufacturer's protocol. To assess the cell viability upon treatments, MTT assay was performed in parallel according to the manufacturer's protocol (VYBRANT, lnvitrogen).

EGFP Flow Cytometry.

Cells were trypsinized, washed with PBS and fixed in 2% paraformaldehyde for 10 min at room temperature, then washed twice with PBS and analyzed using a GUAVA EASYCYTE Mini flow cytometer (Guava Technologies).

Hiv-1 Reporter Virus Preparation and Infections.

HEK293T cells were transfected using LIPOFECTAMINE 2000 reagent (Invitrogen) with pNL4-3-ΔE-EGFP, SF162 and JRFL (NIH AIDS Research and Reference Reagent Program). For pseudotyped pNL4-3-ΔE-EGFP, the VSVG vector was cotransfected. After 48 h, the supernatant was collected, 0.45 μm filtered and tittered in HeLa cells using expressed EGFP as an infection marker. For viral infection, stable Cas9/gRNA TZM-bl cells were incubated 2 h with a diluted viral stock, and washed twice with PBS. At 2 and 4 days post-infection, cells were collected, fixed and analyzed by flow cytometry for EGFP expression, or genomic DNA purification was performed for PCR and whole genome sequencing.

Genomic DNA Purification, PCR, TA-Cloning and Sanger Sequencing.

Genomic DNA was isolated from cells using an Archive-Pure DNA cell/tissue purification kit (SPRIME) according to the protocol recommended by the manufacturer. One hundred ng of extracted DNA were subjected to PCR using a high-fidelity FAILSAFE PCR kit (Epicentre) using primers listed in FIG. 14. Three steps of standard PCR were carried out for 30 cycles with 55° C. annealing and 72° C. extension. The products were resolved in 2% agarose gel. The bands of interest were gel-purified and cloned into pCRll T-A vector (Invitrogen), and the nucleotide sequence of individual clones was determined by sequencing at Genewiz using universal T7 and/or SP6 primers.

Conventional and Real-Time Reverse Transcription (RT)-PCR.

For total RNA extraction, cells were processed with an RNeasy Mini kit (Qiagen) as per manufacturer's instructions. The potentially residual genomic DNA was removed through on-column DNase digestion with an RNase-Free DNase Set (Qiagen). One μg of RNA for each sample was reversely transcribed into cDNAs using random hexanucleotide primers with a High Capacity cDNA Reverse Transcription Kit (Invitrogen, Grand Island, N.Y.). Conventional PCR was performed using a standard protocol. Quantitative PCR (qPCR) analyses were carried out in a LightCycler480 (Roche) using an SYBR® Green PCR Master Mix Kit (Applied Biosystems). The RT reactions were diluted to 5 ng of total RNA per micro-liter of reactions and 2 μl was used in a 20-μl PCR reaction. For qPCR analysis of HIV-1 proviruses, 50 ng of genomic DNA were used. The primers were synthesized in AlphaDNA and shown in FIG. 14. The primers for human housekeeping genes GAPDH and RPL13A were obtained from RealTimePrimers (Elkins Park, Pa.). Each sample was tested in triplicate. Cycle threshold (Ct) values were obtained graphically for the target genes and housekeeping genes. The difference in Ct values between the housekeeping gene and target gene was represented as ΔCt values. The AACt values were obtained by subtracting the ΔCt values of control samples from those of experimental samples. Relative fold or percentage change was calculated as 2−ΔΔCt. In some cases, absolute quantification was performed using the pNL4-3-AE-EGFP plasmid spiked in human genomic DNA as a standard. The number of HIV-1 viral copies was calculated based on standard curve after normalization with housekeeping gene.

GENOMEWALKER Link PCR and Long-Range PCR.

The integration sites of HIV-1 in host cells were identified using a LENTI-X™ Integration Site Analysis kit (Clontech) following the manufacturer's instruction. Briefly, high quality genomic DNAs were extracted from U1 cells using a NUCLEOSPIN Tissue kit (Clontech). To construct the viral integration libraries, each genomic DNA sample was digested with blunt-end-generating digestion enzymes Dra 1, Ssp 1 or Hpal separately overnight at 37° C. The digestion efficiency was verified by electrophoresis on 0.6% agarose. The digested DNA was purified using a NUCLEOSPIN Gel and PCR Clean-Up kit followed by ligation of the digested genomic DNA fragments to GENOMEWALKER™ Adaptor at 16° C. overnight. The ligation reaction was stopped by incubation at 70° C. for 5 min and diluted 5 times with TE buffer. The primary PCR was performed on the DNA segments with adaptor primer 1 (AP1) and LTR-specific primer 1 (LSP1) using Advantage 2 Polymerase Mix followed by a secondary (nested) PCR using AP2 and LSP2 primers (FIG. 14). The secondary PCR products were separated on 1.5% ethidium bromide-containing agarose gel. The major bands were gel-purified and cloned into pCRII T-A vector (Invitrogen), and the nucleotide sequence of individual clones was determined by sequencing at Genewiz using universal T7 and SP6 primers. The sequence reads were analyzed by NCBI BLAST searching. Two integration sites of HIV-1 in U1 cells were identified in chromosomes X and 2. A pair of primers covering each integration site (FIG. 14) was synthesized in AlphaDNA. Long-range PCR using the U1 genomic DNA was performed with a PHUSION High-Fidelity PCR kit (New England Biolabs) following the manufacturer's protocol. The PCR products were visualized on 1% agarose gel and validated by Sanger sequencing.

Surveyor Assay.

The presence of mutations in PCR products was tested using a SURVEYOR Mutation Detection Kit (Transgenomic) according to the protocol of the manufacturer. Briefly heterogeneous PCR products were denatured for 10 min in 95° C. and hybridized by gradual cooling using a thermocycler. Next 300 ng of hybridized DNA (9 ul) was subjected to digestion with 0.25 μl of SURVEYOR Nuclease in the presence of 0.25 μl SURVEYOR Enhancer S and 15 mM $MgCl_2$ for 4h at 42° C. Then Stop Solution was added and samples were resolved in 2% agarose gel together with equal amounts of undigested PCR products.

Some PCR products were used for restriction fragment length polymorphism analysis. Equal amount of PCR products were digested with BsaJl. Digested DNA was separated on an ethidium bromide-contained agarose gel (2%). For sequencing, PCR products were cloned using a TA Cloning® Kit Dual Promoter with pCR™ll vector (Invitrogen). The insert was confirmed by digestion with EcoRl and positive clones were sent to Genwiz for Sanger sequencing.

Selection of LTR Target Sites and Prediction of Potential Off-Target Sites.

For initial studies, we obtained the LTR promoter sequence (−411 to −10) of the integrated lentiviral LTR-luciferase reporter by TA-cloning sequencing of PCR products from the genome of human TZM-bl cells because of potential mutation of LTR during passaging. This promoter sequence has 100% match to the 5'-LTR of pHR'-CMV-LacZ lentiviral vector (AF105229). Thus, sense and anti-sense sequences of the full-length pHR' 5'-LTR (634 bp) were utilized to search for Cas9/gRNA target sites containing 20 bp gRNA targeting sequence plus the PAM sequence (NRG) using Jack Lin's CRISPR/Cas9 gRNA finder tool. The number of potential off-targets with exact match was predicted by blasting each gRNA targeting sequence plus NRG (AGG, TGG, GGG and CGG; AAG, TAG, GAG, CAG) against all available human genomic and transcript sequences using the NCBI/blastn suite with E-value cutoff 1,000 and word size 7. After pressing Control+F, copy/paste the target sequence (1-23 through 9-23 nucleotides) and find the number of genomic targets with 100% match to the target sequence. The number of off-targets for each search was divided by 3 because of repeated genome library.

Whole Genome Sequencing and Bioinformatics Analysis.

The control subclone Cl and experimental subclone AB7 of TZM-bl cells were validated for target cut efficiency and functional suppression of the LTR-luciferase reporter. The genomic DNA was isolated with NUCLEOSPIN Tissue kit (Clontech). The DNA samples were submitted to the Next-Gen sequencing facility at Temple University Fox Chase Cancer Center. Duplicated genomic DNA libraries were prepared from each subclone using a NEBNext Ultra DNA Library Prep Kit for Illumina (New England Biolab) following the manufacturer's instruction. All libraries were sequenced with paired-end 141-bp reads in two Illumina Rapid Run flowcells on HiSeq 2500 instrument (Illumina). Demultiplexed read data from the sequenced libraries were sent to AccuraScience, LLC for professional bioinformatics analysis. Briefly, the raw reads were mapped against human genome (hg19) and HIV-1 genome by using Bowtie2. A genomic analysis toolkit (GATK, version 2.8.1) was used for the duplicated read removal, local alignment, base quality recalibration and indel calling. The confidence scores 10 and 30 were the thresholds for low quality (LowQual) and high confidence calling (PASS). The potential off-target sites of LTR-A and LTR-B with various mismatches were predicted by NCBI/blastn suite as described above and by a CRISPR Design Tool. All the potential gRNA target sites (FIG. 15) were used to map the ±300 bp regions around each indel identified by GATK. The locations of the overlapped regions in the human genome and HIV-1 genome were compared between the control Cl and experimental AB7.

Statistical Analysis.

The quantitative data represented mean±standard deviation from 3-5 independent experiments, and were evaluated by Student's t-test or ANOVA and Newman-Keuls multiple comparison test. A p value that is <0.05 or 0.01 was considered as a statistically significant difference.

Example 2: Cas9/LTR-gRNA Suppresses HIV-1 Reporter Virus Production in CHMES Microglial Cells Latently Infected with HIV-1

Figure 6A:
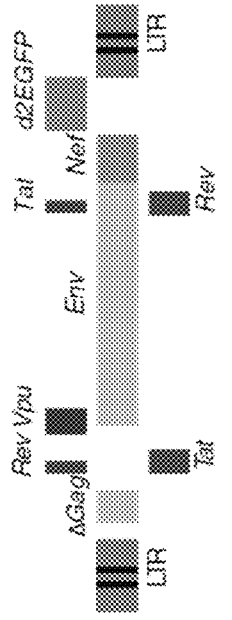
FIGS. 6A-6C show that LTR-C and LTR-D remarkably suppress TSA-induced reactivation of latent pNL4-3-ΔGag-d2EGFP virus in CHMES microglia cells. (6A) Diagram schematically showing pNL4-3-ΔGag-d2EGFP vector containing Tat, Rev, Env, Vpu, and Nef with the reporter gene d2EGFP. (6B) The SURVEYOR assay showing indel mutations in the on-target LTR genome of Cas9/LTR-D but not Cas9/LTR-C transfected cells. (6C) Representative gating diagram of EGFP flow cytometry showing a dramatic reduction in TSA-induced reactivation of latent pNL4-3-ΔGag-d2EGFP reporter viruses by stable expression of Cas9/LTR-C or LTR-D as compared with empty U6-driven gRNA expression vector (U6-CAG).
Figure 6B:
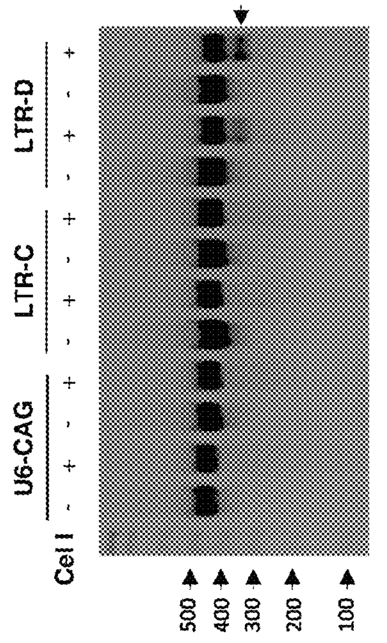
Figure 6C:
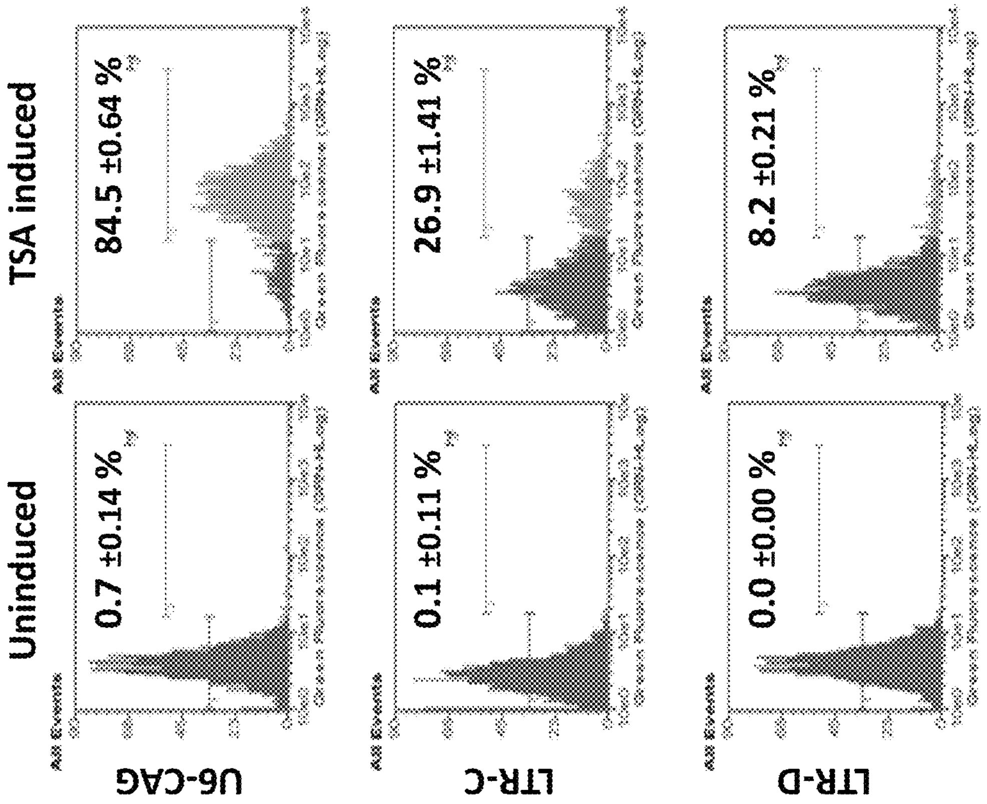
Figure 7A:
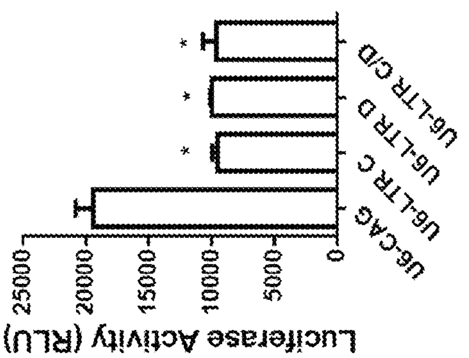
FIGS. 7A-7F show that both LTR-C and LTR-D induced indel mutations and significantly decreased constitutive and TSA/PMA-induced luciferase activity in TZM-bl cells stably incorporated with HIV-1 LTR-firefly luciferase reporter gene. (7A) Functional luciferase reporter assay revealing a significant reduction of LTR reactivation by LTR-C, LTR-D or both. (7B) SURVEYOR assay showing indel mutation in LTR DNA (−453 to +43) induced by LTR-C and LTR-D (upper arrow). A combination of LTR-C and LTR-D generates a 194 bp fragment (lower arrow) resulting from the deletion of 302 bp region between LTR-C and LTR-D. (7C, 7D) Sanger sequencing of 30 clones validating the indel efficiency at 23% for LTR-C and 13% for LTR-D and example chromatograms showing insertion/deletion.
Figure 7B:
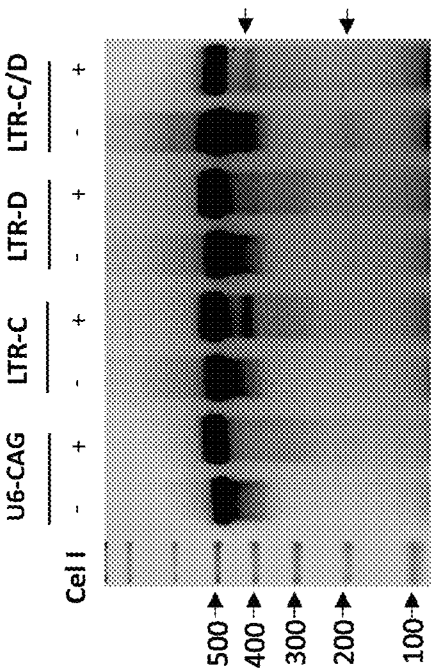
Figure 7C:
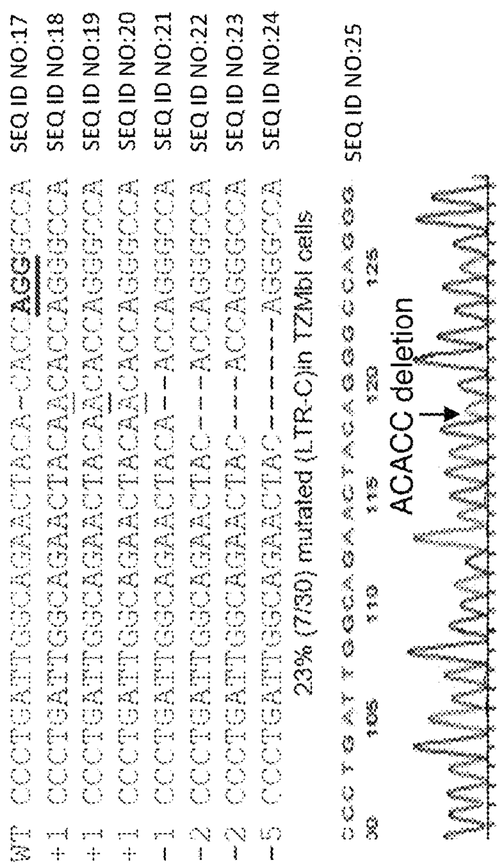
Figure 7D:
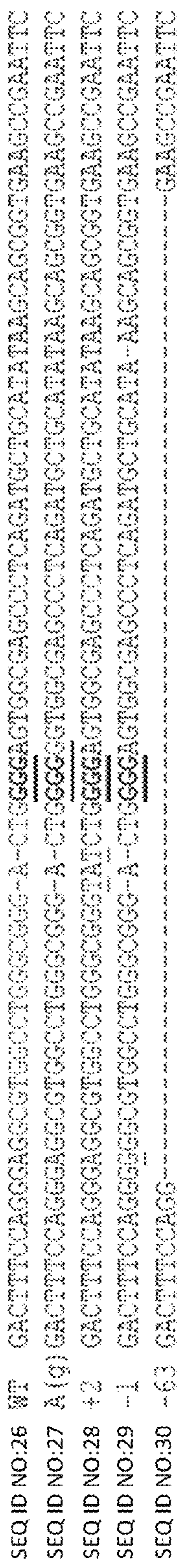
Figure 7E:
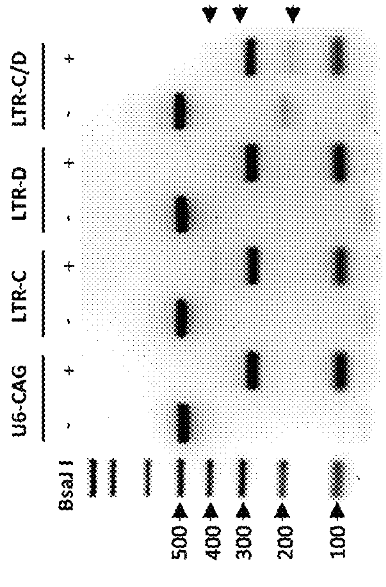
Figure 7F:
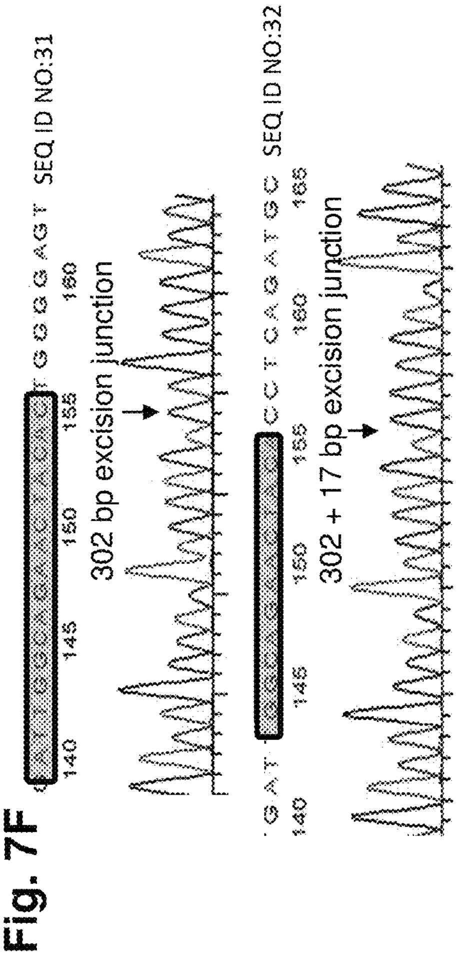

We assessed the ability of HIV-1-directed guide RNAs (gRNAs) to abrogate LTR transcriptional activity and eradicate proviral DNA from the genomes of latently-infected myeloid cells that serve as HIV-1 reservoirs in the brain, a particularly intractable target population. Our strategy was focused on targeting the HIV-1 LTR promoter U3 region. By bioinformatic screening and efficiency/off-target prediction, we identified four gRNA targets (protospacers; LTRs A-D) that avoid conserved transcription factor binding sites, minimizing the likelihood of altering host gene expression (FIGS. 5 and 13). We inserted DNA fragments complementary to gRNAs A-D into a humanized Cas9 expression vector (A/B in pX260; C/D in pX330) and tested their individual and combined abilities to alter the integrated HIV-1 genome activity. We first utilized the microglial cell line CHMES, which harbors integrated copies of a single round HIV-1 vector that includes the 5' and 3' LTRs, and a gene encoding an enhanced green fluorescent protein (EGFP) reporter replacing Gag (pNL4-3-ΔGag-d2EGFP). Treating CHMES cells with trichostatin A (TSA), a histone deacetylase inhibitor, reactivates transcription from the majority of the integrated proviruses and leads to expression of EGFP and the remaining HIV-1 proteome. Expressing of gRNAs plus Cas9 markedly decreased the fraction of TSA-induced EGFP-positive CHMES cells (FIGS. 1A and 6). We detected insertion/deletion gene mutations (indels) for LTRs A-D (FIGS. 1B and 6B) using a Cel 1 nuclease-based heteroduplex-specific SURVEYOR assay. Similarly, expressing gRNAs targeting LTRs C and D in HeLa-derived TZM-bl cells, that contain stably incorporated HIV-1 LTR copies driving a firefly-luciferase reporter gene, suppressed viral promoter activity (FIG. 7A), and elicited indels within the LTR U3 region (FIG. 7B-D) demonstrated by SURVEYOR and Sanger sequencing. Moreover, the combined expression of LTR C/D-targeting gRNAs in these cells caused excision of the predicted 302-bp viral DNA sequence, and emergence of the residual 194-bp fragment (FIG. 7E-F).

Figure 1E:
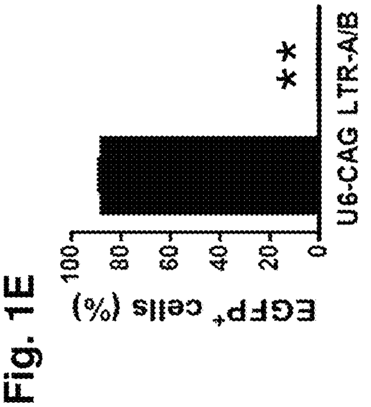
Figure 1F:
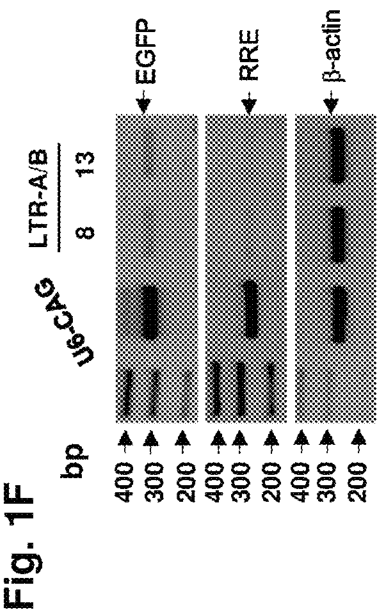
Figure 1G:
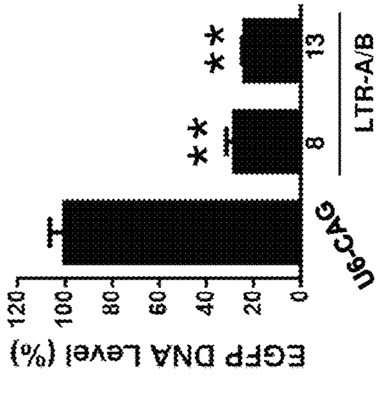
Figure 1H:
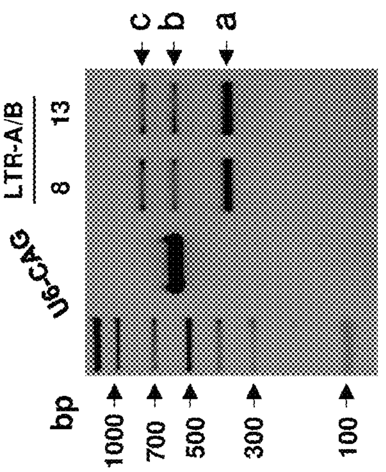
Figures 8A, 8B, 8C:
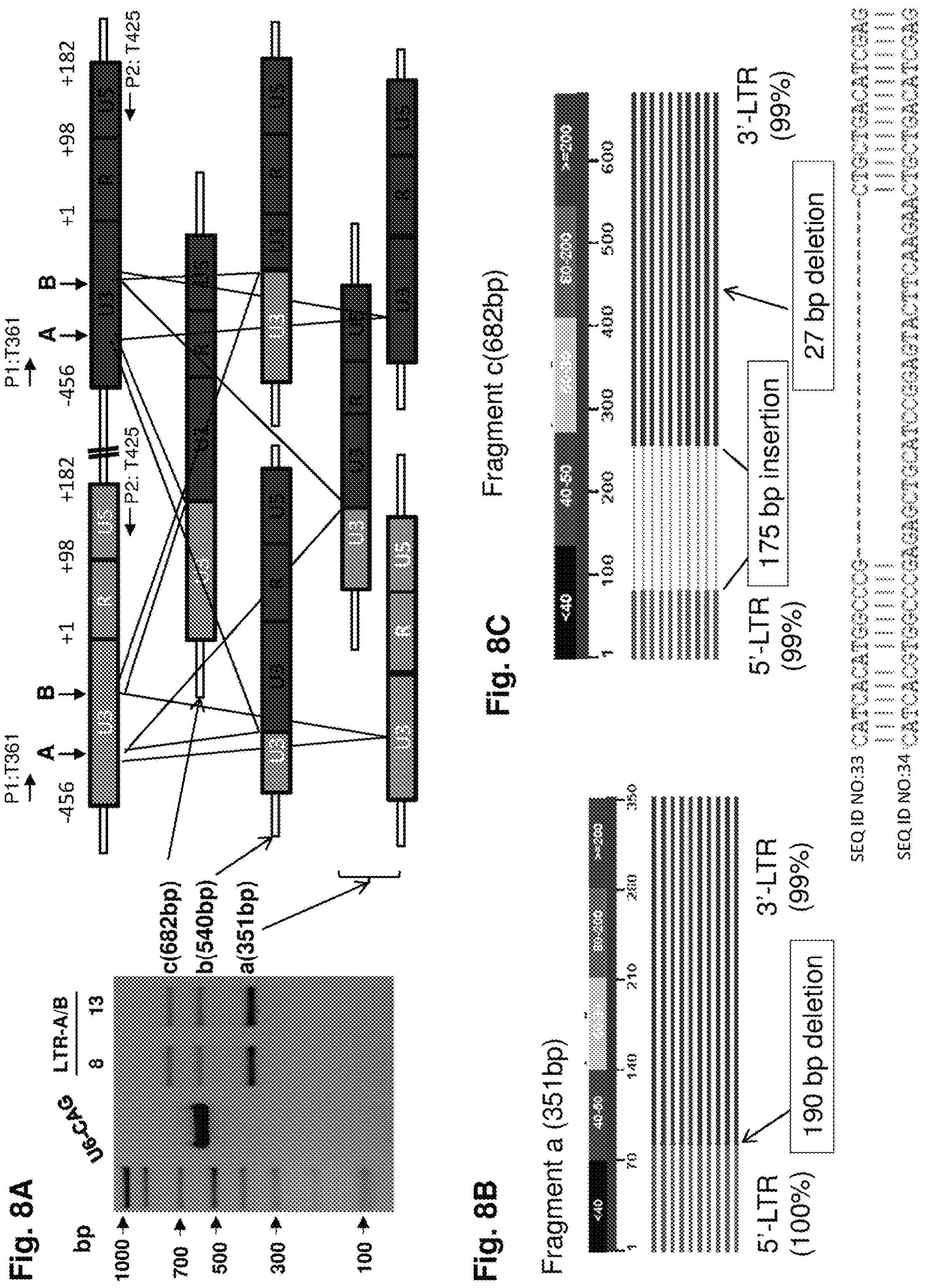
FIGS. 8A-8C illustrate the TA cloning and Sanger sequencing of PCR products from CHMES subclones of LTR-AB and empty U6-CAG control using primers covering HIV-1 LTR U3/R/U5 regions (−411 to +129). (8A) Possible combination of LTR-A and LTR-B cuts on both 5'- and 3'-LTRs generating potential fragments a-c as indicated. (8B) Blasting of fragment a (351 bp) showing 190 bp deletion between LTR-A and LTR-B cut sites. (8C) Blast of fragment c (682 bp) showing a 175 bp insertion at the LTR-A cleavage site and a 27 bp deletion at the LTR-B cleavage site.

Multiplex expression of LTR-A/B gRNAs in mixed clonal CHMES cells caused deletion of a 190-bp fragment between A and B target sites and led to indels to various extents (FIG. 1C-D). Among >20 puromycin-selected stable subclones, we found cell populations with complete blockade of TSA-induced HIV-1 proviral reactivation determined by flow cytometry for EGFP (FIG. 1E). PCR-based analysis for EGFP and HIV-1 Rev response element (RRE) in the proviral genome validated the eradication of HIV-1 genome (FIG. 1F, G). Furthermore, sequencing of the PCR products revealed the entire 5'-3' LTR-spanning viral genome was deleted, yielding a 351-bp fragment via a 190-bp excision between cleavage sites A and B (FIGS. 1G and 8), and a 682-bp fragment with a 175-bp insertion and a 27-bp deletion at the LTR-A and -B sites respectively (FIG. 8C). The residual HIV-1 genome (FIG. 1F-H) may reflect the presence of trace Cas9/gRNA-negative cells. These results indicate that LTR-targeting Cas9/gRNAs A/B eradicates the HIV-1 genome and blocks its reactivation in latently infected microglial cells.

Figure 2A:
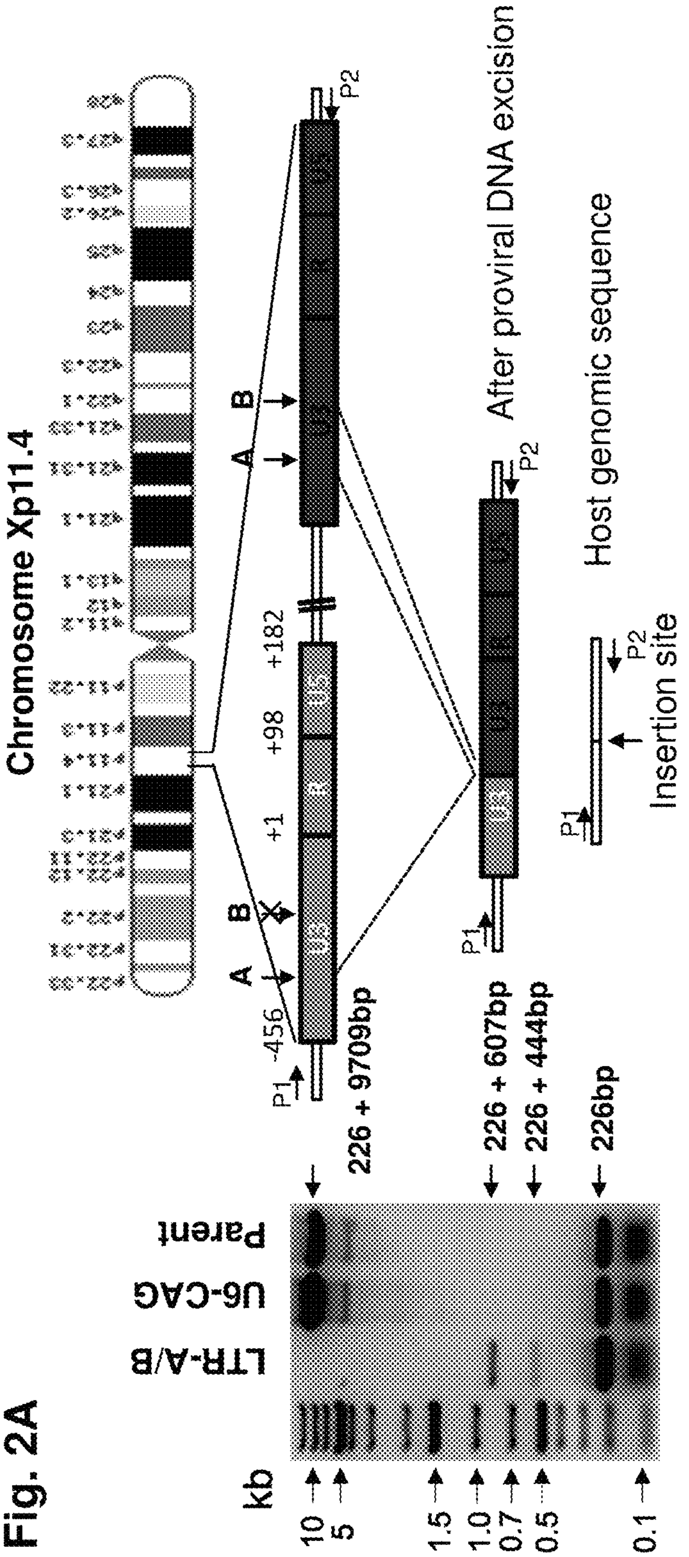
FIGS. 2A-2C show that Cas9/LTR-gRNA efficiently eradicates latent HIV-1 virus from U1 monocytic cells. (2A) Right, diagram showing excision of HIV-1 entire genome in chromosome Xp11.4. HIV-1 integration sites were identified using a Genome-Walker link PCR kit. Left, analysis of PCR amplicon lengths using a primer pair (P1/P2) targeting chromosome X integration site-flanking sequence reveals elimination of the entire HIV-1 genome (9709-bp), leaving two fragments (833- and 670-bp). (2B) TA cloning and sequencing of the LTR fragment (833-bp) showing the host genomic sequence (small letters, 226-bp) and the partial sequences (634−27=607 bp) of 5'-LTR (underlined using dashes) and 3'-LTR (first underlined section) with a 27-bp deletion around the LTR-A targeting site (second underlined section). Bottom, two indel alleles identified from 15 sequenced clonal amplicons. The 670-bp fragment consists of a host sequence (226-bp) and the remaining LTR sequence (634−190=444 bp) after 190-bp excision by simultaneous cutting at LTR-A and B target sites. The underlined and highlighted sequences indicate the gRNA LTR-A target site and PAM.
Figure 2B:
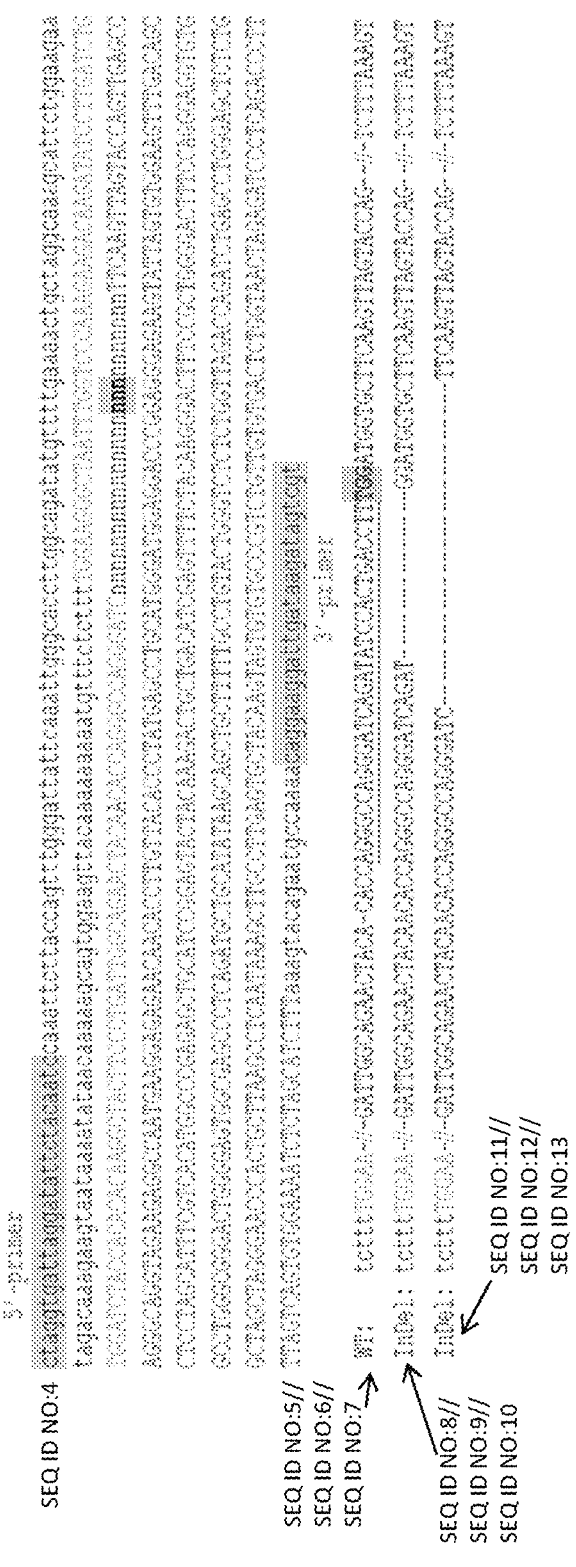
Figure 2C:
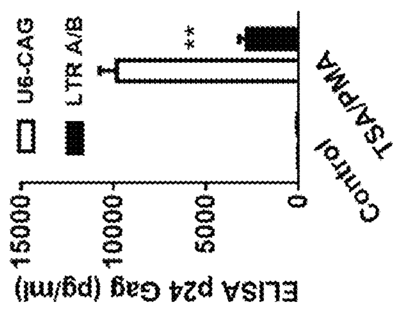
Figures 9A, 9B, 9C, 9D:
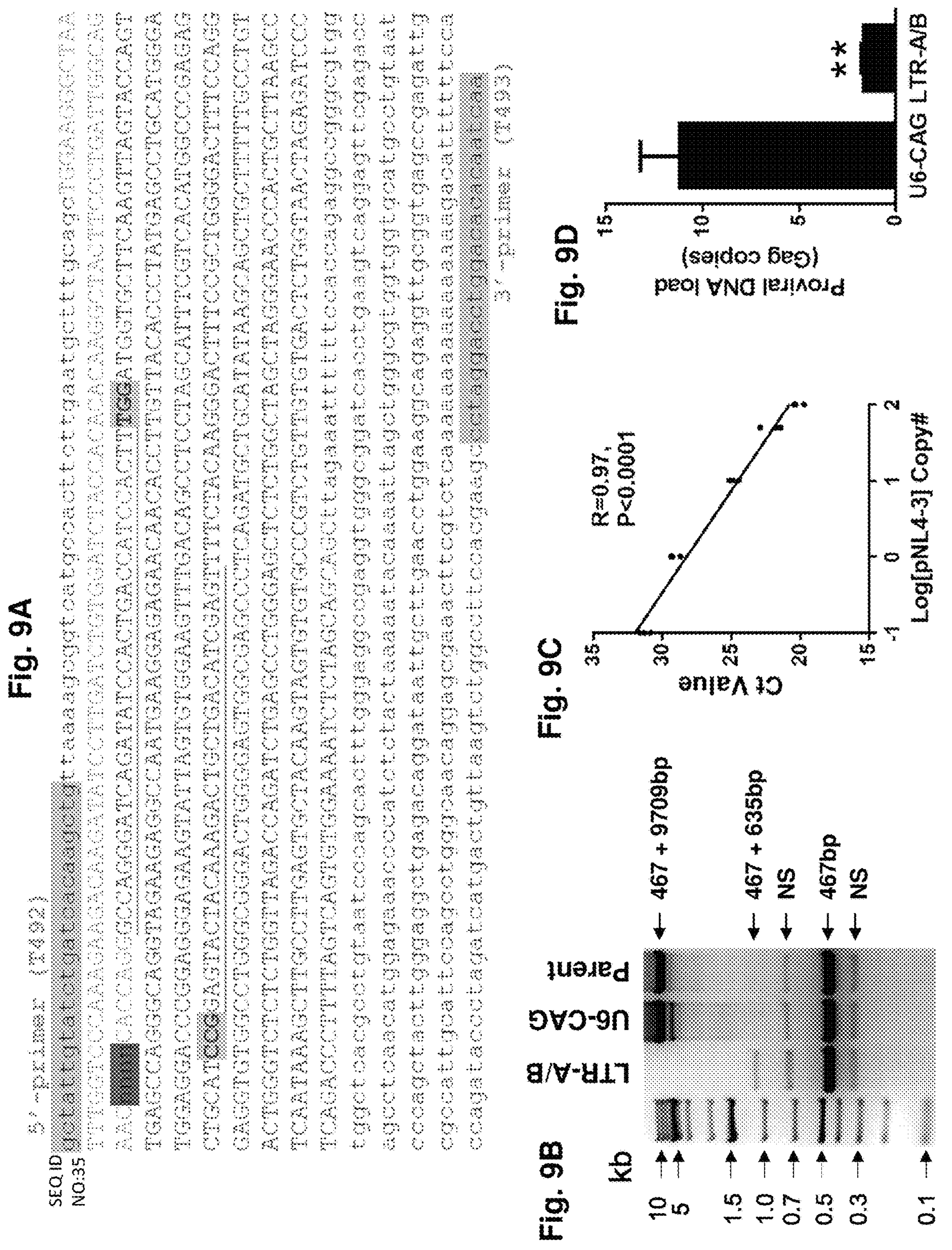
FIGS. 9A-9D demonstrate that Cas9/LTR-gRNA efficiently eradicates latent HIV-1 virus from U1 monocytic cells. (9A) Sanger sequencing of a 1.1 kb fragment from long-range PCR using a primer pair (T492/T493) targeting a chromosome 2 integration site-flanking sequence (small letters, 467-bp) reveals elimination of the entire HIV-1 genome (9709-bp), leaving combined 5'-LTR (underlined using dashes) and 3'-LTR with a 6-bp insertion (boxed) precisely at the third nucleotide from PAM (TGG) LTR-A targeting site (underlined) and a 4-bp deletion (nnnn).
Figure 10A:
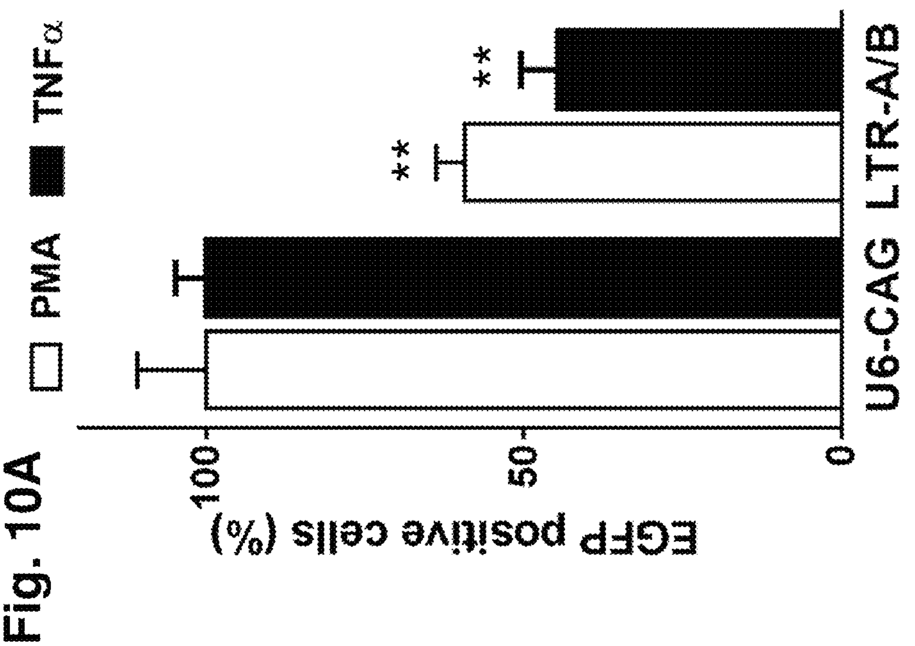
FIGS. 10A-10C show that Cas9/LTR gRNAs effectively eradicates HIV-1 provirus in J-Lat latently infected T cells. (10A) Functional analysis by EGFP flow cytometry reveals approximately 50% reduction of PMA and TNFa-induced reactivation of EGFP reporter viruses. (10B) The SURVEYOR assay shows indel mutations (arrow) in the on-target LTR genome of Cas9/LTR-A/B transfected cells. J-Lat cells were transfected with pX260 empty vector or LTRs-A and -B. After 2-week puromycin selection, cells were treated with PMA or TNFa for 24 h. The genomic DNAs were subject to PCR using primers covering HIV-1 LTR U3/R/U5 regions (−411 to +129) and the SURVEYOR assay was performed. "P<0.01 indicates a significant decrease compared to the U6-CAG control. (10C) PCR fragment analysis using primers covering HIV-1 LTR (−374 to +43) shows a precise deletion of 190-bp region between LTRs A and B cutting sites, leaving 227-bp fragment (arrow). House-keeping gene β-actin serves as a DNA purification and loading control.
Figure 10B:
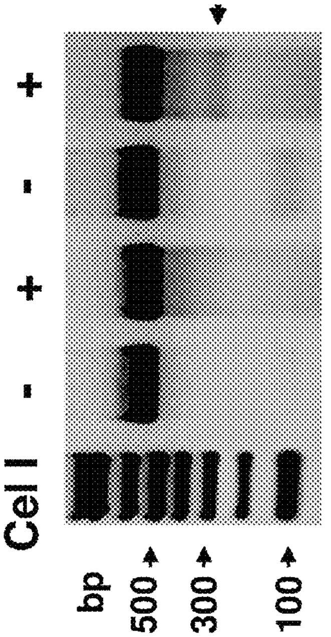
Figure 10C:
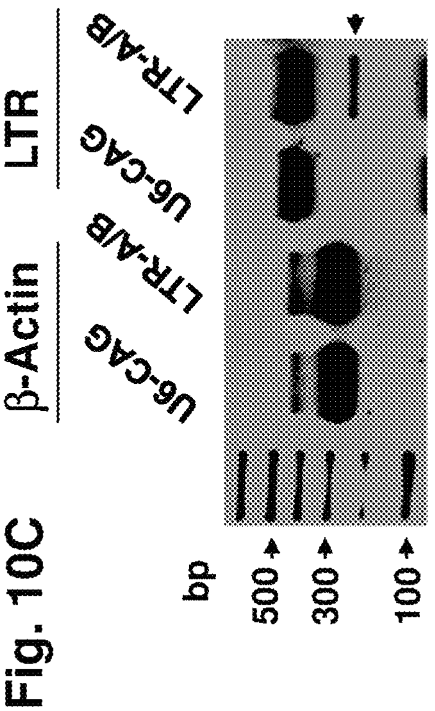

Example 3: Cas9/LTR-gRNA Efficiently Eradicates Latent HIV-1 Virus from U1 Monocytic Cells The promonocytic U-937 cell subclone U1, an HIV-1 latency model for infected perivascular macrophages and monocytes, is chronically HIV-1-infected and exhibits low level constitutive viral gene expression and replication. GENOMEWALKER mapping detected two integrated proviral DNA copies at chromosomes Xp11-4 (FIG. 2A) and 2p21 (FIG. 9A) in U1 cells. A 9935-bp DNA fragment representing the entire 9709-bp proviral HIV-1 DNA plus a flanking 226-bp X-chromosome-derived sequence (FIG. 2A), and a 10176-bp fragment containing 9709-bp HIV-1 genome plus its flanking 2-chromosome-derived 467-bp (FIG. 9A, B) were identified by the long-range PCR analysis of the parental control or empty-vector (U6-CAG) U1 cells. The 226-bp and 467-bp fragments represent the predicted segment from the other copy of chromosome X and 2 respectively, which lacked the integrated proviral DNA. In U1 cells expressing LTR-AB gRNAs and Cas9, we found two additional DNA fragments of 833 and 670 bp in chromosome X and one additional 1102-bp fragment in chromosome 2. Thus, gRNAs AB enabled Cas9 to excise the HIV-1 5'-3' LTR-spanning viral genome segment in both chromosomes. The 833-bp fragment includes the expected 226-bp from the host genome and a 607-bp viral LTR sequence with a 27-bp deletion around the LTR-A site (FIG. 2A-B). The 670-bp fragment encompassed a 226-bp host sequence and residual 444-bp viral LTR sequence after 190-bp fragment excision (FIG. 1D), caused by gRNAs-AB-guided cleavage at both LTRs (FIG. 2A). The additional fragments did not emerge via circular LTR integration, because it was absent in the parental U1 cells, and such circular LTR viral genome configuration occurs immediately after HIV-1 infection but is short lived and intolerant to repeated passaging. These cells exhibited substantially decreased HIV-1 viral load, shown by the functional p24 ELISA replication assay (FIG. 2C) and real-time PCR analysis (FIG. 9C, D). The detectable but low residual viral load and reactivation may result from cell population heterogeneity and/or incomplete genome editing. We also validated the ablation of HIV-1 genome by Cas9/LTR-A/B gRNAs in latently infected J-Lat T cells harboring integrated HIV-R7/E-/EGFP using flow cytometry analysis, SURVEYOR assay and PCR genotyping (FIG. 10), supporting the results of previous reports on HIV-1 proviral deletion in Jurkat T cells by Cas9/gRNA and ZFN. Taken together, our results suggest that the multiplex LTR-gRNAs/Cas9 system efficiently suppress HIV-1 replication and reactivation in latently HIV-1-infected "reservoir" (microglial, monocytic and T) cells typical of human latent HIV-1 infection, and in TZM-bl cells highly sensitive for detecting HIV-1 transcription and reactivation. Single or multiplex gRNAs targeting 5'- and 3T-LTRs effectively eradicated the entire HIV-1 genome.

Figures 3A, 3B, 3C, 3D:
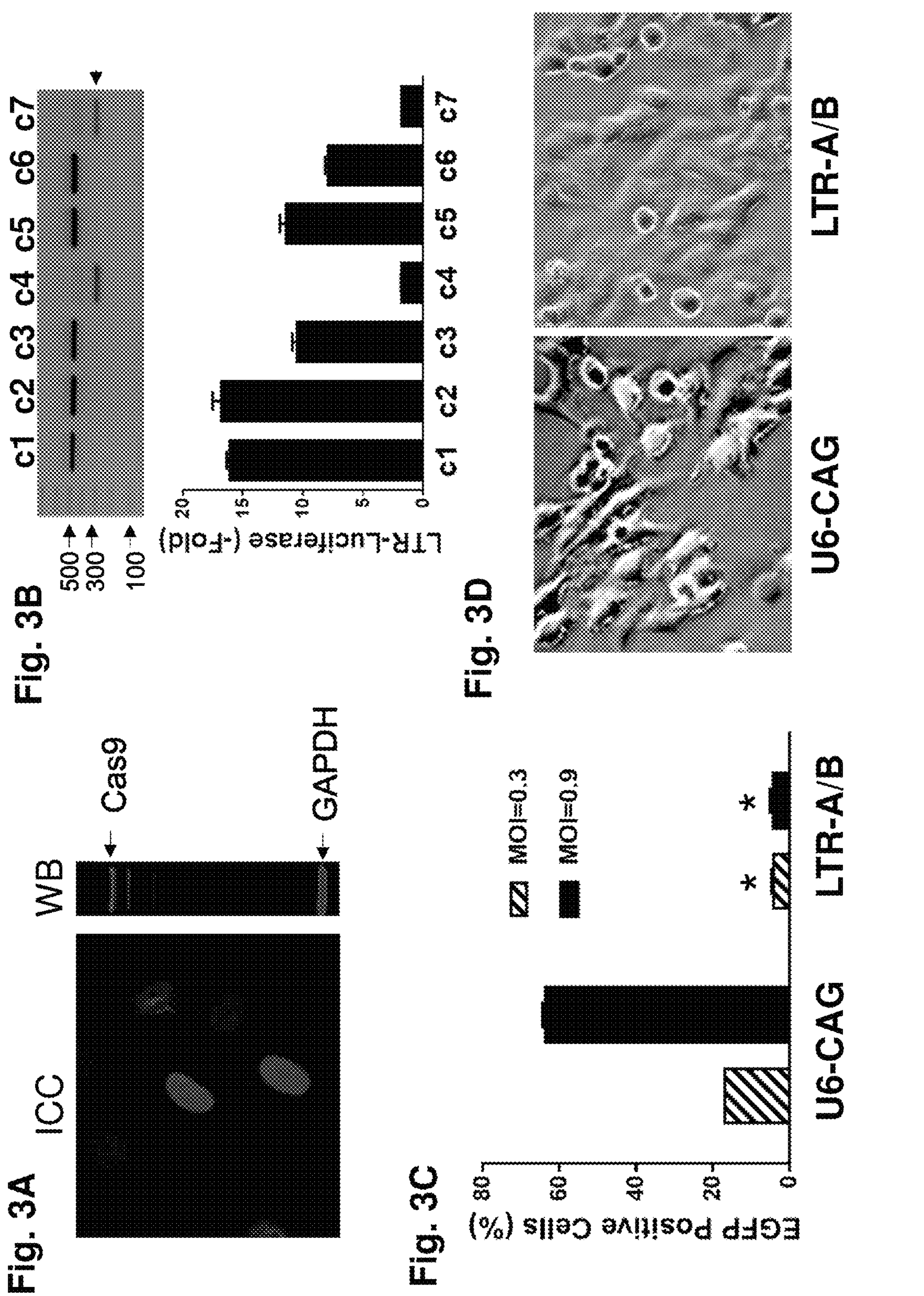
FIGS. 3A-3D show that stable expression of Cas9 plus LTR-A/B vaccinates TZM-bl cells against new HIV-1 virus infection.
Figures 11A, 11B, 11C, 11D:
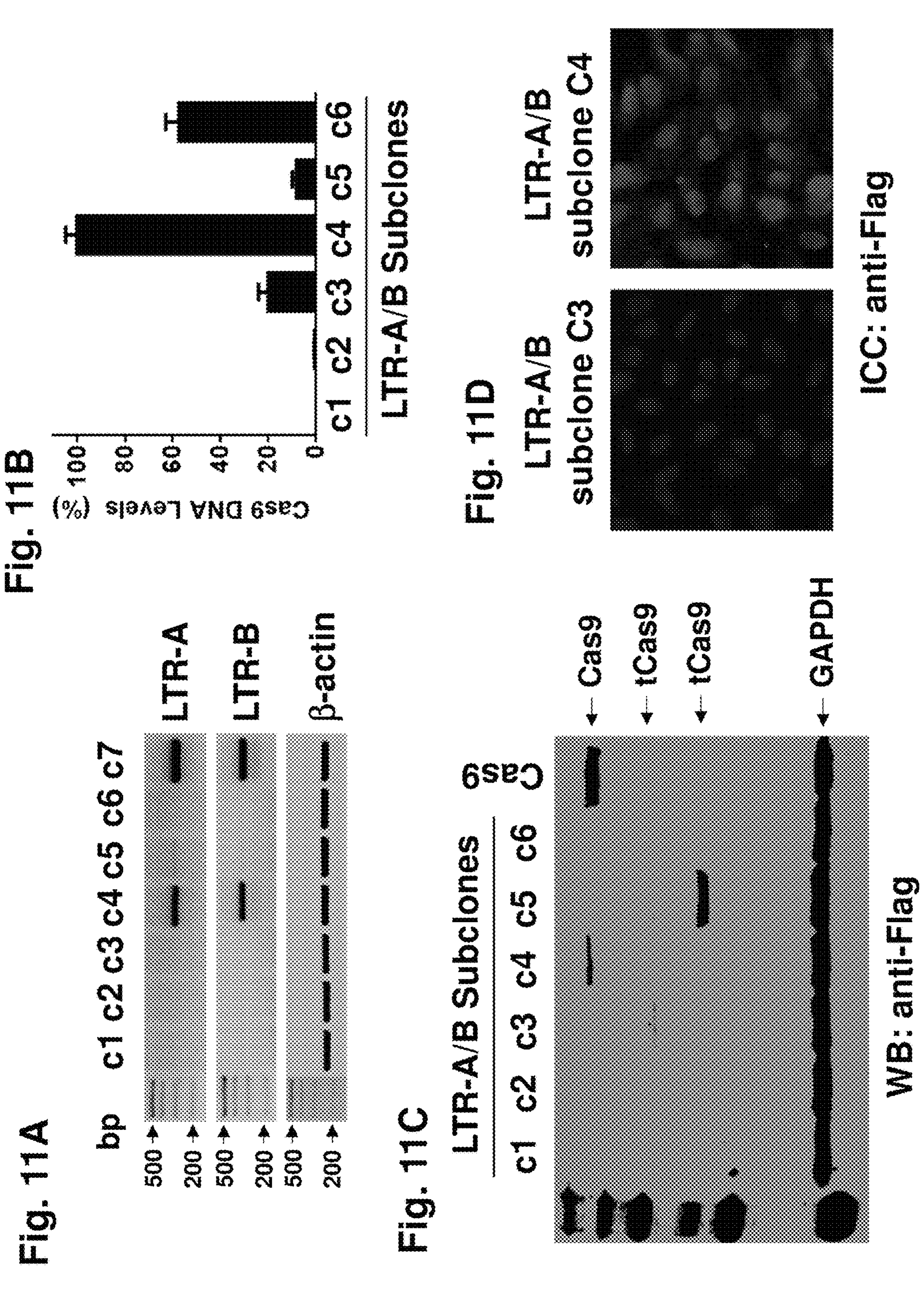
FIGS. 11A-11D show that genome editing efficiency depends upon the presence of Cas9 and gRNAs. (11A, 11B) PCR genotyping reveals the absence of a U6-driven LTR-A or LTR-B expression cassette (11A) and absence/reduction of CMV-driven Cas9 DNA (11B) in puromycin-selected TZM-bl subclones without any indication of genomic editing. Genomic DNAs from indicated subclones were subject to conventional (11A) or real-time (11B) PCR analyses using a primer pair covering U6 promoter (T351) and LTR-A (T354) or -B (T356), and targeting Cas9 (T477/T491). (11C, 11D) Cas9 protein expression is absent in ineffective TZM-bl subclones. The Flag-tagged Cas9 fusion protein was detected by Western blot (WB) and immunocytochemistry (ICC) with anti-Flag monoclonal antibody. HEK293T cell line stably expressing Flag-Cas9 was used as a positive control for WB (11C). GAPDH serves as a protein loading control. Clone c6 contains Cas9 DNA but no Cas9 protein expression, suggesting a potential mechanism of epigenetic repression after puromycin selection. Clone c5 and c3 may represent a truncated Flag-Cas9 (tCas9). Nucleus was stained with Hoechst 33258 (11D).
Figures 12A, 12B, 12C, 12D:
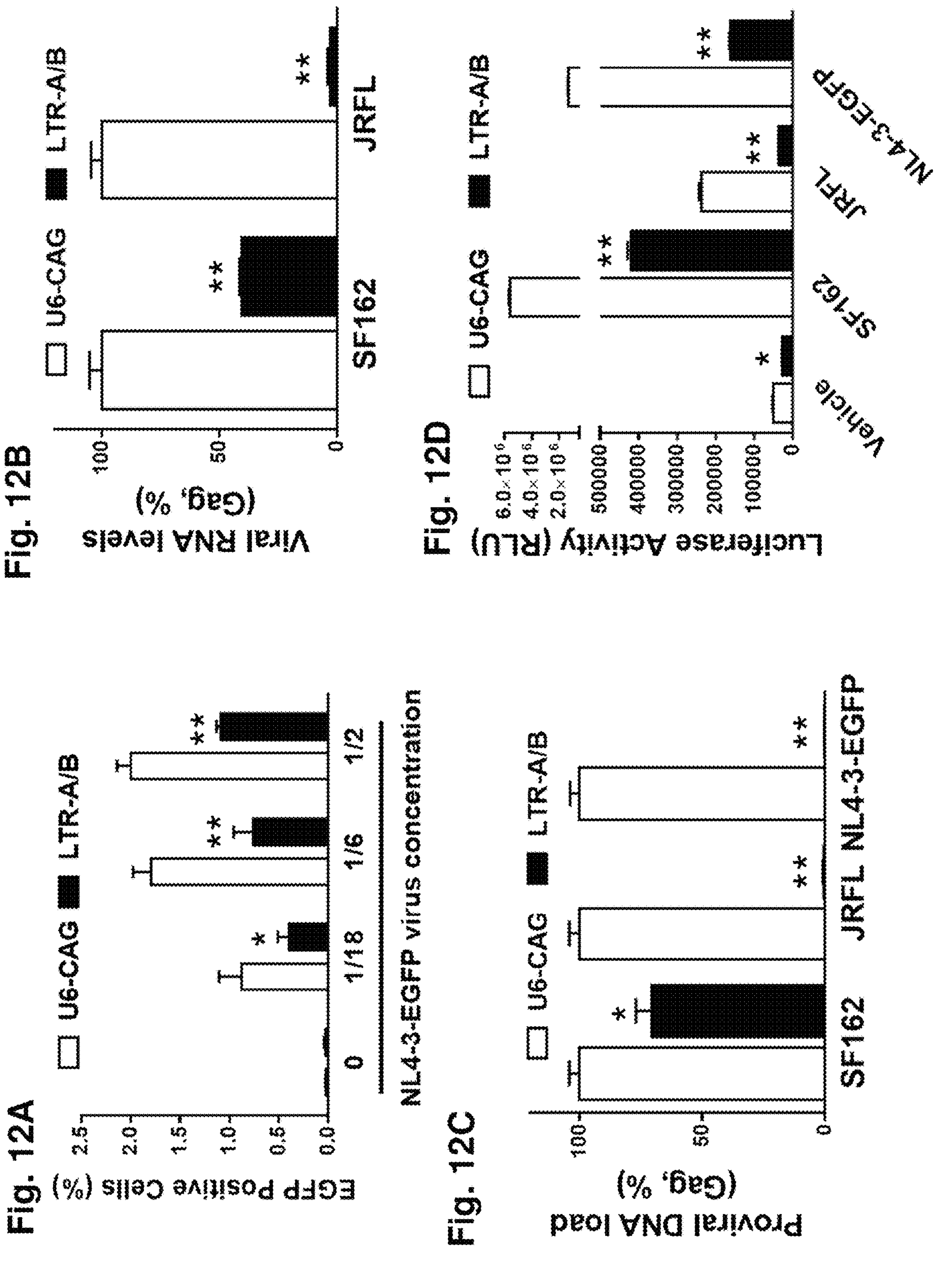
FIGS. 12A-12D demonstrate that stable expression of Cas9/LTR-AB gRNAs in TZM-bl cells vaccinates against pseudotyped or native HIV-1 viruses. (12A) Flow cytometry shows a significant reduction of native pNL4-3-ΔE-EGFP reporter virus infection efficiency in Cas9/LTR-A/B expressing TZM-bl subclones. (12B, 12C) Real-time PCR analysis reveals suppression or elimination of viral RNA (12B) and DNA (12C) by Cas9/LTR-AB gRNAs. (12D) The firefly-luciferase luminescent assay demonstrates dramatic inhibition of virus infection-stimulated LTR promoter activity by Cas9/LTR-AB gRNAs. The stable Cas9/LTR-AB gRNA-expressing TZM-bl cells were infected for 2 hours with indicated native HIV-1 viruses, and washed twice with PBS. At 2 days post-infection, cells were collected, fixed and analyzed by flow cytometry for EGFP expression (12A), or lysed for total RNA extraction and RT-qPCR (12B), genomic DNA purification for qPCR (12C) and luminescence measurement (12D). *P<0.05 and **P<0.01 indicate significant decreases compared to the U6-CAG control.
Figures 16A, 16B, 16C, 16D, 16E:
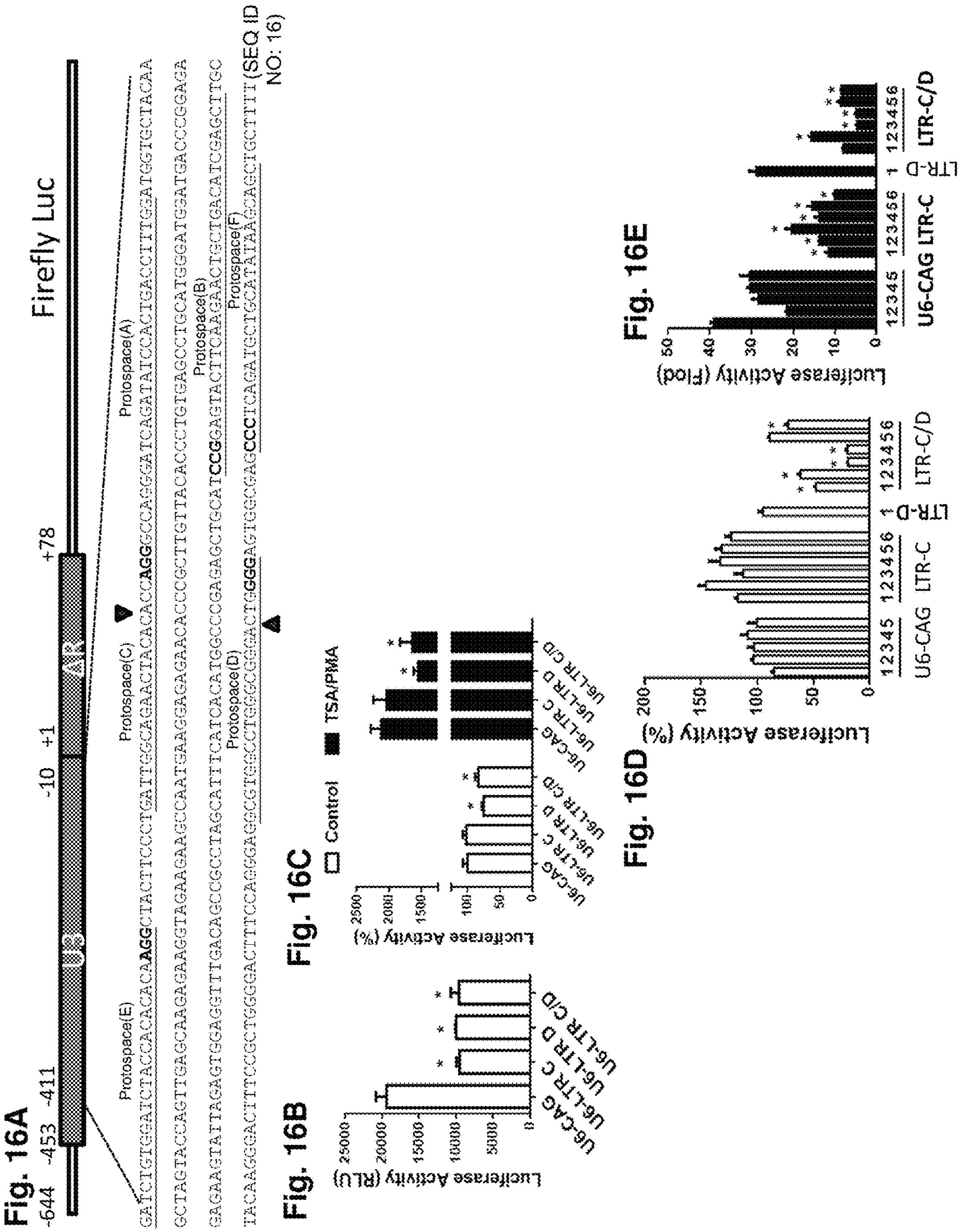
FIGS. 16A-16H show that both LTR-C and LTR-D decreased constitutive and TSA/PMA-induced luciferase activity in TZMBI cells stably incorporated with HIV-1 LTR firefly luciferase reporter gene and combination induced precise genome excision. Six gRNA targets were designed for the promoter region of HIV-LTR (FIG. 16A).
Figure 16F:
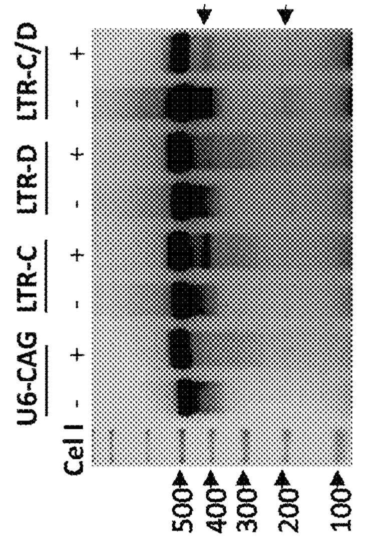
Figure 16G:
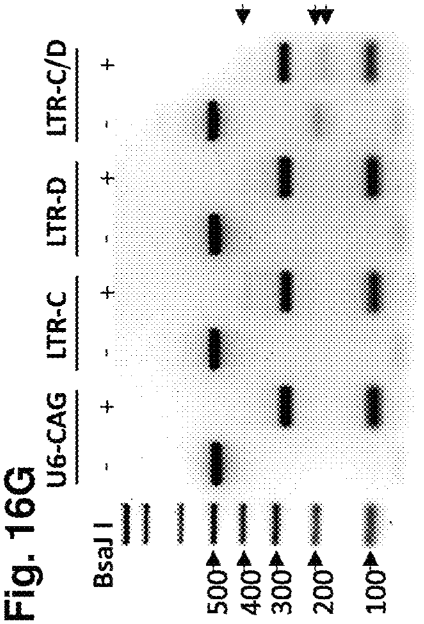
Figure 16H:
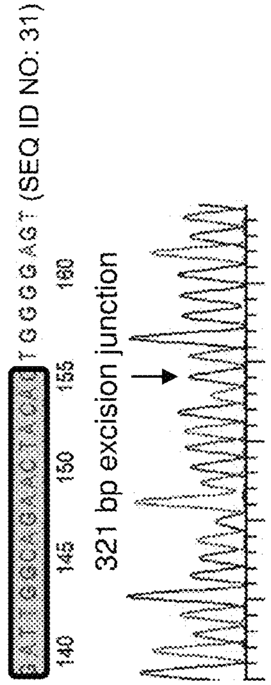
Figures 17A, 17B, 17C, 17D, 17E:
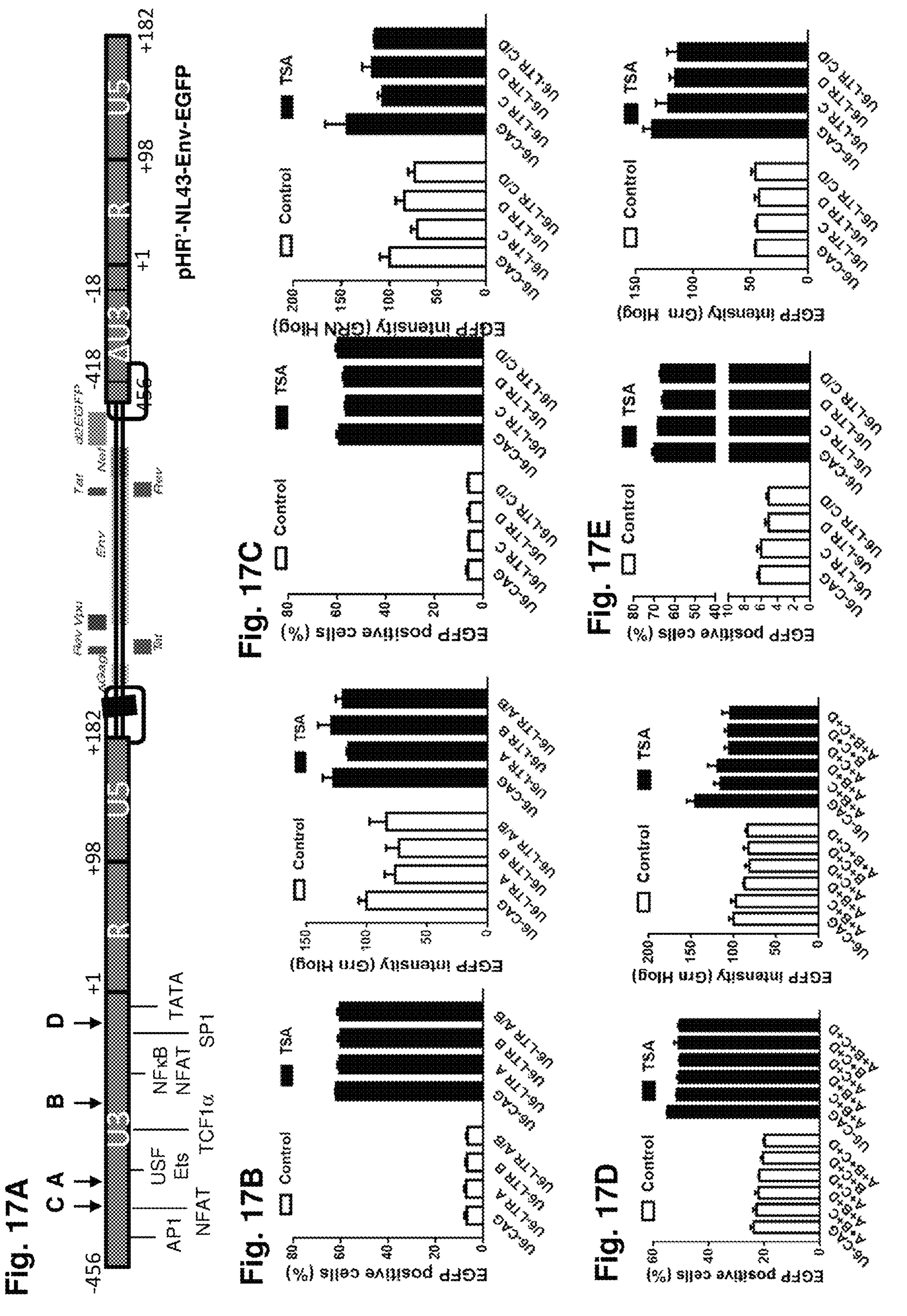
FIGS. 17A-17H show that Cas9/LTR-gRNA inhibited constitutive and inducible production of HIV-1 virus measured by EGFP flow cytometry in HIV-1 latently infected CHMES microglia cell line. The pHR' lentiviral vector containing Tat, Rev, Env, Vpu, and Nef with the reported gene d2EGFP was transduced into human fetal microglia cell line CHME5 and 400 bp deletion in U3 region of 3'-LTR is illustrated (FIG. 17A). After transient transfection of Cas9/gRNA, Human HIV-1 LTR-A, B, C, D alone or combination decreased the intensity but not percentage of EGFP due to suppression of LTR promoter activity (FIGS. 17B, 17C). After antibiotic selection for 1-2 weeks, the percentage of EGFP cells was also reduced (FIGS. 17D, 17E). The PCR product from the stable selected clones were analyzed with Surveyor Cel-1 nuclease assay (FIG. 17F) showing indel mutation dramatically in LTR-A and LTR-B but weakly in the combination of LTR-AB (red arrow). A 331 bp fragment (FIGS. 17F, 17G, black arrow) resulting from the deletion of 190 bp region between LTR-A and LTR-B as predicted (FIG. 17H, red arrowhead) was validated by TA-cloning and sequencing showing precise genomic excision (FIG. 17H).
Figure 17F:
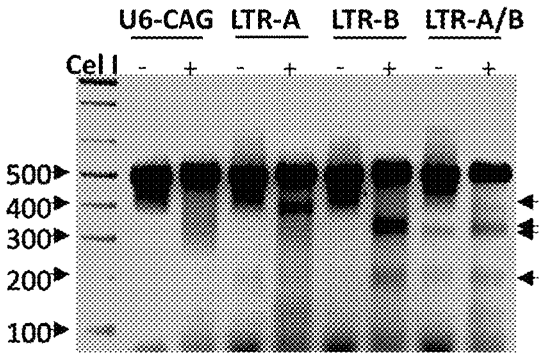
Figure 17G:
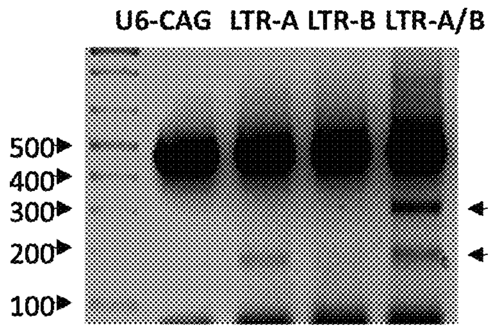
Figure 17H:
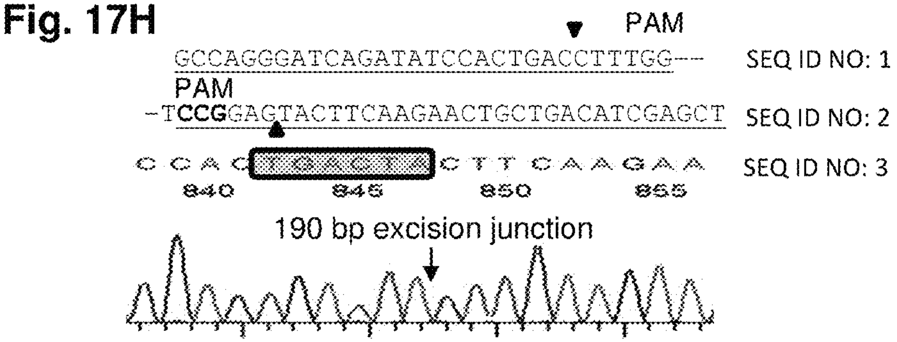

Example 4: Stable Expression of Cas9 Plus LTR-A/B Vaccinates TZM-bl Cells Against New HIV-1 Virus Infection We next tested whether combined Cas9/LTR gRNAs can immunize cells against HIV-1 infection using stable Cas9/gRNAs-A and -B-expressing TZM-bl-based clones (FIG. 3A). Two of 7 puromycin-selected subclones exhibited efficient excision of the 190-bp LTR-A/B site-spanning DNA fragment (FIG. 3B). However, the remaining 5 subclones exhibited no excision (FIG. 3B) and no indel mutations as verified by Sanger sequencing. PCR genotyping using primers targeting Cas9 and U6-LTR showed that none of these ineffective subclones retained the integrated copies of Cas9/LTR-A/B gRNA expression cassettes. (FIG. 11A, B). As a result, no expression of full-length Cas9 was detected (FIG. 11C, D). The long-term expression of Cas9/LTR-A/B gRNAs did not adversely affect cell growth or viability, suggesting a low occurrence of off-target interference with the host genome or Cas9-induced toxicity in this model. We assessed de novo HIV-1 replication by infecting cells with the VSVG-pseudotyped pNL4-3-AE-EGFP reporter virus, with EGFP-positivity by flow cytometry indicating HIV-1 replication. Unlike the control U6-CAG cells, the cells stably expressing Cas9/gRNAs LTRs-A/B failed to support HIV-1 replication at 2 d post infection, indicating that they were immunized effectively against new HIV-1 infection (FIG. 3C-D). A similar immunity against HIV-1 was observed in Cas/LTR-A/B gRNA expressing cells infected with native T-tropic X4 strain pNL4-3-AE-EGFP reporter virus (FIG. 12A) or native M-tropic R5 strains such as SF162 and JRFL (FIG. 12B-D).

Example 5: Off-Target Effects of Cas9/LTR-A/B on Human Genome

The appeal of Cas9/gRNA as an interventional approach rests on its highly specific on-target indel-producing cleavage, but multiplex gRNAs could potentially cause host genome mutagenesis and chromosomal disorders, cytotoxicity, genotoxicity, or oncogenesis. Fairly low viral-human genome homology reduces this risk, but the human genome contains numerous endogenous retroviral genomes that are potentially susceptible to HIV-1-directed gRNAs. Therefore, we assessed off-target effects of selected HIV-1 LTR gRNAs on the human genome. Because the 12-14-bp seed sequence nearest the protospacer-adjacent motif (PAM) region (NGG) is critical for cleavage specificity, we searched >14-bp seed+NGG, and found no off-target candidate sites by LTR gRNAs A-D (FIG. 13). It is not surprising that progressively shorter gRNA segments yielded increasing off-target cleavage sites 100% matched to corresponding on-target sequences (i.e., NGG+13 bp yielded 6, 0, 2 and 9 off-target sites, respectively, whereas NGG+12 bp yielded 16, 5, 16 and 29; FIG. 13). From human genomic DNA we obtained a 500-800-bp sequence covering one of predicted off-target sites using high-fidelity PCR, and analyzed the potential mutations by SURVEYOR and Sanger sequencing. We found no mutations (see representative off-target sites #1, 5 and 6 in TZM-bl and U1 cells; FIG. 4A).

To assess risk of off-target effects comprehensively, we performed whole genome sequencing (WGS) using the stable Cas9/gRNA AB-expressing and control U6-CAG TZM-bl cells (FIG. 4B-D). We identified 676,105 indels, using a genome analysis toolkit (GATK, v.2.8.1) with human (hg19) and HIV-1 genomes as reference sequences. Among the indels, 24% occurred in the U6-CAG control, 26% in LTR-A/B subclone, and 50% in both (FIG. 4B). Such substantial inter-sample indel-calling discrepancy suggests the probable off-target effects, but most likely results from its limited confidence, limited WGS coverage (15-30×), and cellular heterogeneity. GATK reported only confidently-identified indels: some found in the U6-CAG control but not in the LTR-AB subclone, and others in the LTR-A/B but not in the U6-CAG. We expected abundant missing indel calls for both samples due to the limited WGS coverage. Such limited indel-calling confidence also implies the possibility of false negatives: missed indels occurring in LTR-A/B but not U6-CAG controls. Cellular heterogeneity may reflect variability of Cas9/gRNA editing efficiency and effects of passaging. Therefore, we tested whether each indel was LTR-AB gRNA-induced, by analyzing ±300 bp flanking each indel against LTRs-A/-B-targeted sites of the HIV-1 genome and predicted/potential gRNA off-target sites of the host genome (FIG. 15). For sequences 100% matched to one containing the seed (12-bp) plus NRG, we identified only 8 overlapped regions of 92 potential off-target sites against 676,105 indels: 6 indels occurring in both samples, and 2 only in the U6-CAG control (FIG. 4C, D). We also identified 2 indels on HIV-1 LTR that occurred only in the LTR-A/B subclone but, as expected, not in the U6-CAG control (FIG. 4C). The results suggest that LTR-AB gRNAs induce the indicated on-target indels, but no off-target indels, consistent with prior findings using deep sequencing of PCR products covering predicted/potential off-target site.

Our combined approaches minimized off-target effects while achieving high efficiency and complete ablation of the genomically integrated HIV-1 provirus. In addition to an extremely low homology between the foreign viral genome and host cellular genome including endogenous retroviral DNA, the key design attributes in our study included: bioinformatic screening using the strictest 12-bp+NGG target-selection criteria to exclude off-target human transcriptome or (even rarely) untranslated-genomic sites; avoiding transcription factor binding sites within the HIV-1 LTR promoter (potentially conserved in the host genome); selection of LTR-A- and -B-directed, 30-bp gRNAs and also pre-crRNA system reflecting the original bacterial immune mechanism to enhance specificity/efficiency vs. 20-bp gRNA-, chimeric crRNA-tracrRNA-based system; and WGS, Sanger sequencing and SURVEYOR assay, to identify and exclude potential off-target effects. Indeed, the use of newly developed Cas9 double-nicking and RNA-guided Fokl nuclease may further assist identification of new targets within the various conserved regions of HIV-1 with reduced off-target effects.

Our results show that the HIV-1 Cas9/gRNA system has the ability to target more than one copy of the LTR, which are positioned on different chromosomes, suggesting that this genome editing system can alter the DNA sequence of HIV-1 in latently infected patient's cells harboring multiple proviral DNAs. To further ensure high editing efficacy and consistency of our technology, one may consider the most stable region of HIV-1 genome as a target to eradicate HIV-1 in patient samples, which may not harbor only one strain of HIV-1. Alternatively, one may develop personalized treatment modalities based on the data from deep sequencing of the patient-derived viral genome prior to engineering therapeutic Cas9/gRNA molecules.

Our results also demonstrate that Cas9/gRNA genome editing can be used to immunize cells against HIV-1 infection. The preventative vaccination is independent of HIV-1 strain's diversity because the system targets genomic sequences regardless of how the viruses enter the infected cells. The preexistence of the Cas9/gRNA system in cells led to a rapid elimination of the new HIV-1 before it integrates into the host genome. One may explore various systems for delivery of Cas9/LTR-gRNA for immunizing high-risk subjects, e.g., gene therapies (viral vector and nanoparticle) and transplantation of autologous Cas9/gRNA-modified bone marrow stem/progenitor cells or inducible pluripotent stem cells for eradicating HIV-1 infection.

Here, we demonstrated the high specificity of Cas9/gRNAs in editing HIV-1 target genome. Results from subclone data revealed the strict dependence of genome editing on the presence of both Cas9 and gRNA. Moreover, only one nucleotide mismatch in the designed gRNA target will disable the editing potency. In addition, all of our 4 designed LTR gRNAs worked well with different cell lines, indicating that the editing is more efficient in the HIV-1 genome than the host cellular genome, wherein not all designed gRNAs are functional, which may be due to different epigenetic regulation, variable genome accessibility, or other reasons. Given the ease and rapidity of Cas9/gRNA development, even if HIV-1 mutations confer resistance to one Cas9/gRNA-based therapy, as described above, HIV-1 variants can be genotyped to enable another personalized therapy for individual patients.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising:

(a) a Clustered Regularly Interspaced Short Palindromic Repeat (CRISPR)-associated Cas9 endonuclease or a nucleic acid sequence encoding the CRISPR-associated Cas9 endonuclease;

(b) two or more guide RNAs (gRNAs) or one or more nucleic acid sequences encoding the two or more gRNAs, at least two of the two or more gRNAs targeting a cleavage site, (i) a first gRNA or a nucleic acid sequence encoding the first gRNA, the first gRNA being complementary to a first target nucleic acid sequence within a 5' long terminal repeat (LTR) of a human immunodeficiency virus (HIV) sequence;

and (ii) a second gRNA or a nucleic acid sequence encoding the second gRNA, the second gRNA being complementary to a second target nucleic acid sequence within a 3' long terminal repeat (LTR) of the HIV sequence, at least two of the two or more gRNAs being different; and (c) an excipient, wherein the CRISPR-associated Cas9 endonuclease and the two or more gRNAs are capable of excising the HIV sequence between cleavage sites from a genome in a cell.

2. The composition of claim 1, wherein the first target nucleic acid sequence is within sections U3, R, or U5 region of the 5' LTR.

3. The composition of claim 1, wherein the second target nucleic acid sequence is within sections U3, R, or U5 region of the 3' LTR.

4. The composition of claim 1, wherein the nucleic acid sequence encoding the CRISPR-associated endonuclease, the nucleic acid sequence encoding the first gRNA, and the nucleic acid sequence encoding the second gRNA are in a same expression vector.

5. The composition of claim 1, wherein the nucleic acid sequence encoding the CRISPR-associated endonuclease, the nucleic acid sequence encoding the first gRNA, and the nucleic acid sequence encoding the second gRNA are in different expression vectors.

6. The composition of claim 1, wherein the composition comprises the CRISPR-associated Cas9 endonuclease and the two or more gRNAs.

7. The composition of claim 1, wherein the composition comprises the nucleic acid sequence encoding CRISPR-associated Cas9 endonuclease, the nucleic acid sequence encoding the first gRNA, and the nucleic acid sequence encoding the second gRNA.

8. The composition of claim 1, wherein the composition comprises the CRISPR-associated Cas9 endonuclease, the nucleic acid sequence encoding the first gRNA, and the nucleic acid sequence encoding the second gRNA.

9. The composition of claim 1, wherein the composition comprises the nucleic acid sequence encoding CRISPR-associated Cas9 endonuclease and the two or more gRNAs.

10. A nucleic acid encoding:

(a) a Clustered Regularly Interspected Short Palindromic Repeat (CRISPR)-associated Cas9 endonuclease;

(b) two or more guide RNAs (gRNAs), at least two of the two or more gRNAs targeting a cleavage site, (i) a first gRNA, the first gRNA being complementary to a first target nucleic acid sequence within a 5' long terminal repeat (LTR) of a human immunodeficiency virus (HIV) sequence; and (ii) a second gRNA, the second gRNA being complementary to a second target nucleic acid sequence within a 3' long terminal repeat (LTR) of the HIV sequence, at least two of the two or more gRNAs being different, wherein the nucleic acid is capable of excising the HIV sequence between cleavage sites from a genome in a cell.

11. The nucleic acid of claim 10, wherein the first target nucleic acid sequence is within sections U3, R or U5 of the 5' LTR.

12. The nucleic acid of claim 10, wherein the second target nucleic acid sequence is within sections U3, R or U5 of the 3' LTR.

13. A pharmaceutical composition comprising:

(a) a nucleic acid comprising:

i. a first nucleic acid sequence encoding a Clustered Regularly Interspaced Short Palindromic Repeat (CRISPR)-associated Cas9 endonuclease;

ii. a second nucleic acid sequence encoding two or more guide RNAs (gRNAs), at least two of the two or more gRNAs targeting a cleavage site, (i) a first gRNA, the first gRNA being complementary to a first target nucleic acid sequence within a 5' long terminal repeat (LTR) of a human immunodeficiency virus (HIV) sequence; and (ii) a second gRNA, the second gRNA being complementary to a second target nucleic acid sequence within a 3' long terminal repeat (LTR) of the HIV sequence, at least two of the two or more gRNAs being different;

wherein the nucleic acid is capable of excising the HIV sequence between cleavage sites from a genome in a cell; and (b) a pharmaceutically acceptable excipient.

14. The pharmaceutical composition of claim 13, wherein the first target nucleic acid sequence is within sections U3, R, or U5 regions of the 5' LTR.

15. The pharmaceutical composition of claim 13, wherein the second target nucleic acid sequence is within sections U3, R, or U5 regions of the 3' LTR.

* * * * *

SEQUENCE LISTING

```
<160> NUMBER OF SEQ ID NOS: 389

<210> SEQ ID NO 1
<211> LENGTH: 30
<212> TYPE: DNA
<213> ORGANISM: Human immunodeficiency virus 1

<400> SEQUENCE: 1

gccagggatc agatatccac tgacctttgg                                        30


<210> SEQ ID NO 2
<211> LENGTH: 34
<212> TYPE: DNA
<213> ORGANISM: Human immunodeficiency virus 1

<400> SEQUENCE: 2

tccggagtac ttcaagaact gctgacatcg agct                                   34
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
ccactgacta cttcaagaa 19

<210> SEQ ID NO 4
<211> LENGTH: 859
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (289)..(313)
<223> OTHER INFORMATION: a, c, t, g, unknown or other
<220> FEATURE:
<221> NAME/KEY: misc_feature
<222> LOCATION: (289)..(313)
<223> OTHER INFORMATION: n is a, c, g, or t

<400> SEQUENCE: 4
ctaggtgatt aggatattct acaatccaaa ttcttaccag tttgggatta ttcaaattgg 60
gcaccttggc agatatgttt tgaaaactgc taggcaaagc attctggaag aatagacaaa 120
gaagtaataa aatataacaa aaagcagtgg aagttacaaa aaaaaatgtt tctcttttgg 180
aagggctaat ttggtcccaa agaagacaag atatccttga tctgtggatc taccacacac 240
aaggctactt ccctgattgg cagaactaca acaccagggc cagggatcnn nnnnnnnnnn 300
nnnnnnnnnn nnnttcaagt tagtaccagt tgagccaggg caggtagaag aggccaatga 360
aggagagaac aacaccttgt tacaccctat gagcctgcat gggatggagg acccggaggg 420
agaagtatta gtgtggaagt ttgacagcct cctagcattt cgtcacatgg cccgagagct 480
gcatccggag tactacaaag actgctgaca tcgagttttc tacaagggac tttccgctgg 540
ggactttcca gggaggtgtg gcctgggcgg gactggggag tggcgagccc tcagatgctg 600
catataagca gctgcttttt gcctgtactg ggtctctctg gttagaccag atctgagcct 660
gggagctctc tggctagcta gggaacccac tgcttaagcc tcaataaagc ttgccttgag 720
tgctacaagt agtgtgtgcc cgtctgttgt gtgactctgg taactagaga tccctcagac 780
ccttttagtc agtgtggaaa atctctagca tctttaaagt acagaatgcc aaaacaggaa 840
ggattgataa gatagtcgt 859

<210> SEQ ID NO 5
<211> LENGTH: 10
<212> TYPE: DNA
<213> ORGANISM: Human immunodeficiency virus 1

<400> SEQUENCE: 5
tcttttggaa 10

<210> SEQ ID NO 6
<211> LENGTH: 76
<212> TYPE: DNA
<213> ORGANISM: Human immunodeficiency virus 1

<400> SEQUENCE: 6

-continued gattggcaga actacacacc agggccaggg atcagatatc cactgacctt tggatggtgc 60
ttcaagttag taccag 76

<210> SEQ ID NO 7
<211> LENGTH: 10
<212> TYPE: DNA
<213> ORGANISM: Human immunodeficiency virus 1

<400> SEQUENCE: 7
tctttaaagt 10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
tcttttggaa 10

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
gattggcaga actacaacac cagggccagg gatcagatgg atggtgcttc aagttagtac 60
cag 63

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
tctttaaagt 10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
tcttttggaa 10

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
gattggcaga actacaacac cagggccagg gatcttcaag ttagtaccag 50

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tctttaaagt 10

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
gagatcctgt ctcaaaaaaa agtt 24

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
atctatccat gagggcg 17

<210> SEQ ID NO 16
<211> LENGTH: 402
<212> TYPE: DNA
<213> ORGANISM: Human immunodeficiency virus 1

<400> SEQUENCE: 16
gatctgtgga tctaccacac acaaggctac ttccctgatt ggcagaacta cacaccaggg 60
ccagggatca gatatccact gacctttgga tggtgctaca agctagtacc agttgagcaa 120
gagaaggtag aagaagccaa tgaaggagag aacacccgct tgttacaccc tgtgagcctg 180
catgggatgg atgacccgga gagagaagta ttagagtgga ggtttgacag ccgcctagca 240
tttcatcaca tggcccgaga gctgcatccg gagtacttca agaactgctg acatcgagct 300
tgctacaagg gactttccgc tggggacttt ccagggaggc gtggcctggg cgggactggg 360
gagtggcgag ccctcagatg ctgcatataa gcagctgctt tt 402

<210> SEQ ID NO 17
<211> LENGTH: 31
<212> TYPE: DNA
<213> ORGANISM: Human immunodeficiency virus 1

<400> SEQUENCE: 17
ccctgattgg cagaactaca caccagggcc a 31

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
ccctgattgg cagaactaca acaccagggc ca 32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ccctgattgg cagaactaca acaccagggc ca 32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccctgattgg cagaactaca acaccagggc ca 32

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ccctgattgg cagaactaca accagggcca 30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
ccctgattgg cagaactaca ccagggcca 29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
ccctgattgg cagaactaca ccagggcca 29

<210> SEQ ID NO 24
<211> LENGTH: 26
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 24
ccctgattgg cagaactaca gggcca                                           26

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccctgattgg cagaactaca gggccaggg                                        29

<210> SEQ ID NO 26
<211> LENGTH: 86
<212> TYPE: DNA
<213> ORGANISM: Human immunodeficiency virus 1

<400> SEQUENCE: 26
gactttccag ggaggcgtgg cctgggcggg actggggagt ggcgagccct cagatgctgc     60
atataagcag cggtgaagcc gaattc                                           86

<210> SEQ ID NO 27
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gactttccag ggaggcgtgg cctgggcggg actgggggt ggcgagccct cagatgctgc      60
atataagcag cggtgaagcc gaattc                                           86

<210> SEQ ID NO 28
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gactttccag ggaggcgtgg cctgggcggg tatctgggga gtggcgagcc ctcagatgct     60
gcatataagc agcggtgaag ccgaattc                                         88

<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gactttccag gggggcgtgg cctgggcggg actggggagt ggcgagccct cagatgctgc     60
ataaagcagc ggtgaagccg aattc                                            85

<210> SEQ ID NO 30

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

gactttccag ggaagccgaa ttc                                           23


<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

gattggcaga actacactgg ggagt                                         25


<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

gattggcaga actacacctc agatgc                                        26


<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

catcacatgg cccgctgctg acatcgag                                      28


<210> SEQ ID NO 34
<211> LENGTH: 55
<212> TYPE: DNA
<213> ORGANISM: Human immunodeficiency virus 1

<400> SEQUENCE: 34

catcacgtgg cccgagagct gcatccggag tacttcaaga actgctgaca tcgag        55


<210> SEQ ID NO 35
<211> LENGTH: 1106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (152)..(155)
<223> OTHER INFORMATION: a, c, t, g, unknown or other
<220> FEATURE:
<221> NAME/KEY: misc_feature
<222> LOCATION: (152)..(155)
<223> OTHER INFORMATION: n is a, c, g, or t

<400> SEQUENCE: 35
```

```
gctattgtat ctgatcacaa gctgttaaaa gcggtcatgc cacttcttga atgctttgca     60

gctggaaggg ctaatttggt cccaaagaag acaagatatc cttgatctgt ggatctacca    120

cacacaaggc tacttccctg attggcagaa cnnnncacca gggccaggga tcagatatcc    180

actgaccatc cactttggat ggtgcttcaa gttagtacca gttgagccag ggcaggtaga    240

agaggccaat gaaggagaga acaacacctt gttacaccct atgagcctgc atgggatgga    300

ggacccggag ggagaagtat tagtgtggaa gtttgacagc ctcctagcat ttcgtcacat    360

ggcccgagag ctgcatccgg agtactacaa agactgctga catcgagttt tctacaaggg    420

actttccgct ggggactttc cagggaggtg tggcctgggc gggactgggg agtggcgagc    480

cctcagatgc tgcatataag cagctgcttt ttgcctgtac tgggtctctc tggttagacc    540

agatctgagc ctgggagctc tctggctagc tagggaaccc actgcttaag cctcaataaa    600

gcttgccttg agtgctacaa gtagtgtgtg cccgtctgtt gtgtgactct ggtaactaga    660

gatccctcag acccttttag tcagtgtgga aaatctctag cagcagctta gaaatttttt    720

ccaccagagg ccgggcgtgg tggctcacgc ctgtaatccc agcactttgg gaggccgagg    780

tgggcggatc acctgaagtc aggagttcga gaccagcctc aacatggaga aaccccatct    840

ctactaaaaa tacaaaatta gctgggcgtg gtggtgcatg cctgtaatcc cagctacttg    900

ggaggctgag acaggataat tgcttgaacc tggaaggcag aggttgcggt gagccgagat    960

tgcgccattg cattccagcc tggcaacag gagcgaaact tcgtctcaaa aaaaaaaaaa   1020

aaagacattt tttccaccag ataccctaga tcatgactgt taagtctggc cttccacgaa   1080

gccctaggac ctggacacac aatcaa                                          1106


<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

aaacagggcc agggatcaga tatccactga ccttgt                                 36


<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

taaacaaggt cagtggatat ctgatccctg gccct                                  35


<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

aaacagctcg atgtcagcag ttcttgaagt actcgt                                 36


<210> SEQ ID NO 39
```

<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
taaacgagta cttcaagaac tgctgacatc gagct 35

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
caccgattgg cagaactaca cacc 24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
aaacggtgtg tagttctgcc aatc 24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
caccgcgtgg cctgggcggg actg 24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
aaaccagtcc cgcccaggcc acgc 24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
tggaagggct aattcactcc caac 24

<210> SEQ ID NO 45
<211> LENGTH: 24

<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ccgagagctc ccaggctcag atct 24

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
caccgatctg tggatctacc acacaca 27

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
aaacgagtca cacaacagac gggc 24

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cgcctcgagg atccgagggc ctatttccca tgattcc 37

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tgtgaattca ggcgggccat ttaccgtaag ttatg 35

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
acgactatct tatcaatcct tcctg 25

<210> SEQ ID NO 51
<211> LENGTH: 26
<212> TYPE: DNA

<213> ORGANISM: Artificial Sequence
<220> FEATURE:
<223> OTHER INFORMATION: Description of Artificial Sequence: Synthetic
primer

<400> SEQUENCE: 51
ctaggtgatt aggatattct acaatc 26

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
gctattgtat ctgatcacaa gctg 24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
ttgattgtgt gtccaggtcc tagg 24

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
gcaagggcga ggagctgttc acc 23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
ttgtagttgc cgtcgtcctt gaag 24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
aatggtacat caggccatat cac 23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
cccactgtgt ttagcatggt att 23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
cacagcatca agaagaacct gat 23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
tcttccgtct ggtgtatctt cttc 24

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
cgccaagctt gaataggagc tttgttcc 28

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
ctaggatcca ggagctgttg atcctttagg 30

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
gtggactttg gatggtgaga tag 23

<210> SEQ ID NO 63
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 63

gcctggcaag agtgaactga gtc                                              23


<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

aagataatga gttgtggcag agc                                              23


<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

tctacctggt aatccagcat ctgg                                             24


<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

ataggaggaa ggcaccaaga ggg                                              23


<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

aatgatgctt tggtcctact cct                                              23


<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

tgctcttgct actctggcat gtac                                             24


<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 69
aatctacctc tgagagctgc agg 23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
tcagacacag ctgaagcaga ggc 23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
atgccagtgt cagtagatgt cag 23

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
tcaagatcag ccagagtgca catg 24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
tgctcttccg agcctctctg gag 23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
atggactatc atatgcttac cg 22

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
gcttcagcaa gccgagtcct gcgtcgag 28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
gctcctctgg tttccctttc gctttcaa 28

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
gtaatacgac tcactatagg gc 22

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
actatagggc acgcgtggt 19

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
tcagaccctt ttagtcagtg tgg 23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
ttgcttgtac tgggtctctc tgg 23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
cagctgcttt ttgcttgtac tgg 23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
ctgacatcga gcttgctaca agg 23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
ccgcctagca tttcatcaca tgg 23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
cggagagaga agtattagag tgg 23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
agtaccagtt gagcaagaga agg 23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
gatatccact gacctttgga tgg 23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
gattggcaga actacacacc agg 23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
cacaaggcta cttccctgat tgg 23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ctgtggatct accacacaca agg 23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
tgggagctct ctggctaact agg 23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
ggttagacca gatctgagcc tgg 23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
tgctacaagg gactttccgc tgg 23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93

-continued agagagaagt attagagtgg agg 23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
ttacaccctg tgagcctgca tgg 23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 95
aaggtagaag aagccaatga agg 23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
atcagatatc cactgacctt tgg 23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 97
gacaagatat ccttgatctg tgg 23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98
gcccgtctgt tgtgtgactc tgg 23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
atctgagcct gggagctctc tgg 23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
ctttccgctg gggactttcc agg 23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cagaactaca caccagggcc agg 23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
cctgcatggg atggatgacc cgg 23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
ccctgtgagc ctgcatggga tgg 23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
ctttccaggg aggcgtggcc tgg 23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
ggggactttc cagggaggcg tgg 23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
ccgctgggga ctttccaggg agg 23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
catggcccga gagctgcatc cgg 23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
gcctgggcgg gactggggag tgg 23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
aggcgtggcc tgggcgggac tgg 23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
gcgtggcctg ggcgggactg ggg 23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
ccagggaggc gtggcctggg cgg 23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
tgtggtagat ccacagatca agg 23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
ggtgtgtagt tctgccaatc agg 23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
gtcagtggat atctgatccc tgg 23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
tagcaccatc caaaggtcag tgg 23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
tagcttgtag caccatccaa agg 23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
tctaccttct cttgctcaac tgg 23

<210> SEQ ID NO 118

<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
cactctaata cttctctctc cgg 23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
ccatgtgatg aaatgctagg cgg 23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
gggccatgtg atgaaatgct agg 23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
cagcagttct tgaagtactc cgg 23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
ctgcttatat gcagcatctg agg 23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
cacactactt gaagcactca agg 23

<210> SEQ ID NO 124
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

taccagagtc acacaacaga cgg                                        23


<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

acactgacta aaagggtctg agg                                        23


<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

caaggatatc ttgtcttcgt tgg                                        23


<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127

cagggaagta gccttgtgtg tgg                                        23


<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128

gcgggtgttc tctccttcat tgg                                        23


<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

tagttagcca gagagctccc agg                                        23


<210> SEQ ID NO 130
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 130

ctttattgag gcttaagcag tgg                                             23


<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

actcaaggca agctttattg agg                                             23


<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

ggatatctga tccctggccc tgg                                             23


<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

ggctcacagg gtgtaacaag cgg                                             23


<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

tccatcccat gcaggctcac agg                                             23


<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

agtactccgg atgcagctct cgg                                             23


<210> SEQ ID NO 136
<211> LENGTH: 23
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 136
agagctccca ggctcagatc tgg 23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 137
gattttccac actgactaaa agg 23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138
ccgggtcatc catcccatgc agg 23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
cctccctgga aagtccccag cgg 23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
gccactcccc agtcccgccc agg 23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
ccgcccaggc cacgcctccc tgg 23

<210> SEQ ID NO 142
<211> LENGTH: 23
<212> TYPE: DNA
<213> ORGANISM: Human immunodeficiency virus 1

<400> SEQUENCE: 142
atcagatatc cactgacctt tgg 23

<210> SEQ ID NO 143
<211> LENGTH: 22
<212> TYPE: DNA
<213> ORGANISM: Human immunodeficiency virus 1

<400> SEQUENCE: 143
tcagatatcc actgaccttt gg 22

<210> SEQ ID NO 144
<211> LENGTH: 22
<212> TYPE: DNA
<213> ORGANISM: Human immunodeficiency virus 1

<400> SEQUENCE: 144
tcagatatcc actgaccttt gg 22

<210> SEQ ID NO 145
<211> LENGTH: 21
<212> TYPE: DNA
<213> ORGANISM: Human immunodeficiency virus 1

<400> SEQUENCE: 145
cagatatcca ctgacctttg g 21

<210> SEQ ID NO 146
<211> LENGTH: 21
<212> TYPE: DNA
<213> ORGANISM: Human immunodeficiency virus 1

<400> SEQUENCE: 146
cagatatcca ctgacctttg g 21

<210> SEQ ID NO 147
<211> LENGTH: 20
<212> TYPE: DNA
<213> ORGANISM: Human immunodeficiency virus 1

<400> SEQUENCE: 147
agatatccac tgacctttgg 20

<210> SEQ ID NO 148
<211> LENGTH: 20
<212> TYPE: DNA
<213> ORGANISM: Human immunodeficiency virus 1

<400> SEQUENCE: 148
agatatccac tgacctttgg 20

<210> SEQ ID NO 149
<211> LENGTH: 19
<212> TYPE: DNA
<213> ORGANISM: Human immunodeficiency virus 1

<400> SEQUENCE: 149
gatatccact gacctttgg 19

<210> SEQ ID NO 150
<211> LENGTH: 19
<212> TYPE: DNA
<213> ORGANISM: Human immunodeficiency virus 1

<400> SEQUENCE: 150
gatatccact gacctttgg 19

<210> SEQ ID NO 151
<211> LENGTH: 18
<212> TYPE: DNA
<213> ORGANISM: Human immunodeficiency virus 1

<400> SEQUENCE: 151
atatccactg acctttgg 18

<210> SEQ ID NO 152
<211> LENGTH: 18
<212> TYPE: DNA
<213> ORGANISM: Human immunodeficiency virus 1

<400> SEQUENCE: 152
atatccactg acctttgg 18

<210> SEQ ID NO 153
<211> LENGTH: 17
<212> TYPE: DNA
<213> ORGANISM: Human immunodeficiency virus 1

<400> SEQUENCE: 153
tatccactga ccttggg 17

<210> SEQ ID NO 154
<211> LENGTH: 17
<212> TYPE: DNA
<213> ORGANISM: Human immunodeficiency virus 1

<400> SEQUENCE: 154
tatccactga cctttgg 17

<210> SEQ ID NO 155
<211> LENGTH: 17
<212> TYPE: DNA
<213> ORGANISM: Human immunodeficiency virus 1

<400> SEQUENCE: 155
tatccactga cctttgg 17

<210> SEQ ID NO 156
<211> LENGTH: 17
<212> TYPE: DNA
<213> ORGANISM: Human immunodeficiency virus 1

<400> SEQUENCE: 156
tatccactga ccttaag 17

<210> SEQ ID NO 157
<211> LENGTH: 17
<212> TYPE: DNA
<213> ORGANISM: Human immunodeficiency virus 1

<400> SEQUENCE: 157
tatccactga ccttgag 17

<210> SEQ ID NO 158
<211> LENGTH: 16
<212> TYPE: DNA

<213> ORGANISM: Human immunodeficiency virus 1

<400> SEQUENCE: 158
atccactgac cttagg 16

<210> SEQ ID NO 159
<211> LENGTH: 16
<212> TYPE: DNA
<213> ORGANISM: Human immunodeficiency virus 1

<400> SEQUENCE: 159
atccactgac cttagg 16

<210> SEQ ID NO 160
<211> LENGTH: 16
<212> TYPE: DNA
<213> ORGANISM: Human immunodeficiency virus 1

<400> SEQUENCE: 160
atccactgac cttggg 16

<210> SEQ ID NO 161
<211> LENGTH: 16
<212> TYPE: DNA
<213> ORGANISM: Human immunodeficiency virus 1

<400> SEQUENCE: 161
atccactgac cttggg 16

<210> SEQ ID NO 162
<211> LENGTH: 16
<212> TYPE: DNA
<213> ORGANISM: Human immunodeficiency virus 1

<400> SEQUENCE: 162
atccactgac cttggg 16

<210> SEQ ID NO 163
<211> LENGTH: 16
<212> TYPE: DNA
<213> ORGANISM: Human immunodeficiency virus 1

<400> SEQUENCE: 163
atccactgac cttggg 16

<210> SEQ ID NO 164
<211> LENGTH: 16
<212> TYPE: DNA
<213> ORGANISM: Human immunodeficiency virus 1

<400> SEQUENCE: 164
atccactgac ctttgg 16

<210> SEQ ID NO 165
<211> LENGTH: 16
<212> TYPE: DNA
<213> ORGANISM: Human immunodeficiency virus 1

<400> SEQUENCE: 165
atccactgac ctttgg 16

<210> SEQ ID NO 166
<211> LENGTH: 16

<212> TYPE: DNA
<213> ORGANISM: Human immunodeficiency virus 1

<400> SEQUENCE: 166
atccactgac ctttgg 16

<210> SEQ ID NO 167
<211> LENGTH: 16
<212> TYPE: DNA
<213> ORGANISM: Human immunodeficiency virus 1

<400> SEQUENCE: 167
atccactgac cttaag 16

<210> SEQ ID NO 168
<211> LENGTH: 16
<212> TYPE: DNA
<213> ORGANISM: Human immunodeficiency virus 1

<400> SEQUENCE: 168
atccactgac cttaag 16

<210> SEQ ID NO 169
<211> LENGTH: 16
<212> TYPE: DNA
<213> ORGANISM: Human immunodeficiency virus 1

<400> SEQUENCE: 169
atccactgac cttcag 16

<210> SEQ ID NO 170
<211> LENGTH: 16
<212> TYPE: DNA
<213> ORGANISM: Human immunodeficiency virus 1

<400> SEQUENCE: 170
atccactgac cttcag 16

<210> SEQ ID NO 171
<211> LENGTH: 16
<212> TYPE: DNA
<213> ORGANISM: Human immunodeficiency virus 1

<400> SEQUENCE: 171
atccactgac cttgag 16

<210> SEQ ID NO 172
<211> LENGTH: 16
<212> TYPE: DNA
<213> ORGANISM: Human immunodeficiency virus 1

<400> SEQUENCE: 172
atccactgac cttgag 16

<210> SEQ ID NO 173
<211> LENGTH: 15
<212> TYPE: DNA
<213> ORGANISM: Human immunodeficiency virus 1

<400> SEQUENCE: 173
tccactgacc ttagg 15

<210> SEQ ID NO 174

<211> LENGTH: 15
<212> TYPE: DNA
<213> ORGANISM: Human immunodeficiency virus 1

<400> SEQUENCE: 174
tccactgacc ttagg 15

<210> SEQ ID NO 175
<211> LENGTH: 15
<212> TYPE: DNA
<213> ORGANISM: Human immunodeficiency virus 1

<400> SEQUENCE: 175
tccactgacc ttagg 15

<210> SEQ ID NO 176
<211> LENGTH: 15
<212> TYPE: DNA
<213> ORGANISM: Human immunodeficiency virus 1

<400> SEQUENCE: 176
tccactgacc ttagg 15

<210> SEQ ID NO 177
<211> LENGTH: 15
<212> TYPE: DNA
<213> ORGANISM: Human immunodeficiency virus 1

<400> SEQUENCE: 177
tccactgacc ttagg 15

<210> SEQ ID NO 178
<211> LENGTH: 15
<212> TYPE: DNA
<213> ORGANISM: Human immunodeficiency virus 1

<400> SEQUENCE: 178
tccactgacc ttagg 15

<210> SEQ ID NO 179
<211> LENGTH: 15
<212> TYPE: DNA
<213> ORGANISM: Human immunodeficiency virus 1

<400> SEQUENCE: 179
tccactgacc ttggg 15

<210> SEQ ID NO 180
<211> LENGTH: 15
<212> TYPE: DNA
<213> ORGANISM: Human immunodeficiency virus 1

<400> SEQUENCE: 180
tccactgacc ttggg 15

<210> SEQ ID NO 181
<211> LENGTH: 15
<212> TYPE: DNA
<213> ORGANISM: Human immunodeficiency virus 1

<400> SEQUENCE: 181
tccactgacc ttggg 15

<210> SEQ ID NO 182
<211> LENGTH: 15
<212> TYPE: DNA
<213> ORGANISM: Human immunodeficiency virus 1

<400> SEQUENCE: 182
tccactgacc ttggg 15

<210> SEQ ID NO 183
<211> LENGTH: 15
<212> TYPE: DNA
<213> ORGANISM: Human immunodeficiency virus 1

<400> SEQUENCE: 183
tccactgacc ttggg 15

<210> SEQ ID NO 184
<211> LENGTH: 15
<212> TYPE: DNA
<213> ORGANISM: Human immunodeficiency virus 1

<400> SEQUENCE: 184
tccactgacc ttggg 15

<210> SEQ ID NO 185
<211> LENGTH: 15
<212> TYPE: DNA
<213> ORGANISM: Human immunodeficiency virus 1

<400> SEQUENCE: 185
tccactgacc ttggg 15

<210> SEQ ID NO 186
<211> LENGTH: 15
<212> TYPE: DNA
<213> ORGANISM: Human immunodeficiency virus 1

<400> SEQUENCE: 186
tccactgacc ttggg 15

<210> SEQ ID NO 187
<211> LENGTH: 15
<212> TYPE: DNA
<213> ORGANISM: Human immunodeficiency virus 1

<400> SEQUENCE: 187
tccactgacc tttgg 15

<210> SEQ ID NO 188
<211> LENGTH: 15
<212> TYPE: DNA
<213> ORGANISM: Human immunodeficiency virus 1

<400> SEQUENCE: 188
tccactgacc tttgg 15

<210> SEQ ID NO 189
<211> LENGTH: 15
<212> TYPE: DNA
<213> ORGANISM: Human immunodeficiency virus 1

<400> SEQUENCE: 189
tccactgacc tttgg 15

<210> SEQ ID NO 190
<211> LENGTH: 15
<212> TYPE: DNA
<213> ORGANISM: Human immunodeficiency virus 1

<400> SEQUENCE: 190
tccactgacc tttgg 15

<210> SEQ ID NO 191
<211> LENGTH: 15
<212> TYPE: DNA
<213> ORGANISM: Human immunodeficiency virus 1

<400> SEQUENCE: 191
tccactgacc tttgg 15

<210> SEQ ID NO 192
<211> LENGTH: 15
<212> TYPE: DNA
<213> ORGANISM: Human immunodeficiency virus 1

<400> SEQUENCE: 192
tccactgacc tttgg 15

<210> SEQ ID NO 193
<211> LENGTH: 15
<212> TYPE: DNA
<213> ORGANISM: Human immunodeficiency virus 1

<400> SEQUENCE: 193
tccactgacc tttgg 15

<210> SEQ ID NO 194
<211> LENGTH: 15
<212> TYPE: DNA
<213> ORGANISM: Human immunodeficiency virus 1

<400> SEQUENCE: 194
tccactgacc tttgg 15

<210> SEQ ID NO 195
<211> LENGTH: 15
<212> TYPE: DNA
<213> ORGANISM: Human immunodeficiency virus 1

<400> SEQUENCE: 195
tccactgacc tttgg 15

<210> SEQ ID NO 196
<211> LENGTH: 15
<212> TYPE: DNA
<213> ORGANISM: Human immunodeficiency virus 1

<400> SEQUENCE: 196
tccactgacc ttaag 15

<210> SEQ ID NO 197
<211> LENGTH: 15
<212> TYPE: DNA
<213> ORGANISM: Human immunodeficiency virus 1

<400> SEQUENCE: 197
tccactgacc ttaag 15

<210> SEQ ID NO 198
<211> LENGTH: 15
<212> TYPE: DNA
<213> ORGANISM: Human immunodeficiency virus 1

<400> SEQUENCE: 198
tccactgacc ttaag 15

<210> SEQ ID NO 199
<211> LENGTH: 15
<212> TYPE: DNA
<213> ORGANISM: Human immunodeficiency virus 1

<400> SEQUENCE: 199
tccactgacc ttaag 15

<210> SEQ ID NO 200
<211> LENGTH: 15
<212> TYPE: DNA
<213> ORGANISM: Human immunodeficiency virus 1

<400> SEQUENCE: 200
tccactgacc ttaag 15

<210> SEQ ID NO 201
<211> LENGTH: 15
<212> TYPE: DNA
<213> ORGANISM: Human immunodeficiency virus 1

<400> SEQUENCE: 201
tccactgacc ttcag 15

<210> SEQ ID NO 202
<211> LENGTH: 15
<212> TYPE: DNA
<213> ORGANISM: Human immunodeficiency virus 1

<400> SEQUENCE: 202
tccactgacc ttcag 15

<210> SEQ ID NO 203
<211> LENGTH: 15
<212> TYPE: DNA
<213> ORGANISM: Human immunodeficiency virus 1

<400> SEQUENCE: 203
tccactgacc ttcag 15

<210> SEQ ID NO 204
<211> LENGTH: 15
<212> TYPE: DNA
<213> ORGANISM: Human immunodeficiency virus 1

<400> SEQUENCE: 204
tccactgacc ttcag 15

<210> SEQ ID NO 205
<211> LENGTH: 15
<212> TYPE: DNA
<213> ORGANISM: Human immunodeficiency virus 1

<400> SEQUENCE: 205
tccactgacc ttcag 15

<210> SEQ ID NO 206
<211> LENGTH: 15
<212> TYPE: DNA
<213> ORGANISM: Human immunodeficiency virus 1

<400> SEQUENCE: 206
tccactgacc ttcag 15

<210> SEQ ID NO 207
<211> LENGTH: 15
<212> TYPE: DNA
<213> ORGANISM: Human immunodeficiency virus 1

<400> SEQUENCE: 207
tccactgacc ttcag 15

<210> SEQ ID NO 208
<211> LENGTH: 15
<212> TYPE: DNA
<213> ORGANISM: Human immunodeficiency virus 1

<400> SEQUENCE: 208
tccactgacc ttcag 15

<210> SEQ ID NO 209
<211> LENGTH: 15
<212> TYPE: DNA
<213> ORGANISM: Human immunodeficiency virus 1

<400> SEQUENCE: 209
tccactgacc ttcag 15

<210> SEQ ID NO 210
<211> LENGTH: 15
<212> TYPE: DNA
<213> ORGANISM: Human immunodeficiency virus 1

<400> SEQUENCE: 210
tccactgacc ttcag 15

<210> SEQ ID NO 211
<211> LENGTH: 15
<212> TYPE: DNA
<213> ORGANISM: Human immunodeficiency virus 1

<400> SEQUENCE: 211
tccactgacc ttcag 15

<210> SEQ ID NO 212
<211> LENGTH: 15
<212> TYPE: DNA
<213> ORGANISM: Human immunodeficiency virus 1

<400> SEQUENCE: 212
tccactgacc ttcag 15

<210> SEQ ID NO 213
<211> LENGTH: 15
<212> TYPE: DNA
<213> ORGANISM: Human immunodeficiency virus 1

<400> SEQUENCE: 213
tccactgacc ttgag 15

<210> SEQ ID NO 214
<211> LENGTH: 15
<212> TYPE: DNA
<213> ORGANISM: Human immunodeficiency virus 1

<400> SEQUENCE: 214
tccactgacc ttgag 15

<210> SEQ ID NO 215
<211> LENGTH: 15
<212> TYPE: DNA
<213> ORGANISM: Human immunodeficiency virus 1

<400> SEQUENCE: 215
tccactgacc ttgag 15

<210> SEQ ID NO 216
<211> LENGTH: 15
<212> TYPE: DNA
<213> ORGANISM: Human immunodeficiency virus 1

<400> SEQUENCE: 216
tccactgacc ttgag 15

<210> SEQ ID NO 217
<211> LENGTH: 15
<212> TYPE: DNA
<213> ORGANISM: Human immunodeficiency virus 1

<400> SEQUENCE: 217
tccactgacc ttgag 15

<210> SEQ ID NO 218
<211> LENGTH: 15
<212> TYPE: DNA
<213> ORGANISM: Human immunodeficiency virus 1

<400> SEQUENCE: 218
tccactgacc ttgag 15

<210> SEQ ID NO 219
<211> LENGTH: 15
<212> TYPE: DNA
<213> ORGANISM: Human immunodeficiency virus 1

<400> SEQUENCE: 219
tccactgacc ttgag 15

<210> SEQ ID NO 220
<211> LENGTH: 15
<212> TYPE: DNA
<213> ORGANISM: Human immunodeficiency virus 1

<400> SEQUENCE: 220
tccactgacc ttgag 15

<210> SEQ ID NO 221
<211> LENGTH: 15
<212> TYPE: DNA
<213> ORGANISM: Human immunodeficiency virus 1

<400> SEQUENCE: 221
tccactgacc ttgag 15

<210> SEQ ID NO 222
<211> LENGTH: 15
<212> TYPE: DNA
<213> ORGANISM: Human immunodeficiency virus 1

<400> SEQUENCE: 222
tccactgacc tttag 15

<210> SEQ ID NO 223
<211> LENGTH: 15
<212> TYPE: DNA
<213> ORGANISM: Human immunodeficiency virus 1

<400> SEQUENCE: 223
tccactgacc tttag 15

<210> SEQ ID NO 224
<211> LENGTH: 15
<212> TYPE: DNA
<213> ORGANISM: Human immunodeficiency virus 1

<400> SEQUENCE: 224
tccactgacc tttag 15

<210> SEQ ID NO 225
<211> LENGTH: 15
<212> TYPE: DNA
<213> ORGANISM: Human immunodeficiency virus 1

<400> SEQUENCE: 225
tccactgacc tttag 15

<210> SEQ ID NO 226
<211> LENGTH: 15
<212> TYPE: DNA
<213> ORGANISM: Human immunodeficiency virus 1

<400> SEQUENCE: 226
tccactgacc tttag 15

<210> SEQ ID NO 227
<211> LENGTH: 23
<212> TYPE: DNA
<213> ORGANISM: Human immunodeficiency virus 1

<400> SEQUENCE: 227
cagcagttct tgaagtactc cgg 23

<210> SEQ ID NO 228
<211> LENGTH: 22
<212> TYPE: DNA
<213> ORGANISM: Human immunodeficiency virus 1

<400> SEQUENCE: 228
agcagttctt gaagtactcc gg 22

<210> SEQ ID NO 229
<211> LENGTH: 21
<212> TYPE: DNA
<213> ORGANISM: Human immunodeficiency virus 1

<400> SEQUENCE: 229
gcagttcttg aagtactccg g 21

<210> SEQ ID NO 230
<211> LENGTH: 20
<212> TYPE: DNA
<213> ORGANISM: Human immunodeficiency virus 1

<400> SEQUENCE: 230
cagttcttga agtactccgg 20

<210> SEQ ID NO 231
<211> LENGTH: 19
<212> TYPE: DNA
<213> ORGANISM: Human immunodeficiency virus 1

<400> SEQUENCE: 231
agttcttgaa gtactccgg 19

<210> SEQ ID NO 232
<211> LENGTH: 18
<212> TYPE: DNA
<213> ORGANISM: Human immunodeficiency virus 1

<400> SEQUENCE: 232
gttcttgaag tactccgg 18

<210> SEQ ID NO 233
<211> LENGTH: 17
<212> TYPE: DNA
<213> ORGANISM: Human immunodeficiency virus 1

<400> SEQUENCE: 233
ttcttgaagt actccgg 17

<210> SEQ ID NO 234
<211> LENGTH: 16
<212> TYPE: DNA
<213> ORGANISM: Human immunodeficiency virus 1

<400> SEQUENCE: 234
tcttgaagta ctccgg 16

<210> SEQ ID NO 235
<211> LENGTH: 16
<212> TYPE: DNA
<213> ORGANISM: Human immunodeficiency virus 1

<400> SEQUENCE: 235
tcttgaagta ctctag 16

<210> SEQ ID NO 236
<211> LENGTH: 15
<212> TYPE: DNA
<213> ORGANISM: Human immunodeficiency virus 1

<400> SEQUENCE: 236
cttgaagtac tcagg 15

<210> SEQ ID NO 237
<211> LENGTH: 15
<212> TYPE: DNA

<213> ORGANISM: Human immunodeficiency virus 1

<400> SEQUENCE: 237
cttgaagtac tcagg 15

<210> SEQ ID NO 238
<211> LENGTH: 15
<212> TYPE: DNA
<213> ORGANISM: Human immunodeficiency virus 1

<400> SEQUENCE: 238
cttgaagtac tcagg 15

<210> SEQ ID NO 239
<211> LENGTH: 15
<212> TYPE: DNA
<213> ORGANISM: Human immunodeficiency virus 1

<400> SEQUENCE: 239
cttgaagtac tcagg 15

<210> SEQ ID NO 240
<211> LENGTH: 15
<212> TYPE: DNA
<213> ORGANISM: Human immunodeficiency virus 1

<400> SEQUENCE: 240
cttgaagtac tccgg 15

<210> SEQ ID NO 241
<211> LENGTH: 15
<212> TYPE: DNA
<213> ORGANISM: Human immunodeficiency virus 1

<400> SEQUENCE: 241
cttgaagtac tctgg 15

<210> SEQ ID NO 242
<211> LENGTH: 15
<212> TYPE: DNA
<213> ORGANISM: Human immunodeficiency virus 1

<400> SEQUENCE: 242
cttgaagtac tcaag 15

<210> SEQ ID NO 243
<211> LENGTH: 15
<212> TYPE: DNA
<213> ORGANISM: Human immunodeficiency virus 1

<400> SEQUENCE: 243
cttgaagtac tcaag 15

<210> SEQ ID NO 244
<211> LENGTH: 15
<212> TYPE: DNA
<213> ORGANISM: Human immunodeficiency virus 1

<400> SEQUENCE: 244
cttgaagtac tcaag 15

<210> SEQ ID NO 245
<211> LENGTH: 15

<212> TYPE: DNA
<213> ORGANISM: Human immunodeficiency virus 1

<400> SEQUENCE: 245
cttgaagtac tcaag 15

<210> SEQ ID NO 246
<211> LENGTH: 15
<212> TYPE: DNA
<213> ORGANISM: Human immunodeficiency virus 1

<400> SEQUENCE: 246
cttgaagtac tcaag 15

<210> SEQ ID NO 247
<211> LENGTH: 15
<212> TYPE: DNA
<213> ORGANISM: Human immunodeficiency virus 1

<400> SEQUENCE: 247
cttgaagtac tccag 15

<210> SEQ ID NO 248
<211> LENGTH: 15
<212> TYPE: DNA
<213> ORGANISM: Human immunodeficiency virus 1

<400> SEQUENCE: 248
cttgaagtac tccag 15

<210> SEQ ID NO 249
<211> LENGTH: 15
<212> TYPE: DNA
<213> ORGANISM: Human immunodeficiency virus 1

<400> SEQUENCE: 249
cttgaagtac tccag 15

<210> SEQ ID NO 250
<211> LENGTH: 15
<212> TYPE: DNA
<213> ORGANISM: Human immunodeficiency virus 1

<400> SEQUENCE: 250
cttgaagtac tccag 15

<210> SEQ ID NO 251
<211> LENGTH: 15
<212> TYPE: DNA
<213> ORGANISM: Human immunodeficiency virus 1

<400> SEQUENCE: 251
cttgaagtac tctag 15

<210> SEQ ID NO 252
<211> LENGTH: 15
<212> TYPE: DNA
<213> ORGANISM: Human immunodeficiency virus 1

<400> SEQUENCE: 252
cttgaagtac tctag 15

<210> SEQ ID NO 253

<211> LENGTH: 23
<212> TYPE: DNA
<213> ORGANISM: Human immunodeficiency virus 1

<400> SEQUENCE: 253
atcagatatc cactgacctt tgg 23

<210> SEQ ID NO 254
<211> LENGTH: 22
<212> TYPE: DNA
<213> ORGANISM: Human immunodeficiency virus 1

<400> SEQUENCE: 254
tcagatatcc actgaccttt gg 22

<210> SEQ ID NO 255
<211> LENGTH: 22
<212> TYPE: DNA
<213> ORGANISM: Human immunodeficiency virus 1

<400> SEQUENCE: 255
tcagatatcc actgaccttt gg 22

<210> SEQ ID NO 256
<211> LENGTH: 21
<212> TYPE: DNA
<213> ORGANISM: Human immunodeficiency virus 1

<400> SEQUENCE: 256
cagatatcca ctgacctttg g 21

<210> SEQ ID NO 257
<211> LENGTH: 21
<212> TYPE: DNA
<213> ORGANISM: Human immunodeficiency virus 1

<400> SEQUENCE: 257
cagatatcca ctgacctttg g 21

<210> SEQ ID NO 258
<211> LENGTH: 20
<212> TYPE: DNA
<213> ORGANISM: Human immunodeficiency virus 1

<400> SEQUENCE: 258
agatatccac tgacctttgg 20

<210> SEQ ID NO 259
<211> LENGTH: 20
<212> TYPE: DNA
<213> ORGANISM: Human immunodeficiency virus 1

<400> SEQUENCE: 259
agatatccac tgacctttgg 20

<210> SEQ ID NO 260
<211> LENGTH: 19
<212> TYPE: DNA
<213> ORGANISM: Human immunodeficiency virus 1

<400> SEQUENCE: 260
gatatccact gacctttgg 19

<210> SEQ ID NO 261
<211> LENGTH: 19
<212> TYPE: DNA
<213> ORGANISM: Human immunodeficiency virus 1

<400> SEQUENCE: 261
gatatccact gacctttgg 19

<210> SEQ ID NO 262
<211> LENGTH: 18
<212> TYPE: DNA
<213> ORGANISM: Human immunodeficiency virus 1

<400> SEQUENCE: 262
atatccactg acctttgg 18

<210> SEQ ID NO 263
<211> LENGTH: 18
<212> TYPE: DNA
<213> ORGANISM: Human immunodeficiency virus 1

<400> SEQUENCE: 263
atatccactg acctttgg 18

<210> SEQ ID NO 264
<211> LENGTH: 17
<212> TYPE: DNA
<213> ORGANISM: Human immunodeficiency virus 1

<400> SEQUENCE: 264
tatccactga ccttggg 17

<210> SEQ ID NO 265
<211> LENGTH: 17
<212> TYPE: DNA
<213> ORGANISM: Human immunodeficiency virus 1

<400> SEQUENCE: 265
tatccactga cctttgg 17

<210> SEQ ID NO 266
<211> LENGTH: 17
<212> TYPE: DNA
<213> ORGANISM: Human immunodeficiency virus 1

<400> SEQUENCE: 266
tatccactga cctttgg 17

<210> SEQ ID NO 267
<211> LENGTH: 17
<212> TYPE: DNA
<213> ORGANISM: Human immunodeficiency virus 1

<400> SEQUENCE: 267
tatccactga ccttaag 17

<210> SEQ ID NO 268
<211> LENGTH: 17
<212> TYPE: DNA
<213> ORGANISM: Human immunodeficiency virus 1

<400> SEQUENCE: 268
tatccactga ccttgag 17

<210> SEQ ID NO 269
<211> LENGTH: 16
<212> TYPE: DNA
<213> ORGANISM: Human immunodeficiency virus 1

<400> SEQUENCE: 269
atccactgac cttagg 16

<210> SEQ ID NO 270
<211> LENGTH: 16
<212> TYPE: DNA
<213> ORGANISM: Human immunodeficiency virus 1

<400> SEQUENCE: 270
atccactgac cttagg 16

<210> SEQ ID NO 271
<211> LENGTH: 16
<212> TYPE: DNA
<213> ORGANISM: Human immunodeficiency virus 1

<400> SEQUENCE: 271
atccactgac cttggg 16

<210> SEQ ID NO 272
<211> LENGTH: 16
<212> TYPE: DNA
<213> ORGANISM: Human immunodeficiency virus 1

<400> SEQUENCE: 272
atccactgac cttggg 16

<210> SEQ ID NO 273
<211> LENGTH: 16
<212> TYPE: DNA
<213> ORGANISM: Human immunodeficiency virus 1

<400> SEQUENCE: 273
atccactgac cttggg 16

<210> SEQ ID NO 274
<211> LENGTH: 16
<212> TYPE: DNA
<213> ORGANISM: Human immunodeficiency virus 1

<400> SEQUENCE: 274
atccactgac cttggg 16

<210> SEQ ID NO 275
<211> LENGTH: 16
<212> TYPE: DNA
<213> ORGANISM: Human immunodeficiency virus 1

<400> SEQUENCE: 275
atccactgac ctttgg 16

<210> SEQ ID NO 276
<211> LENGTH: 16
<212> TYPE: DNA
<213> ORGANISM: Human immunodeficiency virus 1

<400> SEQUENCE: 276
atccactgac ctttgg 16

<210> SEQ ID NO 277
<211> LENGTH: 16
<212> TYPE: DNA
<213> ORGANISM: Human immunodeficiency virus 1

<400> SEQUENCE: 277
atccactgac ctttgg 16

<210> SEQ ID NO 278
<211> LENGTH: 16
<212> TYPE: DNA
<213> ORGANISM: Human immunodeficiency virus 1

<400> SEQUENCE: 278
atccactgac cttaag 16

<210> SEQ ID NO 279
<211> LENGTH: 16
<212> TYPE: DNA
<213> ORGANISM: Human immunodeficiency virus 1

<400> SEQUENCE: 279
atccactgac cttaag 16

<210> SEQ ID NO 280
<211> LENGTH: 16
<212> TYPE: DNA
<213> ORGANISM: Human immunodeficiency virus 1

<400> SEQUENCE: 280
atccactgac cttcag 16

<210> SEQ ID NO 281
<211> LENGTH: 16
<212> TYPE: DNA
<213> ORGANISM: Human immunodeficiency virus 1

<400> SEQUENCE: 281
atccactgac cttcag 16

<210> SEQ ID NO 282
<211> LENGTH: 16
<212> TYPE: DNA
<213> ORGANISM: Human immunodeficiency virus 1

<400> SEQUENCE: 282
atccactgac cttgag 16

<210> SEQ ID NO 283
<211> LENGTH: 16
<212> TYPE: DNA
<213> ORGANISM: Human immunodeficiency virus 1

<400> SEQUENCE: 283
atccactgac cttgag 16

<210> SEQ ID NO 284
<211> LENGTH: 15
<212> TYPE: DNA
<213> ORGANISM: Human immunodeficiency virus 1

<400> SEQUENCE: 284
tccactgacc ttagg 15

<210> SEQ ID NO 285
<211> LENGTH: 15
<212> TYPE: DNA
<213> ORGANISM: Human immunodeficiency virus 1

<400> SEQUENCE: 285
tccactgacc ttagg 15

<210> SEQ ID NO 286
<211> LENGTH: 15
<212> TYPE: DNA
<213> ORGANISM: Human immunodeficiency virus 1

<400> SEQUENCE: 286
tccactgacc ttagg 15

<210> SEQ ID NO 287
<211> LENGTH: 15
<212> TYPE: DNA
<213> ORGANISM: Human immunodeficiency virus 1

<400> SEQUENCE: 287
tccactgacc ttagg 15

<210> SEQ ID NO 288
<211> LENGTH: 15
<212> TYPE: DNA
<213> ORGANISM: Human immunodeficiency virus 1

<400> SEQUENCE: 288
tccactgacc ttagg 15

<210> SEQ ID NO 289
<211> LENGTH: 15
<212> TYPE: DNA
<213> ORGANISM: Human immunodeficiency virus 1

<400> SEQUENCE: 289
tccactgacc ttagg 15

<210> SEQ ID NO 290
<211> LENGTH: 15
<212> TYPE: DNA
<213> ORGANISM: Human immunodeficiency virus 1

<400> SEQUENCE: 290
tccactgacc ttggg 15

<210> SEQ ID NO 291
<211> LENGTH: 15
<212> TYPE: DNA
<213> ORGANISM: Human immunodeficiency virus 1

<400> SEQUENCE: 291
tccactgacc ttggg 15

<210> SEQ ID NO 292
<211> LENGTH: 15
<212> TYPE: DNA
<213> ORGANISM: Human immunodeficiency virus 1

<400> SEQUENCE: 292
tccactgacc ttggg 15

<210> SEQ ID NO 293
<211> LENGTH: 15
<212> TYPE: DNA
<213> ORGANISM: Human immunodeficiency virus 1

<400> SEQUENCE: 293
tccactgacc ttggg 15

<210> SEQ ID NO 294
<211> LENGTH: 15
<212> TYPE: DNA
<213> ORGANISM: Human immunodeficiency virus 1

<400> SEQUENCE: 294
tccactgacc ttggg 15

<210> SEQ ID NO 295
<211> LENGTH: 15
<212> TYPE: DNA
<213> ORGANISM: Human immunodeficiency virus 1

<400> SEQUENCE: 295
tccactgacc ttggg 15

<210> SEQ ID NO 296
<211> LENGTH: 15
<212> TYPE: DNA
<213> ORGANISM: Human immunodeficiency virus 1

<400> SEQUENCE: 296
tccactgacc ttggg 15

<210> SEQ ID NO 297
<211> LENGTH: 15
<212> TYPE: DNA
<213> ORGANISM: Human immunodeficiency virus 1

<400> SEQUENCE: 297
tccactgacc ttggg 15

<210> SEQ ID NO 298
<211> LENGTH: 15
<212> TYPE: DNA
<213> ORGANISM: Human immunodeficiency virus 1

<400> SEQUENCE: 298
tccactgacc tttgg 15

<210> SEQ ID NO 299
<211> LENGTH: 15
<212> TYPE: DNA
<213> ORGANISM: Human immunodeficiency virus 1

<400> SEQUENCE: 299
tccactgacc tttgg 15

<210> SEQ ID NO 300
<211> LENGTH: 15
<212> TYPE: DNA
<213> ORGANISM: Human immunodeficiency virus 1

-continued

<400> SEQUENCE: 300
tccactgacc tttgg 15

<210> SEQ ID NO 301
<211> LENGTH: 15
<212> TYPE: DNA
<213> ORGANISM: Human immunodeficiency virus 1

<400> SEQUENCE: 301
tccactgacc tttgg 15

<210> SEQ ID NO 302
<211> LENGTH: 15
<212> TYPE: DNA
<213> ORGANISM: Human immunodeficiency virus 1

<400> SEQUENCE: 302
tccactgacc tttgg 15

<210> SEQ ID NO 303
<211> LENGTH: 15
<212> TYPE: DNA
<213> ORGANISM: Human immunodeficiency virus 1

<400> SEQUENCE: 303
tccactgacc tttgg 15

<210> SEQ ID NO 304
<211> LENGTH: 15
<212> TYPE: DNA
<213> ORGANISM: Human immunodeficiency virus 1

<400> SEQUENCE: 304
tccactgacc tttgg 15

<210> SEQ ID NO 305
<211> LENGTH: 15
<212> TYPE: DNA
<213> ORGANISM: Human immunodeficiency virus 1

<400> SEQUENCE: 305
tccactgacc tttgg 15

<210> SEQ ID NO 306
<211> LENGTH: 15
<212> TYPE: DNA
<213> ORGANISM: Human immunodeficiency virus 1

<400> SEQUENCE: 306
tccactgacc tttgg 15

<210> SEQ ID NO 307
<211> LENGTH: 15
<212> TYPE: DNA
<213> ORGANISM: Human immunodeficiency virus 1

<400> SEQUENCE: 307
tccactgacc ttaag 15

<210> SEQ ID NO 308
<211> LENGTH: 15
<212> TYPE: DNA
<213> ORGANISM: Human immunodeficiency virus 1

<400> SEQUENCE: 308
tccactgacc ttaag 15

<210> SEQ ID NO 309
<211> LENGTH: 15
<212> TYPE: DNA
<213> ORGANISM: Human immunodeficiency virus 1

<400> SEQUENCE: 309
tccactgacc ttaag 15

<210> SEQ ID NO 310
<211> LENGTH: 15
<212> TYPE: DNA
<213> ORGANISM: Human immunodeficiency virus 1

<400> SEQUENCE: 310
tccactgacc ttaag 15

<210> SEQ ID NO 311
<211> LENGTH: 15
<212> TYPE: DNA
<213> ORGANISM: Human immunodeficiency virus 1

<400> SEQUENCE: 311
tccactgacc ttaag 15

<210> SEQ ID NO 312
<211> LENGTH: 15
<212> TYPE: DNA
<213> ORGANISM: Human immunodeficiency virus 1

<400> SEQUENCE: 312
tccactgacc ttcag 15

<210> SEQ ID NO 313
<211> LENGTH: 15
<212> TYPE: DNA
<213> ORGANISM: Human immunodeficiency virus 1

<400> SEQUENCE: 313
tccactgacc ttcag 15

<210> SEQ ID NO 314
<211> LENGTH: 15
<212> TYPE: DNA
<213> ORGANISM: Human immunodeficiency virus 1

<400> SEQUENCE: 314
tccactgacc ttcag 15

<210> SEQ ID NO 315
<211> LENGTH: 15
<212> TYPE: DNA
<213> ORGANISM: Human immunodeficiency virus 1

<400> SEQUENCE: 315
tccactgacc ttcag 15

<210> SEQ ID NO 316
<211> LENGTH: 15
<212> TYPE: DNA

<213> ORGANISM: Human immunodeficiency virus 1

<400> SEQUENCE: 316
tccactgacc ttcag 15

<210> SEQ ID NO 317
<211> LENGTH: 15
<212> TYPE: DNA
<213> ORGANISM: Human immunodeficiency virus 1

<400> SEQUENCE: 317
tccactgacc ttcag 15

<210> SEQ ID NO 318
<211> LENGTH: 15
<212> TYPE: DNA
<213> ORGANISM: Human immunodeficiency virus 1

<400> SEQUENCE: 318
tccactgacc ttcag 15

<210> SEQ ID NO 319
<211> LENGTH: 15
<212> TYPE: DNA
<213> ORGANISM: Human immunodeficiency virus 1

<400> SEQUENCE: 319
tccactgacc ttcag 15

<210> SEQ ID NO 320
<211> LENGTH: 15
<212> TYPE: DNA
<213> ORGANISM: Human immunodeficiency virus 1

<400> SEQUENCE: 320
tccactgacc ttcag 15

<210> SEQ ID NO 321
<211> LENGTH: 15
<212> TYPE: DNA
<213> ORGANISM: Human immunodeficiency virus 1

<400> SEQUENCE: 321
tccactgacc ttcag 15

<210> SEQ ID NO 322
<211> LENGTH: 15
<212> TYPE: DNA
<213> ORGANISM: Human immunodeficiency virus 1

<400> SEQUENCE: 322
tccactgacc ttcag 15

<210> SEQ ID NO 323
<211> LENGTH: 15
<212> TYPE: DNA
<213> ORGANISM: Human immunodeficiency virus 1

<400> SEQUENCE: 323
tccactgacc ttcag 15

<210> SEQ ID NO 324
<211> LENGTH: 15

<212> TYPE: DNA
<213> ORGANISM: Human immunodeficiency virus 1

<400> SEQUENCE: 324
tccactgacc ttgag 15

<210> SEQ ID NO 325
<211> LENGTH: 15
<212> TYPE: DNA
<213> ORGANISM: Human immunodeficiency virus 1

<400> SEQUENCE: 325
tccactgacc ttgag 15

<210> SEQ ID NO 326
<211> LENGTH: 15
<212> TYPE: DNA
<213> ORGANISM: Human immunodeficiency virus 1

<400> SEQUENCE: 326
tccactgacc ttgag 15

<210> SEQ ID NO 327
<211> LENGTH: 15
<212> TYPE: DNA
<213> ORGANISM: Human immunodeficiency virus 1

<400> SEQUENCE: 327
tccactgacc ttgag 15

<210> SEQ ID NO 328
<211> LENGTH: 15
<212> TYPE: DNA
<213> ORGANISM: Human immunodeficiency virus 1

<400> SEQUENCE: 328
tccactgacc ttgag 15

<210> SEQ ID NO 329
<211> LENGTH: 15
<212> TYPE: DNA
<213> ORGANISM: Human immunodeficiency virus 1

<400> SEQUENCE: 329
tccactgacc ttgag 15

<210> SEQ ID NO 330
<211> LENGTH: 15
<212> TYPE: DNA
<213> ORGANISM: Human immunodeficiency virus 1

<400> SEQUENCE: 330
tccactgacc ttgag 15

<210> SEQ ID NO 331
<211> LENGTH: 15
<212> TYPE: DNA
<213> ORGANISM: Human immunodeficiency virus 1

<400> SEQUENCE: 331
tccactgacc ttgag 15

<210> SEQ ID NO 332

<211> LENGTH: 15
<212> TYPE: DNA
<213> ORGANISM: Human immunodeficiency virus 1

<400> SEQUENCE: 332
tccactgacc ttgag 15

<210> SEQ ID NO 333
<211> LENGTH: 15
<212> TYPE: DNA
<213> ORGANISM: Human immunodeficiency virus 1

<400> SEQUENCE: 333
tccactgacc tttag 15

<210> SEQ ID NO 334
<211> LENGTH: 15
<212> TYPE: DNA
<213> ORGANISM: Human immunodeficiency virus 1

<400> SEQUENCE: 334
tccactgacc tttag 15

<210> SEQ ID NO 335
<211> LENGTH: 15
<212> TYPE: DNA
<213> ORGANISM: Human immunodeficiency virus 1

<400> SEQUENCE: 335
tccactgacc tttag 15

<210> SEQ ID NO 336
<211> LENGTH: 15
<212> TYPE: DNA
<213> ORGANISM: Human immunodeficiency virus 1

<400> SEQUENCE: 336
tccactgacc tttag 15

<210> SEQ ID NO 337
<211> LENGTH: 15
<212> TYPE: DNA
<213> ORGANISM: Human immunodeficiency virus 1

<400> SEQUENCE: 337
tccactgacc tttag 15

<210> SEQ ID NO 338
<211> LENGTH: 23
<212> TYPE: DNA
<213> ORGANISM: Human immunodeficiency virus 1

<400> SEQUENCE: 338
cagcagttct tgaagtactc cgg 23

<210> SEQ ID NO 339
<211> LENGTH: 22
<212> TYPE: DNA
<213> ORGANISM: Human immunodeficiency virus 1

<400> SEQUENCE: 339
agcagttctt gaagtactcc gg 22

<210> SEQ ID NO 340
<211> LENGTH: 21
<212> TYPE: DNA
<213> ORGANISM: Human immunodeficiency virus 1

<400> SEQUENCE: 340
gcagttcttg aagtactccg g 21

<210> SEQ ID NO 341
<211> LENGTH: 20
<212> TYPE: DNA
<213> ORGANISM: Human immunodeficiency virus 1

<400> SEQUENCE: 341
cagttcttga agtactccgg 20

<210> SEQ ID NO 342
<211> LENGTH: 19
<212> TYPE: DNA
<213> ORGANISM: Human immunodeficiency virus 1

<400> SEQUENCE: 342
agttcttgaa gtactccgg 19

<210> SEQ ID NO 343
<211> LENGTH: 18
<212> TYPE: DNA
<213> ORGANISM: Human immunodeficiency virus 1

<400> SEQUENCE: 343
gttcttgaag tactccgg 18

<210> SEQ ID NO 344
<211> LENGTH: 17
<212> TYPE: DNA
<213> ORGANISM: Human immunodeficiency virus 1

<400> SEQUENCE: 344
ttcttgaagt actccgg 17

<210> SEQ ID NO 345
<211> LENGTH: 16
<212> TYPE: DNA
<213> ORGANISM: Human immunodeficiency virus 1

<400> SEQUENCE: 345
tcttgaagta ctccgg 16

<210> SEQ ID NO 346
<211> LENGTH: 16
<212> TYPE: DNA
<213> ORGANISM: Human immunodeficiency virus 1

<400> SEQUENCE: 346
tcttgaagta ctctag 16

<210> SEQ ID NO 347
<211> LENGTH: 15
<212> TYPE: DNA
<213> ORGANISM: Human immunodeficiency virus 1

<400> SEQUENCE: 347
cttgaagtac tcagg 15

<210> SEQ ID NO 348
<211> LENGTH: 15
<212> TYPE: DNA
<213> ORGANISM: Human immunodeficiency virus 1

<400> SEQUENCE: 348
cttgaagtac tcagg 15

<210> SEQ ID NO 349
<211> LENGTH: 15
<212> TYPE: DNA
<213> ORGANISM: Human immunodeficiency virus 1

<400> SEQUENCE: 349
cttgaagtac tcagg 15

<210> SEQ ID NO 350
<211> LENGTH: 15
<212> TYPE: DNA
<213> ORGANISM: Human immunodeficiency virus 1

<400> SEQUENCE: 350
cttgaagtac tcagg 15

<210> SEQ ID NO 351
<211> LENGTH: 15
<212> TYPE: DNA
<213> ORGANISM: Human immunodeficiency virus 1

<400> SEQUENCE: 351
cttgaagtac tccgg 15

<210> SEQ ID NO 352
<211> LENGTH: 15
<212> TYPE: DNA
<213> ORGANISM: Human immunodeficiency virus 1

<400> SEQUENCE: 352
cttgaagtac tctgg 15

<210> SEQ ID NO 353
<211> LENGTH: 15
<212> TYPE: DNA
<213> ORGANISM: Human immunodeficiency virus 1

<400> SEQUENCE: 353
cttgaagtac tcaag 15

<210> SEQ ID NO 354
<211> LENGTH: 15
<212> TYPE: DNA
<213> ORGANISM: Human immunodeficiency virus 1

<400> SEQUENCE: 354
cttgaagtac tcaag 15

<210> SEQ ID NO 355
<211> LENGTH: 15
<212> TYPE: DNA
<213> ORGANISM: Human immunodeficiency virus 1

<400> SEQUENCE: 355
cttgaagtac tcaag 15

<210> SEQ ID NO 356
<211> LENGTH: 15
<212> TYPE: DNA
<213> ORGANISM: Human immunodeficiency virus 1

<400> SEQUENCE: 356
cttgaagtac tcaag 15

<210> SEQ ID NO 357
<211> LENGTH: 15
<212> TYPE: DNA
<213> ORGANISM: Human immunodeficiency virus 1

<400> SEQUENCE: 357
cttgaagtac tcaag 15

<210> SEQ ID NO 358
<211> LENGTH: 15
<212> TYPE: DNA
<213> ORGANISM: Human immunodeficiency virus 1

<400> SEQUENCE: 358
cttgaagtac tccag 15

<210> SEQ ID NO 359
<211> LENGTH: 15
<212> TYPE: DNA
<213> ORGANISM: Human immunodeficiency virus 1

<400> SEQUENCE: 359
cttgaagtac tccag 15

<210> SEQ ID NO 360
<211> LENGTH: 15
<212> TYPE: DNA
<213> ORGANISM: Human immunodeficiency virus 1

<400> SEQUENCE: 360
cttgaagtac tccag 15

<210> SEQ ID NO 361
<211> LENGTH: 15
<212> TYPE: DNA
<213> ORGANISM: Human immunodeficiency virus 1

<400> SEQUENCE: 361
cttgaagtac tccag 15

<210> SEQ ID NO 362
<211> LENGTH: 15
<212> TYPE: DNA
<213> ORGANISM: Human immunodeficiency virus 1

<400> SEQUENCE: 362
cttgaagtac tctag 15

<210> SEQ ID NO 363
<211> LENGTH: 15
<212> TYPE: DNA
<213> ORGANISM: Human immunodeficiency virus 1

<400> SEQUENCE: 363
cttgaagtac tctag 15

<210> SEQ ID NO 364
<211> LENGTH: 23
<212> TYPE: DNA
<213> ORGANISM: Human immunodeficiency virus 1

<400> SEQUENCE: 364
gatctgtgga tctaccacac aca 23

<210> SEQ ID NO 365
<211> LENGTH: 26
<212> TYPE: DNA
<213> ORGANISM: Human immunodeficiency virus 1

<400> SEQUENCE: 365
gatctgtgga tctaccacac acaagg 26

<210> SEQ ID NO 366
<211> LENGTH: 20
<212> TYPE: DNA
<213> ORGANISM: Human immunodeficiency virus 1

<400> SEQUENCE: 366
gattggcaga actacacacc 20

<210> SEQ ID NO 367
<211> LENGTH: 23
<212> TYPE: DNA
<213> ORGANISM: Human immunodeficiency virus 1

<400> SEQUENCE: 367
gattggcaga actacacacc agg 23

<210> SEQ ID NO 368
<211> LENGTH: 27
<212> TYPE: DNA
<213> ORGANISM: Human immunodeficiency virus 1

<400> SEQUENCE: 368
gccagggatc agatatccac tgacctt 27

<210> SEQ ID NO 369
<211> LENGTH: 30
<212> TYPE: DNA
<213> ORGANISM: Human immunodeficiency virus 1

<400> SEQUENCE: 369
gccagggatc agatatccac tgacctttgg 30

<210> SEQ ID NO 370
<211> LENGTH: 30
<212> TYPE: DNA
<213> ORGANISM: Human immunodeficiency virus 1

<400> SEQUENCE: 370
gagtacttca agaactgctg acatcgagct 30

<210> SEQ ID NO 371
<211> LENGTH: 33
<212> TYPE: DNA
<213> ORGANISM: Human immunodeficiency virus 1

<400> SEQUENCE: 371
ccggagtact tcaagaactg ctgacatcga gct 33

<210> SEQ ID NO 372
<211> LENGTH: 20
<212> TYPE: DNA
<213> ORGANISM: Human immunodeficiency virus 1

<400> SEQUENCE: 372
gcgtggcctg ggcgggactg 20

<210> SEQ ID NO 373
<211> LENGTH: 23
<212> TYPE: DNA
<213> ORGANISM: Human immunodeficiency virus 1

<400> SEQUENCE: 373
gcgtggcctg ggcgggactg ggg 23

<210> SEQ ID NO 374
<211> LENGTH: 22
<212> TYPE: DNA
<213> ORGANISM: Human immunodeficiency virus 1

<400> SEQUENCE: 374
tcagatgctg catataagca gc 22

<210> SEQ ID NO 375
<211> LENGTH: 25
<212> TYPE: DNA
<213> ORGANISM: Human immunodeficiency virus 1

<400> SEQUENCE: 375
ccctcagatg ctgcatataa gcagc 25

<210> SEQ ID NO 376
<211> LENGTH: 634
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 376
tggaagggct aattcactcc caacgaagac aagatatcct tgatctgtgg atctaccaca 60
cacaaggcta cttccctgat tggcagaact acacaccagg gccagggatc agatatccac 120
tgacctttgg atggtgctac aagctagtac cagttgagca agagaaggta gaagaagcca 180
atgaaggaga gaacacccgc ttgttacacc ctgtgagcct gcatgggatg gatgacccgg 240
agagagaagt attagagtgg aggtttgaca gccgcctagc atttcatcac atggcccgag 300
agctgcatcc ggagtacttc aagaactgct gacatcgagc ttgctacaag ggactttccg 360
ctggggactt tccagggagg cgtggcctgg gcgggactgg ggagtggcga gccctcagat 420
gctgcatata agcagctgct ttttgcttgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agca 634

<210> SEQ ID NO 377
<211> LENGTH: 453

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 377
tggaagggct aattcactcc caacgaagac aagatatcct tgatctgtgg atctaccaca 60
cacaaggcta cttccctgat tggcagaact acacaccagg gccagggatc agatatccac 120
tgacctttgg atggtgctac aagctagtac cagttgagca agagaaggta gaagaagcca 180
atgaaggaga gaacacccgc ttgttacacc ctgtgagcct gcatgggatg gatgacccgg 240
agagagaagt attagagtgg aggtttgaca gccgcctagc atttcatcac atggcccgag 300
agctgcatcc ggagtacttc aagaactgct gacatcgagc ttgctacaag ggactttccg 360
ctggggactt tccagggagg cgtggcctgg gcgggactgg ggagtggcga gccctcagat 420
gctgcatata agcagctgct ttttgcttgt act 453

<210> SEQ ID NO 378
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 378
gggtctctct ggttagacca gatctgagcc tgggagctct ctggctaact agggaaccca 60
ctgcttaagc ctcaataaag cttgccttga gtgcttc 97

<210> SEQ ID NO 379
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 379
aagtagtgtg tgcccgtctg ttgtgtgact ctggtaacta gagatccctc agaccctttt 60
agtcagtgtg gaaaatctct agca 84

<210> SEQ ID NO 380
<211> LENGTH: 818
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 380
tggaagggat ttattacagt gcaagaagac atagaatctt agacatatac ttagaaaagg 60
aagaaggcat cataccagat tggcaggatt acacctcagg accaggaatt agatacccaa 120
agacatttgg ctggctatgg aaattagtcc ctgtaaatgt atcagatgag gcacaggagg 180
atgaggagca ttatttaatg catccagctc aaacttccca gtgggatgac ccttggggag 240
aggttctagc atggaagttt gatccaactc tggcctacac ttatgaggca tatgttagat 300
acccagaaga gtttggaagc aagtcaggcc tgtcagagga agaggttaga agaaggctaa 360
ccgcaagagg ccttcttaac atggctgaca agaaggaaac tcgctgaaac agcagggact 420
ttccacaagg ggatgttacg gggaggtact ggggaggagc cggtcgggaa cgcccacttt 480
cttgatgtat aaatatcact gcatttcgct ctgtattcag tcgctctgcg gagaggctgg 540
cagattgagc cctgggaggt tctctccagc actagcaggt agagcctggg tgttccctgc 600
tagactctca ccagcacttg gccggtgctg ggcagagtga ctccacgctt gcttgcttaa 660
agccctcttc aataaagctg ccattttaga agtaagctag tgtgtgttcc catctctcct 720
agccgccgcc tggtcaactc ggtactcaat aataagaaga ccctggtctg ttaggaccct 780
ttctgctttg ggaaaccgaa gcaggaaaat ccctagca 818

<210> SEQ ID NO 381
<211> LENGTH: 517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 381
tggaagggat ttattacagt gcaagaagac atagaatctt agacatatac ttagaaaagg 60
aagaaggcat cataccagat tggcaggatt acacctcagg accaggaatt agatacccaa 120
agacatttgg ctggctatgg aaattagtcc ctgtaaatgt atcagatgag gcacaggagg 180
atgaggagca ttatttaatg catccagctc aaacttccca gtgggatgac ccttggggag 240
aggttctagc atggaagttt gatccaactc tggcctacac ttatgaggca tatgttagat 300
acccagaaga gtttggaagc aagtcaggcc tgtcagagga agaggttaga agaaggctaa 360
ccgcaagagg ccttcttaac atggctgaca agaaggaaac tcgctgaaac agcagggact 420
ttccacaagg ggatgttacg gggaggtact ggggaggagc cggtcgggaa cgcccacttt 480
cttgatgtat aaatatcact gcatttcgct ctgtatt 517

<210> SEQ ID NO 382
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 382
cagtcgctct gcggagaggc tggcagattg agccctggga ggttctctcc agcactagca 60
ggtagagcct gggtgttccc tgctagactc tcaccagcac ttggccggtg ctgggcagag 120
tgactccacg cttgcttgct taaagccctc ttcaataaag ctgccatttt agaagt 176

<210> SEQ ID NO 383
<211> LENGTH: 125
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 383
aagctagtgt gtgttcccat ctctcctagc cgccgcctgg tcaactcggt actcaataat 60
aagaagaccc tggtctgtta ggaccctttc tgctttggga aaccgaagca ggaaaatccc 120
tagca 125

<210> SEQ ID NO 384

-continued

<211> LENGTH: 14825
<212> TYPE: DNA
<213> ORGANISM: Human immunodeficiency virus 1

<400> SEQUENCE: 384
tggaagggct aatttggtcc caaaaaagac aagagatcct tgatctgtgg atctaccaca 60
cacaaggcta cttccctgat tggcagaact acacaccagg gccagggatc agatatccac 120
tgacctttgg atggtgcttc aagttagtac cagttgaacc agagcaagta gaagaggcca 180
atgaaggaga gaacaacagc ttgttacacc ctatgagcca gcatgggatg gaggacccgg 240
agggagaagt attagtgtgg aagtttgaca gcctcctagc atttcgtcac atggcccgag 300
agctgcatcc ggagtactac aaagactgct gacatcgagc tttctacaag ggactttccg 360
ctggggactt tccagggagg tgtggcctgg gcgggactgg ggagtggcga gccctcagat 420
gctacatata agcagctgct tttgcctgt actgggtctc tctggttaga ccagatctga 480
gcctgggagc tctctggcta actagggaac ccactgctta agcctcaata aagcttgcct 540
tgagtgctca aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagtaaa gccagaggag atctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcggta ttaagcgggg gagaattaga taaatgggaa 840
aaaattcggt taaggccagg gggaaagaaa caatataaac taaaacatat agtatgggca 900
agcagggagc tagaacgatt cgcagttaat cctggccttt tagagacatc agaaggctgt 960
agacaaatac tgggacagct acaaccatcc cttcagacag gatcagaaga acttagatca 1020
ttatataata caatagcagt cctctattgt gtgcatcaaa ggatagatgt aaaagacacc 1080
aaggaagcct tagataagat agaggaagag caaaacaaaa gtaagaaaaa ggcacagcaa 1140
gcagcagctg acacaggaaa caacagccag gtcagccaaa attaccctat agtgcagaac 1200
ctccaggggc aaatggtaca tcaggccata tcacctagaa ctttaaatgc atgggtaaaa 1260
gtagtagaag agaaggcttt cagcccagaa gtaataccca tgttttcagc attatcagaa 1320
ggagccaccc cacaagattt aaataccatg ctaaacacag tgggggggaca tcaagcagcc 1380 atgcaaatgt taaaagagac catcaatgag gaagctgcag aatgggatag attgcatcca 1440
gtgcatgcag ggcctattgc accaggccag atgagagaac caaggggaag tgacatagca 1500
ggaactacta gtacccttca ggaacaaata ggatggatga cacataatcc acctatccca 1560
gtaggagaaa tctataaaag atggataatc ctgggattaa ataaaatagt aagaatgtat 1620
agccctacca gcattctgga cataagacaa ggaccaaagg aaccctttag agactatgta 1680
gaccgattct ataaaactct aagagccgag caagcttcac aagaggtaaa aaattggatg 1740
acagaaacct tgttggtcca aaatgcgaac ccagattgta agactatttt aaaagcattg 1800
ggaccaggag cgacactaga agaaatgatg acagcatgtc agggagtggg gggacccggc 1860
cataaagcaa gagttttggc tgaagcaatg agccaagtaa caaatccagc taccataatg 1920
atacagaaag gcaattttag gaaccaaaga aagactgtta agtgtttcaa ttgtggcaaa 1980
gaagggcaca tagccaaaaa ttgcagggcc cctaggaaaa agggctgttg gaaatgtgga 2040
aaggaaggac accaaatgaa agattgtact gagagacagg ctaatttttt agggaagatc 2100
tggccttccc acaagggaag gccagggaat tttcttcaga gcagaccaga gccaacagcc 2160
ccaccagaag agagcttcag gtttggggaa gagacaacaa ctccctctca gaagcaggag 2220

```
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta agacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaagta tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagataaat   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
```

-continued aaacagtaca tacagacaat ggcagcaatt tcaccagtac tacagttaag gccgcctgtt 4620
ggtgggcggg gatcaagcag gaatttggca ttccctacaa tccccaaagt caaggagtaa 4680
tagaatctat gaataaagaa ttaaagaaaa ttataggaca ggtaagagat caggctgaac 4740
atcttaagac agcagtacaa atggcagtat tcatccacaa ttttaaaaga aaagggggga 4800
ttggggggta cagtgcaggg gaaagaatag tagacataat agcaacagac atacaaacta 4860
aagaattaca aaaacaaatt acaaaaattc aaaattttcg ggtttattac agggacagca 4920
gagatccagt ttggaaagga ccagcaaagc tcctctggaa aggtgaaggg gcagtagtaa 4980
tacaagataa tagtgacata aaagtagtgc caagaagaaa agcaaagatc atcagggatt 5040
atggaaaaca gatggcaggt gatgattgtg tggcaagtag acaggatgag gattaacaca 5100
tggaaaagat tagtaaaaca ccatatgtat atttcaagga aagctaagga ctggttttat 5160
agacatcact atgaaagtac taatccaaaa ataagttcag aagtacacat cccactaggg 5220
gatgctaaat tagtaataac aacatattgg ggtctgcata caggagaaag agactggcat 5280
ttgggtcagg gagtctccat agaatggagg aaaaagagat atagcacaca agtagaccct 5340
gacctagcag accaactaat tcatctgcac tattttgatt gtttttcaga atctgctata 5400
agaaatacca tattaggacg tatagttagt cctaggtgtg aatatcaagc aggacataac 5460
aaggtaggat ctctacagta cttggcacta gcagcattaa taaaaccaaa acagataaag 5520
ccacctttgc ctagtgttag gaaactgaca gaggacagat ggaacaagcc ccagaagacc 5580
aagggccaca gagggagcca tacaatgaat ggacactaga gcttttagag gaacttaaga 5640
gtgaagctgt tagacatttt cctaggatat ggctccataa cttaggacaa catatctatg 5700
aaacttacgg ggatacttgg gcaggagtgg aagccataat aagaattctg caacaactgc 5760
tgtttatcca tttcagaatt gggtgtcgac atagcagaat aggcgttact cgacagagga 5820
gagcaagaaa tggagccagt agatcctaga ctagagccct ggaagcatcc aggaagtcag 5880
cctaaaactg cttgtaccaa ttgctattgt aaaaagtgtt gctttcattg ccaagtttgt 5940
ttcatgacaa aagccttagg catctcctat ggcaggaaga agcggagaca gcgacgaaga 6000
gctcatcaga acagtcagac tcatcaagct tctctatcaa agcagtaagt agtacatgta 6060
atgcaaccta taatagtagc aatagtagca ttagtagtag caataataat agcaatagtt 6120
gtgtggtcca tagtaatcat agaatatagg aaaatattaa gacaaagaaa aatagacagg 6180
ttaattgata gactaataga aagagcagaa gacagtggca atgagagtga aggagaagta 6240
tcagcacttg tggagatggg ggtggaaatg gggcaccatg ctccttggga tattgatgat 6300
ctgtagtgct acagaaaaat tgtgggtcac agtctattat ggggtacctg tgtggaagga 6360
agcaaccacc actctatttt gtgcatcaga tgctaaagca tatgatacag aggtacataa 6420
tgtttgggcc acacatgcct gtgtacccac agaccccaac ccacaagaag tagtattggt 6480
aaatgtgaca gaaaatttta acatgtggaa aaatgacatg gtagaacaga tgcatgagga 6540
tataatcagt ttatgggatc aaagcctaaa gccatgtgta aaattaaccc cactctgtgt 6600
tagtttaaag tgcactgatt tgaagaatga tactaatacc aatagtagta gcgggagaat 6660
gataatggag aaaggagaga taaaaaactg ctctttcaat atcagcacaa gcataagaga 6720
taaggtgcag aaagaatatg cattctttta taaacttgat atagtaccaa tagataatac 6780
cagctatagg ttgataagtt gtaacacctc agtcattaca caggcctgtc caaaggtatc 6840
ctttgagcca attcccatac attattgtgc cccggctggt tttgcgattc taaaatgtaa 6900
taataagacg ttcaatggaa caggaccatg tacaaatgtc agcacagtac aatgtacaca 6960
tggaatcagg ccagtagtat caactcaact gctgttaaat ggcagtctag cagaagaaga 7020
tgtagtaatt agatctgcca atttcacaga caatgctaaa accataatag tacagctgaa 7080
cacatctgta gaaattaatt gtacaagacc caacaacaat acaagaaaaa gtatccgtat 7140
ccagagggga ccagggagag catttgttac aataggaaaa ataggaaata tgagacaagc 7200
acattgtaac attagtagag caaaatggaa tgccacttta aaacagatag ctagcaaatt 7260
aagagaacaa tttggaaata ataaaacaat aatctttaag caatcctcag gaggggaccc 7320
agaaattgta acgcacagtt ttaattgtgg aggggaattt ttctactgta attcaacaca 7380
actgtttaat agtacttggt ttaatagtac ttggagtact gaagggtcaa ataacactga 7440
aggaagtgac acaatcacac tcccatgcag aataaaacaa tttataaaca tgtggcagga 7500
agtaggaaaa gcaatgtatg cccctcccat cagtggacaa attagatgtt catcaaatat 7560
tactgggctg ctattaacaa gagatggtgg taataacaac aatgggtccg agatcttcag 7620
acctggagga ggcgatatga gggacaattg gagaagtgaa ttatataaat ataaagtagt 7680
aaaaattgaa ccattaggag tagcacccac caaggcaaag agaagagtgg tgcagagaga 7740
aaaaagagca gtgggaatag gagctttgtt ccttgggttc ttgggagcag caggaagcac 7800
tatgggcgca gcgtcaatga cgctgacggt acaggccaga caattattgt ctgatatagt 7860
gcagcagcag aacaatttgc tgagggctat tgaggcgcaa cagcatctgt tgcaactcac 7920
agtctggggc atcaaacagc tccaggcaag aatcctggct gtggaaagat acctaaagga 7980
tcaacagctc ctggggattt ggggttgctc tggaaaactc atttgcacca ctgctgtgcc 8040
ttggaatgct agttggagta ataaatctct ggaacagatt tggaataaca tgacctggat 8100
ggagtgggac agagaaatta acaattacac aagcttaata cactccttaa ttgaagaatc 8160
gcaaaaccag caagaaaaga atgaacaaga attattggaa ttagataaat gggcaagttt 8220
gtggaattgg tttaacataa caaattggct gtggtatata aaattattca taatgatagt 8280
aggaggcttg gtaggtttaa gaatagtttt tgctgtactt tctatagtga atagagttag 8340
gcagggatat tcaccattat cgtttcagac ccacctccca atcccgaggg gacccgacag 8400
gcccgaagga atagaagaag aaggtggaga gagagacaga gacagatcca ttcgattagt 8460
gaacggatcc ttagcactta tctgggacga tctgcggagc ctgtgcctct tcagctacca 8520
ccgcttgaga gacttactct tgattgtaac gaggattgtg gaacttctgg gacgcagggg 8580
gtgggaagcc ctcaaatatt ggtggaatct cctacagtat tggagtcagg aactaaagaa 8640
tagtgctgtt aacttgctca atgccacagc catagcagta gctgagggga cagatagggt 8700
tatagaagta ttacaagcag cttatagagc tattcgccac atacctagaa gaataagaca 8760
gggcttggaa aggattttgc tataagatgg gtggcaagtg gtcaaaaagt agtgtgattg 8820
gatggcctgc tgtaagggaa agaatgagac gagctgagcc agcagcagat ggggtgggag 8880
cagtatctcg agacctagaa aaacatggag caatcacaag tagcaataca gcagctaaca 8940
atgctgcttg tgcctggcta gaagcacaag aggaggaaga ggtgggtttt ccagtcacac 9000
ctcaggtacc tttaagacca atgacttaca aggcagctgt agatcttagc cactttttaa 9060
aagaaaaggg gggactggaa gggctaattc actcccaaag aagacaagat atccttgatc 9120
tgtggatcta ccacacacaa ggctacttcc ctgattggca gaactacaca ccagggccag 9180
ggtcagata tccactgacc tttggatggt gctacaagct agtaccagtt gagccagata 9240
aggtagaaga ggccaataaa ggagagaaca ccagcttgtt acaccctgtg agcctgcatg 9300

```
gaatggatga ccctgagaga gaagtgttag agtggaggtt tgacagccgc ctagcatttc   9360
atcacgtggc ccgagagctg catccggagt acttcaagaa ctgctgacat cgagcttgct   9420
acaagggact ttccgctggg gactttccag ggaggcgtgg cctgggcggg actggggagt   9480
ggcgagccct cagatgctgc atataagcag ctgctttttg cctgtactgg gtctctctgg   9540
ttagaccaga tctgagcctg ggagctctct ggctaactag ggaacccact gcttaagcct   9600
caataaagct tgccttgagt gcttcaagta gtgtgtgccc gtctgttgtg tgactctggt   9660
aactagagat ccctcagacc cttttagtca gtgtggaaaa tctctagcac ccaggaggta   9720
gaggttgcag tgagccaaga tcgcgccact gcattccagc ctgggcaaga aaacaagact   9780
gtctaaaata ataataataa gttaagggta ttaaatatat ttatacatgg aggtcataaa   9840
aatatatata tttgggctgg gcgcagtggc tcacacctgc gcccggccct ttgggaggcc   9900
gaggcaggtg gatcacctga gtttgggagt tccagaccag cctgaccaac atggagaaac   9960
cccttctctg tgtattttta gtagatttta ttttatgtgt attttattca caggtatttc  10020
tggaaaactg aaactgtttt tcctctactc tgataccaca agaatcatca gcacagagga  10080
agacttctgt gatcaaatgt ggtgggagag ggaggttttc accagcacat gagcagtcag  10140
ttctgccgca gactcggcgg gtgtccttcg gttcagttcc aacaccgcct gcctggagag  10200
aggtcagacc acagggtgag ggctcagtcc ccaagacata aacacccaag acataaacac  10260
ccaacaggtc caccccgcct gctgcccagg cagagccgat tcaccaagac gggaattagg  10320
atagagaaag agtaagtcac acagagccgg ctgtgcggga gaacggagtt ctattatgac  10380
tcaaatcagt ctccccaagc attcggggat cagagttttt aaggataact tagtgtgtag  10440
ggggccagtg agttggagat gaaagcgtag ggagtcgaag gtgtcctttt gcgccgagtc  10500
agttcctggg tgggggccac aagatcggat gagccagttt atcaatccgg gggtgccagc  10560
tgatccatgg agtgcagggt ctgcaaaata tctcaagcac tgattgatct taggttttac  10620
aatagtgatg ttaccccagg aacaatttgg ggaaggtcag aatcttgtag cctgtagctg  10680
catgactcct aaaccataat ttcttttttg tttttttttt tttatttttg agacagggtc  10740
tcactctgtc acctaggctg gagtgcagtg gtgcaatcac agctcactgc agcctcaacg  10800
tcgtaagctc aagcgatcct cccacctcag cctgcctggt agctgagact acaagcgacg  10860
ccccagttaa tttttgtatt tttggtagag gcagcgtttt gccgtgtggc cctggctggt  10920
ctcgaactcc tgggctcaag tgatccagcc tcagcctccc aaagtgctgg gacaaccggg  10980
gccagtcact gcacctggcc ctaaaccata atttctaatc ttttggctaa tttgttagtc  11040
ctacaaaggc agtctagtcc ccaggcaaaa agggggtttg tttcgggaaa gggctgttac  11100
tgtctttgtt tcaaactata aactaagttc ctcctaaact tagttcggcc tacacccagg  11160
aatgaacaag gagagcttgg aggttagaag cacgatggaa ttggttaggt cagatctctt  11220
tcactgtctg agttataatt ttgcaatggt ggttcaaaga ctgcccgctt ctgacaccag  11280
tcgctgcatt aatgaatcgg ccaacgcgcg gggagaggcg gtttgcgtat tgggcgctct  11340
tccgcttcct cgctcactga ctcgctgcgc tcggtcgttc ggctgcggcg agcggtatca  11400
gctcactcaa aggcggtaat acggttatcc acagaatcag gggataacgc aggaaagaac  11460
atgtgagcaa aaggccagca aaaggccagg aaccgtaaaa aggccgcgtt gctggcgttt  11520
ttccataggc tccgcccccc tgacgagcat cacaaaaatc gacgctcaag tcagaggtgg  11580
cgaaacccga caggactata aagataccag gcgtttcccc ctggaagctc cctcgtgcgc  11640
tctcctgttc cgaccctgcc gcttaccgga tacctgtccg cctttctccc ttcgggaagc  11700
```

-continued

```
gtggcgcttt ctcatagctc acgctgtagg tatctcagtt cggtgtaggt cgttcgctcc  11760
aagctgggct gtgtgcacga accccccgtt cagcccgacc gctgcgcctt atccggtaac  11820
tatcgtcttg agtccaaccc ggtaagacac gacttatcgc cactggcagc agccactggt  11880
aacaggatta gcagagcgag gtatgtaggc ggtgctacag agttcttgaa gtggtggcct  11940
aactacggct acactagaag aacagtattt ggtatctgcg ctctgctgaa gccagttacc  12000
ttcggaaaaa gagttggtag ctcttgatcc ggcaaacaaa ccaccgctgg tagcggtggt  12060
tttttgttt gcaagcagca gattacgcgc agaaaaaaag gatctcaaga agatcctttg  12120
atcttttcta cggggtctga cgctcagtgg aacgaaaact cacgttaagg gattttggtc  12180
atgagattat caaaaaggat cttcacctag atccttttaa attaaaaatg aagttttaaa  12240
tcaatctaaa gtatatatga gtaaacttgg tctgacagtt accaatgctt aatcagtgag  12300
gcacctatct cagcgatctg tctatttcgt tcatccatag ttgcctgact ccccgtcgtg  12360
tagataacta cgatacggga gggcttacca tctggcccca gtgctgcaat gataccgcga  12420
gacccacgct caccggctcc agatttatca gcaataaacc agccagccgg aagggccgag  12480
cgcagaagtg gtcctgcaac tttatccgcc tccatccagt ctattaattg ttgccgggaa  12540
gctagagtaa gtagttcgcc agttaatagt ttgcgcaacg ttgttgccat tgctacaggc  12600
atcgtggtgt cacgctcgtc gtttggtatg gcttcattca gctccggttc ccaacgatca  12660
aggcgagtta catgatcccc catgttgtgc aaaaaagcgg ttagctcctt cggtcctccg  12720
atcgttgtca gaagtaagtt ggccgcagtg ttatcactca tggttatggc agcactgcat  12780
aattctctta ctgtcatgcc atccgtaaga tgcttttctg tgactggtga gtactcaacc  12840
aagtcattct gagaatagtg tatgcggcga ccgagttgct cttgcccggc gtcaatacgg  12900
gataataccg cgccacatag cagaacttta aaagtgctca tcattggaaa acgttcttcg  12960
gggcgaaaac tctcaaggat cttaccgctg ttgagatcca gttcgatgta acccactcgt  13020
gcacccaact gatcttcagc atcttttact ttcaccagcg tttctgggtg agcaaaaaca  13080
ggaaggcaaa atgccgcaaa aaagggaata agggcgacac ggaaatgttg aatactcata  13140
ctcttccttt ttcaatatta ttgaagcatt tatcagggtt attgtctcat gagcggatac  13200
atatttgaat gtatttagaa aaataaacaa ataggggttc cgcgcacatt tccccgaaaa  13260
gtgccacctg acgtctaaga aaccattatt atcatgacat taacctataa aaataggcgt  13320
atcacgaggc cctttcgtct cgcgcgtttc ggtgatgacg gtgaaaacct ctgacacatg  13380
cagctcccgg agacggtcac agcttgtctg taagcggatg ccgggagcag acaagcccgt  13440
cagggcgcgt cagcgggtgt tggcgggtgt cggggctggc ttaactatgc ggcatcagag  13500
cagattgtac tgagagtgca ccatatgcgg tgtgaaatac cgcacagatg cgtaaggaga  13560
aaataccgca tcaggcgcca ttcgccattc aggctgcgca actgttggga agggcgatcg  13620
gtgcgggcct cttcgctatt acgccagggg aggcagagat tgcagtaagc tgagatcgca  13680
gcactgcact ccagcctggg cgacagagta agactctgtc tcaaaaataa aataaataaa  13740
tcaatcagat attccaatct tttcctttat ttatttattt attttctatt ttggaaacac  13800
agtccttcct tattccagaa ttacacatat attctatttt tctttatatg ctccagtttt  13860
ttttagacct tcacctgaaa tgtgtgtata caaaatctag gccagtccag cagagcctaa  13920
aggtaaaaaa taaaataata aaaaataaat aaaatctagc tcactccttc acatcaaaat  13980
ggagatacag ctgttagcat taaataccaa ataacccatc ttgtcctcaa taattttaag  14040
```

```
cgcctctctc caccacatct aactcctgtc aaaggcatgt gccccttccg ggcgctctgc  14100

tgtgctgcca accaactggc atgtggactc tgcagggtcc ctaactgcca agccccacag  14160

tgtgccctga ggctgcccct tccttctagc ggctgccccc actcggcttt gctttcccta  14220

gtttcagtta cttgcgttca gccaaggtct gaaactaggt gcgcacagag cggtaagact  14280

gcgagagaaa gagaccagct ttacaggggg tttatcacag tgcaccctga cagtcgtcag  14340

cctcacaggg ggtttatcac attgcaccct gacagtcgtc agcctcacag gggggtttatc  14400

acagtgcacc cttacaatca ttccatttga ttcacaattt ttttagtctc tactgtgcct  14460

aacttgtaag ttaaatttga tcagaggtgt gttcccagag gggaaaacag tatatacagg  14520

gttcagtact atcgcatttc aggcctccac ctgggtcttg gaatgtgtcc cccgaggggt  14580

gatgactacc tcagttggat ctccacaggt cacagtgaca caagataacc aagacacctc  14640

ccaaggctac cacaatgggc cgccctccac gtgcacatgg ccggaggaac tgccatgtcg  14700

gaggtgcaag cacacctgcg catcagagtc cttggtgtgg agggagggac cagcgcagct  14760

tccagccatc cacctgatga acagaaccta gggaaagccc cagttctact tacaccagga  14820

aaggc                                                              14825
```

<210> SEQ ID NO 385
<211> LENGTH: 10535
<212> TYPE: DNA
<213> ORGANISM: Simian immunodeficiency virus

<400> SEQUENCE: 385

```
gcatgcacat tttaaaggct tttgctaaat atagccaaaa gtccttctac aaattttcta     60

agagttctga ttcaaagcag taacaggcct tgtctcatca tgaactttgg catttcatct    120

acagctaagt ttatatcata aatagttctt tacaggcagc accaacttat acccttatag    180

catactttac tgtgtgaaaa ttgcatcttt cattaagctt actgtaaatt tactggctgt    240

cttccttgca ggtttctgga agggatttat tacagtgcaa gaagacatag aatcttagac    300

atatacttag aaaaggaaga aggcatcata ccagattggc aggattacac ctcaggacca    360

ggaattagat acccaaagac atttggctgg ctatggaaat tagtccctgt aaatgtatca    420

gatgaggcac aggaggatga ggagcattat ttaatgcatc cagctcaaac ttcccagtgg    480

gatgaccctt ggggagaggt tctagcatgg aagtttgatc caactctggc ctacacttat    540

gaggcatatg ttagataccc agaagagttt ggaagcaagt caggcctgtc agaggaagag    600

gttagaagaa ggctaaccgc aagaggcctt cttaacatgg ctgacaagaa ggaaactcgc    660

tgaaacagca gggactttcc acaaggggat gttacgggga ggtactgggg aggagccggt    720

cgggaacgcc cactttcttg atgtataaat atcactgcat ttcgctctgt attcagtcgc    780

tctgcggaga ggctggcaga ttgagccctg ggaggttctc tccagcacta gcaggtagag    840

cctgggtgtt ccctgctaga ctctcaccag cacttggccg gtgctgggca gagtgactcc    900

acgcttgctt gcttaaagcc ctcttcaata aagctgccat tttagaagta agctagtgtg    960

tgttcccatc tctcctagcc gccgcctggt caactcggta ctcaataata agaagaccct   1020

ggtctgttag gaccctttct gctttgggaa accgaagcag gaaaatccct agcagattgg   1080

cgcctgaaca gggacttgaa ggagagtgag agactcctga gtacggctga gtgaaggcag   1140

taagggcggc aggaaccaac cacgacggag tgctcctata aaggcgcggg tcggtaccag   1200

acggcgtgag gagcgggaga ggaagaggcc tccggttgca ggtaagtgca acacaaaaaa   1260

gaaatagctg tcttttatcc aggaaggggt aataagatag agtgggagat gggcgtgaga   1320
```

```
aactccgtct tgtcagggaa gaaagcagat gaattagaaa aaattaggct acgacccaac   1380
ggaaagaaaa agtacatgtt gaagcatgta gtatgggcag caaatgaatt agatagattt   1440
ggattagcag aaagcctgtt ggagaacaaa gaaggatgtc aaaaaatact ttcggtctta   1500
gctccattag tgccaacagg ctcagaaaat ttaaaaagcc tttataatac tgtctgcgtc   1560
atctggtgca ttcacgcaga agagaaagtg aaacacactg aggaagcaaa acagatagtg   1620
cagagacacc tagtggtgga aacaggaaca acagaaacta tgccaaaaac aagtagacca   1680
acagcaccat ctagcggcag aggaggaaat tacccagtac aacaaatagg tggtaactat   1740
gtccacctgc cattaagccc gagaacatta aatgcctggg taaaattgat agaggaaaag   1800
aaatttggag cagaagtagt gccaggattt caggcactgt cagaaggttg cacccccctat   1860
gacattaatc agatgttaaa ttgtgtggga gaccatcaag cggctatgca gattatcaga   1920
gatattataa acgaggaggc tgcagattgg gacttgcagc acccacaacc agctccacaa   1980
caaggacaac ttagggagcc gtcaggatca gatattgcag gaacaactag ttcagtagat   2040
gaacaaatcc agtggatgta cagacaacag aaccccatac cagtaggcaa catttacagg   2100
agatggatcc aactggggtt gcaaaaatgt gtcagaatgt ataacccaac aaacattcta   2160
gatgtaaaac aagggccaaa agagccattt cagagctatg tagacaggtt ctacaaaagt   2220
ttaagagcag aacagacaga tgcagcagta aagaattgga tgactcaaac actgctgatt   2280
caaaatgcta acccagattg caagctagtg ctgaaggggc tgggtgtgaa tcccacccta   2340
gaagaaatgc tgacggcttg tcaaggagta ggggggccgg gacagaaggc tagattaatg   2400
gcagaagccc tgaaagaggc cctcgcacca gtgccaatcc cttttgcagc agcccaacag   2460
aggggaccaa gaaagccaat taagtgttgg aattgtggga aagagggaca ctctgcaagg   2520
caatgcagag ccccaagaag acagggatgc tggaaatgtg gaaaaatgga ccatgttatg   2580
gccaaatgcc cagacagaca ggcgggtttt ttaggccttg gtccatgggg aaagaagccc   2640
cgcaatttcc ccatggctca agtgcatcag ggcctgatgc caactgctcc cccagaggac   2700
ccagctgtgg atctgctaaa gaactacatg cagttgggca agcagcagag agaaaagcag   2760
agagaaagca gagagaagcc ttacaaggag gtgacagagg atttgctgca cctcaattct   2820
ctctttggag gagaccagta gtcactgctc atattgaagg acagcctgta gaagtattac   2880
tggatacagg ggctgatgat tctattgtaa caggaataga gttaggtcca cattataccc   2940
caaaaatagt aggaggaata ggaggtttta ttaatactaa agaatacaaa aatgtagaaa   3000
tagaagtttt aggcaaaagg attaaaggga caatcatgac aggggacacc ccgattaaca   3060
tttttggtag aaatttgcta acagctctgg ggatgtctct aaattttccc atagctaaag   3120
tagagcctgt aaaagtcgcc ttaaagccag gaaaggatgg accaaaattg aagcagtggc   3180
cattatcaaa agaaaagata gttgcattaa gagaaatctg tgaaaagatg gaaaaggatg   3240
gtcagttgga ggaagctccc ccgaccaatc catacaacac cccccacattt gctataaaga   3300
aaaaggataa gaacaaatgg agaatgctga tagattttag ggaactaaat agggtcactc   3360
aggactttac ggaagtccaa ttaggaatac cacaccctgc aggactagca aaaaggaaaa   3420
gaattacagt actggatata ggtgatgcat atttctccat acctctagat gaagaattta   3480
ggcagtacac tgcctttact ttaccatcag taaataatgc agagccagga aaacgataca   3540
tttataaggt tctgcctcag ggatggaagg ggtcaccagc catcttccaa tacactatga   3600
gacatgtgct agaacccttc aggaaggcaa atccagatgt gaccttagtc cagtatatgg   3660
```

-continued

```
atgacatctt aatagctagt gacaggacag acctggaaca tgacagggta gttttacagt   3720
caaaggaact cttgaatagc atagggtttt ctaccccaga agagaaattc caaaaagatc   3780
ccccatttca atggatgggg tacgaattgt ggccaacaaa atggaagttg caaaagatag   3840
agttgccaca aagagagacc tggacagtga atgatataca gaagttagta ggagtattaa   3900
attgggcagc tcaaatttat ccaggtataa aaaccaaaca tctctgtagg ttaattagag   3960
gaaaaatgac tctaacagag gaagttcagt ggactgagat ggcagaagca gaatatgagg   4020
aaaataaaat aattctcagt caggaacaag aaggatgtta ttaccaagaa ggcaagccat   4080
tagaagccac ggtaataaag agtcaggaca atcagtggtc ttataaaatt caccaagaag   4140
acaaaatact gaaagtagga aaatttgcaa agataaagaa tacacatacc aatggagtga   4200
gactattagc acatgtaata cagaaaatag gaaaggaagc aatagtgatc tggggacagg   4260
tcccaaaatt ccacttacca gttgagaagg atgtatggga acagtggtgg acagactatt   4320
ggcaggtaac ctggataccg gaatgggatt ttatctcaac accaccgcta gtaagattag   4380
tcttcaatct agtgaaggac cctatagagg gagaagaaac ctattataca gatggatcat   4440
gtaataaaca gtcaaaagaa gggaaagcag gatatatcac agataggggc aaagacaaag   4500
taaaagtgtt agaacagact actaatcaac aagcagaatt ggaagcattt ctcatggcat   4560
tgacagactc agggccaaag gcaaatatta tagtagattc acaatatgtt atgggaataa   4620
taacaggatg ccctacagaa tcagagagca ggctagttaa tcaaataata gaagaaatga   4680
ttaaaaagtc agaaatttat gtagcatggg taccagcaca caaaggtata ggaggaaacc   4740
aagaaataga ccacctagtt agtcaaggga ttagacaagt tctcttcttg gaaaagatag   4800
agccagcaca agaagaacat gataaatacc atagtaatgt aaaagaattg gtattcaaat   4860
ttggattacc cagaatagtg gccagacaga tagtagacac ctgtgataaa tgtcatcaga   4920
aaggagaggc tatacatggg caggcaaatt cagatctagg gacttggcaa atggattgta   4980
cccatctaga gggaaaaata atcatagttg cagtacatgt agctagtgga ttcatagaag   5040
cagaggtaat tccacaagag acaggaagac agacagcact atttctgtta aaattggcag   5100
gcagatggcc tattacacat ctacacacag ataatggtgc taactttgct tcgcaagaag   5160
taaagatggt tgcatggtgg gcagggatag agcacacctt tggggtacca tacaatccac   5220
agagtcaggg agtagtggaa gcaatgaatc accacctgaa aaatcaaata gatagaatca   5280
gggaacaagc aaattcagta gaaaccatag tattaatggc agttcattgc atgaatttta   5340
aaagaagggg aggaataggg gatatgactc cagcagaaag attaattaac atgatcacta   5400
cagaacaaga gatacaattt caacaatcaa aaaactcaaa atttaaaaat tttcgggtct   5460
attacagaga aggcagagat caactgtgga agggacccgg tgagctattg tggaaagggg   5520
aaggagcagt catcttaaag gtagggacag acattaaggt agtacccaga agaaaggcta   5580
aaattatcaa agattatgga ggaggaaaag aggtggatag cagttcccac atggaggata   5640
ccggagaggc tagagaggtg gcatagcctc ataaaatatc tgaaatataa aactaaagat   5700
ctacaaaagg tttgctatgt gccccatttt aaggtcggat gggcatggtg gacctgcagc   5760
agagtaatct tcccactaca ggaaggaagc catttagaag tacaagggta ttggcatttg   5820
acaccagaaa aagggtggct cagtacttat gcagtgagga taacctggta ctcaaagaac   5880
ttttggacag atgtaacacc aaactatgca gacattttac tgcatagcac ttatttccct   5940
tgctttacag cgggagaagt gagaagggcc atcaggggag aacaactgct gtcttgctgc   6000
aggttcccga gagctcataa gtaccaggta ccaagcctac agtacttagc actgaaagta   6060
```

gtaagcgatg tcagatccca gggagagaat cccacctgga aacagtggag aagagacaat 6120
aggagaggcc ttcgaatggc taaacagaac agtagaggag ataaacagag aggcggtaaa 6180
ccacctacca agggagctaa ttttccaggt ttggcaaagg tcttgggaat actggcatga 6240
tgaacaaggg atgtcaccaa gctatgtaaa atacagatac ttgtgtttaa tacaaaaggc 6300
tttatttatg cattgcaaga aaggctgtag atgtctaggg gaaggacatg ggcaggggg 6360 atggagacca ggacctcctc ctcctccccc tccaggacta gcataaatgg aagaaagacc 6420
tccagaaaat gaaggaccac aaagggaacc atgggatgaa tgggtagtgg aggttctgga 6480
agaactgaaa gaagaagctt taaaacattt tgatcctcgc ttgctaactg cacttggtaa 6540
tcatatctat aatagacatg gagacaccct tgagggagca ggagaactca ttagaatcct 6600
ccaacgagcg ctcttcatgc atttcagagg cggatgcatc cactccagaa tcggccaacc 6660
tgggggagga aatcctctct cagctatacc gccctctaga agcatgctat aacacatgct 6720
attgtaaaaa gtgttgctac cattgccagt tttgttttct taaaaaaggc ttggggatat 6780
gttatgagca atcacgaaag agaagaagaa ctccgaaaaa ggctaaggct aatacatctt 6840
ctgcatcaaa caagtaagta tgggatgtct tgggaatcag ctgcttatcg ccatcttgct 6900
tttaagtgtc tatgggatct attgtactct atatgtcaca gtcttttatg gtgtaccagc 6960
ttggaggaat gcgacaattc ccctcttttg tgcaaccaag aatagggata cttggggaac 7020
aactcagtgc ctaccagata atggtgatta ttcagaagtg gcccttaatg ttacagaaag 7080
ctttgatgcc tggaataata cagtcacaga acaggcaata gaggatgtat ggcaactctt 7140
tgagacctca ataaagcctt gtgtaaaatt atccccatta tgcattacta tgagatgcaa 7200
taaaagtgag acagatagat ggggattgac aaaatcaata acaacaacag catcaacaac 7260
atcaacgaca gcatcagcaa aagtagacat ggtcaatgag actagttctt gtatagccca 7320
ggataattgc acaggcttgg aacaagagca aatgataagc tgtaaattca acatgacagg 7380
gttaaaaaga gacaagaaaa aagagtacaa tgaaacttgg tactctgcag atttggtatg 7440
tgaacaaggg aataacactg gtaatgaaag tagatgttac atgaaccact gtaacacttc 7500
tgttatccaa gagtcttgtg acaaacatta ttgggatgct attagattta ggtattgtgc 7560
acctccaggt tatgctttgc ttagatgtaa tgacacaaat tattcaggct ttatgcctaa 7620
atgttctaag gtggtggtct cttcatgcac aaggatgatg gagacacaga cttctacttg 7680
gtttggcttt aatggaacta gagcagaaaa tagaacttat atttactggc atggtaggga 7740
taataggact ataattagtt taaataagta ttataatcta acaatgaaat gtagaagacc 7800
aggaaataag acagttttac cagtcaccat tatgtctgga ttggttttcc actcacaacc 7860
aatcaatgat aggccaaagc aggcatggtg ttggtttgga ggaaaatgga aggatgcaat 7920
aaaagaggtg aagcagacca ttgtcaaaca tcccaggtat actggaacta acaatactga 7980
taaaatcaat ttgacggctc ctggaggagg agatccggaa gttaccttca tgtggacaaa 8040
ttgcagagga gagttcctct actgtaaaat gaattggttt ctaaattggg tagaagatag 8100
gaatacagct aaccagaagc caaaggaaca gcataaaagg aattacgtgc catgtcatat 8160
tagacaaata atcaacactt ggcataaagt aggcaaaaat gtttatttgc ctccaagaga 8220
gggagacctc acgtgtaact ccacagtgac cagtctcata gcaaacatag attggattga 8280
tggaaaccaa actaatatca ccatgagtgc agaggtggca gaactgtatc gattggaatt 8340
gggagattat aaattagtag agatcactcc aattggcttg gcccccacag atgtgaagag 8400

```
gtacactact ggtggcacct caagaaataa aagaggggtc tttgtgctag ggttcttggg   8460
ttttctcgca acggcaggtt ctgcaatggg cgcggcgtcg ttgacgctga ccgctcagtc   8520
ccgaacttta ttggctggga tagtgcagca acagcaacag ctgttggacg tggtcaagag   8580
acaacaagaa ttgttgcgac tgaccgtctg ggaacaaag aacctccaga ctagggtcac   8640
tgccatcgag aagtacttaa aggaccaggc gcagctgaat gcttggggat gtgcgtttag   8700
acaagtctgc cacactactg taccatggcc aaatgcaagt ctaacaccaa agtggaacaa   8760
tgagacttgg caagagtggg agcgaaaggt tgacttcttg gaagaaaata taacagccct   8820
cctagaggag gcacaaattc aacaagagaa gaacatgtat gaattacaaa agttgaatag   8880
ctgggatgtg tttggcaatt ggtttgacct tgcttcttgg ataaagtata tacaatatgg   8940
agtttatata gttgtaggag taatactgtt aagaatagtg atctatatag tacaaatgct   9000
agctaagtta aggcaggggt ataggccagt gttctcttcc ccaccctctt atttccagca   9060
gacccatatc caacaggacc cggcactgcc aaccagagaa ggcaaagaaa gagacggtgg   9120
agaaggcggt ggcaacagct cctggccttg gcagatagaa tatattcatt tcctgatccg   9180
ccaactgata cgcctcttga cttggctatt cagcaactgc agaaccttgc tatcgagagt   9240
ataccagatc ctccaaccaa tactccagag gctctctgcg accctacaga ggattcgaga   9300
agtcctcagg actgaactga cctacctaca atatgggtgg agctatttcc atgaggcggt   9360
ccaggccgtc tggagatctg cgacagagac tcttgcgggc gcgtggggag acttatggga   9420
gactcttagg agaggtggaa gatggatact cgcaatcccc aggaggatta gacaagggct   9480
tgagctcact ctcttgtgag ggacagaaat acaatcaggg acagtatatg aatactccat   9540
ggagaaaccc agctgaagag agagaaaaat tagcatacag aaaacaaaat atggatgata   9600
tagatgagta agatgatgac ttggtagggg tatcagtgag gccaaaagtt cccctaagaa   9660
caatgagtta caaattggca atagacatgt ctcattttat aaaagaaaag gggggactgg   9720
aagggattta ttacagtgca agaagacata gaatcttaga catatactta gaaaaggaag   9780
aaggcatcat accagattgg caggattaca cctcaggacc aggaattaga tacccaaaga   9840
catttggctg gctatggaaa ttagtccctg taaatgtatc agatgaggca caggaggatg   9900
aggagcatta tttaatgcat ccagctcaaa cttcccagtg ggatgaccct tggggagagg   9960
ttctagcatg gaagtttgat ccaactctgg cctacactta tgaggcatat gttagatacc  10020
cagaagagtt tggaagcaag tcaggcctgt cagaggaaga ggttagaaga aggctaaccg  10080
caagaggcct tcttaacatg gctgacaaga aggaaactcg ctgaaacagc agggactttc  10140
cacaagggga tgttacgggg aggtactggg gaggagccgg tcgggaacgc ccactttctt  10200
gatgtataaa tatcactgca tttcgctctg tattcagtcg ctctgcggag aggctggcag  10260
attgagccct gggaggttct ctccagcact agcaggtaga gcctgggtgt tccctgctag  10320
actctcacca gcacttggcc ggtgctgggc agagtgactc cacgcttgct tgcttaaagc  10380
cctcttcaat aaagctgcca ttttagaagt aagctagtgt gtgttcccat ctctcctagc  10440
cgccgcctgg tcaactcggt actcaataat aagaagaccc tggtctgtta ggaccctttc  10500
tgctttggga aaccgaagca ggaaaatccc tagca                             10535
```

<210> SEQ ID NO 386
<211> LENGTH: 9713
<212> TYPE: DNA
<213> ORGANISM: Human immunodeficiency virus 2

<400> SEQUENCE: 386

-continued

```
agtcgctctg cggagaggct ggcagattga gccctgggag gttctctcca gcactagcag      60
gtagagcctg ggtgttccct gctagactct caccggtgct tggccggcac tgggcagacg     120
gctccacgct tgcttgctta aaagacctct taataaagct gccagttaga agcaagttaa     180
gtgtgtgttc ccatctctcc tagtcgccgc ctggtcattc ggtgttcatc tgaataacaa     240
gaccctggtc tgttaggacc ctttctgctt tgggaaacca aagcaggaaa atccctagca     300
ggttggcgcc cgaacaggga cttagagaag actgaaaagc cttggaacac ggctgagtga     360
aggcagtaag ggcggcagga acaaaccacg acggagtgct cctagaaagg cgcaggccaa     420
ggtaccaaag gcggcgtgtg gagcgggagt aaagaggcct ccgggtgaag gtaagtacct     480
acaccaaaaa attgtagcca ggaagggctt gttatcctac ctttagacag gtagaagatt     540
gtgggagatg ggcgcgagaa actccgtctt gaaagggaaa aaagcagacg aattagaaac     600
aattaggtta cggcccggcg gaaagaaaaa atacaggcta aagcatattg tgtgggcagc     660
gaatgaattg gacagattcg gattagcaga gagcctgttg gagtcaaaag aaggttgcca     720
aagaattctt acagttttag gtccattagt accgacaggt tcagaaaatt taaaaagcct     780
ttttaatact gtctgcgtca tttggtgcat acacgcagaa gagaaagtga aagatactga     840
aggagcaaaa caaatagtac agagacatct agcggcagaa acaggaactg cagagaaaat     900
gccaaataca agtagaccaa cagcaccacc tagcgggaag ggaggaaact tccccgtaca     960
acaagtaggc ggcaattata cccatgtgcc gctgagtcct cgaaccctaa atgcttgggt    1020
aaaattagta gaggaaaaga agttcggggc agaggtagtg ccaggatttc aggcactctc    1080
agaaggctgc acgccctatg atatcaacca aatgcttaat tgtgtgggcg accatcaagc    1140
agctatgcaa ataatcaggg agatcgttaa tgaagaagca gcagattggg atgtgcaaca    1200
tccaatacca ggtcccttac cagcggggca gcttagagaa ccaagagggt ctgacatagc    1260
agggacaaca agcacagtag atgaacagat ccagtggatg tttaggccac aaaatcccgt    1320
accagtggga aacatctata ggagatggat ccagatagga ctgcagaagt gcgtcaggat    1380
gtacaacccg accaacatcc tagacataaa acaaggacca aaggaaccat tccaaagtta    1440
tgtagataga ttctacaaaa gcttgagggc agaacaaaca gatccagcag tgaagaattg    1500
gatgacccag acactactag tacagaatgc caacccagac tgtaaattag tactaaaagg    1560
actagggatg aatcctacct tagaagagat gctaaccgcc tgccaagggg taggtgggcc    1620
aggccagaaa gctagactaa tggcagaagc cttaaaagag gccttgacac cagcccctat    1680
cccatttgca gcagcccagc agaaaaggac aattaaatgc tggaattgtg gaaaggaagg    1740
acactcggca agacaatgcc gagcacctag aagacagggc tgctggaagt gtggtaaacc    1800
aggacatgtc atagcaaatt gcccagatag acaggtgggt tttttaggga tgggcccccg    1860
gggaaagaag ccccgcaact tccccgtggc ccaagtcccg caggggctaa caccaacagc    1920
acccccagta gatccagcag tggacctact ggagaattat atgcagcaag gaaaaagaca    1980
aagagaacag agagagagac catacaaaga agtgacagag gacttactgc acctcgagca    2040
gggagaggca ccatgcagag agacgacaga ggacttgctg cacctcaatt ctctcttttg    2100
aaaagaccag tagtcacggc atacgtcgag ggccagccag tagaagttct gctagacacg    2160
ggggctgacg actcaatagt agcagggata gagttaggga gcaattatag tccaaagata    2220
gtaggaggaa tagggggatt cataaatacc aaggaatata aaaatgtaaa aatagaagtt    2280
ttaggtaaaa aggtaagggc caccataatg acaggtgaca ccccaatcaa catttttggc    2340
```

-continued

```
agaaatattc tgacagcctt aggcatgtca ttaaatttac cagtcgccaa aatagaacca   2400
ataaaaataa tgttaaagcc aggaaaagat ggaccaaaac tgaggcaatg gcccttaaca   2460
aaagaaaaaa tagaggcact aaaagaaatc tgtgaaaaaa tggaaagaga aggccagcta   2520
gaggaagcgc ctccaactaa tccttataac accccacat ttgcaatcaa gaaaaaggac   2580
aaaaataaat ggaggatgct aatagatttt agagaactaa acaaggtaac tcaagatttc   2640
acagaaattc agttaggaat tccacaccca gcaggattgg ccaagaaaaa aagaattact   2700
gtactagata taggggatgc ttacttttcc ataccactac atgaagactt tagacagtat   2760
actgcattta ctttaccatc aataaacaat gcagaaccag gaaaaagata tatatataag   2820
gtcctgcctc agggatggaa ggggtcacca gcaatttttc aatacacaat gaggcaggtc   2880
ttagaaccat tcagaaaagc aaacctagat gtcattatca ttcagtacat ggatgatatc   2940
ctaatagcta gtgacaggac agatctagaa catgacaagg tggtcctgca gctaaaggaa   3000
cttctaaata acctaggatt ttctacccca gatgagaagt tccaaaagga ccctccatac   3060
cactggatgg gctatgaact gtggccaact aagtggaagc tgcagaagat acagttgccc   3120
caaaaagatg tatggacagt aaatgacatc caaaagttag tgggtgtctt aaactgggca   3180
gcacaaatct acccagggat aaaaaccaga cacttatgta agctaattag aggaaaaatg   3240
acactcacag aagaagtaca gtggacagaa ctagcagagg cggagttaga agagaacaag   3300
attatcttaa gccaggagca agagggacac tattaccaag aagaaaaaga gttagaagca   3360
acagtccaaa aggatcaaga caatcagtgg acatataaag tacaccaggg agagaaaatt   3420
ctaaaagtag ggaaatatgc aaagataaaa aatacccata ccaatggggt cagattgtta   3480
gcacaagtag ttcaaaagat aggaaaagaa gcactaatca tttggggacg aataccaaaa   3540
tttcacctac cagtagaaag agagacatgg gaacagtggt gggatgacta ctggcaggtg   3600
acatggatcc ctgactggga cttcgtatct accccgccgc tggtcagact agcatttaac   3660
ctggtaaaag atcctatacc aagaacagag actttctaca cagatggatc ctgcaatagg   3720
caatcaaagg aaggaaaagc aggatatgta acagatagag ggagagacaa ggtaaggatg   3780
ctagaacaaa ctaccaatca gcaagcagaa ttagaagcct ttgcaatggc actaacagac   3840
tcaggtccaa aagccaatat tatagtagac tcacagtatg taatggggat agtagcaggc   3900
cagccaacag aatcagagag tagaatagta aatcaaatca tagaggagat gataaaaaag   3960
gaagcaatct atgttgcatg ggtcccagcc cataaaggca taggagggaa tcaggaggta   4020
gatcagttag taagtcaggg catcagacaa gtgttgttcc tggaaaaaat agagcccgct   4080
caggaagaac atgagaaata ccatagcaat gtaaaagaac tatcccataa atttggattg   4140
cccaaattag tagcaagaca aatagtaaac acatgtgccc aatgtcaaca gaaaggggag   4200
gctatacatg ggcaagtaga tgcagaatta ggcacttggc aaatggactg cacacactta   4260
gaaggaaaga tcattatagt agcagtacat gttgcaagtg gattcataga agcagaagtc   4320
atcccacagg aatcaggaag gcagacagca ctcttcctat taaaactggc cagtaggtgg   4380
ccaataacac acttgcacac agataatggt gccaacttca cttcacagga agtaaaaatg   4440
gtagcatggt gggtaggtat agaacaatct ttcggagtac cttacaatcc acaaagccaa   4500
ggagtagtag aagcaatgaa tcaccaccta aaaaatcaga taagtagaat tagagaacag   4560
gcaaatacag tagaaacaat agtactgatg gcaacacact gcatgaattt taaaagaagg   4620
ggaggaatag ggatatgac cccagcagaa agactaatca atatgatcac cacagaacaa   4680
gaaatacaat tcctccacgc caaaaattca aaattaaaaa attttcgggt ctatttcaga   4740
```

gaaggcagag atcagctgtg gaaaggaccc ggggaactac tgtggaaggg agacggagca 4800
gtcatagtca aggtagggac agacataaaa gtagtaccaa ggaggaaagc caagatcatc 4860
aaagactatg gaggaaggca agaactggat agtggttccc acttggaggg tgccagggag 4920
gatggagaaa tggcatagcc ttgtcaaata tctaaaatac agaacaaaag atctagaaga 4980
cgtgtgctat gttccccacc ataaagtagg atgggcatgg tggacttgca gcagggtaat 5040
attcccatta aagggaaaca gtcatctaga aatacaggca tattggaacc taacgccaga 5100
aaaaggatgg ctctcctctt attcagtaag aatgacttgg tatacggaaa ggttctggac 5160
agatgttacc ccagactgtg cagactccct aatacatagc acttatttct cttgctttac 5220
agcaggtgaa gtaagaagag ccatcagagg ggaaaagtta ttgtcctgct gcaattatcc 5280
ccaagcccat agagcccagg taccgtcact ccaatttttg gccttagtgg tagtgcagca 5340
aaatgacaga ccccagagaa acggtacccc caggaaacag tggcgaagag actatcgaag 5400
aggccttcaa ttggctagac aggacggtag aagccataaa cagagaggca gtgaatcacc 5460
tgccccgaga gcttattttc caggtgtggc agaggtcctg gagatactgg catgatgaac 5520
aagggatgtc acaaagttac acaaagtata gatatttgtg cttaatacag aaggctatgt 5580
tcacacattg taagagaggg tgcacttgcc tgggggggagg acatgggcca ggagggtgga 5640
gaccaggacc tccccctcct cccccctccag gtctagtcta atgactgaag caccaacaga 5700
gtttcccccg gaggatggga ccccaccgag ggaaccaggg gatgagtgga taatagaaat 5760
cctgagaaaa ataaagaaag aagctttaaa gcattttgac cctcgcttgc taactgctct 5820
tggcaactat atccatacta gacatggaga cacccttgaa ggcgccagag agctcattaa 5880
tgtcctacaa cgagccctct tcatgcactt cagagcggga tgtaggctct caagaattgg 5940
ccaaacaggg ggaagaactc ctttcccagc tacatcgacc cctagaacca tgcaataaca 6000
aatgctattg taaaggatgc tgcttccact gccagctgtg ttttttaaac aaggggctcg 6060
ggatatgtta tgaccggaag ggcagacgaa gaagaactcc gaagaaaact aaggctcatt 6120
catcttctgc atcagacaag tgagtatgat gggtggtaga aatcagctgc ttgttgccat 6180
tttgctaact agtacttgct tgatatattg caccaattat gtgactgttt tctatggcat 6240
acccgcgtgg agaaatgcat ccattcccct cttttgtgca accaagaata gggatacttg 6300
gggaaccata cagtgcttgc cagacaatga tgattatcag gagataactt tgaatgtgac 6360
agaggctttc gatgcatggg ataatacagt aacagaacaa gcaatagaag atgtctggaa 6420
tctatttgag acatcaataa aaccatgtgt caaattaacg cctttatgtg tagcaatgag 6480
atgtaacaac acagatgcaa ggaacacaac cacacccaca acagcatccc cgcgtacaat 6540
aaaacccgtg acagagataa gtgagaattc ctcatgcata cgcgcaaaca actgctcagg 6600
attgggagaa gaagaggtgg tcaattgtca attcaatatg acaggattag agagagataa 6660
gaaaaagcaa tatagtgaga catggtactc gaaggatgta gtttgtgaag gaaatggcac 6720
cacagataca tgttacatga accattgcaa cacatcggtc atcacagagt catgtgacaa 6780
gcactattgg gatgctatga ggtttagata ctgtgcacca ccaggttttg ccctactaag 6840
atgcaatgat accaattatt caggctttgc gcccaattgc tctaaggtag tagctgctac 6900
atgcaccaga atgatggaaa cgcaaacttc tacatggttt ggctttaatg gcactagagc 6960
agaaaataga acatttatct attggcatgg tagggataac agaactatca tcagcttaaa 7020
caaatattat aatctcacta tacattgtaa gaggccagga aataagacag tggtaccaat 7080
aacacttatg tcagggttaa ggtttcactc ccagccggtc atcaataaaa gacccagaca 7140
agcatggtgt tggttcaaag gtgaatggaa gggagccatg caggaggtga aggaaaccct 7200
tgcaaaacat cccaggtata aaggaaccaa tgaaacaaag aatattaact ttacagcacc 7260
aggaaagggc tcagacccag aggtggcata catgtggact aactgcagag gagaatttct 7320
ctactgcaac atgacttggt tcctcaattg gatagaaaat aagacacacc gcaattatgt 7380
accgtgccat ataagacaaa taattaacac ctggcataag gtagggaaaa atgtatattt 7440
gcctcccagg gaaggggagt tgacctgcaa ctcaacagta actagcataa ttgctaacat 7500
tgatgcaaat ggaaataata caaatattac ctttagtgca gaggtggcag aactataccg 7560
attagagttg ggagattata aattggtaga aataacacca attggcttcg cacctacagc 7620
agaaaaaaga tactcctcta ctccaatgag gaacaagaga ggtgtgttcg tgctagggtt 7680
cttgggtttt ctcgcaacag caggctctgc aatgggcgcg gcgtccttaa cgctgtcggc 7740
tcagtctcgg actttactgg ccgggatagt gcagcaacag caacagctgt tggacgtggt 7800
caagagacaa caggaaatgt tgcgactgac cgtctgggga acaaaaaatc tccaggcaag 7860
agtcactgct atcgagaagt acttaaagga ccaggcgcaa ctaaattcat ggggatgtgc 7920
atttagacaa gtctgccaca ctactgtacc atgggtaaat gataccttaa cgcctgagtg 7980
gaacaatatg acgtggcaag aatgggaagg caaaatccgc gacctggagg caaatatcag 8040
tcaacaatta gaacaagcac aaattcagca agagaagaat atgtatgaac tacaaaagtt 8100
aaatagctgg gatgtttttg gtaactggtt tgacttaacc tcctggatca agtatattca 8160
atatggagtt tatataataa taggaatagt agttcttaga atagtaatat atatagtaca 8220
gatgttaagt agacttagaa agggctatag gcctgttttc tcttcccccc ccggttacct 8280
ccaacagatc catatccaca aggactggga acagccagcc agagaagaaa cagaagaaga 8340
cgttggaaac aacgttggag acagctcgtg gccttggccg ataagatata tacatttcct 8400
gatccaccag ctgattcgcc tcttggccgg actatacaac atctgcagga acttactatc 8460
caggatctcc ctgaccctcc gaccagtttt ccagagtctt cagagggcac tgacagcaat 8520
cagagactgg ctaagaactg acgcagccta cttgcagtat gggtgcgagt ggatccaagg 8580
agcgttccag gccttcgcaa gggctacgag agagactctt gcgggcacgt ggagagactt 8640
gtggggggca ctgcagcgga tcgggagggg aatacttgca gtcccaagaa gaatcaggca 8700
gggagcagag atcgccctcc tatgagggac agcggtatca gcagggagac tttatgaata 8760
ccccatggag aaccccagca aaagaagggg agaaagaatt gtacaagcaa caaaatagag 8820
atgatgtaga ttcggatgat gatgacctag taggggtctc tgtcacacca agagtaccac 8880
taagagaatt gacacataga ttagcaatag atgtgtcaca ttttataaaa gaaaaagggg 8940
gactggaagg gatgtattac agtgagagaa gacatagaat cttagacata taccttgaaa 9000
aggaagaagg gataattgca gattggcaga actatactca tgggccagga ataagatacc 9060
caatgttctt tgggtggcta tggaagctag taccagtaga tgtcacacga caggaggagg 9120
acgatgggac tcactgttta ctacacccag cacaaacaag caggtttgat gacccgcatg 9180
gggaaacact gatatggaag tttgacccca cgctggctca tgattacaag gcttttatcc 9240
tgcacccaga ggaatttggg cataagtcag gcctgccaga agaagactgg aaggcaagac 9300
tgaaagcaag agggatacca tttagttaga gacaggaaca gctatatttg gccagggcag 9360
gaaataacta ctgaaaacag ctgagactgc agggactttc cgaaggggct gtaaccaggg 9420
gagggacatg ggaggagccg gtggggaacg ccctcatact ttctgtataa agatacccgc 9480

-continued

```
tgcttgcatt gtacttcagt cgctctgcgg agaggctggc agattgagcc ctgggaggtt   9540

ctctccagca ctagcaggta gagcctgggt gttccctgct agactctcac cggtgcttgg   9600

ccggcactgg gcagacggct ccacgcttgc ttgcttaaaa gacctcttaa taaagctgcc   9660

agttagaagc aagttaagtg tgtgttccca tctctcctag tcgccgcctg gtc          9713
```

```
<210> SEQ ID NO 387
<211> LENGTH: 11878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387

gcctcactga ttaagcattg gtaactgtca gaccaagttt actcatatat actttagatt     60

gatttaaaac ttcattttta atttaaaagg atctaggtga agatcctttt tgataatctc    120

atgaccaaaa tcccttaacg tgagttttcg ttccactgag cgtcagaccc cgtagaaaag    180

atcaaaggat cttcttgaga tccttttttt ctgcgcgtaa tctgctgctt gcaaacaaaa    240

aaaccaccgc taccagcggt ggtttgtttg ccggatcaag agctaccaac tctttttccg    300

aaggtaactg gcttcagcag agcgcagata ccaaatactg ttcttctagt gtagccgtag    360

ttaggccacc acttcaagaa ctctgtagca ccgcctacat acctcgctct gctaatcctg    420

ttaccagtgg ctgctgccag tggcgataag tcgtgtctta ccgggttgga ctcaagacga    480

tagttaccgg ataaggcgca gcggtcgggc tgaacggggg gttcgtgcac acagcccagc    540

ttggagcgaa cgacctacac cgaactgaga tacctacagc gtgagctatg agaaagcgcc    600

acgcttcccg aagggagaaa ggcggacagg tatccggtaa gcggcagggt cggaacagga    660

gagcgcacga gggagcttcc agggggaaac gcctggtatc tttatagtcc tgtcgggttt    720

cgccacctct gacttgagcg tcgatttttg tgatgctcgt caggggggcg gagcctatgg    780

aaaaacgcca gcaacgcggc ctttttacgg ttcctggcct tttgctggcc ttttgctcac    840

atgttctttc ctgcgttatc ccctgattct gtggataacc gtattaccgc ctttgagtga    900

gctgataccg ctcgccgcag ccgaacgacc gagcgcagcg agtcagtgag cgaggaagcg    960

gaagagcgcc caatacgcaa accgcctctc cccgcgcgtt ggccgattca ttaatgcagc   1020

tggcacgaca ggtttcccga ctggaaagcg ggcagtgagc gcaacgcaat taatgtgagt   1080

tagctcactc attaggcacc ccaggcttta cactttatgc ttccggctcg tatgttgtgt   1140

ggaattgtga gcggataaca atttcacaca ggaaacagct atgaccatga ttacgccaag   1200

ctatttaggt gacactatag aatactcaag cttgggggga tcctctagag tcgacctgca   1260

ggcatgctat ttgatgaatt aactacactt aaaataatac aattattatt aaattttttt   1320

ttgatttatt tattaatttt taaacttaat catttgtatt tgggaggaat tatatatatc   1380

tttataatta ttttattttt ttttattttt ttattttttt attattatta ttttttttta   1440

ttttttttt ttactgtatc aaagaaaaac ctttaaaaaa aaaattataa tttccccatc   1500

ttactatatt tttaatacat acgttttaag gaattaaatt agacaaaagc tatattatgc   1560

tttacatata attagaattt ataaacgttt ggttattaga tatttcatgt ctcagtaaag   1620

tctttcaata catatgtaaa aaaatatata tgaatacaca taagttgtta atatatttta   1680

tatgcataaa tgtataaata tatatatata tatatatata tgtatgtatg tatatgtgtg   1740

tatatgaaat tatttcaatg tttaattttt taaattttaa ttttttttt ttttttttt   1800
```

```
tttattatgt atattgatct ttattattta aatattactt ttttcgtttt ttcttctttt   1860
tattattttt tttttttttt atattttata caaatggtaa ttcaaataaa aggtataaat   1920
ttatatttaa ttttctttta tggataaata aaagaaaaat ataaatatat aaaaatataa   1980
aaatatatat atgtatattg gggtgatgat aaaatgaaag ataaatatata tatatatata   2040
tctttatttt tttttttttg tagaccccat tgtgagtaca taaatatatt atataactcg   2100
ggagcatcag tcatggaatt cttatttctt tttctttttt gcctggccgg ccttttttcgt   2160
ggccgccggc cttttgtcgc ctcccagctg agacaggtcg atccgtgtct cgtacaggcc   2220
ggtgatgctc tggtggatca gggtggcgtc cagcacctct ttggtgctgg tgtacctctt   2280
ccggtcgatg gtggtgtcaa agtacttgaa ggcggcaggg gctcccagat tggtcagggt   2340
aaacaggtgg atgatattct cggcctgctc tctgatgggc ttatcccggt gcttgttgta   2400
ggcggacagc actttgtcca gattagcgtc ggccaggatc actctcttgg agaactcgct   2460
gatctgctcg atgatctcgt ccaggtagtg cttgtgctgt tccacaaaca gctgtttctg   2520
ctcattatcc tcgggggagc ccttcagctt ctcatagtgg ctggccaggt acaggaagtt   2580
cacatatttg gagggcaggg ccagttcgtt tcccttctgc agttcgccgg cagaggccag   2640
cattctcttc cggccgtttt ccagctcgaa cagggagtac ttaggcagct tgatgatcag   2700
gtccttttttc acttctttgt agcccttggc ttccagaaag tcgatgggat tcttctcgaa   2760
gctgcttctt tccatgatgg tgatccccag cagctctttc acactcttca gtttcttgga   2820
cttgcccttt tccactttgg ccaccaccag cacagaatag gccacggtgg ggctgtcgaa   2880
gccgccgtac ttcttagggt cccagtcctt ctttctggcg atcagcttat cgctgttcct   2940
cttgggcagg atagactctt tgctgaagcc gcctgtctgc acctcggtct ttttcacgat   3000
attcacttgg ggcatgctca gcactttccg cacggtggca aaatcccggc ccttatccca   3060
cacgatctcc ccggtttcgc cgtttgtctc gatcagaggc cgcttccgga tctcgccgtt   3120
ggccagggta atctcggtct tgaaaaagtt catgatgttg ctgtagaaga agtacttggc   3180
ggtagccttg ccgatttcct gctcgctctt ggcgatcatc ttccgcacgt cgtacacctt   3240
gtagtcgccg tacacgaact cgctttccag cttagggtac tttttgatca gggcggttcc   3300
cacgacggcg ttcaggtagg cgtcgtgggc gtggtggtag ttgttgatct cgcgcacttt   3360
gtaaaactgg aaatccttcc ggaaatcgga caccagcttg gacttcaggg tgatcacttt   3420
cacttcccgg atcagcttgt cattctcgtc gtacttagtg ttcatccggg agtccaggat   3480
ctgtgccacg tgctttgtga tctgccgggt ttccaccagc tgtctcttga tgaagccggc   3540
cttatccagt tcgctcaggc cgcctctctc ggccttggtc agattgtcga actttctctg   3600
ggtaatcagc ttggcgttca gcagctgccg ccagtagttc ttcatcttct tcacgacctc   3660
ttcggagggc acgttgtcgc tcttgccccg gttcttgtcg cttctggtca gcaccttgtt   3720
gtcgatggag tcgtccttca gaaagctctg aggcacgata tggtccacat cgtagtcgga   3780
cagccggttg atgtccagtt cctggtccac gtacatatcc cgcccattct gcaggtagta   3840
caggtacagc ttctcgttct gcagctgggt gttttccacg gggtgttctt tcaggatctg   3900
gctgcccagc tctttgatgc cctcttcgat ccgcttcatt ctctcgcggc tgttcttctg   3960
tcccttctgg gtggtctggt tctctctggc catttcgatc acgatgttct cgggcttgtg   4020
ccggcccatc actttcacga gctcgtccac caccttcact gtctgcagga tgcccttctt   4080
aatggcgggg ctgccggcca gattggcaat gtgctcgtgc aggctatcgc cctggccgga   4140
```

-continued

```
cacctgggct ttctggatgt cctctttaaa ggtcaggctg tcgtcgtgga tcagctgcat   4200
gaagtttctg ttggcgaagc cgtcggactt caggaaatcc aggattgtct tgccggactg   4260
cttgtcccgg atgccgttga tcagcttccg gctcagcctg ccccagccgg tgtatctccg   4320
ccgcttcagc tgcttcatca ctttgtcgtc gaacaggtgg gcataggttt tcagccgttc   4380
ctcgatcatc tctctgtcct caaacagtgt cagggtcagc acgatatctt ccagaatgtc   4440
ctcgttttcc tcattgtcca ggaagtcctt gtccttgata attttcagca gatcgtggta   4500
tgtgcccagg gaggcgttga accgatcttc cacgccggag atttccacgg agtcgaagca   4560
ctcgattttc ttgaagtagt cctctttcag ctgcttcacg gtcactttcc ggttggtctt   4620
gaacagcagg tccacgatgg ccttttttctg ctcgccgctc aggaaggcgg gctttctcat   4680
tccctcggtc acgtatttca ctttggtcag ctcgttatac acggtgaagt actcgtacag   4740
caggctgtgc ttgggcagca ccttctcgtt gggcaggttc ttatcgaagt tggtcatccg   4800
ctcgatgaag ctctgggcgg aagcgccctt gtccaccact tcctcgaagt tccagggggt   4860
gatggtttcc tcgctctttc tggtcatcca ggcgaatctg ctgtttcccc tggccagagg   4920
gcccacgtag taggggatgc ggaaggtcag gatcttctcg atcttttccc ggttgtcctt   4980
caggaatggg taaaaatctt cctgccgccg cagaatggcg tgcagctctc ccaggtggat   5040
ctggtggggg atgctgccgt tgtcgaaggt ccgctgcttc cgcagcaggt cctctctgtt   5100
cagcttcacg agcagttcct cggtgccgtc catcttttcc aggatgggct tgatgaactt   5160
gtagaactct tcctggctgg ctccgccgtc aatgtagccg gcgtagccgt tcttgctctg   5220
gtcgaagaaa atctctttgt acttctcagg cagctgctgc cgcacgagag ctttcagcag   5280
ggtcaggtcc tggtggtgct cgtcgtatct cttgatcata gaggcgctca ggggggcctt   5340
ggtgatctcg gtgttcactc tcaggatgtc gctcagcagg atggcgtcgg acaggttctt   5400
ggcggccaga aacaggtcgg cgtactggtc gccgatctgg gccagcaggt tgtccaggtc   5460
gtcgtcgtag gtgtccttgc tcagctgcag tttggcatcc tcggccaggt cgaagttgct   5520
cttgaagttg gggtcaggc ccaggctcag ggcaatcagg tttccgaaca ggccattctt   5580
cttctcgccg ggcagctggg cgatcagatt ttccagccgt ctgctcttgc tcagtctggc   5640
agacaggatg gccttggcgt ccacgccgct ggcgttgatg gggttttcct cgaacagctg   5700
gttgtaggtc tgcaccagct ggatgaacag cttgtccacg tcgctgttgt cggggttcag   5760
gtcgccctcg atcaggaagt ggccccggaa cttgatcatg tgggccaggg ccagatagat   5820
cagccgcagg tcggccttgt cggtgctgtc caccagtttc tttctcaggt ggtagatggt   5880
ggggtacttc tcgtggtagg ccacctcgtc cacgatgttg ccgaagatgg ggtgccgctc   5940
gtgcttctta tcctcttcca ccaggaagga ctcttccagt ctgtggaaga agctgtcgtc   6000
caccttggcc atctcgttgc tgaagatctc ttgcagatag cagatccggt tcttccgtct   6060
ggtgtatctt cttctggcgg ttctcttcag ccgggtggcc tcggctgttt cgccgctgtc   6120
gaacagcagg gctccgatca ggttcttctt gatgctgtgc cggtcggtgt tgcccagcac   6180
cttgaatttc ttgctgggca ccttgtactc gtcggtgatc acggcccagc ccacagagtt   6240
ggtgccgatg tccaggccga tgctgtactt cttgtcggct gctgggactc cgtggatacc   6300
gaccttccgc ttcttctttg gggccatctt atcgtcatcg tctttgtaat caatatcatg   6360
atccttgtag tctccgtcgt ggtccttata gtccattttt ctcgagggat cctgatatat   6420
ttctattagg tatttattat tataaaatat aaatcttgaa tgataataaa taaaatatta   6480
gttattcctt ttctagttta aaatatacat attataaata tatatatata tatatatatt   6540
```

```
tttattgtga caagaatata taattataaa ttatattatt tatttttgta ttttttttt   6600
ttttttttt tttttctttt tttgttttat ttttcttttt ttttataaat attattttt   6660
tcttttatca tgcacattgg aataatacat taatatatat atatatatta tattatacat   6720
atattgaata atgtttataa aaaatgcata acttatatga atataatttt ttttaaatat   6780
gacaaaaaga aaaaaaaaaa aaaccaaaaa aaattaaaat tgaaatgaaa tatataaata   6840
tattatttat atatattata cattgtttaa tactactaca tgtatatata tatattatat   6900
atatatatat atatcaattt tttcaaaaat aaattaatat aaaaagaggg gaaaaaaaaa   6960
aaaaaaaaaa aaaaaagata attaagtaag catttaaaaa tatataaatt gataatatat   7020
aaaattaatc acatataaaa gcttataaac actaggttag ctaattcgct tgtaagaggt   7080
actctcgttt atgcaaaact atttgatata gcattttaac aagtacacat atatatatgt   7140
aatatatata ctatatatat ctattgcatg tgtactaagc atgtgcatgg catccccttt   7200
ttctcgtgtt taaaacagtt tgtatgataa aatataaagg atttgaaaaa gagaaaaaaa   7260
tatatgatct catcctatat agcgccataa tttttatttg ggttgaataa aattttctac   7320
taaatttagg tgtaagtaaa ataatggaat atatataagt acaataaaaa agtgcataaa   7380
ttaaaaaatt tttataataa atattttttt taaaaaagtc aataataata ttaaatatat   7440
ataacacagg attatatatg ttcactacaa tttttttatat tataatataa attcttttca   7500
attttcattt tattttacat acactttcct tttttgtcac tatattttaa tattcacata   7560
tttagtttaa atactggcta tttctttcta catttgctag taacaattgt gtagtgctta   7620
aatatataca cacacctaaa acttacaaag tatcctagga ccatggccaa gcctttgtct   7680
caagaagaat ccaccctcat tgaaagagca acggctacaa tcaacagcat ccccatctct   7740
gaagactaca gcgtcgccag cgcagctctc tctagcgacg gccgcatctt cactggtgtc   7800
aatgtatatc attttactgg gggaccttgt gcagaactcg tggtgctggg cactgctgct   7860
gctgcggcag ctggcaacct gacttgtatc gtcgcgatcg gaaatgagaa caggggcatc   7920
ttgagcccct gcggacggtg ccgacaggtg cttctcgatc tgcatcctgg gatcaaagcc   7980
atagtgaagg acagtgatgg acagccgacg gcagttggga ttcgtgaatt gctgccctct   8040
ggttatgtgt gggagggcta accgcgggta ccccattaaa tttatttaat aatagattaa   8100
aaatattata aaaataaaaa cataaacaca gaaattacaa aaaaaataca tatgaatttt   8160
tttttgtaa tcttccttat aaatatagaa taatgaatca tataaaacat atcattattc   8220
atttatttac atttaaaatt attgtttcag tatctttaat ttattatgta tatataaaaa   8280
taacttacaa ttttattaat aaacaatata tgtttattaa ttcatgtttt gtaatttatg   8340
ggatagcgat ttttttact gtctgtattt tcttttttaa ttatgtttta attgtattta   8400
ttttattttt attattgttc tttttatagt attattttaa aacaaaatgt attttctaag   8460
aacttataat aataataata taaattttaa taaaaattat atttatcttt tacaatatga   8520
acataaagta caacattaat atatagcttt taatattttt attcctaatc atgtaaatct   8580
taaatttttc tttttaaaca tatgttaaat atttatttct cattatatat aagaacatat   8640
ttattacatc tagaggtacc gagctcgttt tcgacactgg atggcggcgt tagtatcgaa   8700
tcgacagcag tatagcgacc agcattcaca tacgattgac gcatgatatt actttctgcg   8760
cacttaactt cgcatctggg cagatgatgt cgaggcgaaa aaaaatataa atcacgctaa   8820
catttgatta aaatagaaca actacaatat aaaaaaacta tacaaatgac aagttcttga   8880
```

aaacaagaat ctttttattg tcagtactga ttagaaaaac tcatcgagca tcaaatgaaa 8940
ctgcaattta ttcatatcag gattatcaat accatatttt tgaaaaagcc gtttctgtaa 9000
tgaaggagaa aactcaccga ggcagttcca taggatggca agatcctggt atcggtctgc 9060
gattccgact cgtccaacat caatacaacc tattaatttc ccctcgtcaa aaataaggtt 9120
atcaagtgag aaatcaccat gagtgacgac tgaatccggt gagaatggca aaagcttatg 9180
catttctttc cagacttgtt caacaggcca gccattacgc tcgtcatcaa aatcactcgc 9240
atcaaccaaa ccgttattca ttcgtgattg cgcctgagcg agacgaaata cgcgatcgct 9300
gttaaaagga caattacaaa caggaatcga atgcaaccgg cgcaggaaca ctgccagcgc 9360
atcaacaata ttttcacctg aatcaggata ttcttctaat acctggaatg ctgttttgcc 9420
ggggatcgca gtggtgagta accatgcatc atcaggagta cggataaaat gcttgatggt 9480
cggaagaggc ataaattccg tcagccagtt tagtctgacc atctcatctg taacatcatt 9540
ggcaacgcta cctttgccat gtttcagaaa caactctggc gcatcgggct tcccatacaa 9600
tcgatagatt gtcgcacctg attgcccgac attatcgcga gcccatttat acccatataa 9660
atcagcatcc atgttggaat ttaatcgcgg cctcgaaacg tgagtctttt ccttacccat 9720
ggttgtttat gttcggatgt gatgtgagaa ctgtatccta gcaagatttt aaaaggaagt 9780
atatgaaaga agaacctcag tggcaaatcc taacctttta tatttctcta caggggcgcg 9840
gcgtggggac aattcaacgc gtctgtgagg ggagcgtttc cctgctcgca ggtctgcagc 9900
gaggagccgt aatttttgct tcgcgccgtg cggccatcaa aatgtatgga tgcaaatgat 9960
tatacatggg gatgtatggg ctaaatgtac gggcgacagt cacatcatgc ccctgagctg 10020
cgcacgtcaa gactgtcaag gagggtattc tgggcctcca tgtcgctggc ctaacattag 10080
taatgtaggt ctgactttca ctcatataag tcttatggta actaaactaa ggtcttacct 10140
ttactgatat atgtcttact ttcactaact taggtattac ttttactaac ttaggtctta 10200
aattcagtaa ctaaggtcat acttcgacta actaaggtct tacattcact gatataggtc 10260
ttatgattac taacttaggt cctaatttga ctaacataag tcctaacatt agtaatgtag 10320
gtcttaactt aactaactta ggtcttacct tcactaatat aggtcttaat attactgact 10380
taagtaatta aggtactaac ttaggtcgta aggtaactaa tatataggtc ttaaggtaac 10440
taatttaggt cttgacttaa taaatatagg tcctaacata aatagtatag gtcctaatat 10500
aagtactata ggccttaact taaccaacat aggtcctaac ataagttata taggtcttaa 10560
cgtaactaac ataagtcatt aaggtactaa gtttggtctt aatttaacaa taacatgtcg 10620
ctggcctaac attagtaatg taggtctgac tttcactcat ataagtctta tggtaactaa 10680
actaaggtct tacctttact gatatatgtc ttactttcac taacttaggt attactttta 10740
ctaacttagg tcttaaattc agtaactaag gtcatacttc gactaactaa ggtcttacat 10800
tcactgatat aggtcttatg attactaact taggtcctaa tttgactaac ataagtccta 10860
acattagtaa tgtaggtctt aacttaacta acttaggtct taccttcact aatataggtc 10920
ttaatattac tgacttaagt aattaaggta ctaacttagg tcgtaaggta actaatatat 10980
aggtcttaag gtaactaatt taggtcttga cttaataaat ataggtccta acataaatag 11040
tataggtcct aatataagta ctataggcct taacttaacc aacataggtc ctaacataag 11100
ttatataggt cttaacgtaa ctaacataag tcattaaggt actaagtttg gtcttaattt 11160
aacaataacc atgtcgctgg ccgggtggtc ttaatttaac aaatatagac catgtcgctg 11220
gccgggtgac ccggcgggga cgaggcaagc taaacagatc ctcgtgatac gcctattttt 11280
ataggttaat gtcatgataa taatggtttc ttaggacgga tcgcttgcct gtaacttaca 11340
cgcgcctcgt atcttttaat gatggaataa tttgggaatt tactctgtgt ttatttattt 11400
ttatgttttg tatttggatt ttagaaagta aataaagaag gtagaagagt tacggaatga 11460
agaaaaaaaa ataaacaaag gtttaaaaaa tttcaacaaa aagcgtactt tacatatata 11520
tttattagac aagaaaagca gattaaatag atatacattc gattaacgat aagtaaaatg 11580
taaaatcaca ggattttcgt gtgtggtctt ctacacagac aagatgaaac aattcggcat 11640
taatacctga gagcaggaag agcaagataa aaggtagtat ttgttggcga tccccctaga 11700
gtcttttaca tcttcggaaa acaaaaacta ttttttcttt aatttctttt tttactttct 11760
atttttaatt tatatattta tattaaaaaa tttaaattat aattattttt atagcacgtg 11820
atgaaaagga cccaggtggc acttttcggg gaaatctcga cctgcagcgt acgaagct 11878

<210> SEQ ID NO 388
<211> LENGTH: 12044
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 388
gcctcactga ttaagcattg gtaactgtca gaccaagttt actcatatat actttagatt 60
gatttaaaac ttcattttta atttaaaagg atctaggtga agatcctttt tgataatctc 120
atgaccaaaa tcccttaacg tgagttttcg ttccactgag cgtcagaccc cgtagaaaag 180
atcaaaggat cttcttgaga tccttttttt ctgcgcgtaa tctgctgctt gcaaacaaaa 240
aaaccaccgc taccagcggt ggtttgtttg ccggatcaag agctaccaac tctttttccg 300
aaggtaactg gcttcagcag agcgcagata ccaaatactg ttcttctagt gtagccgtag 360
ttaggccacc acttcaagaa ctctgtagca ccgcctacat acctcgctct gctaatcctg 420
ttaccagtgg ctgctgccag tggcgataag tcgtgtctta ccgggttgga ctcaagacga 480
tagttaccgg ataaggcgca gcggtcgggc tgaacggggg gttcgtgcac acagcccagc 540
ttggagcgaa cgacctacac cgaactgaga tacctacagc gtgagctatg agaaagcgcc 600
acgcttcccg aagggagaaa ggcggacagg tatccggtaa gcggcagggt cggaacagga 660
gagcgcacga gggagcttcc agggggaaac gcctggtatc tttatagtcc tgtcgggttt 720
cgccacctct gacttgagcg tcgatttttg tgatgctcgt caggggggcg gagcctatgg 780
aaaaacgcca gcaacgcggc ctttttacgg ttcctggcct tttgctggcc ttttgctcac 840
atgttctttc ctgcgttatc ccctgattct gtggataacc gtattaccgc ctttgagtga 900
gctgataccg ctcgccgcag ccgaacgacc gagcgcagcg agtcagtgag cgaggaagcg 960
gaagagcgcc caatacgcaa accgcctctc cccgcgcgtt ggccgattca ttaatgcagc 1020
tggcacgaca ggtttcccga ctggaaagcg ggcagtgagc gcaacgcaat taatgtgagt 1080
tagctcactc attaggcacc ccaggcttta cactttatgc ttccggctcg tatgttgtgt 1140
ggaattgtga gcggataaca atttcacaca ggaaacagct atgaccatga ttacgccaag 1200
ctatttaggt gacactatag aatactcaag cttgggggga tcctctagag tcgactaata 1260
cgactcacta taggaacata atctatagcg gcgttttaga gctagaaata gcaagttaaa 1320
ataaggctag tccgttatca acttgaaaaa gtggcaccga gtcggtgcta gcataacccc 1380
ttggggcctc taaacgggtc ttgaggggtt ttttggtcga cctgcaggca tgctatttga 1440

```
tgaattaact acacttaaaa taatacaatt attattaaat ttttttttga tttatttatt   1500
aatttttaaa cttaatcatt tgtatttggg aggaattata tatatcttta taattatttt   1560
attttttttt atttttttat ttttttatta ttattatttt tttttatttt tttttttttac   1620
tgtatcaaag aaaaaccttt aaaaaaaaaa ttataatttc cccatcttac tatattttta   1680
atacatacgt tttaaggaat taaattagac aaaagctata ttatgcttta catataatta   1740
gaatttataa acgtttggtt attagatatt tcatgtctca gtaaagtctt tcaatacata   1800
tgtaaaaaaa tatatatgaa tacacataag ttgttaatat attttatatg cataaatgta   1860
taaatatata tatatatata tatatatgta tgtatgtata tgtgtgtata tgaaattatt   1920
tcaatgttta attttttaaa ttttaatttt tttttttttt tttttttta ttatgtatat   1980
tgatctttat tatttaaata ttactttttt cgtttttttct tctttttatt attttttttt   2040
tttttatat tttatacaaa tggtaattca aataaaaggt ataaatttat atttaatttt   2100
cttttatgga taaataaaag aaaaatataa atatataaaa atataaaaat atatatatgt   2160
atattggggt gatgataaaa tgaaagataa tatatatata tatatatctt tatttttttt   2220
tttttgtaga ccccattgtg agtacataaa tatattatat aactcgggag catcagtcat   2280
ggaattctta tttcttttttc tttttgcct ggccggcctt tttcgtggcc gccggccttt   2340
tgtcgcctcc cagctgagac aggtcgatcc gtgtctcgta caggccggtg atgctctggt   2400
ggatcagggt ggcgtccagc acctctttgg tgctggtgta cctcttccgg tcgatggtgg   2460
tgtcaaagta cttgaaggcg gcaggggctc ccagattggt cagggtaaac aggtggatga   2520
tattctcggc ctgctctctg atgggcttat cccggtgctt gttgtaggcg gacagcactt   2580
tgtccagatt agcgtcggcc aggatcactc tcttggagaa ctcgctgatc tgctcgatga   2640
tctcgtccag gtagtgcttg tgctgttcca caaacagctg tttctgctca ttatcctcgg   2700
gggagccctt cagcttctca tagtggctgg ccaggtacag gaagttcaca tatttggagg   2760
gcagggccag ttcgtttccc ttctgcagtt cgccggcaga ggccagcatt ctcttccggc   2820
cgttttccag ctcgaacagg gagtacttag gcagcttgat gatcaggtcc tttttcactt   2880
ctttgtagcc cttggcttcc agaaagtcga tgggattctt ctcgaagctg cttctttcca   2940
tgatggtgat ccccagcagc tctttcacac tcttcagttt cttggacttg ccctttttcca   3000
ctttggccac caccagcaca gaataggcca cggtggggct gtcgaagccg ccgtacttct   3060
tagggtccca gtccttcttt ctggcgatca gcttatcgct gttcctcttg ggcaggatag   3120
actctttgct gaagccgcct gtctgcacct cggtcttttt cacgatattc acttggggca   3180
tgctcagcac tttccgcacg gtggcaaaat cccggccctt atcccacacg atctccccgg   3240
tttcgccgtt tgtctcgatc agaggccgct tccggatctc gccgttggcc agggtaatct   3300
cggtcttgaa aaagttcatg atgttgctgt agaagaagta cttggcggta gccttgccga   3360
tttcctgctc gctcttggcg atcatcttcc gcacgtcgta caccttgtag tcgccgtaca   3420
cgaactcgct ttccagctta gggtactttt tgatcagggc ggttcccacg acggcgttca   3480
ggtaggcgtc gtgggcgtgg tggtagttgt tgatctcgcg cactttgtaa aactggaaat   3540
ccttccggaa atcggacacc agcttggact tcagggtgat cactttcact tcccggatca   3600
gcttgtcatt ctcgtcgtac ttagtgttca tccgggagtc caggatctgt gccacgtgct   3660
ttgtgatctg ccgggtttcc accagctgtc tcttgatgaa gccggcctta tccagttcgc   3720
tcaggccgcc tctctcggcc ttggtcagat tgtcgaactt tctctgggta atcagcttgg   3780
```

-continued

```
cgttcagcag ctgccgccag tagttcttca tcttcttcac gacctcttcg gagggcacgt   3840
tgtcgctctt gccccggttc ttgtcgcttc tggtcagcac cttgttgtcg atggagtcgt   3900
ccttcagaaa gctctgaggc acgatatggt ccacatcgta gtcggacagc cggttgatgt   3960
ccagttcctg gtccacgtac atatcccgcc cattctgcag gtagtacagg tacagcttct   4020
cgttctgcag ctgggtgttt tccacggggt gttctttcag gatctggctg cccagctctt   4080
tgatgccctc ttcgatccgc ttcattctct cgcggctgtt cttctgtccc ttctgggtgg   4140
tctggttctc tctggccatt tcgatcacga tgttctcggg cttgtgccgg cccatcactt   4200
tcacgagctc gtccaccacc ttcactgtct gcaggatgcc cttcttaatg gcggggctgc   4260
cggccagatt ggcaatgtgc tcgtgcaggc tatcgccctg gccggacacc tgggctttct   4320
ggatgtcctc tttaaaggtc aggctgtcgt cgtggatcag ctgcatgaag tttctgttgg   4380
cgaagccgtc ggacttcagg aaatccagga ttgtcttgcc ggactgcttg tcccggatgc   4440
cgttgatcag cttccggctc agcctgcccc agccggtgta tctccgccgc ttcagctgct   4500
tcatcacttt gtcgtcgaac aggtgggcat aggttttcag ccgttcctcg atcatctctc   4560
tgtcctcaaa cagtgtcagg gtcagcacga tatcttccag aatgtcctcg ttttcctcat   4620
tgtccaggaa gtccttgtcc ttgataattt tcagcagatc gtggtatgtg cccagggagg   4680
cgttgaaccg atcttccacg ccggagattt ccacggagtc gaagcactcg attttcttga   4740
agtagtcctc tttcagctgc ttcacggtca ctttccggtt ggtcttgaac agcaggtcca   4800
cgatggcctt tttctgctcg ccgctcagga aggcgggctt tctcattccc tcggtcacgt   4860
atttcacttt ggtcagctcg ttatacacgg tgaagtactc gtacagcagg ctgtgcttgg   4920
gcagcacctt ctcgttgggc aggttcttat cgaagttggt catccgctcg atgaagctct   4980
gggcggaagc gcccttgtcc accacttcct cgaagttcca gggggtgatg gtttcctcgc   5040
tctttctggt catccaggcg aatctgctgt ttcccctggc cagagggccc acgtagtagg   5100
ggatgcggaa ggtcaggatc ttctcgatct tttcccggtt gtccttcagg aatgggtaaa   5160
aatcttcctg ccgccgcaga atggcgtgca gctctcccag gtggatctgg tgggggatgc   5220
tgccgttgtc gaaggtccgc tgcttccgca gcaggtcctc tctgttcagc ttcacgagca   5280
gttcctcggt gccgtccatc ttttccagga tgggcttgat gaacttgtag aactcttcct   5340
ggctggctcc gccgtcaatg tagccggcgt agccgttctt gctctggtcg aagaaaatct   5400
ctttgtactt ctcaggcagc tgctgccgca cgagagcttt cagcagggtc aggtcctggt   5460
ggtgctcgtc gtatctcttg atcatagagg cgctcagggg ggccttggtg atctcggtgt   5520
tcactctcag gatgtcgctc agcaggatgg cgtcggacag gttcttggcg gccagaaaca   5580
ggtcggcgta ctggtcgccg atctgggcca gcaggttgtc caggtcgtcg tcgtaggtgt   5640
ccttgctcag ctgcagtttg gcatcctcgg ccaggtcgaa gttgctcttg aagttggggg   5700
tcaggcccag gctcagggca atcaggtttc cgaacaggcc attcttcttc tcgccgggca   5760
gctgggcgat cagattttcc agccgtctgc tcttgctcag tctggcagac aggatggcct   5820
tggcgtccac gccgctggcg ttgatggggt tttcctcgaa cagctggttg taggtctgca   5880
ccagctggat gaacagcttg tccacgtcgc tgttgtcggg gttcaggtcg ccctcgatca   5940
ggaagtggcc ccggaacttg atcatgtggg ccagggccag atagatcagc cgcaggtcgg   6000
ccttgtcggt gctgtccacc agtttctttc tcaggtggta gatggtgggg tacttctcgt   6060
ggtaggccac ctcgtccacg atgttgccga agatggggtg ccgctcgtgc ttcttatcct   6120
cttccaccag gaaggactct tccagtctgt ggaagaagct gtcgtccacc ttggccatct   6180
```

cgttgctgaa gatctcttgc agatagcaga tccggttctt ccgtctggtg tatcttcttc 6240
tggcggttct cttcagccgg gtggcctcgg ctgtttcgcc gctgtcgaac agcagggctc 6300
cgatcaggtt cttcttgatg ctgtgccggt cggtgttgcc cagcaccttg aatttcttgc 6360
tgggcacctt gtactcgtcg gtgatcacgg cccagcccac agagttggtg ccgatgtcca 6420
ggccgatgct gtacttcttg tcggctgctg ggactccgtg gataccgacc ttccgcttct 6480
tctttggggc catcttatcg tcatcgtctt tgtaatcaat atcatgatcc ttgtagtctc 6540
cgtcgtggtc cttatagtcc atttttctcg agggatcctg atatatttct attaggtatt 6600
tattattata aaatataaat cttgaatgat aataaataaa atattagtta ttcctttttct 6660 agtttaaaat atacatatta taaatatata tatatatata tatattttta ttgtgacaag 6720
aatatataat tataaattat attatttatt tttgtatttt tttttttttt tttttttttt 6780
tctttttttg ttttattttt cttttttttt ataaatatta tttttttctt ttatcatgca 6840
cattggaata atacattaat atatatatat atattatatt atacatatat tgaataatgt 6900
ttataaaaaa tgcataactt atatgaatat aatttttttt aaatatgaca aaaagaaaaa 6960
aaaaaaaaac caaaaaaaat taaaattgaa atgaaatata taaatatatt atttatatat 7020
attatacatt gtttaatact actacatgta tatatatata ttatatatat atatatatat 7080 caatttttttc aaaaataaat taatataaaa agaggggaaa aaaaaaaaaa aaaaaaaaaa 7140
aagataatta agtaagcatt taaaaatata taaattgata atatataaaa ttaatcacat 7200
ataaaagctt ataaacacta ggttagctaa ttcgcttgta agaggtactc tcgtttatgc 7260
aaaactattt gatatagcat tttaacaagt acacatatat atatgtaata tatatactat 7320
atatatctat tgcatgtgta ctaagcatgt gcatggcatc cccttttttct cgtgtttaaa 7380 acagtttgta tgataaaata taaaggattt gaaaaagaga aaaaaatata tgatctcatc 7440
ctatatagcg ccataatttt tatttgggtt gaataaaatt ttctactaaa tttaggtgta 7500
agtaaaataa tggaatatat ataagtacaa taaaaaagtg cataaattaa aaaattttta 7560
taataaatat tttttttaaa aaagtcaata ataatattaa atatatataa cacaggatta 7620
tatatgttca ctacaatttt ttatattata atataaattc ttttcaattt tcattttatt 7680
ttacatacac tttccttttt tgtcactata ttttaatatt cacatattta gtttaaatac 7740
tggctatttc tttctacatt tgctagtaac aattgtgtag tgcttaaata tatacacaca 7800
cctaaaactt acaaagtatc ctaggaccat ggccaagcct ttgtctcaag aagaatccac 7860
cctcattgaa agagcaacgg ctacaatcaa cagcatcccc atctctgaag actacagcgt 7920
cgccagcgca gctctctcta gcgacggccg catcttcact ggtgtcaatg tatatcattt 7980
tactggggga ccttgtgcag aactcgtggt gctgggcact gctgctgctg cggcagctgg 8040
caacctgact tgtatcgtcg cgatcggaaa tgagaacagg ggcatcttga gcccctgcgg 8100
acggtgccga caggtgcttc tcgatctgca tcctgggatc aaagccatag tgaaggacag 8160
tgatggacag ccgacggcag ttgggattcg tgaattgctg ccctctggtt atgtgtggga 8220
gggctaaccg cgggtacccc attaaattta tttaataata gattaaaaat attataaaaa 8280
taaaaacata aacacagaaa ttacaaaaaa aatacatatg aatttttttt ttgtaatctt 8340
ccttataaat atagaataat gaatcatata aaacatatca ttattcattt atttacattt 8400
aaaattattg tttcagtatc tttaatttat tatgtatata taaaaataac ttacaatttt 8460
attaataaac aatatatgtt tattaattca tgttttgtaa tttatgggat agcgattttt 8520

```
tttactgtct gtattttctt ttttaattat gttttaattg tatttatttt atttttatta   8580
ttgttctttt tatagtatta ttttaaaaca aaatgtattt tctaagaact tataataata   8640
ataatataaa ttttaataaa aattatattt atcttttaca atatgaacat aaagtacaac   8700
attaatatat agcttttaat atttttattc ctaatcatgt aaatcttaaa tttttctttt   8760
taaacatatg ttaaatattt atttctcatt atatataaga acatatttat tacatctaga   8820
ggtaccgagc tcgttttcga cactggatgg cggcgttagt atcgaatcga cagcagtata   8880
gcgaccagca ttcacatacg attgacgcat gatattactt tctgcgcact taacttcgca   8940
tctgggcaga tgatgtcgag gcgaaaaaaa atataaatca cgctaacatt tgattaaaat   9000
agaacaacta caatataaaa aaactataca aatgacaagt tcttgaaaac aagaatcttt   9060
ttattgtcag tactgattag aaaaactcat cgagcatcaa atgaaactgc aatttattca   9120
tatcaggatt atcaatacca tatttttgaa aaagccgttt ctgtaatgaa ggagaaaact   9180
caccgaggca gttccatagg atggcaagat cctggtatcg gtctgcgatt ccgactcgtc   9240
caacatcaat acaacctatt aatttcccct cgtcaaaaat aaggttatca agtgagaaat   9300
caccatgagt gacgactgaa tccggtgaga atggcaaaag cttatgcatt tctttccaga   9360
cttgttcaac aggccagcca ttacgctcgt catcaaaatc actcgcatca accaaaccgt   9420
tattcattcg tgattgcgcc tgagcgagac gaaatacgcg atcgctgtta aaaggacaat   9480
tacaaacagg aatcgaatgc aaccggcgca ggaacactgc cagcgcatca acaatatttt   9540
cacctgaatc aggatattct tctaatacct ggaatgctgt tttgccgggg atcgcagtgg   9600
tgagtaacca tgcatcatca ggagtacgga taaaatgctt gatggtcgga agaggcataa   9660
attccgtcag ccagtttagt ctgaccatct catctgtaac atcattggca acgctacctt   9720
tgccatgttt cagaaacaac tctggcgcat cgggcttccc atacaatcga tagattgtcg   9780
cacctgattg cccgacatta tcgcgagccc atttataccc atataaatca gcatccatgt   9840
tggaatttaa tcgcggcctc gaaacgtgag tcttttcctt acccatggtt gtttatgttc   9900
ggatgtgatg tgagaactgt atcctagcaa gattttaaaa ggaagtatat gaaagaagaa   9960
cctcagtggc aaatcctaac cttttatatt tctctacagg ggcgcggcgt ggggacaatt  10020
caacgcgtct gtgaggggag cgtttccctg ctcgcaggtc tgcagcgagg agccgtaatt  10080
tttgcttcgc gccgtgcggc catcaaaatg tatggatgca aatgattata catggggatg  10140
tatgggctaa atgtacgggc gacagtcaca tcatgcccct gagctgcgca cgtcaagact  10200
gtcaaggagg gtattctggg cctccatgtc gctggcctaa cattagtaat gtaggtctga  10260
ctttcactca tataagtctt atggtaacta aactaaggtc ttacctttac tgatatatgt  10320
cttactttca ctaacttagg tattactttt actaacttag gtcttaaatt cagtaactaa  10380
ggtcatactt cgactaacta aggtcttaca ttcactgata taggtcttat gattactaac  10440
ttaggtccta atttgactaa cataagtcct aacattagta atgtaggtct taacttaact  10500
aacttaggtc ttaccttcac taatataggt cttaatatta ctgacttaag taattaaggt  10560
actaacttag gtcgtaaggt aactaatata taggtcttaa ggtaactaat ttaggtcttg  10620
acttaataaa tataggtcct aacataaata gtataggtcc taatataagt actataggcc  10680
ttaacttaac caacataggt cctaacataa gttatatagg tcttaacgta actaacataa  10740
gtcattaagg tactaagttt ggtcttaatt taacaataac atgtcgctgg cctaacatta  10800
gtaatgtagg tctgactttc actcatataa gtcttatggt aactaaacta aggtcttacc  10860
tttactgata tatgtcttac tttcactaac ttaggtatta cttttactaa cttaggtctt  10920
```

```
aaattcagta actaaggtca tacttcgact aactaaggtc ttacattcac tgatataggt  10980

cttatgatta ctaacttagg tcctaatttg actaacataa gtcctaacat tagtaatgta  11040

ggtcttaact taactaactt aggtcttacc ttcactaata taggtcttaa tattactgac  11100

ttaagtaatt aaggtactaa cttaggtcgt aaggtaacta atatataggt cttaaggtaa  11160

ctaatttagg tcttgactta ataaatatag gtcctaacat aaatagtata ggtcctaata  11220

taagtactat aggccttaac ttaaccaaca taggtcctaa cataagttat ataggtctta  11280

acgtaactaa cataagtcat taaggtacta agtttggtct taatttaaca ataaccatgt  11340

cgctggccgg gtggtcttaa tttaacaaat atagaccatg tcgctggccg ggtgacccgg  11400

cggggacgag gcaagctaaa cagatcctcg tgatacgcct atttttatag gttaatgtca  11460

tgataataat ggtttcttag gacggatcgc ttgcctgtaa cttacacgcg cctcgtatct  11520

tttaatgatg gaataatttg ggaatttact ctgtgtttat ttattttat gttttgtatt  11580

tggattttag aaagtaaata aagaaggtag aagagttacg gaatgaagaa aaaaaaataa  11640

acaaaggttt aaaaaatttc aacaaaaagc gtactttaca tatatattta ttagacaaga  11700

aaagcagatt aaatagatat acattcgatt aacgataagt aaaatgtaaa atcacaggat  11760

tttcgtgtgt ggtcttctac acagacaaga tgaaacaatt cggcattaat acctgagagc  11820

aggaagagca agataaaagg tagtatttgt tggcgatccc cctagagtct tttacatctt  11880

cggaaaacaa aaactatttt ttctttaatt tcttttttta ctttctattt ttaatttata  11940

tatttatatt aaaaaattta aattataatt atttttatag cacgtgatga aaaggaccca  12000

ggtggcactt ttcggggaaa tctcgacctg cagcgtacga agct                  12044
```

<210> SEQ ID NO 389
<211> LENGTH: 12044
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 389

```
gcctcactga ttaagcattg gtaactgtca gaccaagttt actcatatat actttagatt     60

gatttaaaac ttcattttta atttaaaagg atctaggtga agatcctttt tgataatctc    120

atgaccaaaa tcccttaacg tgagttttcg ttccactgag cgtcagaccc cgtagaaaag    180

atcaaaggat cttcttgaga tccttttttt ctgcgcgtaa tctgctgctt gcaaacaaaa    240

aaaccaccgc taccagcggt ggtttgtttg ccggatcaag agctaccaac tctttttccg    300

aaggtaactg gcttcagcag agcgcagata ccaaatactg ttcttctagt gtagccgtag    360

ttaggccacc acttcaagaa ctctgtagca ccgcctacat acctcgctct gctaatcctg    420

ttaccagtgg ctgctgccag tggcgataag tcgtgtctta ccgggttgga ctcaagacga    480

tagttaccgg ataaggcgca gcggtcgggc tgaacggggg gttcgtgcac acagcccagc    540

ttggagcgaa cgacctacac cgaactgaga tacctacagc gtgagctatg agaaagcgcc    600

acgcttcccg aagggagaaa ggcggacagg tatccggtaa gcggcagggt cggaacagga    660

gagcgcacga gggagcttcc agggggaaac gcctggtatc tttatagtcc tgtcgggttt    720

cgccacctct gacttgagcg tcgatttttg tgatgctcgt caggggggcg gagcctatgg    780

aaaaacgcca gcaacgcggc ctttttacgg ttcctggcct tttgctggcc ttttgctcac    840

atgttctttc ctgcgttatc ccctgattct gtggataacc gtattaccgc ctttgagtga    900
```

-continued gctgataccg ctcgccgcag ccgaacgacc gagcgcagcg agtcagtgag cgaggaagcg 960
gaagagcgcc caatacgcaa accgcctctc cccgcgcgtt ggccgattca ttaatgcagc 1020
tggcacgaca ggtttcccga ctggaaagcg ggcagtgagc gcaacgcaat taatgtgagt 1080
tagctcactc attaggcacc ccaggcttta cactttatgc ttccggctcg tatgttgtgt 1140
ggaattgtga gcggataaca atttcacaca ggaaacagct atgaccatga ttacgccaag 1200
ctatttaggt gacactatag aatactcaag cttgggggga tcctctagag tcgactaata 1260
cgactcacta taggaaatga tatggatttt gggttttaga gctagaaata gcaagttaaa 1320
ataaggctag tccgttatca acttgaaaaa gtggcaccga gtcggtgcta gcataacccc 1380
ttggggcctc taaacgggtc ttgaggggtt ttttggtcga cctgcaggca tgctatttga 1440
tgaattaact acacttaaaa taatacaatt attattaaat tttttttga tttatttatt 1500 aatttttaaa cttaatcatt tgtatttggg aggaattata tatatcttta taattatttt 1560
attttttttt atttttttat ttttttatta ttattatttt tttttatttt tttttttac 1620 tgtatcaaag aaaaaccttt aaaaaaaaaa ttataatttc cccatcttac tatattttta 1680
atacatacgt tttaaggaat taaattagac aaaagctata ttatgcttta catataatta 1740
gaatttataa acgtttggtt attagatatt tcatgtctca gtaaagtctt tcaatacata 1800
tgtaaaaaaa tatatatgaa tacacataag ttgttaatat attttatatg cataaatgta 1860
taaatatata tatatatata tatatatgta tgtatgtata tgtgtgtata tgaaattatt 1920
tcaatgttta attttttaaa ttttaatttt tttttttttt ttttttttta ttatgtatat 1980
tgatctttat tatttaaata ttactttttt cgtttttttct tctttttatt attttttttt 2040 tttttttatat tttatacaaa tggtaattca aataaaaggt ataaatttat atttaatttt 2100
cttttatgga taaataaaag aaaaatataa atatataaaa atataaaaat atatatatgt 2160
atattggggt gatgataaaa tgaaagataa tatatatata tatatatctt tatttttttt 2220
tttttgtaga ccccattgtg agtacataaa tatattatat aactcgggag catcagtcat 2280
ggaattctta tttcttttttc ttttttgcct ggccggcctt tttcgtggcc gccggccttt 2340
tgtcgcctcc cagctgagac aggtcgatcc gtgtctcgta caggccggtg atgctctggt 2400
ggatcagggt ggcgtccagc acctctttgg tgctggtgta cctcttccgg tcgatggtgg 2460
tgtcaaagta cttgaaggcg gcaggggctc ccagattggt cagggtaaac aggtggatga 2520
tattctcggc ctgctctctg atgggcttat cccggtgctt gttgtaggcg gacagcactt 2580
tgtccagatt agcgtcggcc aggatcactc tcttggagaa ctcgctgatc tgctcgatga 2640
tctcgtccag gtagtgcttg tgctgttcca caaacagctg tttctgctca ttatcctcgg 2700
gggagccctt cagcttctca tagtggctgg ccaggtacag gaagttcaca tatttggagg 2760
gcagggccag ttcgtttccc ttctgcagtt cgccggcaga ggccagcatt ctcttccggc 2820
cgttttccag ctcgaacagg gagtacttag gcagcttgat gatcaggtcc tttttcactt 2880
ctttgtagcc cttggcttcc agaaagtcga tgggattctt ctcgaagctg cttctttcca 2940
tgatggtgat ccccagcagc tctttcacac tcttcagttt cttggacttg cccttttcca 3000
ctttggccac caccagcaca gaataggcca cggtggggct gtcgaagccg ccgtacttct 3060
tagggtccca gtccttcttt ctggcgatca gcttatcgct gttcctcttg ggcaggatag 3120
actctttgct gaagccgcct gtctgcacct cggtcttttt cacgatattc acttggggca 3180
tgctcagcac tttccgcacg gtggcaaaat cccggccctt atcccacacg atctccccgg 3240

```
tttcgccgtt tgtctcgatc agaggccgct tccggatctc gccgttggcc agggtaatct   3300
cggtcttgaa aaagttcatg atgttgctgt agaagaagta cttggcggta gccttgccga   3360
tttcctgctc gctcttggcg atcatcttcc gcacgtcgta caccttgtag tcgccgtaca   3420
cgaactcgct ttccagctta gggtactttt tgatcagggc ggttcccacg acggcgttca   3480
ggtaggcgtc gtgggcgtgg tggtagttgt tgatctcgcg cactttgtaa aactggaaat   3540
ccttccggaa atcggacacc agcttggact tcagggtgat cactttcact tcccggatca   3600
gcttgtcatt ctcgtcgtac ttagtgttca tccgggagtc caggatctgt gccacgtgct   3660
ttgtgatctg ccgggtttcc accagctgtc tcttgatgaa gccggcctta tccagttcgc   3720
tcaggccgcc tctctcggcc ttggtcagat tgtcgaactt tctctgggta atcagcttgg   3780
cgttcagcag ctgccgccag tagttcttca tcttcttcac gacctcttcg gagggcacgt   3840
tgtcgctctt gccccggttc ttgtcgcttc tggtcagcac cttgttgtcg atggagtcgt   3900
ccttcagaaa gctctgaggc acgatatggt ccacatcgta gtcggacagc cggttgatgt   3960
ccagttcctg gtccacgtac atatcccgcc cattctgcag gtagtacagg tacagcttct   4020
cgttctgcag ctgggtgttt tccacggggt gttctttcag gatctggctg cccagctctt   4080
tgatgccctc ttcgatccgc ttcattctct cgcggctgtt cttctgtccc ttctgggtgg   4140
tctggttctc tctggccatt tcgatcacga tgttctcggg cttgtgccgg cccatcactt   4200
tcacgagctc gtccaccacc ttcactgtct gcaggatgcc cttcttaatg gcggggctgc   4260
cggccagatt ggcaatgtgc tcgtgcaggc tatcgccctg gccggacacc tgggctttct   4320
ggatgtcctc tttaaaggtc aggctgtcgt cgtggatcag ctgcatgaag tttctgttgg   4380
cgaagccgtc ggacttcagg aaatccagga ttgtcttgcc ggactgcttg tcccggatgc   4440
cgttgatcag cttccggctc agcctgcccc agccggtgta tctccgccgc ttcagctgct   4500
tcatcacttt gtcgtcgaac aggtgggcat aggttttcag ccgttcctcg atcatctctc   4560
tgtcctcaaa cagtgtcagg gtcagcacga tatcttccag aatgtcctcg ttttcctcat   4620
tgtccaggaa gtccttgtcc ttgataattt tcagcagatc gtggtatgtg cccagggagg   4680
cgttgaaccg atcttccacg ccggagattt ccacggagtc gaagcactcg attttcttga   4740
agtagtcctc tttcagctgc ttcacggtca ctttccggtt ggtcttgaac agcaggtcca   4800
cgatggcctt tttctgctcg ccgctcagga aggcgggctt tctcattccc tcggtcacgt   4860
atttcacttt ggtcagctcg ttatacacgg tgaagtactc gtacagcagg ctgtgcttgg   4920
gcagcacctt ctcgttgggc aggttcttat cgaagttggt catccgctcg atgaagctct   4980
gggcggaagc gcccttgtcc accacttcct cgaagttcca gggggtgatg gtttcctcgc   5040
tctttctggt catccaggcg aatctgctgt ttcccctggc cagagggccc acgtagtagg   5100
ggatgcggaa ggtcaggatc ttctcgatct tttcccggtt gtccttcagg aatgggtaaa   5160
aatcttcctg ccgccgcaga atggcgtgca gctctcccag gtggatctgg tgggggatgc   5220
tgccgttgtc gaaggtccgc tgcttccgca gcaggtcctc tctgttcagc ttcacgagca   5280
gttcctcggt gccgtccatc ttttccagga tgggcttgat gaacttgtag aactcttcct   5340
ggctggctcc gccgtcaatg tagccggcgt agccgttctt gctctggtcg aagaaaatct   5400
ctttgtactt ctcaggcagc tgctgccgca cgagagcttt cagcagggtc aggtcctggt   5460
ggtgctcgtc gtatctcttg atcatagagg cgctcagggg ggccttggtg atctcggtgt   5520
tcactctcag gatgtcgctc agcaggatgg cgtcggacag gttcttggcg gccagaaaca   5580
ggtcggcgta ctggtcgccg atctgggcca gcaggttgtc caggtcgtcg tcgtaggtgt   5640
```

ccttgctcag ctgcagtttg gcatcctcgg ccaggtcgaa gttgctcttg aagttggggg 5700
tcaggcccag gctcagggca atcaggtttc cgaacaggcc attcttcttc tcgccgggca 5760
gctgggcgat cagattttcc agccgtctgc tcttgctcag tctggcagac aggatggcct 5820
tggcgtccac gccgctggcg ttgatggggt tttcctcgaa cagctggttg taggtctgca 5880
ccagctggat gaacagcttg tccacgtcgc tgttgtcggg gttcaggtcg ccctcgatca 5940
ggaagtggcc ccggaacttg atcatgtggg ccagggccag atagatcagc cgcaggtcgg 6000
ccttgtcggt gctgtccacc agtttctttc tcaggtggta gatggtgggg tacttctcgt 6060
ggtaggccac ctcgtccacg atgttgccga agatggggtg ccgctcgtgc ttcttatcct 6120
cttccaccag gaaggactct tccagtctgt ggaagaagct gtcgtccacc ttggccatct 6180
cgttgctgaa gatctcttgc agatagcaga tccggttctt ccgtctggtg tatcttcttc 6240
tggcggttct cttcagccgg gtggcctcgg ctgtttcgcc gctgtcgaac agcagggctc 6300
cgatcaggtt cttcttgatg ctgtgccggt cggtgttgcc cagcaccttg aatttcttgc 6360
tgggcacctt gtactcgtcg gtgatcacgg cccagcccac agagttggtg ccgatgtcca 6420
ggccgatgct gtacttcttg tcggctgctg ggactccgtg gataccgacc ttccgcttct 6480
tctttggggc catcttatcg tcatcgtctt tgtaatcaat atcatgatcc ttgtagtctc 6540
cgtcgtggtc cttatagtcc atttttctcg agggatcctg atatatttct attaggtatt 6600
tattattata aaatataaat cttgaatgat aataaataaa atattagtta ttcctttttct 6660
agtttaaaat atacatatta taaatatata tatatatata tatattttta ttgtgacaag 6720
aatatataat tataaattat attatttatt tttgtatttt tttttttttt tttttttttt 6780
tcttttttttg ttttattttt cttttttttt ataaatatta ttttttttctt ttatcatgca 6840
cattggaata atacattaat atatatatat atattatatt atacatatat tgaataatgt 6900
ttataaaaaa tgcataactt atatgaatat aatttttttt aaatatgaca aaaagaaaaa 6960
aaaaaaaaac caaaaaaaat taaaattgaa atgaaatata taaatatatt atttatatat 7020
attatacatt gtttaatact actacatgta tatatatata ttatatatat atatatatat 7080
caattttttc aaaaataaat taatataaaa agaggggaaa aaaaaaaaaa aaaaaaaaaa 7140
aagataatta agtaagcatt taaaaatata taaattgata atatataaaa ttaatcacat 7200
ataaaagctt ataaacacta ggttagctaa ttcgcttgta agaggtactc tcgtttatgc 7260
aaaactattt gatatagcat tttaacaagt acacatatat atatgtaata tatatactat 7320
atatatctat tgcatgtgta ctaagcatgt gcatggcatc ccctttttct cgtgtttaaa 7380
acagtttgta tgataaaata taaaggattt gaaaaagaga aaaaaatata tgatctcatc 7440
ctatatagcg ccataatttt tatttgggtt gaataaaatt ttctactaaa tttaggtgta 7500
agtaaaataa tggaatatat ataagtacaa taaaaaagtg cataaattaa aaaattttta 7560
taataaatat ttttttttaaa aaagtcaata ataatattaa atatatataa cacaggatta 7620
tatatgttca ctacaatttt ttatattata atataaattc ttttcaattt tcattttatt 7680
ttacatacac tttccttttt tgtcactata ttttaatatt cacatattta gtttaaatac 7740
tggctatttc tttctacatt tgctagtaac aattgtgtag tgcttaaata tatacacaca 7800
cctaaaactt acaaagtatc ctaggaccat ggccaagcct ttgtctcaag aagaatccac 7860
cctcattgaa agagcaacgg ctacaatcaa cagcatcccc atctctgaag actacagcgt 7920
cgccagcgca gctctctcta gcgacggccg catcttcact ggtgtcaatg tatatcattt 7980

-continued

```
tactggggga ccttgtgcag aactcgtggt gctgggcact gctgctgctg cggcagctgg   8040
caacctgact tgtatcgtcg cgatcggaaa tgagaacagg ggcatcttga gcccctgcgg   8100
acggtgccga caggtgcttc tcgatctgca tcctgggatc aaagccatag tgaaggacag   8160
tgatggacag ccgacggcag ttgggattcg tgaattgctg ccctctggtt atgtgtggga   8220
gggctaaccg cgggtacccc attaaattta tttaataata gattaaaaat attataaaaa   8280
taaaaacata aacacagaaa ttacaaaaaa aatacatatg aatttttttt ttgtaatctt   8340
ccttataaat atagaataat gaatcatata aaacatatca ttattcattt atttacattt   8400
aaaattattg tttcagtatc tttaatttat tatgtatata taaaaataac ttacaatttt   8460
attaataaac aatatatgtt tattaattca tgttttgtaa tttatgggat agcgattttt   8520
tttactgtct gtattttctt ttttaattat gttttaattg tatttatttt atttttatta   8580
ttgttctttt tatagtatta ttttaaaaca aaatgtattt tctaagaact tataataata   8640
ataatataaa ttttaataaa aattatattt atcttttaca atatgaacat aaagtacaac   8700
attaatatat agcttttaat atttttattc ctaatcatgt aaatcttaaa tttttctttt   8760
taaacatatg ttaaatattt atttctcatt atatataaga acatatttat tacatctaga   8820
ggtaccgagc tcgttttcga cactggatgg cggcgttagt atcgaatcga cagcagtata   8880
gcgaccagca ttcacatacg attgacgcat gatattactt tctgcgcact taacttcgca   8940
tctgggcaga tgatgtcgag gcgaaaaaaa atataaatca cgctaacatt tgattaaaat   9000
agaacaacta caatataaaa aaactataca aatgacaagt tcttgaaaac aagaatcttt   9060
ttattgtcag tactgattag aaaaactcat cgagcatcaa atgaaactgc aatttattca   9120
tatcaggatt atcaatacca tatttttgaa aaagccgttt ctgtaatgaa ggagaaaact   9180
caccgaggca gttccatagg atggcaagat cctggtatcg gtctgcgatt ccgactcgtc   9240
caacatcaat acaacctatt aatttcccct cgtcaaaaat aaggttatca agtgagaaat   9300
caccatgagt gacgactgaa tccggtgaga atggcaaaag cttatgcatt tctttccaga   9360
cttgttcaac aggccagcca ttacgctcgt catcaaaatc actcgcatca accaaaccgt   9420
tattcattcg tgattgcgcc tgagcgagac gaaatacgcg atcgctgtta aaaggacaat   9480
tacaaacagg aatcgaatgc aaccggcgca ggaacactgc cagcgcatca acaatatttt   9540
cacctgaatc aggatattct tctaatacct ggaatgctgt tttgccgggg atcgcagtgg   9600
tgagtaacca tgcatcatca ggagtacgga taaaatgctt gatggtcgga agaggcataa   9660
attccgtcag ccagtttagt ctgaccatct catctgtaac atcattggca acgctacctt   9720
tgccatgttt cagaaacaac tctggcgcat cgggcttccc atacaatcga tagattgtcg   9780
cacctgattg cccgacatta tcgcgagccc atttataccc atataaatca gcatccatgt   9840
tggaatttaa tcgcggcctc gaaacgtgag tcttttcctt acccatggtt gtttatgttc   9900
ggatgtgatg tgagaactgt atcctagcaa gattttaaaa ggaagtatat gaaagaagaa   9960
cctcagtggc aaatcctaac cttttatatt tctctacagg ggcgcggcgt ggggacaatt  10020
caacgcgtct gtgaggggag cgtttccctg ctcgcaggtc tgcagcgagg agccgtaatt  10080
tttgcttcgc gccgtgcggc catcaaaatg tatggatgca aatgattata catggggatg  10140
tatgggctaa atgtacgggc gacagtcaca tcatgcccct gagctgcgca cgtcaagact  10200
gtcaaggagg gtattctggg cctccatgtc gctggcctaa cattagtaat gtaggtctga  10260
ctttcactca tataagtctt atggtaacta aactaaggtc ttacctttac tgatatatgt  10320
cttactttca ctaacttagg tattactttt actaacttag gtcttaaatt cagtaactaa  10380
```

-continued

```
ggtcatactt cgactaacta aggtcttaca ttcactgata taggtcttat gattactaac  10440
ttaggtccta atttgactaa cataagtcct aacattagta atgtaggtct taacttaact  10500
aacttaggtc ttaccttcac taatataggt cttaatatta ctgacttaag taattaaggt  10560
actaacttag gtcgtaaggt aactaatata taggtcttaa ggtaactaat ttaggtcttg  10620
acttaataaa tataggtcct aacataaata gtataggtcc taatataagt actataggcc  10680
ttaacttaac caacataggt cctaacataa gttatatagg tcttaacgta actaacataa  10740
gtcattaagg tactaagttt ggtcttaatt taacaataac atgtcgctgg cctaacatta  10800
gtaatgtagg tctgactttc actcatataa gtcttatggt aactaaacta aggtcttacc  10860
tttactgata tatgtcttac tttcactaac ttaggtatta cttttactaa cttaggtctt  10920
aaattcagta actaaggtca tacttcgact aactaaggtc ttacattcac tgatataggt  10980
cttatgatta ctaacttagg tcctaatttg actaacataa gtcctaacat tagtaatgta  11040
ggtcttaact taactaactt aggtcttacc ttcactaata taggtcttaa tattactgac  11100
ttaagtaatt aaggtactaa cttaggtcgt aaggtaacta atatataggt cttaaggtaa  11160
ctaatttagg tcttgactta ataaatatag gtcctaacat aaatagtata ggtcctaata  11220
taagtactat aggccttaac ttaaccaaca taggtcctaa cataagttat ataggtctta  11280
acgtaactaa cataagtcat taaggtacta agtttggtct taatttaaca ataaccatgt  11340
cgctggccgg gtggtcttaa tttaacaaat atagaccatg tcgctggccg ggtgacccgg  11400
cggggacgag gcaagctaaa cagatcctcg tgatacgcct atttttatag gttaatgtca  11460
tgataataat ggtttcttag gacggatcgc ttgcctgtaa cttacacgcg cctcgtatct  11520
tttaatgatg gaataatttg ggaatttact ctgtgtttat ttatttttat gttttgtatt  11580
tggattttag aaagtaaata aagaaggtag aagagttacg gaatgaagaa aaaaaaataa  11640
acaaaggttt aaaaaatttc aacaaaaagc gtactttaca tatatattta ttagacaaga  11700
aaagcagatt aaatagatat acattcgatt aacgataagt aaaatgtaaa atcacaggat  11760
tttcgtgtgt ggtcttctac acagacaaga tgaaacaatt cggcattaat acctgagagc  11820
aggaagagca agataaaagg tagtatttgt tggcgatccc cctagagtct tttacatctt  11880
cggaaaacaa aaactatttt ttctttaatt tcttttttta ctttctattt ttaatttata  11940
tatttatatt aaaaaattta aattataatt atttttatag cacgtgatga aaaggaccca  12000
ggtggcactt ttcggggaaa tctcgacctg cagcgtacga agct                  12044
```

UNITED STATES PATENT AND TRADEMARK OFFICE
CERTIFICATE OF CORRECTION

PATENT NO. : 11,291,710 B2
APPLICATION NO. : 16/874295
DATED : April 5, 2022
INVENTOR(S) : Kamel Khalili and Wenhui Hu It is certified that error appears in the above-identified patent and that said Letters Patent is hereby corrected as shown below:

In the Specification

At Column 1, Line numbers 27-31, should read "This invention was made with government support under P30 MH092177, R01 MH093271, and R01 NS087971 awarded by the National Institutes of Health. The government has certain rights in the invention."

Signed and Sealed this
Twenty-fourth Day of June, 2025

Coke Morgan Stewart
*Acting Director of the United States Patent and Trademark Office*